US010870627B2

United States Patent
Xia et al.

(10) Patent No.: US 10,870,627 B2
(45) Date of Patent: Dec. 22, 2020

(54) SALT OF QUINAZOLINE DERIVATIVE, PREPARATION METHOD THEREFOR AND APPLICATION THEREOF

(71) Applicant: SHANGHAI PHARMACEUTICALS HOLDING CO., LTD., Shanghai (CN)

(72) Inventors: Guangxin Xia, Shanghai (CN); Di Li, Shanghai (CN); Ning Zhou, Shanghai (CN); Ao Chen, Shanghai (CN); Liang Zhao, Shanghai (CN); Jiansheng Han, Shanghai (CN); Yanjun Liu, Shanghai (CN)

(73) Assignee: SHANGHAI PHARMACEUTICALS HOLDING CO., LTD., Shanghai (CN)

( * ) Notice: Subject to any disclaimer, the term of this patent is extended or adjusted under 35 U.S.C. 154(b) by 0 days.

(21) Appl. No.: 16/335,622

(22) PCT Filed: Sep. 22, 2017

(86) PCT No.: PCT/CN2017/102998
§ 371 (c)(1),
(2) Date: Mar. 21, 2019

(87) PCT Pub. No.: WO2018/054359
PCT Pub. Date: Mar. 29, 2018

(65) Prior Publication Data
US 2019/0300491 A1 Oct. 3, 2019

(30) Foreign Application Priority Data

Sep. 23, 2016 (CN) .......................... 2016 1 0847951

(51) Int. Cl.
| | | |
|---|---|---|
| *C07D 239/94* | (2006.01) | |
| *A61P 35/00* | (2006.01) | |
| *C07C 59/265* | (2006.01) | |
| *C07C 309/05* | (2006.01) | |
| *C07C 309/29* | (2006.01) | |

(Continued)

(52) U.S. Cl.
CPC .......... *C07D 239/94* (2013.01); *A61K 31/517* (2013.01); *A61K 31/5377* (2013.01); *A61P 35/00* (2018.01); *C07C 55/08* (2013.01); *C07C 55/10* (2013.01); *C07C 57/145* (2013.01); *C07C 59/105* (2013.01); *C07C 59/255* (2013.01); *C07C 59/265* (2013.01); *C07C 59/305* (2013.01); *C07C 59/347* (2013.01); *C07C 65/11* (2013.01); *C07C 69/38* (2013.01); *C07C 69/40* (2013.01); *C07C 309/05* (2013.01); *C07C 309/29* (2013.01); *C07C 309/35* (2013.01); *C07C 309/39* (2013.01); *C07D 307/06* (2013.01); *C07D 307/08* (2013.01); *C07D 319/12* (2013.01); *C07D 401/12* (2013.01); *C07D 403/12* (2013.01); *C07D 405/12* (2013.01); *C07D 413/12* (2013.01);

(Continued)

(58) Field of Classification Search
CPC .. C07D 239/94; C07D 319/12; C07D 401/12; C07D 405/12; C07D 413/12; C07D 307/06; C07D 307/08; C07D 403/12; C07C 65/11; C07C 309/39; C07C 69/38; C07C 55/08; C07C 59/347; C07C 59/255; C07C 309/05; C07C 69/40; A61K 31/517; A61K 31/5377; A61P 35/00
See application file for complete search history.

(56) References Cited

U.S. PATENT DOCUMENTS

| | | | |
|---|---|---|---|
| 2004/0158065 A1 | 8/2004 | Barth | |
| 2014/0206687 A1* | 7/2014 | Xia | ...................... C07D 403/12 514/234.5 |
| 2015/0126550 A1 | 5/2015 | Li et al. | |

FOREIGN PATENT DOCUMENTS

| | | |
|---|---|---|
| CN | 1745073 A | 3/2006 |
| CN | 102020639 A | 4/2011 |

(Continued)

OTHER PUBLICATIONS

International Search Report of PCT/CN2017/102998 dated Dec. 27, 2017.

(Continued)

*Primary Examiner* — Mark L Shibuya
*Assistant Examiner* — Ebenezer O Sackey
(74) *Attorney, Agent, or Firm* — Houston Beshining Law Office PLLC; Liangang Ye

(57) ABSTRACT

A salt of a quinazoline derivative (N-[4-(3-chlorine-4-fluoroanilino)]-7-(3-morpholinepropanol)-6-(2-fluoroacrylamide)-quinazoline, the structure thereof is as represented by formula I). Compared with a known quinazoline derivative, the salt of the quinazoline derivative has one or more improved properties and at least has better water solubility, wherein a citrate, a benzene sulfonate, and an ethanedisulphonate thereof further have better crystallinity and are not easy to absorb moisture.

(I)

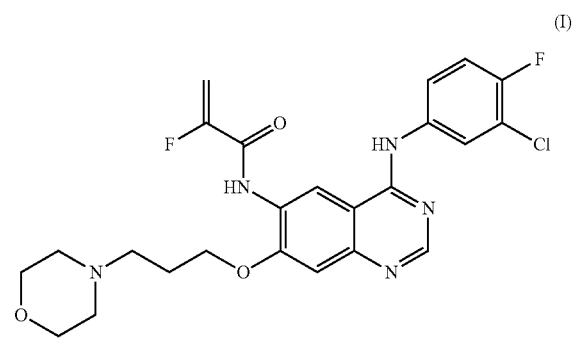

12 Claims, 46 Drawing Sheets

(51) Int. Cl.
| | | |
|---|---|---|
| *C07C 59/105* | (2006.01) | |
| *C07C 59/255* | (2006.01) | |
| *C07C 65/11* | (2006.01) | |
| *C07C 309/35* | (2006.01) | |
| *C07C 59/305* | (2006.01) | |
| *C07C 69/38* | (2006.01) | |
| *C07C 69/40* | (2006.01) | |
| *C07C 59/347* | (2006.01) | |
| *C07C 57/145* | (2006.01) | |
| *C07C 55/08* | (2006.01) | |
| *C07C 55/10* | (2006.01) | |
| *C07C 309/39* | (2006.01) | |
| *C07D 401/12* | (2006.01) | |
| *C07D 405/12* | (2006.01) | |
| *C07D 413/12* | (2006.01) | |
| *C07D 319/12* | (2006.01) | |
| *C07D 307/06* | (2006.01) | |
| *C07D 403/12* | (2006.01) | |
| *C07F 9/6512* | (2006.01) | |
| *C07D 307/08* | (2006.01) | |
| *C07F 9/6558* | (2006.01) | |
| *A61K 31/5377* | (2006.01) | |
| *A61K 31/517* | (2006.01) | |

(52) U.S. Cl.
CPC .......... *C07F 9/6512* (2013.01); *C07F 9/6558* (2013.01); *C07B 2200/13* (2013.01)

(56) References Cited

FOREIGN PATENT DOCUMENTS

| | | |
|---|---|---|
| CN | 102898386 A | 1/2013 |
| CN | 103965120 A | 8/2014 |
| CN | 104109186 A | 10/2014 |
| JP | 2014521613 A | 8/2014 |
| WO | 2013013640 A1 | 1/2013 |

OTHER PUBLICATIONS

Written Opinion of PCT/CN2017/102998 dated Dec. 27, 2017.
Extended European Search Report issued in the counterpart European application No. 17852427.8 dated May 6, 2020.

\* cited by examiner

SALT OF QUINAZOLINE DERIVATIVE, PREPARATION METHOD THEREFOR AND APPLICATION THEREOF

The present application is a National Stage of International Application No. PCT/CN2017/102998, filed on Sep. 22, 2017, which claims priority of the Chinese Patent Application No. CN201610847951.1 filed on Sep. 23, 2016, the contents of which are incorporated herein by reference in their entireties.

FIELD OF INVENTION

The present invention relates to a salt of a quinazoline derivative, a preparation method and a use thereof.

PRIOR ARTS

A quinazoline derivative, the chemical name of which is (N-[4-(3-chloro-4-fluoroanilino)]-7-(3-morpholino-propoxy)-6-(2-fluoroacrylamido)-quinazoline, of which the molecular formula is $C_{24}H_{24}ClF_2N_5O_3$ and the structure is represented by the following formula:

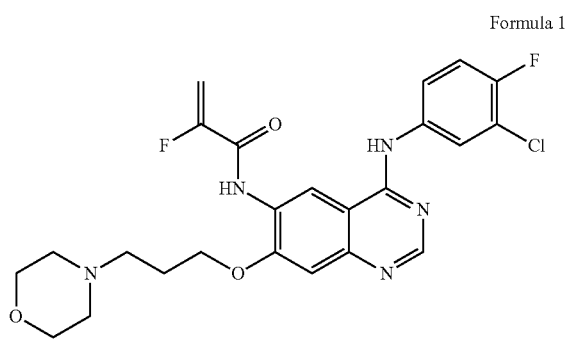 [SMILES: C=C(F)C(=O)Nc1cc2c(Nc3ccc(F)c(Cl)c3)ncnc2cc1OCCCN1CCOCC1]

Formula 1

The quinazoline derivative (i.e., the compound of formula 1) and the preparation method thereof have been disclosed in US2014206687, WO2013013640, CN102898386 and JP2014521613. The compound of the formula 1 is a pale yellow or off-white powdery solid with poor water solubility.

CONTENT OF THE PRESENT INVENTION

The technical problem to be solved in the present invention is to overcome the defects of poor water solubility of conventional quinazoline derivatives in the prior art, therefore, the present invention provides a salt of a quinazoline derivative, a preparation method thereof and a use thereof. Compared with known quinazoline derivatives, the salt of the quinazoline derivative has one or more improved properties, at least has better water solubility.

The present invention provides a salt of a quinazoline derivative which is monocitrate represented by formula 2, monocitrate hemiethanolate represented by formula 2-1, monocitrate ditetrahydrofuran complex represented by formula 2-2, monocitrate hemi-1,4-dioxane complex represented by formula 2-3, monocitrate dihydrate represented by formula 2-4, monocitrate hemichloroform complex represented by formula 2-5, monocitrate trihydrate represented by formula 2-6, monocitrate hemi(pentahydrate) represented by formula 2-7, monobenzenesulfonate represented by formula 3, monoethanedisulfonate represented by formula 4, mono-L-tartrate represented by formula 5, mono-L-tartrate tetrahydrate represented by formula 5-1, monohydrochloride monohydrate represented by formula 6, monosulfate represented by formula 7, mono-D-gluconate represented by formula 8, mono-α-ketoglutarate represented by formula 9, di-α-ketoglutarate represented by formula 10, diphosphonate represented by formula 11, dimaleate represented by formula 12, monosuccinate represented by formula 13, trisuccinate represented by formula 14, diglycolate represented by formula 15, monomalonate represented by formula 16, dimalonate represented by formula 17, trimalonate represented by formula 18, disulfate represented by formula 19, di-1,5-naphthalenedisulfonate represented by formula 20, monopamoate represented by formula 21, mono-p-toluenesulfonate represented by formula 22, mono-1,5-naphthalenedisulfonate represented by formula 23, or mono-p-chlorobenzenesulfonate represented by formula 24;

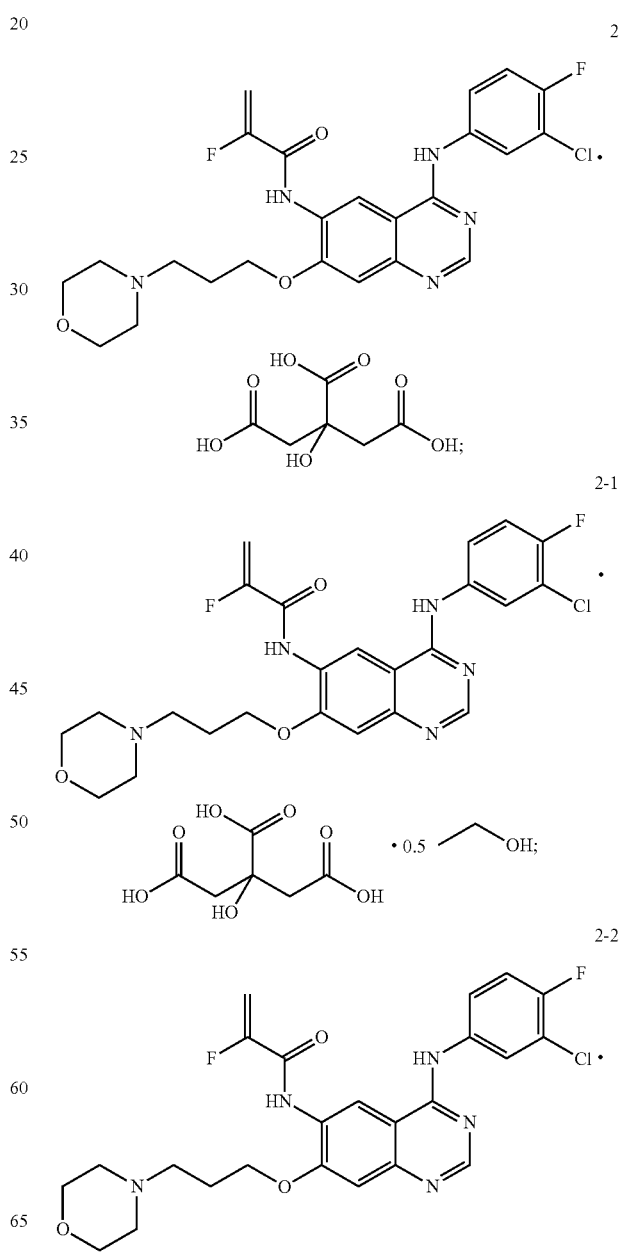

3

-continued

· 2 [tetrahydrofuran] ;

2-3

[2-fluoroacrylamide-morpholinopropoxy-quinazoline-(3-chloro-4-fluoroanilino) structure]

· 0.5 [1,4-dioxane] ;

2-4

[same quinazoline structure]

· 2 H₂O ;

2-5

[same quinazoline structure]

· 0.5 CHCl₃ ;

4

-continued 2-6

[same quinazoline structure]

· 3 H₂O ;

2-7

[same quinazoline structure]

· 2.5 H₂O ;

3

[same quinazoline structure] · [benzenesulfonic acid] ;

4

[same quinazoline structure]

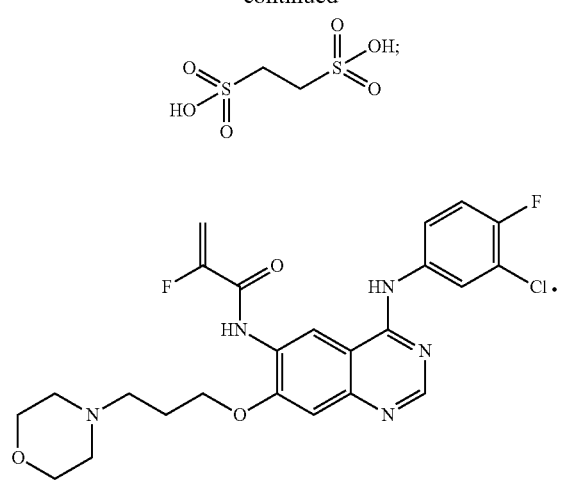
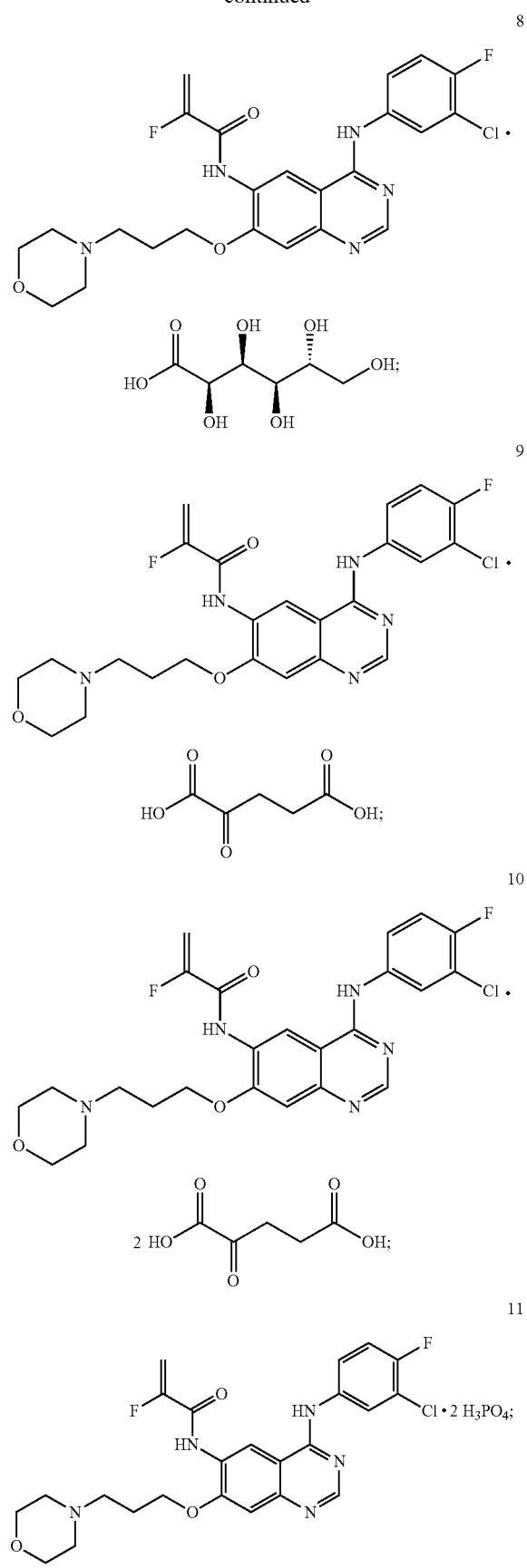

-continued
12
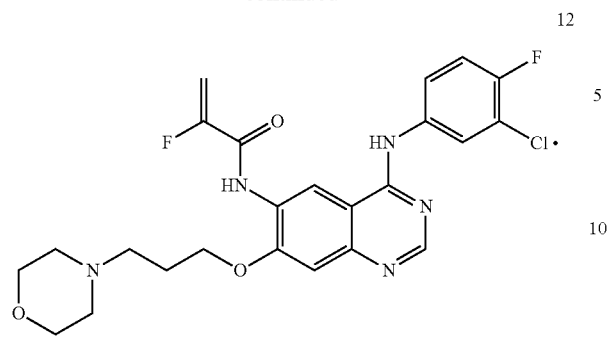
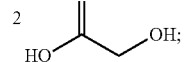
13
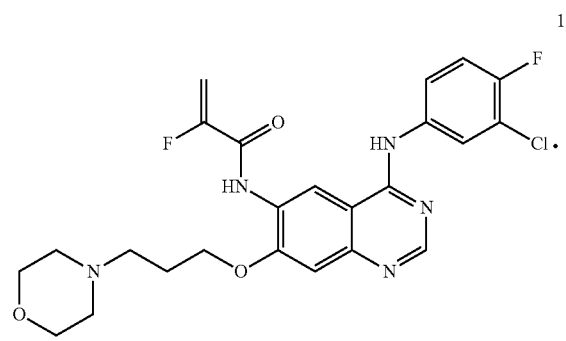
14
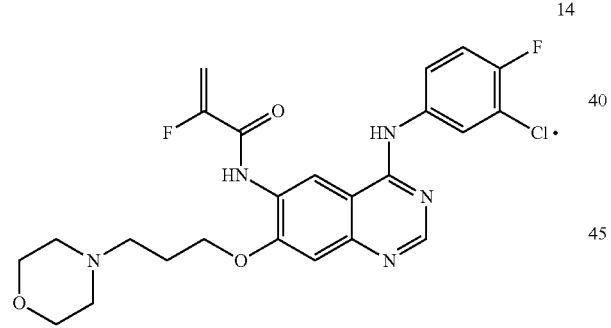
15
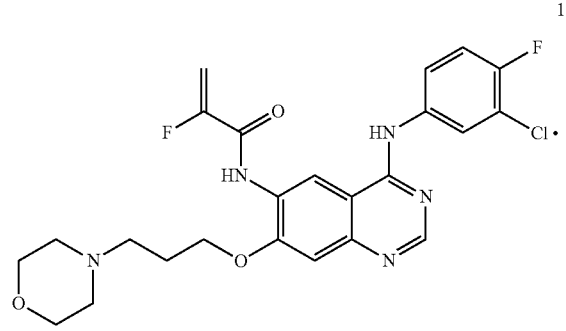
-continued
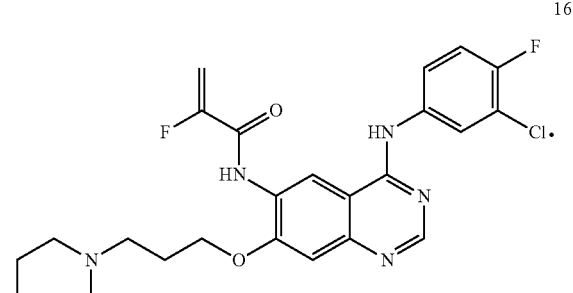
16
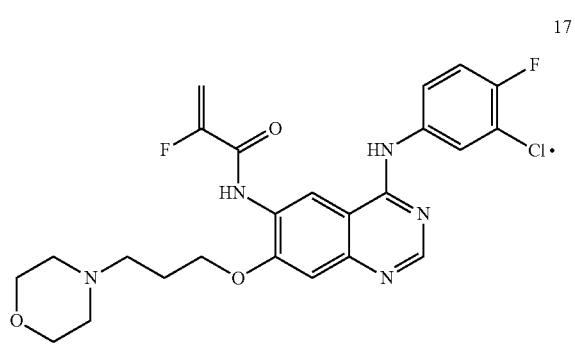
17
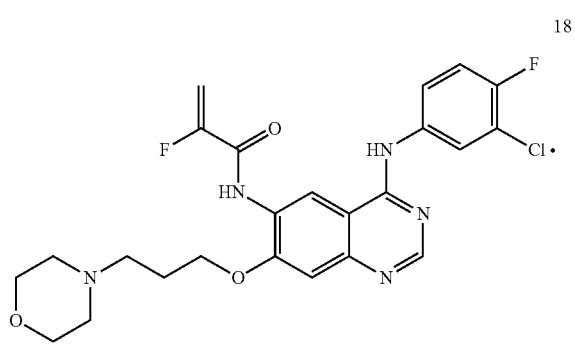
18
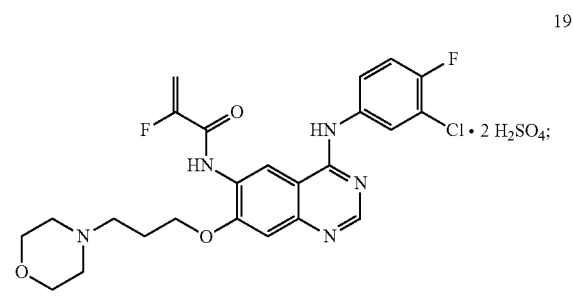
19

20

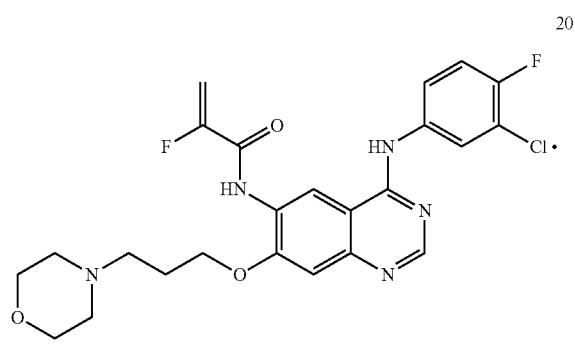

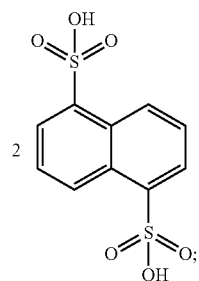
2

21

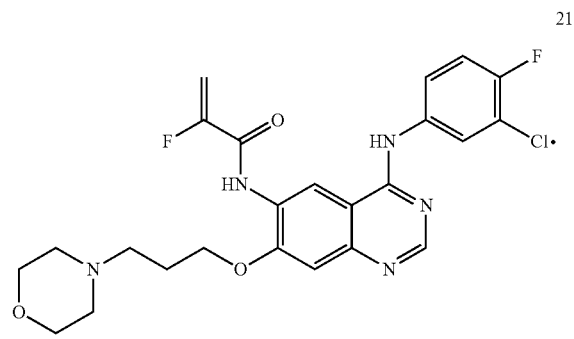

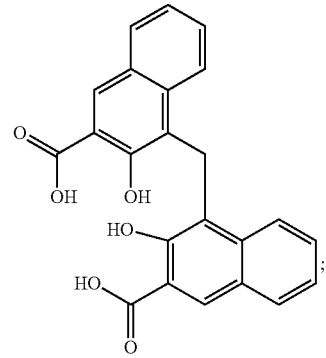

22

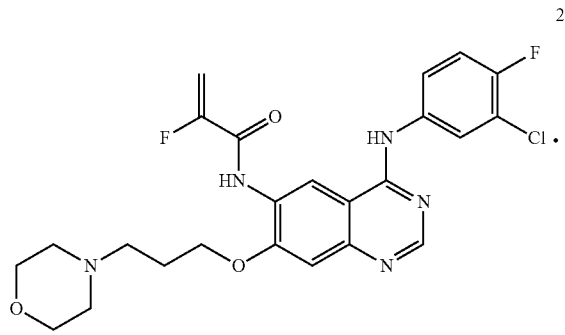 [SMILES: C=C(F)C(=O)Nc1cc2c(Nc3ccc(F)c(Cl)c3)ncnc2cc1OCCCN1CCOCC1]

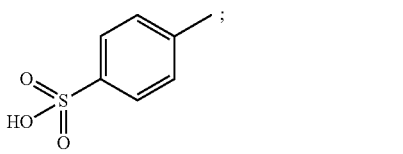

23

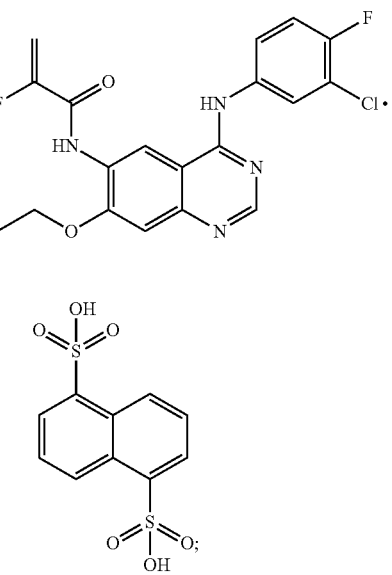

24

The structural formulas of the monocitrate 2, monocitrate hemiethanolate 2-1, monocitrate ditetrahydrofuran complex 2-2, the monocitrate hemi-1,4-dioxane complex 2-3, monocitrate dihydrate 2-4, monocitrate hemichloroform complex 2-5, monocitrate trihydrate 2-6, monocitrate hemi (pentahydrate) 2-7, monobenzenesulfonate 3, monoethanedisulfonate 4, mono-L-tartrate tetrahydrate 5-1, monohydrochloride monohydrate 6, monosulfate 7, mono-D-gluconate 8, trisuccinate 14, trimalonate 18 and mono-p-toluenesulfonate 22 represent that they only consist of the quinazoline derivatives and the acids shown therein, or only consist of the quinazoline derivatives, the acids and the solvent molecules shown therein.

The structural formulas of the di-α-ketoglutarate 10, dimaleate 12, monosuccinate 13, diglycolate 15, dimalonate 17, disulfate 19, di-1,5-naphthalenedisulfonate 20, monopamoate 21, mono-1,5-naphthalenedisulfonate 23, and monop-chlorobenzenesulfonate 24 represent that they comprise the quinazoline derivatives and the acids shown therein (i.e., they may also contain solvent molecules not shown therein <which may be water or an organic solvent>). In one embodiment, their structural formulas represent that they only consist of the quinazoline derivatives and the acids shown therein.

The structural formulas of the mono-L-tartrate 5, mono-α-ketoglutarate 9, diphosphonate 11 and monomalonate 16 represents that they comprise the quinazoline derivatives and the acids shown therein (i.e., they may also contain solvent molecules not shown therein <which may be water or an organic solvent>). In one embodiment, their structural formulas represent that they only consist of the quinazoline derivatives, the acids and water shown therein.

The monocitrate represented by formula 2 also may has the following parameters: ① the X-ray powder diffraction pattern thereof comprises characteristic peaks at diffraction angle 2θ of 8.280±0.2°, 8.720±0.2°, 16.962±0.2°, 19.124±0.2°, 19.742±0.2° and 25.222±0.2° (also may be 8.280±0.2°, 8.720±0.2°, 13.621±0.2°, 14.043±0.2°, 16.522±0.2°, 16.962±0.2°, 19.124±0.2°, 19.742±0.2°, 21.367±0.2°, 23.439±0.2°, 25.222±0.2° and 26.842±0.2°; also may be 5.278±0.2°, 8.280±0.2°, 8.720±0.2°, 9.862±0.2°, 10.740±0.2°, 11.564±0.2°, 13.621±0.2°, 14.043±0.2°, 14.853±0.2°, 16.522±0.2°, 16.962±0.2°, 19.124±0.2°, 19.742±0.2°, 20.501±0.2°, 20.802±0.2°, 21.367±0.2°, 23.439±0.2°, 23.799±0.2°, 25.222±0.2°, 26.359±0.2°, 26.842±0.2°, 27.494±0.2°, 28.919±0.2°, 32.383±0.2° and 32.764±0.2°; still may be 8.280±0.2°, 8.720±0.2°, 9.862±0.2°, 10.740±0.2°, 11.564±0.2°, 13.621±0.2°, 14.043±0.2°, 16.522±0.2°, 16.962±0.2°, 19.124±0.2°, 19.742±0.2°, 20.802±0.2°, 21.367±0.2°, 23.439±0.2° and 25.222±0.2°) (i.e., crystal form 1); or ② the X-ray powder diffraction pattern thereof comprises characteristic peaks at diffraction angle 2θ of 6.757±0.2°, 11.521±0.2°, 15.926±0.2°, 18.400±0.2°, 21.520±0.2°, 22.942±0.2°, 24.584±0.2° and 26.943±0.2° (also may be 6.757±0.2°, 10.441±0.2°, 11.521±0.2°, 13.084±0.2°, 13.406±0.2°, 15.926±0.2°, 17.540±0.2°, 18.400±0.2°, 21.520±0.2°, 22.942±0.2°, 24.584±0.2° and 26.943±0.2°; also may be 6.757±0.2°, 10.441±0.2°, 11.521±0.2°, 13.084±0.2°, 13.406±0.2°, 14.003±0.2°, 14.594±0.2°, 15.097±0.2°, 15.926±0.2°, 17.540±0.2°, 18.400±0.2°, 20.898±0.2°, 21.520±0.2°, 22.942±0.2°, 23.562±0.2°, 24.584±0.2° and 26.943±0.2°) (i.e., crystal form 13).

The monocitrate hemiethanolate represented by formula 2-1 also has the following parameter: the X-ray powder diffraction pattern thereof comprises characteristic peaks at diffraction angle 2θ of 4.700±0.2°, 7.400±0.2°, 7.801±0.2°, 11.340±0.2°, 13.298±0.2°, 13.799±0.2°, 18.464±0.2° and 22.618±0.2° (also may be 4.700±0.2°, 7.400±0.2°, 7.801±0.2°, 11.340±0.2°, 13.298±0.2°, 13.799±0.2°, 14.397±0.2°, 15.719±0.2°, 18.464±0.2°, 20.036±0.2°, 22.618±0.2°, 31.385±0.2° and 31.604±0.2°) (i.e., crystal form 2).

The monocitrate ditetrahydrofuran complex represented by formula 2-2 also may has the following parameter: the X-ray powder diffraction pattern thereof comprises characteristic peaks at diffraction angle 2θ of 6.939±0.2°, 7.462±0.2°, 18.603±0.2°, 19.183±0.2°, 24.803±0.2° and 25.983±0.2° (also may be 6.939±0.2°, 7.462±0.2°, 15.181±0.2°, 15.976±0.2°, 18.603±0.2°, 19.183±0.2°, 20.861±0.2°, 21.444±0.2°, 22.321±0.2°, 23.040±0.2°, 24.803±0.2° and 25.983±0.2°; also may be 6.939±0.2°, 7.462±0.2°, 13.042±0.2°, 15.181±0.2°, 15.976±0.2°, 16.502±0.2°, 17.318±0.2°, 18.603±0.2°, 19.183±0.2°, 20.861±0.2°, 21.444±0.2°, 22.321±0.2°, 23.040±0.2°, 24.803±0.2°, 25.983±0.2°, 27.106±0.2°, 28.244±0.2° and 29.713±0.2°; still may be 6.939±0.2°, 7.462±0.2°, 13.042±0.2°, 15.181±0.2°, 15.976±0.2°, 16.502±0.2°, 17.076±0.2°, 17.318±0.2°, 18.603±0.2°, 19.183±0.2°, 20.498±0.2°, 20.861±0.2°, 21.444±0.2°, 22.321±0.2°, 23.040±0.2°, 24.803±0.2°, 25.983±0.2°, 27.106±0.2°, 28.244±0.2° and 29.713±0.2°) (i.e., crystal form 3).

The monocitrate hemi-1,4-dioxane complex represented by formula 2-3 also may has the following parameter: the X-ray powder diffraction pattern thereof comprises characteristic peaks at diffraction angle 2θ of 6.962±0.2°, 7.821±0.2°, 8.560±0.2°, 8.999±0.2°, 17.262±0.2° and 19.441±0.2° (also may be 6.962±0.2°, 7.821±0.2°, 8.560±0.2°, 8.999±0.2°, 15.712±0.2°, 17.262±0.2°, 19.441±0.2°, 20.037±0.2°, 20.754±0.2°, 24.062±0.2° and 25.407±0.2°; still may be 6.962±0.2°, 7.821±0.2°, 8.560±0.2°, 8.999±0.2°, 15.712±0.2°, 17.262±0.2°, 19.441±0.2°, 20.037±0.2°, 20.754±0.2°, 21.540±0.2°, 24.062±0.2° and 25.407±0.2°) (i.e., crystal form 4).

The monocitrate dihydrate represented by formula 2-4 also may has the following parameters: ① the X-ray powder diffraction pattern thereof comprises characteristic peaks at diffraction angle 2θ of 6.443±0.2°, 10.780±0.2°, 12.808±0.2°, 16.230±0.2°, 18.683±0.2°, 19.262±0.2°, 24.519±0.2°, 25.885±0.2° and 28.743±0.2° (also may be 6.443±0.2°, 7.801±0.2°, 10.780±0.2°, 12.808±0.2°, 13.211±0.2°, 14.221±0.2°, 16.230±0.2°, 18.683±0.2°, 19.262±0.2°, 19.744±0.2°, 21.042±0.2°, 21.540±0.2°, 24.519±0.2°, 25.885±0.2° and 28.743±0.2% also may be 6.443±0.2°, 7.801±0.2°, 8.140±0.2°, 10.780±0.2°, 12.808±0.2°, 13.211±0.2°, 14.221±0.2°, 16.230±0.2°, 16.543±0.2°, 18.683±0.2°, 19.262±0.2°, 24.519±0.2°, 25.886±0.2° and 28.743±0.2% still may be 6.443±0.2°, 7.801±0.2°, 8.140±0.2°, 10.780±0.2°, 11.202±0.2°, 12.808±0.2°, 12.564±0.2°, 13.211±0.2°, 14.221±0.2°, 16.230±0.2°, 16.543±0.2°, 17.176±0.2°, 18.237±0.2°, 18.683±0.2°, 19.262±0.2°, 19.744±0.2°, 20.205±0.2°, 21.042±0.2°, 21.540±0.2°, 24.519±0.2°, 25.601±0.2°, 25.886±0.2°, 26.888±0.2°, and 28.743±0.2°) (i.e., crystal form 5); or, ② the X-ray powder diffraction pattern thereof comprises characteristic peaks at diffraction angle 2θ of 8.542±0.2°, 12.659±0.2°, 13.843±0.2°, 18.638±0.2°, 19.822±0.2° and 25.300±0.2° (also may be 8.542±0.2°, 12.659±0.2°, 13.843±0.2°, 18.120±0.2°, 18.638±0.2°, 18.916±0.2°, 19.822±0.2°, 20.637±0.2°, 23.763±0.2°, 24.157±0.2°, 24.528±0.2°, 25.300±0.2° and 25.659±0.2°; also may be 8.261±0.2°, 8.542±0.2°, 10.920±0.2°, 12.659±0.2°, 13.024±0.2°, 13.843±0.2°, 14.713±0.2°, 15.986±0.2°, 16.980±0.2°, 18.120±0.2°, 18.638±0.2°, 18.916±0.2°, 19.822±0.2°, 20.637±0.2°, 23.763±0.2°, 24.157±0.2°, 24.528±0.2°, 25.300±0.2°, 25.659±0.2°, 28.241±0.2°, 28.802±0.2°, 32.263±0.2°, 32.782±0.2°, 33.743±0.2° and 35.629±0.2°) (i.e., crystal form 7); or, ③ the X-ray powder diffraction pattern thereof comprises characteristic peaks at diffraction angle 2θ of 4.602±0.2°, 7.641±0.2°, 13.651±0.2°, 15.264±0.2°, 19.182±0.2° and 23.321±0.2° (i.e., crystal form 11).

The monocitrate hemichloroform complex represented by formula 2-5 also may has the following parameter: the X-ray powder diffraction pattern thereof comprises characteristic peaks at diffraction angle 2θ of 7.682±0.2°, 19.122±0.2° and 26.044±0.2° (also may be 7.682±0.2°, 8.101±0.2°, 16.705±0.2°, 17.138±0.2°, 19.122±0.2° and 26.044±0.2°) (i.e., crystal form 6).

The monocitrate trihydrate represented by formula 2-6 also may has the following parameter: the X-ray powder diffraction pattern thereof comprises characteristic peaks at diffraction angle 2θ of 5.659±0.2°, 5.920±0.2°, 9.064±0.2°, 11.760±0.2°, 17.600±0.2°, 27.103±0.2° and 27.623±0.2° (also may be 5.659±0.2°, 5.920±0.2°, 8.107±0.2°, 9.064±0.2°, 11.760±0.2°, 12.795±0.2°, 13.047±0.2°, 13.454±0.2°, 17.600±0.2°, 18.705±0.2°, 19.161±0.2°, 20.039±0.2°, 22.182±0.2°, 27.103±0.2° and 27.623±0.2°; also may be 5.659±0.2°, 5.920±0.2°, 8.107±0.2°, 9.064±0.2°, 11.760±0.2°, 13.047±0.2°, 13.454±0.2°, 17.016±0.2°, 17.600±0.2°, 18.705±0.2°, 19.161±0.2°, 20.039±0.2°, 22.182±0.2°, 23.831±0.2°, 25.723±0.2°, 27.103±0.2° and 27.623±0.2% still may be 5.659±0.2°, 5.920±0.2°, 8.107±0.2°, 9.064±0.2°, 11.760±0.2°, 13.047±0.2°, 13.454±0.2°, 17.016±0.2°, 17.600±0.2°, 12.795±0.2°, 18.705±0.2°, 19.161±0.2°, 20.039±0.2°, 22.182±0.2°, 23.831±0.2°, 24.304±0.2°, 25.723±0.2°, 27.103±0.2°, 27.623±0.2° and 27.936±0.2°) (i.e., crystal form 10).

The monocitrate hemi(pentahydrate) represented by formula 2-7 also may has the following parameter: the X-ray powder diffraction pattern thereof comprises characteristic peaks at diffraction angle 2θ of 7.852±0.2°, 14.859±0.2°, 15.605±0.2°, 19.448±0.2°, 23.439±0.2° and 25.604±0.2° (also may be 7.852±0.2°, 14.128±0.2°, 14.859±0.2°, 15.605±0.2°, 16.580±0.2°, 19.448±0.2°, 20.221±0.2°, 23.439±0.2° and 25.604±0.2°) (i.e., crystal form 14).

The monobenzenesulfonate represented by formula 3 also may has the following parameter: the X-ray powder diffraction pattern thereof comprises characteristic peaks at diffraction angle 2θ of 7.642±0.2°, 13.639±0.2°, 14.861±0.2°, 15.445±0.2°, 16.182±0.2°, 16.904±0.2°, 17.542±0.2°, 18.821±0.2°, 19.160±0.2°, 20.563±0.2°, 21.643±0.2°, 22.843±0.2°, 23.542±0.2°, 25.252±0.2° and 26.201±0.2°.

The monoethanedisulfonate represented by formula 4 also may has the following parameter: the X-ray powder diffraction pattern thereof comprises characteristic peaks at diffraction angle 2θ of 5.447±0.2°, 8.286±0.2°, 13.734±0.2°, 18.614±0.2°, 20.686±0.2°, 22.596±0.2°, 24.179±0.2°, 24.908±0.2° and 29.606±0.2°.

The mono-L-tartrate represented by formula 5 also may has the following parameter: the X-ray powder diffraction pattern thereof comprises characteristic peaks at diffraction angle 2θ of 5.738±0.2°, 7.332±0.2°, 8.817±0.2°, 11.084±0.2°, 13.060±0.2°, 17.063±0.2°, 17.814±0.2°, 19.841±0.2°, 20.469±0.2°, 21.844±0.2° and 24.123±0.2° (i.e., crystal form 15).

The mono-L-tartrate tetrahydrate represented by formula 5-1 also may has the following parameter: the X-ray powder diffraction pattern thereof comprises characteristic peaks at diffraction angle 2θ of 7.357±0.2°, 8.696±0.2°, 9.437±0.2°, 12.725±0.2°, 16.543±0.2°, 17.444±0.2°, 18.959±0.2°, 21.847±0.2°, 22.101±0.2°, 24.819±0.2°, 29.444±0.2° and 33.501±0.2° (i.e., crystal form 16).

The monohydrochloride monohydrate represented by formula 6 also may has the following parameter: having an X-ray powder diffraction pattern represented by diffraction angle 2θ comprising characteristic peaks at 8.862±0.2°, 13.860±0.2°, 17.127±0.2°, 17.516±0.2°, 21.452±0.2°, 23.545±0.2°, 25.421±0.2° and 27.985±0.2°.

The monosulfate represented by formula 7 also may has the following parameter: the X-ray powder diffraction pattern thereof comprises characteristic peaks at diffraction angle 2θ of 6.102±0.2°, 6.982±0.2°, 13.336±0.2°, 14.340±0.2°, 14.857±0.2°, 21.585±0.2°, 23.009±0.2°, 24.254±0.2° and 25.783±0.2°.

The mono-D-gluconate represented by formula 8 also may has the following parameter: the X-ray powder diffraction pattern thereof comprises characteristic peaks at diffraction angle 2θ of 6.280±0.2°, 7.901±0.2°, 12.403±0.2°, 15.719±0.2°, 16.106±0.2°, 18.001±0.2°, 19.581±0.2°, 21.601±0.2°, 22.760±0.2°, 23.980±0.2°, 24.461±0.2°, 25.140±0.2°, 26.764±0.2°, 27.419±0.2° and 28.902±0.2°.

The mono-α-ketoglutarate represented by formula 9 also may has the following parameter: the X-ray powder diffraction pattern thereof comprises characteristic peaks at diffraction angle 2θ of 5.349±0.2°, 7.186±0.2°, 7.818±0.2°, 8.446±0.2°, 9.259±0.2°, 11.114±0.2°, 15.968±0.2°, 16.851±0.2°, 17.411±0.2°, 20.408±0.2°, 22.381±0.2°, 23.943±0.2° and 24.198±0.2°.

The di-α-ketoglutarate represented by formula 10 also may has the following parameter: the X-ray powder diffraction pattern thereof comprises characteristic peaks at diffraction angle 2θ of 5.738±0.2°, 7.003±0.2°, 9.537±0.2°, 12.779±0.2°, 14.379±0.2°, 15.815±0.2°, 17.042±0.2°, 17.765±0.2°, 19.121±0.2°, 23.343±0.2°, 24.722±0.2°, 25.821±0.2°, 26.379±0.2°, 27.162±0.2° and 36.062±0.2°.

The diphosphonate represented by formula 11 also may has the following parameter: the X-ray powder diffraction pattern thereof comprises characteristic peaks at diffraction angle 2θ of 5.080±0.2°, 14.304±0.2°, 15.552±0.2°, 19.781±0.2°, 22.580±0.2° and 24.720±0.2°.

The dimaleate represented by formula 12 also may has the following parameter: the X-ray powder diffraction pattern thereof comprises characteristic peaks at diffraction angle 2θ of 4.777±0.2°, 6.094±0.2°, 9.750±0.2°, 10.397±0.2°, 12.279±0.2°, 15.573±0.2°, 16.264±0.2°, 17.230±0.2°, 18.594±0.2°, 18.928±0.2°, 19.662±0.2°, 20.505±0.2°, 21.751±0.2°, 24.098±0.2°, 25.698±0.2°, 26.314±0.2°, 27.871±0.2°, 28.759±0.2° and 29.767±0.2°.

The monosuccinate represented by formula 13 also may has the following parameter: the X-ray powder diffraction pattern thereof comprises characteristic peaks at diffraction angle 2θ of 4.060±0.2°, 7.998±0.2°, 13.866±0.2°, 19.763±0.2°, 21.820±0.2°, 22.543±0.2°, 25.667±0.2°, 27.851±0.2° and 31.700±0.2°.

The trisuccinate represented by formula 14 also may has the following parameter: the X-ray powder diffraction pattern thereof comprises characteristic peaks at diffraction angle 2θ of 4.920±0.2°, 8.941±0.2°, 16.988±0.2°, 20.302±0.2°, 23.799±0.2°, 26.384±0.2°, 27.862±0.2° and 31.802±0.2°.

The diglycolate represented by formula 15 also may has the following parameter: the X-ray powder diffraction pattern thereof comprises characteristic peaks at diffraction angle 2θ of 10.121±0.2°, 11.700±0.2°, 13.863±0.2°, 14.360±0.2°, 15.116±0.2°, 15.977±0.2°, 16.421±0.2°, 17.484±0.2°, 18.642±0.2°, 20.341±0.2°, 21.163±0.2°, 21.822±0.2°, 22.622±0.2°, 23.401±0.2°, 24.481±0.2°, 26.405±0.2°, 27.083±0.2°, 27.865±0.2°, 28.682±0.2° and 30.023±0.2°.

The monomalonate represented by formula 16 also may has the following parameter: the X-ray powder diffraction pattern thereof comprises characteristic peaks at diffraction angle 2θ of 7.018±0.2°, 13.866±0.2°, 17.541±0.2°, 19.127±0.2°, 20.342±0.2°, 21.184±0.2°, 23.183±0.2°, 24.981±0.2°, 27.852±0.2° and 28.444±0.2°.

The dimalonate represented by formula 17 also may has the following parameter: the X-ray powder diffraction pattern thereof comprises characteristic peaks at diffraction angle 2θ of 5.180±0.2°, 7.141±0.2°, 13.876±0.2°, 14.742±0.2°, 16.424±0.2°, 16.840±0.2°, 18.485±0.2°, 19.299±0.2°, 20.024±0.2°, 21.940±0.2°, 23.845±0.2°, 25.003±0.2°, 26.962±0.2° and 27.847±0.2°.

The trimalonate represented by formula 18 also may has the following parameter: the X-ray powder diffraction pattern thereof comprises characteristic peaks at diffraction angle 2θ of 5.062±0.2°, 7.181±0.2°, 13.843±0.2°, 14.731±0.2°, 15.700±0.2°, 16.158±0.2°, 16.841±0.2°, 17.923±0.2°, 19.042±0.2°, 19.722±0.2°, 22.123±0.2°, 23.303±0.2°, 26.621±0.2° and 27.480±0.2°.

The disulfate represented by formula 19 also may has the following parameter: the X-ray powder diffraction pattern thereof comprises characteristic peaks at diffraction angle 2θ of 6.896±0.2°, 13.362±0.2°, 14.516±0.2°, 14.981±0.2°, 18.179±0.2°, 18.622±0.2°, 19.806±0.2°, 20.983±0.2°, 22.801±0.2°, 24.062±0.2°, 24.783±0.2°, 25.662±0.2°, 26.503±0.2°, 27.543±0.2° and 28.143±0.2°.

The di-1,5-naphthalenedisulfonate represented by formula 20 also may has the following parameter: the X-ray powder diffraction pattern thereof comprises characteristic peaks at diffraction angle 2θ of 6.740±0.2°, 7.660±0.2°, 8.821±0.2°, 10.582±0.2°, 11.921±0.2°, 13.420±0.2°, 16.200±0.2°, 17.061±0.2°, 17.481±0.2°, 18.024±0.2°, 18.520±0.2°, 19.003±0.2°, 20.905±0.2°, 21.603±0.2°, 22.518±0.2°, 22.921±0.2°, 23.841±0.2°, 24.722±0.2°, 26.339±0.2° and 26.902±0.2°.

The monopamoate represented by formula 21 also may has the following parameter: the X-ray powder diffraction pattern thereof comprises characteristic peaks at diffraction angle 2θ of 4.861±0.2°, 7.501±0.2°, 8.220±0.2°, 9.119±0.2°, 12.723±0.2°, 14.203±0.2°, 15.821±0.2°, 16.960±0.2°, 19.382±0.2°, 21.661±0.2°, 23.082±0.2°, 23.461±0.2° and 27.343±0.2°.

The mono-p-toluenesulfonate represented by formula 22 also may has the following parameter: the X-ray powder diffraction pattern thereof comprises characteristic peaks at diffraction angle 2θ of 7.560±0.2°, 15.224±0.2°, 16.002±0.2°, 16.903±0.2°, 17.421±0.2°, 18.857±0.2°, 20.141±0.2°, 21.143±0.2°, 22.564±0.2°, 23.023±0.2°, 29.621±0.2° and 31.325±0.2°.

The mono-1,5-naphthalenedisulfonate represented by formula 23 also may has the following parameter: the X-ray powder diffraction pattern thereof comprises characteristic peaks at diffraction angle 2θ of 5.566±0.2°, 7.363±0.2°, 7.914±0.2°, 8.784±0.2°, 9.354±0.2°, 10.617±0.2°, 12.534±0.2°, 15.926±0.2°, 17.584±0.2°, 18.004±0.2°, 19.779±0.2°, 20.506±0.2°, 20.725±0.2°, 22.798±0.2°, 24.138±0.2° and 25.541±0.2°.

The mono-p-chlorobenzenesulfonate represented by formula 24 also may has the following parameter: the X-ray powder diffraction pattern thereof comprises characteristic peaks at diffraction angle 2θ of 7.623±0.2°, 15.244±0.2°, 15.994±0.2°, 17.046±0.2°, 17.487±0.2°, 18.885±0.2°, 20.197±0.2°, 21.267±0.2°, 21.487±0.2°, 22.501±0.2°, 23.154±0.2°, 23.423±0.2°, 24.662±0.2° and 29.617±0.2°.

Unrestrictedly, the crystal form 1 of the monocitrate in an exemplary embodiment has an X-ray powder diffraction pattern as shown in FIG. 1. Further, the crystal form 1 of the monocitrate has a thermogravimetric analysis (TGA) pattern as shown in FIG. 2, indicating that the crystal form 1 of the monocitrate is an anhydrate. Further, the crystal form 1 of the monocitrate has a differential scanning calorimetry (DSC) pattern as shown in FIG. 3, indicating that the melting point thereof is 165-169° C. and the melting is accompanied by decomposition. Further, the crystal form 1 of the monocitrate has a dynamic vapor sorption (DVS) pattern as shown in FIG. 4, indicating that 0.21% of water is absorbed by the crystal form 1 of the monocitrate in a relative humidity range of 20-80%.

Unrestrictedly, the crystal form 2 of the hemiethanolate in an exemplary embodiment has an X-ray powder diffraction pattern as shown in FIG. 29. Further, the crystal form 2 of the hemiethanolate has a thermogravimetric analysis (TGA) pattern as shown in FIG. 30, indicating that the decomposition temperature of the crystal form 2 of the hemiethanolate is 142° C., and the weight loss before decomposition is 3.2%, containing 0.5 mole of ethanol. Further, the crystal form 2 of the hemiethanolate has a differential scanning calorimetry (DSC) pattern as shown in FIG. 31, indicating that the crystal form 2 of the hemiethanolate has an endothermic peak of ethanol elimination between 89-120° C.

Unrestrictedly, the crystal form 3 of the ditetrahydrofuran complex in an exemplary embodiment has an X-ray powder diffraction pattern as shown in FIG. 32. Further, the crystal form 3 of the ditetrahydrofuran complex has a thermogravimetric analysis (TGA) pattern as shown in FIG. 33, indicating that the decomposition temperature of the crystal form 3 of the ditetrahydrofuran complex is 169° C., and the weight loss before decomposition is 17.3%, containing 2 moles of tetrahydrofuran.

Unrestrictedly, the crystal form 4 of the hemi-1,4-dioxane complex in an exemplary embodiment has an X-ray powder diffraction pattern as shown in FIG. 34. Further, the crystal form 4 of the hemi-1,4-dioxane complex has a thermogravimetric analysis (TGA) pattern as shown in FIG. 35, indicating that the decomposition temperature of the crystal form 4 of the hemi-1,4-dioxane complex is 173° C., and the weight loss before decomposition is 6.6%, containing 0.5 mole of dioxane.

Unrestrictedly, the crystal form 5 of the dihydrate in an exemplary embodiment has an X-ray powder diffraction pattern as shown in FIG. 5. Further, the crystal form 5 of the dihydrate has a thermogravimetric analysis (TGA) pattern as shown in FIG. 6, indicating that the crystal form 5 of the dihydrate is a hydrate, the decomposition temperature of which is 145° C., and the weight loss before decomposition is 5.3%, approximately containing 2 moles of water. Further, the crystal form 5 of the dihydrate has a differential scanning calorimetry (DSC) pattern as shown in FIG. 7, indicating that the crystal form 5 of the dihydrate has an endothermic peak of water elimination before 123° C. Further, the crystal form 5 of the dihydrate has a dynamic vapor sorption (DVS) pattern as shown in FIG. 8, indicating that 0.4% of water is absorbed by the crystal form 5 of the dihydrate in a relative humidity range of 0-80%.

Unrestrictedly, the crystal form 6 of the hemichloroform complex in an exemplary embodiment has an X-ray powder diffraction pattern as shown in FIG. 36. Further, the crystal form 6 of the hemichloroform complex has a thermogravimetric analysis (TGA) pattern as shown in FIG. 37, indicating that the decomposition temperature of the crystal form 6 of the hemichloroform complex is 173° C., and the weight loss before decomposition is 7.3%, containing 0.5 mole of chloroform.

Unrestrictedly, the crystal form 7 of the dihydrate in an exemplary embodiment has an X-ray powder diffraction pattern as shown in FIG. 17. Further, the crystal form 7 of the dihydrate has a thermogravimetric analysis (TGA) pattern as shown in FIG. 18, indicating that the decomposition temperature of the crystal form 7 of the dihydrate is 145° C., and the weight loss before decomposition is 4.7%, containing 2 moles of water. Further, the crystal form 7 of the dihydrate has a differential scanning calorimetry (DSC) pattern as shown in FIG. 19, indicating that the crystal form 7 of the dihydrate has two endothermic peaks of water elimination below 79° C. and between 115-117° C. Further, the crystal form 7 of the dihydrate has a dynamic vapor sorption (DVS) pattern as shown in FIG. 20, indicating that 0.38% of water is absorbed by the crystal form 7 of the dihydrate in a relative humidity range of 10-80% and one water molecule is eliminated below a relative humidity of 10%. The eliminated water molecules are recombined at the relative humidity of 30%.

Unrestrictedly, the crystal form 10 of the trihydrate in an exemplary embodiment has an X-ray powder diffraction pattern as shown in FIG. 21. Further, the crystal form 10 of the trihydrate has a thermogravimetric analysis (TGA) pattern as shown in FIG. 22, indicating that the decomposition temperature of the crystal form 10 of the trihydrate is 159° C., and the weight loss before decomposition is 7.7%, containing 3 moles of water. Further, the crystal form 10 of the trihydrate has a differential scanning calorimetry (DSC) pattern as shown in FIG. 23, indicating that the crystal form 10 of the trihydrate has an endothermic peak of water elimination below 117° C. Further, the crystal form 10 of the trihydrate has a dynamic vapor sorption (DVS) pattern as shown in FIG. 24, indicating that 3.5% of water is eliminated from the crystal form 10 of the trihydrate below a relative humidity of 50%. However, the hydrate is stable in a relative humidity range of 50-80% and 1.1% of water is absorbed.

Unrestrictedly, the crystal form 11 of the dihydrate in an exemplary embodiment has an X-ray powder diffraction pattern as shown in FIG. 25. Further, the crystal form 11 of the dihydrate has a thermogravimetric analysis (TGA) pattern as shown in FIG. 26, indicating that the decomposition temperature of the crystal form 11 of the dihydrate is 142° C., and the weight loss before decomposition is 4.8%, containing 2 moles of water. Further, the crystal form 11 of the dihydrate has a differential scanning calorimetry (DSC) pattern as shown in FIG. 27, indicating that the crystal form 11 of the dihydrate has an endothermic peak of water elimination below 71° C. Further, the crystal form 11 of the dihydrate has a dynamic vapor sorption (DVS) pattern as shown in FIG. 28, indicating that the crystal form 11 of the dihydrate is stable in a relative humidity range of 50-80% and 5.3% of water is absorbed. The hydrate water is eliminated below the relative humidity of 50%.

Unrestrictedly, the crystal form 13 of the monocitrate in an exemplary embodiment has an X-ray powder diffraction pattern as shown in FIG. 9. Further, the crystal form 13 of the monocitrate has a thermogravimetric analysis (TGA) pattern as shown in FIG. 10, indicating that the decomposition temperature of the crystal form 13 of the monocitrate is 144° C., and the crystal form 13 of the monocitrate is an anhydrate. Further, the crystal form 13 of the monocitrate has a differential scanning calorimetry (DSC) pattern as shown in FIG. 11, indicating that the melting point of the crystal form 13 of the monocitrate is 127-138° C. Further, the crystal form 13 of the monocitrate has a dynamic vapor sorption (DVS) pattern as shown in FIG. 12, indicating that 0.2% of water is absorbed by the crystal form 13 of the monocitrate in a relative humidity range of 20-80%.

Unrestrictedly, the crystal form 14 of the hemi(pentahydrate) in an exemplary embodiment has an X-ray powder diffraction pattern as shown in FIG. 13. Further, the crystal form 14 of the hemi(pentahydrate) has a thermogravimetric analysis (TGA) pattern as shown in FIG. 14, indicating that the decomposition temperature of the crystal form 14 of the hemi(pentahydrate) is 144° C., and the weight loss before decomposition is 6.3%, containing 2.5 moles of water. Further, the crystal form 14 of the hemipentahydrate has a differential scanning calorimetry (DSC) pattern as shown in FIG. 15, indicating that the crystal form 14 of the hemi (pentahydrate) has an endothermic peak of water elimination below 130° C. Further, the crystal form 14 of the hemi (pentahydrate) has a dynamic vapor sorption (DVS) pattern as shown in FIG. 16, indicating that 0.7% of water is absorbed by the crystal form 14 of the hemi(pentahydrate) in a relative humidity range of 10-80% and the hydrate water is partially eliminated below the relative humidity of 10%.

Unrestrictedly, the monobenzenesulfonate of the quinazoline derivative in an exemplary embodiment has an X-ray powder diffraction pattern as shown in FIG. 50. Further, the monobenzenesulfonate of the quinazoline derivative has a thermogravimetric analysis (TGA) pattern as shown in FIG. 51, indicating that there is no significant weight loss before the decomposition of the monobenzenesulfonate of the quinazoline, and the monobenzenesulfonate of the quinazoline derivative is an anhydrate with a decomposition temperature of 199° C. Further, the monobenzenesulfonate of the quinazoline derivative has a differential scanning calorimetry (DSC) pattern as shown in FIG. 52, indicating that the melting point of the monobenzenesulfonate of the quinazoline derivative is 199° C. and the decomposition occurs spontaneously after melting. Further, the monobenzenesulfonate of the quinazoline derivative has a dynamic vapor sorption (DVS) pattern as shown in FIG. 53, indicating that the weight change of the monobenzenesulfonate of the quinazoline derivative in a relative humidity range of 20-80% is about 0.3%.

Unrestrictedly, the monoethanedisulfonate of the quinazoline derivative in an exemplary embodiment has an X-ray powder diffraction pattern as shown in FIG. 38. Further, the monoethanedisulfonate of the quinazoline derivative has a thermogravimetric analysis (TGA) pattern as shown in FIG. 39, indicating that the decomposition of the monoethanedisulfonate of the quinazoline derivative occurs above 250° C., and the slow weight loss before decomposition is 1.2%. Further, the monoethanedisulfonate of the quinazoline derivative has a differential scanning calorimetry (DSC) pattern as shown in FIG. 40, indicating that the monoethanedisulfonate of the quinazoline derivative has no melting point. Further, the monoethanedisulfonate of the quinazoline derivative has a dynamic vapor sorption (DVS) pattern as shown in FIG. 41, indicating that the weight change of the monoethanedisulfonate of the quinazoline derivative in a relative humidity range of 20-80% is about 1.46%.

Unrestrictedly, the mono-L-tartrate (crystal form 15) in an exemplary embodiment has an X-ray powder diffraction pattern as shown in FIG. 62. Further, the mono-L-tartrate (crystal form 15) has a thermogravimetric analysis (TGA) pattern as shown in FIG. 63, indicating that the decomposition of the mono-L-tartrate (crystal form 15) occurs at 198° C., and the weight loss before decomposition is 8.1%, which appears to be the elimination of the solvent or water.

Unrestrictedly, the mono-L-tartrate tetrahydrate (crystal form 16) in an exemplary embodiment has an X-ray powder diffraction pattern as shown in FIG. 64. Further, the mono-L-tartrate tetrahydrate (crystal form 16) has a thermogravimetric analysis (TGA) pattern as shown in FIG. 65, indicating that the decomposition of the mono-L-tartrate tetrahydrate (crystal form 16) occurs at 190° C., and the weight loss before decomposition is 9.5%, containing 4 moles of water. Further, the mono-L-tartrate tetrahydrate (crystal form 16) has a differential scanning calorimetry (DSC) pattern as shown in FIG. 66, indicating that the mono-L-tartrate tetrahydrate (crystal form 16) has an endothermic peak of solvent elimination below 106° C. and the sample has no melting point. Further, the mono-L-tartrate tetrahydrate (crystal form 16) has a dynamic vapor sorption (DVS) pattern as shown in FIG. 67, indicating that the weight change of the mono-L-tartrate tetrahydrate (crystal form 16) in a relative humidity range of 20-80% is about 0.8% and large amounts of water is eliminated rapidly at the relative humidity of 10%.

Unrestrictedly, the monohydrochloride monohydrate of the quinazoline derivative in an exemplary embodiment has an X-ray powder diffraction pattern as shown in FIG. 54. Further, the monohydrochloride monohydrate of the quinazoline derivative has a thermogravimetric analysis (TGA) pattern as shown in FIG. 55, indicating that the decomposition of the monohydrochloride monohydrate of the quinazoline derivative occurs slightly at 156° C. and massively at 228° C., and the weight loss before decomposition is 3.3%, containing 1 mole of water. Further, the monohydrochloride monohydrate of the quinazoline derivative has a differential scanning calorimetry (DSC) pattern as shown in FIG. 56, indicating that the monohydrochloride monohydrate of the quinazoline derivative has no melting point, wherein the decomposition results in the heat change at 220° C. Further, the monohydrochloride monohydrate of the quinazoline derivative has a dynamic vapor sorption (DVS) pattern as shown in FIG. 57, indicating that the weight change of the monohydrochloride monohydrate of the quinazoline derivative in a relative humidity range of 20-80% is about 0.17%.

Unrestrictedly, the monosulfate of the quinazoline derivative in an exemplary embodiment has an X-ray powder diffraction pattern as shown in FIG. 42. Further, the monosulfate of the quinazoline derivative has a thermogravimetric analysis (TGA) pattern as shown in FIG. 43, indicating that the decomposition of the monosulfate of the quinazoline derivative occurs at 230° C., and the weight loss before decomposition is 7.5%. Further, the monosulfate of the quinazoline derivative has a differential scanning calorimetry (DSC) pattern as shown in FIG. 44, indicating that the melting point of the monosulfate of the quinazoline derivative is 165° C. Further, the monosulfate of the quinazoline derivative has a dynamic vapor sorption (DVS) pattern as shown in FIG. 45, indicating that the weight change of the monosulfate of the quinazoline derivative in a relative humidity range of 20-80% is about 11.68% and the monosulfate of the quinazoline derivative is fairly hygroscopic.

Unrestrictedly, the mono-D-gluconate of the quinazoline derivative in an exemplary embodiment has an X-ray powder diffraction pattern as shown in FIG. 58. Further, the mono-D-gluconate of the quinazoline derivative has a thermogravimetric analysis (TGA) pattern as shown in FIG. 59, indicating that the decomposition of the mono-D-gluconate of the quinazoline derivative occurs at 180° C., and there is no weight loss before decomposition. Further, the mono-D-gluconate of the quinazoline derivative has a differential scanning calorimetry (DSC) pattern as shown in FIG. 60, indicating that the endothermic peak at 193° C. refers to the melting point of the mono-D-gluconate of the quinazoline derivative, and the decomposition of the sample occurs after melting. Further, the mono-D-gluconate of the quinazoline derivative has a dynamic vapor sorption (DVS) pattern as shown in FIG. 61, indicating that the weight change of the mono-D-gluconate of the quinazoline derivative in a relative humidity range of 20-80% is about 0.12%.

Unrestrictedly, the mono-α-ketoglutarate of the quinazoline derivative in an exemplary embodiment has an X-ray powder diffraction pattern as shown in FIG. 77. Further, the mono-α-ketoglutarate of the quinazoline derivative has a thermogravimetric analysis (TGA) pattern as shown in FIG. 78, indicating that the decomposition of the mono-α-ketoglutarate of the quinazoline derivative occurs at 193° C., and the weight loss before decomposition is 9.8%.

Unrestrictedly, the di-α-ketoglutarate of the quinazoline derivative in an exemplary embodiment has an X-ray powder diffraction pattern as shown in FIG. 90. Further, the di-α-ketoglutarate of the quinazoline derivative has a thermogravimetric analysis (TGA) pattern as shown in FIG. 91, indicating that the decomposition of the di-α-ketoglutarate of the quinazoline derivative occurs at 140° C., and the weight loss before decomposition is 4.7%.

Unrestrictedly, the diphosphonate of the quinazoline derivative in an exemplary embodiment has an X-ray powder diffraction pattern as shown in FIG. 68. Further, the diphosphonate of the quinazoline derivative has a thermogravimetric analysis (TGA) pattern as shown in FIG. 69, indicating that the decomposition of the diphosphonate of the quinazoline derivative occurs at 234° C., and the weight loss before decomposition is 7.1%.

Unrestrictedly, the dimaleate of the quinazoline derivative in an exemplary embodiment has an X-ray powder diffraction pattern as shown in FIG. 79. Further, the dimaleate of the quinazoline derivative has a thermogravimetric analysis (TGA) pattern as shown in FIG. 80, the stagewise weight loss of the dimaleate of the quinazoline derivative occurs at 75° C. and 136° C., and the decomposition thereof occurs massively at 167° C.

Unrestrictedly, the monosuccinate of the quinazoline derivative in an exemplary embodiment has an X-ray powder diffraction pattern as shown in FIG. 76.

Unrestrictedly, the trisuccinate of the quinazoline derivative in an exemplary embodiment has an X-ray powder diffraction pattern as shown in FIG. 88. Further, the trisuccinate of the quinazoline derivative has a thermogravimetric analysis (TGA) pattern as shown in FIG. 89, indicating that the decomposition of the trisuccinate of the quinazoline derivative occurs at 173° C.

Unrestrictedly, the diglycolate of the quinazoline derivative in an exemplary embodiment has an X-ray powder diffraction pattern as shown in FIG. 73.

Unrestrictedly, the monomalonate of the quinazoline derivative in an exemplary embodiment has an X-ray powder diffraction pattern as shown in FIG. 74. Further, the monomalonate of the quinazoline derivative has a thermogravimetric analysis (TGA) pattern as shown in FIG. 75, indicating that the decomposition of the monomalonate of the quinazoline derivative occurs at 88° C.

Unrestrictedly, the dimalonate of the quinazoline derivative in an exemplary embodiment has an X-ray powder diffraction pattern as shown in FIG. 82. Further, the dimalonate of the quinazoline derivative has a thermogravimetric analysis (TGA) pattern as shown in FIG. 83, indicating that the decomposition of the dimalonate of the quinazoline derivative occurs at 135° C.

Unrestrictedly, the trimalonate of the quinazoline derivative in an exemplary embodiment has an X-ray powder diffraction pattern as shown in FIG. 84. Further, the trimalonate of the quinazoline derivative has a thermogravimetric analysis (TGA) pattern as shown in FIG. 85, indicating that the decomposition of the trimalonate of the quinazoline derivative occurs at 140° C.

Unrestrictedly, the disulfate of the quinazoline derivative in an exemplary embodiment has an X-ray powder diffraction pattern as shown in FIG. 46. Further, the disulfate of the quinazoline derivative has a thermogravimetric analysis (TGA) pattern as shown in FIG. 47, indicating that the decomposition of the disulfate of the quinazoline derivative occurs at 250° C., and the weight loss below 150° C. is 3%. Further, the disulfate of the quinazoline derivative has a differential scanning calorimetry (DSC) pattern as shown in FIG. 48, indicating that the disulfate of the quinazoline derivative has endothermic peaks below 74° C. and between 114-160° C., which appear to be the peaks of solvent elimination, there is no melting peak below 200° C. Further, the disulfate of the quinazoline derivative has a dynamic vapor sorption (DVS) pattern as shown in FIG. 49, indicating that the weight change of the disulfate of the quinazoline derivative in a relative humidity range of 20-80% is about 2%.

Unrestrictedly, the di-1,5-naphthalenedisulfonate of the quinazoline derivative in an exemplary embodiment has an X-ray powder diffraction pattern as shown in FIG. 86. Further, the di-1,5-naphthalenedisulfonate of the quinazoline derivative has a thermogravimetric analysis (TGA) pattern as shown in FIG. 87, indicating that the decomposition of the di-1,5-naphthalenedisulfonate of the quinazoline derivative occurs at 223° C.

Unrestrictedly, the monopamoate of the quinazoline derivative in an exemplary embodiment has an X-ray powder diffraction pattern as shown in FIG. 70.

Unrestrictedly, the mono-p-toluenesulfonate of the quinazoline derivative in an exemplary embodiment has an X-ray powder diffraction pattern as shown in FIG. 71. Further, the mono-p-toluenesulfonate of the quinazoline derivative has a thermogravimetric analysis (TGA) pattern as shown in FIG. 72, indicating that the decomposition of the mono-p-toluenesulfonate of the quinazoline derivative occurs at 245° C. and there is no weight loss before decomposition.

Unrestrictedly, the mono-1,5-naphthalenedisulfonate of the quinazoline derivative in an exemplary embodiment has an X-ray powder diffraction pattern as shown in FIG. 81.

Unrestrictedly, the mono-p-chlorobenzenesulfonate of the quinazoline derivative in an exemplary embodiment has an X-ray powder diffraction pattern as shown in FIG. 92.

The present invention also provides a preparation method for the salt of the quinazoline derivative as described above:

(1) when the salt is the monocitrate 2 (e.g. crystal form 1), comprising the following procedure: carrying out a salt formation reaction on the quinazoline derivative and the citric acid in tetrahydrofuran to give the monocitrate 2 (e.g. crystal form 1);

(2) when the salt is the monocitrate hemiethanolate 2-1 (e.g. crystal 2), comprising the following procedure: slurring the monocitrate 2 (e.g. crystal form 1) in ethanol to give the monocitrate hemiethanolate 2-1 (e.g. crystal 2);

(3) when the salt is the monocitrate ditetrahydrofuran complex 2-2 (e.g. crystal 3), comprising the following procedure: slurring the monocitrate 2 (e.g. crystal form 1) in tetrahydrofuran to give the monocitrate ditetrahydrofuran complex 2-2 (e.g. crystal form 3);

(4) when the salt is the monocitrate hemi-1,4-dioxane complex 2-3 (e.g. crystal form 4), comprising the following procedure: recrystalling the monocitrate 2 (e.g. crystal form 1) in 1,4-dioxane to give the monocitrate hemi-1,4-dioxane complex 2-3 (e.g. crystal form 4);

(5) when the salt is the monocitrate dihydrate 2-4 (e.g. crystal form 5), comprising the following procedure: slurring the monocitrate 2 (e.g. crystal form 1) in n-butanol or water to give the monocitrate dihydrate 2-4 (e.g. crystal form 5);

(5-1) when the salt is the monocitrate dihydrate 2-4 (e.g. crystal form 5), comprising the following procedure: carrying out evaporative crystallization on the monocitrate 2 (e.g. crystal form 1) in a solvent to give the monocitrate dihydrate 2-4 (e.g. crystal form 5), wherein the solvent is aqueous methanol solution, aqueous ethanol solution or aqueous isopropanol solution;

(5-2) when the salt is the monocitrate dihydrate 2-4 (e.g. crystal form 5), comprising the following procedure: recrystalling the monocitrate 2 (e.g. crystal form 1) in a solvent to give the monocitrate dihydrate 2-4 (e.g. crystal form 5), wherein the solvent is methanol and acetone, or 1,4-dioxane and acetone;

(6) when the salt is the monocitrate hemichloroform complex 2-5 (e.g. crystal form 6), comprising the following procedure: slurring the monocitrate 2 (e.g. crystal form 1) in chloroform to give the monocitrate hemichloroform complex 2-5 (e.g. crystal form 6);

(7) when the salt is the monocitrate dihydrate 2-4 (e.g. crystal form 7), comprising the following procedure: slurring the monocitrate 2 (e.g. crystal form 1) in chloroform to give the monocitrate dihydrate 2-4 (e.g. crystal form 7);

(8) when the salt is the trihydrate 2-6 (e.g. crystal form 10), comprising the following procedure: carrying out evaporative crystallization on the monocitrate 2 (e.g. crystal form 1) in a solvent to give the trihydrate 2-6 (e.g. crystal form 10), wherein the solvent is aqueous methanol solution, aqueous n-propanol solution, aqueous tetrahydrofuran solution or aqueous acetonitrile solution;

(9) when the salt is the monocitrate dihydrate 2-4 (e.g. crystal form 11), comprising the following procedure: recrystalling the monocitrate 2 (e.g. crystal form 1) in a solvent to give the monocitrate dihydrate 2-4 (e.g. crystal form 11), wherein the solvent is methanol and ethanol, nitromethane and ethanol, acetonitrile and ethanol, n-propanol, or isopropanol;

(9-2) when the salt is the monocitrate dihydrate 2-4 (e.g. crystal form 11), comprising the following procedure: slurring the monocitrate 2 (e.g. crystal form 1) in a solvent to give the monocitrate dihydrate 2-4 (e.g. crystal form 11), wherein the solvent is methanol and ethanol, nitromethane and ethanol, or acetonitrile and ethanol;

(10) when the salt is the monocitrate 2 (e.g. crystal form 13), comprising the following procedure: recrystalling the monocitrate 2 (e.g. crystal form 1) in n-butanol to give the monocitrate 2 (e.g. crystal form 13);

(10-2) when the salt is the monocitrate 2 (e.g. crystal form 13), comprising the following procedure: carrying out evaporative crystallization on the monocitrate 2 (e.g. crystal form 1) in water and acetonitrile to give the monocitrate 2 (e.g. crystal form 13);

(11) when the salt is the hemi(pentahydrate) 2-7 (e.g. crystal form 14), comprising the following procedure: recrystalling the monocitrate 2 (e.g. crystal form 1) in water and dimethyl sulfoxide to give the hemi(pentahydrate) 2-7 (e.g. crystal form 14);

(11-2) when the salt is the hemi(pentahydrate) 2-7 (e.g. crystal form 14), comprising the following procedure: carrying out evaporative crystallization on the monocitrate 2 (e.g. crystal form 1) in water and acetone to give the hemi(pentahydrate) 2-7 (e.g. crystal form 14);

(12) when the salt is the monoethanedisulfonate, comprising the following procedure: carrying out a salt formation reaction on the quinazoline derivative and the ethanedisulfonic acid in tetrahydrofuran to give the monoethanedisulfonate;

(13) when the salt is the monosulfate, comprising the following procedure: carrying out a salt formation reaction on the quinazoline derivative and the sulfuric acid in tetrahydrofuran to give the monosulfate; the molar ratio of the sulfuric acid to the quinazoline derivative is 1-1.3;

(14) when the salt is the disulfate, comprising the following procedure: carrying out a salt formation reaction on the quinazoline derivative and the sulfuric acid in tetrahydrofuran to give the disulfate; the molar ratio of the sulfuric acid to the quinazoline derivative is 2.2-2.3;

(15) when the salt is the monobenzenesulfonate, comprising the following procedure: carrying out a salt formation reaction on the quinazoline derivative and the benzenesulfonic acid in tetrahydrofuran to give the monobenzenesulfonate;

(16) when the salt is the monohydrochloride monohydrate, comprising the following procedure: carrying out a salt formation reaction on the quinazoline derivative and the hydrochloride in tetrahydrofuran and water to give the monohydrochloride monohydrate;

(17) when the salt is the mono-D-gluconate, comprising the following procedure: carrying out a salt formation reaction on the quinazoline derivative and the D-gluconic acid in dichloromethane to give the mono-D-gluconate;

(18) when the salt is the mono-L-tartrate (crystal form 15), comprising the following procedure: carrying out a salt formation reaction on the quinazoline derivative and the L-tartaric acid in tetrahydrofuran to give the mono-L-tartrate (crystal form 15);

(19) when the salt is the mono-L-tartrate tetrahydrate (crystal form 16), comprising the following procedure: recrystalling the mono-L-tartrate (crystal form 15) in water to give the mono-L-tartrate tetrahydrate (crystal form 16);

(20) when the salt is the diphosphonate, comprising the following procedure: carrying out a salt formation reaction on the quinazoline derivative and the phosphoric acid in tetrahydrofuran to give the diphosphonate;

(21) when the salt is the monopamoate, comprising the following procedure: carrying out a salt formation reaction on the quinazoline derivative and the pamoic acid in tetrahydrofuran to give the monopamoate;

(22) when the salt is the mono-p-toluenesulfonate, comprising the following procedure: carrying out a salt formation reaction on the quinazoline derivative and the p-toluenesulfonic acid in chloroform and ethanol to give the mono-p-toluenesulfonate;

(23) when the salt is the diglycolate, comprising the following procedure: carrying out a salt formation reaction on the quinazoline derivative and the glycolic acid in dichloromethane to give the diglycolate;

(24) when the salt is the monomalonate, comprising the following procedure: carrying out a salt formation reaction on the quinazoline derivative and the malonic acid in dichloromethane to give the monomalonate; the molar ratio of the malonic acid to the quinazoline derivative is 1-1.2;

(25) when the salt is the monosuccinate, comprising the following procedure: carrying out a salt formation reaction on the quinazoline derivative and the succinic acid in dichloromethane to give the monosuccinate; the molar ratio of the succinic acid to the quinazoline derivative is 1-1.2;

(26) when the salt is the mono-α-ketoglutarate, comprising the following procedure: carrying out a salt formation reaction on the quinazoline derivative and the α-ketoglutaric acid in tetrahydrofuran to give the mono-α-ketoglutarate; the molar ratio of the α-ketoglutaric acid to the quinazoline derivative is 1-1.2;

(27) when the salt is the dimaleate, comprising the following procedure: carrying out a salt formation reaction on the quinazoline derivative and the maleic acid in tetrahydrofuran to give the dimaleate;

(28) when the salt is the mono-1,5-naphthalenedisulfonate, comprising the following procedure: carrying out a salt formation reaction on the quinazoline derivative and the 1,5-naphthalenedisulfonic acid in tetrahydrofuran to give the mono-1,5-naphthalenedisulfonate; the molar ratio of the 1,5-naphthalenedisulfonic acid to the quinazoline derivative is 1.1-1.5;

(29) when the salt is the dimalonate, comprising the following procedure: carrying out a salt formation reaction on the quinazoline derivative and the malonic acid in dichloromethane to give the dimalonate; the molar ratio of the malonic acid to the quinazoline derivative is 2.0-2.3;

(30) when the salt is the trimalonate, comprising the following procedure: carrying out a salt formation reaction on the quinazoline derivative and the malonic acid in dichloromethane to give the trimalonate; the molar ratio of the malonic acid to the quinazoline derivative is 3.0-3.4;

(31) when the salt is the di-1,5-naphthalenedisulfonate, comprising the following procedure: carrying out a salt formation reaction on the quinazoline derivative and the 1,5-naphthalenedisulfonic acid in tetrahydrofuran to give the di-1,5-naphthalenedisulfonate; the molar ratio of the 1,5-naphthalenedisulfonic acid to the quinazoline derivative is 2.2-3.3;

(32) when the salt is the trisuccinate, comprising the following procedure: carrying out a salt formation reaction on the quinazoline derivative and the succinic acid in dichloromethane to give the trisuccinate; the molar ratio of the succinic acid to the quinazoline derivative is 2.2-3.3;

(33) when the salt is the di-α-ketoglutarate, comprising the following procedure: carrying out a salt formation reaction on the quinazoline derivative and the α-ketoglutaric acid in tetrahydrofuran to give the di-α-ketoglutarate; the molar ratio of the α-ketoglutaric acid to the quinazoline derivative is 2.2-3.3;

(34) when the salt is the mono-p-chlorobenzenesulfonate, comprising the following procedure: carrying out a salt formation reaction on the quinazoline derivative and the p-chlorobenzenesulfonic acid in tetrahydrofuran to give the mono-p-chlorobenzenesulfonate;

wherein, the structure of the quinazoline derivative is represented by formula

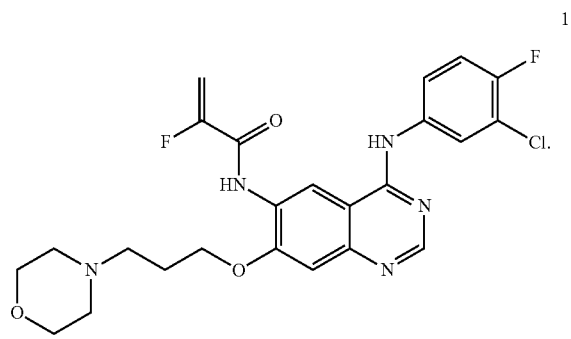 [SMILES: C=C(F)C(=O)Nc1cc2c(Nc3ccc(F)c(Cl)c3)ncnc2cc1OCCCN1CCOCC1]

In the method, the quinazoline derivative can be in any crystal form or amorphous form, for example, a quinazoline derivative given via the method described in CN102898386.

In the method (1), the volume/mass ratio of the tetrahydrofuran to the quinazoline derivative can be 25-50 mL/g, also can be 26-48 mL/g.

In the method (1), the molar ratio of the citric acid to the quinazoline derivative can be 1-1.5.

In the method (1), the temperature of the salt formation can be 10-30° C.

In the method (1), the duration of the salt formation can be 0.5-24 hours.

In the method (1), the operation of the salt formation reaction can be that commonly used in the art. For example, mixing the solution of citric acid in tetrahydrofuran with the solution of the quinazoline derivative in tetrahydrofuran (for example, adding the solution of citric acid in tetrahydrofuran into the solution of the quinazoline derivative in tetrahydrofuran). The concentration of the solution of the quinazoline derivative in tetrahydrofuran can be 25-50 mg/mL. The concentration of the solution of citric acid in tetrahydrofuran can be 50-100 mg/mL.

In the method (1), the post-treatment of the salt formation reaction can be that commonly used for this kind of reactions in the art, for example, filtration and drying. The temperature for drying can be 40-50° C., also can be 40-45° C. The drying can be vacuum drying.

The method (1) may comprises the following procedure: mixing the solution of citric acid in tetrahydrofuran with the solution of the quinazoline derivative in tetrahydrofuran, reacting, followed by isolating the precipitated solids and drying to give the product (wherein, the concentration of the solution of the quinazoline derivative in tetrahydrofuran is preferably 25-50 mg/mL; the concentration of the solution of citric acid in tetrahydrofuran is preferably 50.8-101.6 mg/mL; the molar ratio of the quinazoline derivative to the citric acid is preferably 1:1-1:1.5; the duration of the reaction is preferably 0.5-24 hours).

In the method (2), the volume/mass ratio of the ethanol to the monocitrate 2 (e.g. crystal form 1) can be 35-45 mL/g, also can be 40-45 mL/g.

In the method (2), the monocitrate 2 (e.g. crystal form 1) can be prepared according to the method (1).

In the method (2), the temperature of the slurring can be 55-65° C., also can be 60° C.

In the method (2), the duration of the slurring can be 8-16 hours.

The method (2) may comprises the following procedure: preparing a suspension by mixing the monocitrate 2 (e.g. crystal form 1) with ethanol and stirring at 55-65° C. to give the product (wherein, the concentration of the monocitrate 2 (e.g. crystal form 1) in the ethanol is preferably 10-50 mg/mL; the duration for stirring is preferably 8-16 hous; the temperature for stirring is preferably 60° C.).

In the method (3), the volume/mass ratio of the tetrahydrofuran to the monocitrate 2 (e.g. crystal form 1) can be 35-45 mL/g, also can be 40-45 mL/g.

In the method (3), the monocitrate 2 (e.g. crystal form 1) can be prepared according to the method (1).

In the method (3), the temperature of the slurring can be 10-60° C.

In the method (3), the duration of the slurring can be 8-16 hours.

The method (3) may comprises the following procedure: preparing a suspension by mixing the monocitrate 2 (e.g. crystal form 1) with tetrahydrofuran and stirring at 10-60° C. to give the product (wherein, the concentration of the monocitrate 2 (e.g. crystal form 1) in the tetrahydrofuran is preferably 10-50 mg/mL; the duration for stirring is preferably 8-16 hous).

In the method (4), the volume/mass ratio of the 1,4-dioxane to the monocitrate 2 (e.g. crystal form 1) can be 80-120 mL/g, also can be 100-120 mL/g.

In the method (4), the monocitrate 2 (e.g. crystal form 1) can be prepared according to the method (1).

In the method (4), the recrystalling can be performed as cooling recrystallization, wherein the temperature for dissolution can be 50-60° C. and the target temperature for cooling can be 10-30° C.

The method (4) may comprises the following procedure: preparing a solution by mixing the monocitrate 2 (e.g. crystal form 1) with the dioxane at the temperature above 60° C. and naturally cooling while stirring to give the product (wherein, the concentration of the monocitrate 2 (e.g. crystal form 1) is preferably 8.3-16.7 mg/mL; the naturally cooling refers to cooling under room temperature).

In the method (5), the volume/mass ratio of the water to the monocitrate 2 (e.g. crystal form 1) can be 60-70 mL/g, also can be 66-70 mL/g.

In the method (5), the volume/mass ratio of the tetrahydrofuran to the monocitrate 2 (e.g. crystal form 1) can be 80-120 mL/g, also can be 100-120 mL/g.

In the method (5), the monocitrate 2 (e.g. crystal form 1) may be prepared according to the method (1).

In the method (5), the temperature of the slurring can be 10-60° C.

In the method (5), the duration of the slurring can be 8-16 hours.

The method (5) may comprises the following procedure: preparing a suspension by mixing the monocitrate 2 (e.g. crystal form 1) with the solvent and stirring at 10-60° C. to give the product; the solvent is water or n-butanol (wherein, the concentration of the monocitrate 2 (e.g. crystal form 1) in the solvent is preferably 5-40 mg/mL, more preferably 10-20 mg/mL; the duration for stirring is preferably 5-16 hous).

In the method (5-1), the volume/mass ratio of the solvent to the monocitrate 2 (e.g. crystal form 1) can be 20-200 mL/g.

In the method (5-1), the volume ratio of the alcohol to the water in the solvent can be 1.

In the method (5-1), the monocitrate 2 (e.g. crystal form 1) may be prepared according to the method (1).

In the method (5-1), the temperature of the evaporation can be 10-60° C.

The method (5-1) may comprises the following procedure: preparing a solution by mixing the monocitrate 2 (e.g. crystal form 1) with the solvent, and the solvent was evaporated to dry at 10-60° C. to give the product; the solvent is aqueous methanol solution, aqueous ethanol solution or aqueous isopropanol solution (wherein, the concentration of the monocitrate 2 (e.g. crystal form 1) is preferably 5-50 mg/mL).

In the method (5-2), the volume/mass ratio of the solvent to the monocitrate 2 (e.g. crystal form 1) can be 160-240 mL/g, also can be 200-240 mL/g.

In the method (5-2), the volume ratio of the methanol to the acetone can be 1.

In the method (5-2), the volume ratio of the 1,4-dioxane to the acetone can be 1.

In the method (5-2), the monocitrate 2 (e.g. crystal form 1) may be prepared according to the method (1).

In the method (5-2), the recrystalling can be performed as cooling crystallization, wherein the temperature for dissolution can be 50-60° C. and the target temperature for cooling can be 10-30° C.

In the method (6), the volume/mass ratio of the chloroform to the monocitrate 2 (e.g. crystal form 1) can be 35-45 mL/g, also can be 40-45 mL/g.

In the method (6), the monocitrate 2 (e.g. crystal form 1) may be prepared according to the method (1).

In the method (6), the temperature of the slurring can be 55-66° C., also can be 60° C.

In the method (6), the duration of the slurring can be 8-16 hours.

The method (6) may comprises the following procedure: preparing a suspension by mixing the monocitrate 2 (e.g. crystal form 1) with the chloroform and stirring at room temperature to give the product (wherein, the concentration of the monocitrate 2 (e.g. crystal form 1) in the chloroform is preferably 10-50 mg/mL; the duration for stirring is preferably 8-16 hous).

In the method (7), the volume/mass ratio of the chloroform to the monocitrate 2 (e.g. crystal form 1) can be 80-120 mL/g, also can be 100-120 mL/g.

In the method (7), the monocitrate 2 (e.g. crystal form 1) may be prepared according to the method (1).

In the method (7), the temperature of the slurring can be 10-30° C.

In the method (7), the duration of the slurring can be 8-16 hours.

The method (7) may comprises the following procedure: preparing a suspension by mixing the monocitrate 2 (e.g. crystal form 1) with the water and stirring at room temperature to give the product (wherein, the concentration of the monocitrate 2 (e.g. crystal form 1) in the water is preferably 5-40 mg/mL, more preferably 10-20 mg/mL; the duration for stirring is preferably 8-16 hous).

In the method (8), the volume/mass ratio of the solvent to the monocitrate 2 (e.g. crystal form 1) can be 100-200 mL/g.

In the method (8), the volume ratio of the non-aqueous solvent to the water in the solvent can be 1.

In the method (8), the monocitrate 2 (e.g. crystal form 1) may be prepared according to the method (1).

In the method (8), the temperature of the evaporation is 10-30° C.

The method (8) may comprises the following procedure: preparing a solution by mixing the monocitrate 2 (e.g. crystal form 1) with the solvent and followed by natural evaporation at room temperature to give the product (wherein, the concentration of the monocitrate 2 (e.g. crystal form 1) is preferably 5-10 mg/mL; the natural evaporation can be the uncovered evaporation or covered evaporation with punching. The volume ratio of the n-propanol to the water in the aqueous n-propanol solution is preferably 1:1; the volume ratio of the tetrahydrofuran to the water in the aqueous tetrahydrofuran solution is preferably 1:1; the volume ratio of the acetonitrile to the water in the aqueous acetonitrile solution is preferably 1:1).

In the method (9), the volume/mass ratio of the solvent to the monocitrate 2 (e.g. crystal form 1) can be 200-600 mL/g, also can be 200-500 mL/g.

In the method (9), the monocitrate 2 (e.g. crystal form 1) may be prepared according to the method (1).

In the method (9), the recrystalling can be performed as cooling crystallization, wherein the temperature for dissolution can be 50-60° C. and the target temperature for cooling can be 10-30° C.

The method (9) may comprises the following procedure: preparing a solution by mixing the monocitrate 2 (e.g. crystal form 1) with the organic solvent containing alcohols at the temperature above 60° C. and naturally cooling while stirring to give the product (wherein, the organic solvent containing alcohols is preferably n-propanol, isopropanol, the solution of methanol in ethanol, the solution of acetonitrile in ethanol or the solution of nitromethane in ethanol; the volume ratio of the methanol to the ethanol in the solution of methanol in ethanol is preferably 1:1; the volume ratio of the acetonitrile to the ethanol in the solution of acetonitrile in ethanol is preferably 1:1; the volume ratio of the nitromethane to the ethanol in the solution of nitromethane in ethanol is preferably 1:1).

In the method (9-2), the volume/mass ratio of the solvent to the monocitrate 2 (e.g. crystal form 1) can be 160-240 mL/g, also can be 200-240 mL/g.

In the method (9-2), the volume ratio of the methanol to the ethanol in the solvent can be 1.

In the method (9-2), the volume ratio of the nitromethane to the ethanol in the solvent can be 1.

In the method (9-2), the volume ratio of the acetonitrile to the ethanol in the solvent can be 1.

In the method (9-2), the monocitrate 2 (e.g. crystal form 1) may be prepared according to the method (1).

In the method (9-2), the temperature of the slurring can be 10-30° C.

In the method (9-2), the duration of the slurring can be 8-16 hours.

The method (9-2) may comprises the following procedure: preparing a suspension by mixing the monocitrate 2 (e.g. crystal form 1) with the organic solvent containing alcohols and stirring at room temperature to give the product (wherein, the organic solvent containing alcohols is preferably the solution of methanol in ethanol, the solution of acetonitrile in ethanol or the solution of nitromethane in ethanol; the volume ratio of the methanol to the ethanol in the solution of methanol in ethanol is preferably 1:1; the volume ratio of the acetonitrile to the ethanol in the solution of acetonitrile in ethanol is preferably 1:1; the volume ratio of the nitromethane to the ethanol in the solution of nitromethane in ethanol is preferably 1:1; the duration for stirring is preferably 8-16 hours).

In the method (10), the volume/mass ratio of the n-butanol to the monocitrate 2 (e.g. crystal form 1) can be 200-300 mL/g, also can be 240-300 mL/g.

In the method (10), the monocitrate 2 (e.g. crystal form 1) may be prepared according to the method (1).

In the method (10), the recrystalling can be performed as cooling crystallization, wherein the temperature for dissolution can be 50-60° C. and the target temperature for cooling can be 10-30° C.

The method (10) may comprises the following procedure: preparing a solution by mixing the monocitrate 2 (e.g. crystal form 1) with the n-butanol at 50-60° C. and naturally cooling to room temperature while stirring to give the product (wherein, the concentration of the monocitrate 2 (e.g. crystal form 1) is preferably 4.1-8.3 mg/mL).

In the method (10-2), the volume/mass ratio of the "water and acetonitrile" to the monocitrate 2 (e.g. crystal form 1) can be 100-200 mL/g.

In the method (10-2), the volume ratio of the acetonitrile to the water in the solvent can be 1.

In the method (10-2), the monocitrate 2 (e.g. crystal form 1) may be prepared according to the method (1).

In the method (10-2), the temperature of the evaporation can be 50-60° C.

The method (10-2) may comprises the following procedure: preparing a solution by mixing the monocitrate 2 (e.g. crystal form 1) with the acetonitrile and water at 55-65° C. and the solvent was evaporated to dry to give the product (wherein, the concentration of the monocitrate 2 (e.g. crystal form 1) is preferably 5-50 mg/mL; the volume ratio of the acetonitrile to the water is preferably 1:1).

In the method (11), the volume/mass ratio of the "water and dimethyl sulfoxide" to the monocitrate 2 (e.g. crystal form 1) can be 200-300 mL/g, also can be 240-300 mL/g.

In the method (11-2), the volume ratio of the water to the dimethyl sulfoxide in the solvent can be 60.

In the method (11), the monocitrate 2 (e.g. crystal form 1) may be prepared according to the method (1).

In the method (11), the recrystalling can be performed as antisolvent recrystallization, for example, dissolving with dimethyl sulfoxide, followed by mixing with water.

The method (11) may comprises the following procedure: preparing a solution by mixing the monocitrate 2 (e.g. crystal form 1) with the dimethyl sulfoxide and then adding into the water, stirring at room temperature to give the product (wherein, the concentration of the monocitrate 2 (e.g. crystal form 1) in the solution is preferably 200-400 mg/mL; the volume ratio of the water to the dimethyl sulfoxide is preferably 5-10; the duration for stirring is preferably 5-30 minutes).

In the method (11-2), the volume/mass ratio of the "water and acetone" to the monocitrate 2 (e.g. crystal form 1) can be 110-200 mL/g.

In the method (11-2), the volume ratio of the acetone to the water in the solvent can be 1.

In the method (11-2), the monocitrate 2 (e.g. crystal form 1) may be prepared according to the method (1).

In the method (11-2), the temperature of the evaporation can be 50-60° C.

In the method (12), the volume/mass ratio of the tetrahydrofuran to the quinazoline derivative can be 20-100 mL/g.

In the method (12), the molar ratio of the ethanedisulfonic acid to the quinazoline derivative can be 1.1-2.2.

In the method (12), the temperature of the salt formation can be 10-30° C.

In the method (12), the duration of the salt formation can be 0.5-24 hours.

In the method (12), the operation of the salt formation reaction can be that commonly used in the art. For example, mixing the solution of ethanedisulfonic acid in tetrahydrofuran with the solution of quinazoline derivative in tetrahydrofuran (for example, adding the solution of ethanedisulfonic acid in tetrahydrofuran into the solution of quinazoline derivative in tetrahydrofuran). The concentration of the solution of quinazoline derivative in tetrahydrofuran can be 12.5-25 mg/mL. The concentration of the solution of ethanedisulfonic acid in tetrahydrofuran can be 20.75-41.5 mg/mL.

The method (12) may comprises the following procedure: mixing the solution of ethanedisulfonic acid in tetrahydrofuran with the solution of quinazoline derivative in tetrahydrofuran, reacting, followed by the isolation of the precipitated solids and drying to give the product (wherein, the methods and conditions for mixing can be those commonly used in the art. The mixing is preferably that: adding the solution of ethanedisulfonic acid in tetrahydrofuran dropwise into the solution of quinazoline derivative in tetrahydrofuran. The concentration of the solution of the quinazoline derivative in tetrahydrofuran is preferably 12.5-25 mg/mL; the concentration of solution of the ethanedisulfonic acid in tetrahydrofuran is preferably 20.75-41.5 mg/mL; the molar ratio of the quinazoline derivative to the ethanedisulfonic acid is preferably 1:1.1-1:2.2; the duration of the reaction is preferably 0.5-24 hours).

In the method (13), the volume/mass ratio of the tetrahydrofuran to the quinazoline derivative can be 50-100 mL/g.

In the method (13), the sulfuric acid is used in form of the concentrated sulfuric acid.

In the method (13), the temperature of the salt formation can be 10-30° C.

In the method (13), the duration of the salt formation can be 0.5-24 hours.

In the method (13), the operation of the salt formation reaction can be that commonly used in the art. For example, mixing the solution of sulfuric acid in tetrahydrofuran with the solution of the quinazoline derivative in tetrahydrofuran (for example, adding the solution of sulfuric acid in tetrahydrofuran into the solution of the quinazoline derivative in tetrahydrofuran.). The concentration of the solution of the quinazoline derivative in tetrahydrofuran can be 12.5-25 mg/mL. The concentration of the solution of sulfuric acid in tetrahydrofuran can be 9.75-19.5 mg/mL.

The method (13) may comprises the following procedure: mixing the solution of sulfuric acid in tetrahydrofuran with the solution of the quinazoline derivative in tetrahydrofuran, reacting, followed by the isolation of the precipitated solids and drying to give the product, wherein the molar ratio of the quinazoline derivative to the sulfuric acid is 1:1-1:1.3 (wherein, the methods and conditions for mixing are that commonly used in the art. The mixing is preferably that: adding the solution of sulfuric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of sulfuric acid in tetrahydrofuran is preferably 9.75-19.5 mg/mL; the duration of the reaction is preferably 0.5-24 hours).

In the method (14), the volume/mass ratio of the tetrahydrofuran to the quinazoline derivative can be 50-100 mL/g.

In the method (14), the sulfuric acid is used in form of concentrated sulfuric acid.

In the method (14), the temperature of the salt formation can be 10-30° C.

In the method (14), the duration of the salt formation can be 0.5-24 hours.

The method (14) may comprises the following procedure: mixing the solution of sulfuric acid in tetrahydrofuran with the solution of the quinazoline derivative in tetrahydrofuran, reacting, followed by the isolation of the precipitated solids and drying to give the product, wherein the molar ratio of the quinazoline derivative to the sulfuric acid is 1:2.2-1:3.3 (wherein, the methods and conditions for mixing are that commonly used in the art. The mixing is preferably that: adding the solution of sulfuric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of sulfuric acid in tetrahydrofuran is preferably 29.25-58.5 mg/mL; the molar ratio of the quinazoline derivative to the sulfuric acid is preferably 1:3.3; the duration of the reaction is preferably 0.5-24 hours).

In the method (15), the volume/mass ratio of the tetrahydrofuran to the quinazoline derivative can be 50-100 mL/g.

In the method (15), the molar ratio of the benzenesulfonic acid to the quinazoline derivative can be 1-1.3.

In the method (15), the temperature of the salt formation can be 10-30° C.

In the method (15), the duration of the salt formation can be 0.5-24 hours.

In the method (15), the operation of the salt formation reaction is that commonly used in the art. For example, mixing the solution of benzenesulfonic acid in tetrahydrofuran with the solution of the quinazoline derivative in tetrahydrofuran (for example, adding the solution of benzenesulfonic acid in tetrahydrofuran into the solution of the quinazoline derivative in tetrahydrofuran). The concentration of the solution of the quinazoline derivative in tetrahydrofuran can be 12.5-25 mg/mL. The concentration of the solution of benzenesulfonic acid in tetrahydrofuran can be 15.7-31.4 mg/mL.

The method (15) may comprises the following procedure: mixing the solution of benzenesulfonic acid in tetrahydrofuran with the solution of the quinazoline derivative in tetrahydrofuran, reacting, followed by the isolation of the precipitated solids and drying to give the product (wherein, the methods and conditions for mixing are that commonly used in the art. The mixing is preferably that: adding the solution of benzenesulfonic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of benzenesulfonic acid in tetrahydrofuran is preferably 15.7-31.4 mg/mL; the molar ratio of the quinazoline derivative to the benzenesulfonic acid is preferably 1:1-1.3; the duration of the reaction is preferably 0.5-24 hours).

In the method (16), the volume/mass ratio of the tetrahydrofuran to the quinazoline derivative can be 50-100 mL/g.

In the method (16), the hydrochloride is used with the water in the form of concentrated hydrochloride acid (saturated aqueous hydrochloride solution).

In the method (16), the molar ratio of the hydrochloride to the quinazoline derivative can be 1.1-3.3.

In the method (16), the temperature of the salt formation can be 10-30° C.

In the method (16), the duration of the salt formation can be 0.5-24 hours.

The method (16) may comprises the following procedure: mixing the solution of the quinazoline derivative in tetrahydrofuran with the solution of hydrochloride acid in tetrahydrofuran, reacting, followed by the isolation of the precipitated solids and drying to give the product (wherein, the methods and conditions for mixing can be those commonly used in the art. The mixing is preferably that: adding the solution of hydrochloride acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of hydrochloride acid in tetrahydrofuran is preferably 11-22 mg/mL; the molar ratio of the quinazoline derivative to the hydrochloride acid is preferably 1:1.1-1:3.3; the duration of the reaction is preferably 0.5-24 hours).

In the method (17), the volume/mass ratio of the tetrahydrofuran to the quinazoline derivative can be 230-400 mL/g.

In the method (17), the molar ratio of the D-gluconic acid to the quinazoline derivative can be 1.1-3.3.

In the method (17), the temperature of the salt formation can be 10-30° C.

In the method (17), the duration of the salt formation can be 0.5-24 hours.

The method (17) may comprises the following procedure: mixing the solution of the quinazoline derivative in dichloromethane with the suspension of D-gluconic acid in dichloromethane, reacting, followed by the isolation of the precipitated solids and drying to give the product (wherein, the methods and conditions for mixing can be those commonly used in the art. The mixing is preferably that: adding the solution of the quinazoline derivative in dichloromethane dropwise into the suspension of D-gluconic acid in dichloromethane. The concentration of the solution of the quinazoline derivative in dichloromethane is preferably 5-10 mg/mL; the content of D-gluconic acid in the suspension of D-gluconic acid in dichloromethane is preferably 3-5 mg/mL; the molar ratio of the quinazoline derivative to the D-gluconic acid is preferably 1:1.1-1:3.3; the duration of the reaction is preferably 16-24 hours).

In the method (18), the volume/mass ratio of the tetrahydrofuran to the quinazoline derivative can be 100-300 mL/g.

In the method (18), the molar ratio of the L-tartaric acid to the quinazoline derivative can be 1-1.3.

In the method (18), the temperature of the salt formation can be 10-30° C.

In the method (18), the duration of the salt formation can be 0.5-24 hours.

The method (18) may comprises the following procedure: mixing the solution of the quinazoline derivative in tetrahydrofuran with the solution of L-tartaric acid in tetrahydrofuran, reacting, followed by the isolation of the precipitated solids and drying to give the product (wherein, the methods and conditions for mixing can be those commonly used in the art. The mixing is preferably that: adding the solution of L-tartaric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of L-tartaric acid in tetrahydrofuran is preferably 14.9-29.8 mg/mL; the molar ratio of the quinazoline derivative to the L-tartaric acid is preferably 1:1-1:1.3; the duration of the reaction is preferably 0.5-24 hours).

In the method (19), the recrystalling can be performed as stirring recrystallization.

In the method (19), the mono-L-tartrate (crystal form 15) may be prepared according to method (18).

In the method (19), the duration of the recrystallization can be 6-12 hours.

The method (19) may comprises the following procedure: mixing the mono-L-tartrate (crystal form 15) with water to form a clear solution, and stirring until the solid was completely precipitated, followed by the isolation of the precipitated solids and drying to give the product (wherein, the duration for stirring is preferably 6-12 hours).

In the method (20), the volume/mass ratio of the tetrahydrofuran to the quinazoline derivative can be 50-130 mL/g.

In the method (20), the phosphoric acid is used in form of 85% aqueous phosphoric acid solution.

In the method (20), the molar ratio of the phosphoric acid to the quinazoline derivative can be 1.1-3.3.

In the method (20), the temperature of the salt formation can be 10-30° C.

In the method (20), the duration of the salt formation can be 0.5-24 hours.

The method (20) may comprises the following procedure: mixing the solution of the quinazoline derivative in tetrahydrofuran with the solution of phosphoric acid in tetrahydrofuran, reacting, followed by the isolation of the precipitated solids and drying to give the product (wherein, the methods and conditions for mixing are those commonly used in the art. The mixing is preferably that: adding the solution of phosphoric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of phosphoric acid in tetrahydrofuran is preferably 7.75-15.5 mg/mL; the molar ratio of the quinazoline derivative to the phosphoric acid is preferably 1:1.1-1:3.3; the duration of the reaction is preferably 0.5-24 hours).

In the method (21), the volume/mass ratio of the tetrahydrofuran to the quinazoline derivative can be 65-130 mL/g.

In the method (21), the molar ratio of the pamoic acid to the quinazoline derivative can be 1-1.3.

In the method (21), the temperature of the salt formation can be 10-30° C.

In the method (21), the duration of the salt formation can be 16-24 hours.

The method (21) may comprises the following procedure: mixing the solution of the quinazoline derivative in tetrahydrofuran with the suspension of pamoic acid in tetrahydrofuran, reacting, followed by the isolation of the precipitated solids and drying to give the product (wherein, the methods and conditions for mixing are those commonly used in the art. The mixing is preferably that: adding the solution of the quinazoline derivative in tetrahydrofuran dropwise into the suspension of pamoic acid in tetrahydrofuran. The concentration of the solution of the quinazoline derivative in tetrahydrofuran is preferably 12.5-25 mg/mL; the content of the pamoic acid in the suspension of pamoic acid in tetrahydrofuran is preferably 10-20 mg/mL; the molar ratio of the quinazoline derivative to the pamoic acid is preferably 1:1-1:1.3; the duration of the reaction is preferably 16-24 hours).

In the method (22), the volume/mass ratio of the "chloroform and ethanol" to the quinazoline derivative can be 45-90 mL/g.

In the method (22), the volume ratio of the chloroform to the ethanol can be 8-10.

In the method (22), the molar ratio of the p-toluenesulfonic acid to the quinazoline derivative can be 1-1.3.

In the method (22), the temperature of the salt formation can be 10-30° C.

In the method (22), the duration of the salt formation can be 16-24 hours.

The method (22) may comprises the following procedure: mixing the solution of the quinazoline derivative in chloroform with the solution of p-toluenesulfonic acid in ethanol, reacting, followed by the isolation of the precipitated solids and drying to give the product (wherein, the methods and conditions for mixing are those commonly used in the art. The mixing is preferably that: adding the solution of p-toluenesulfonic acid in ethanol dropwise into the solution of the quinazoline derivative in chloroform. The concentration of the solution of the quinazoline derivative in chloroform is preferably 12.5-25 mg/mL; the concentration of the solution of p-toluenesulfonic acid in ethanol is preferably 41-82 mg/mL; the molar ratio of the quinazoline derivative to the p-toluenesulfonic acid is preferably 1:1.1-1:1.3; the duration of the reaction is preferably 16-24 hours).

In the method (23), the volume/mass ratio of the dichloromethane to the quinazoline derivative can be 125-250 mL/g.

In the method (23), the molar ratio of the glycolic acid to the quinazoline derivative can be 2.0-2.2.

In the method (23), the temperature of the salt formation can be 10-30° C.

In the method (23), the duration of the salt formation can be 16-24 hours.

The method (23) may comprises the following procedure: mixing the solution of the quinazoline derivative in dichloromethane with the suspension of glycolic acid in dichloromethane, reacting, followed by the isolation of the precipitated solids and drying to give the product (wherein, the methods and conditions for mixing are those commonly used in the art. The mixing is preferably that: adding the solution of the quinazoline derivative in dichloromethane dropwise into the suspension of glycolic acid in dichloromethane. The concentration of the solution of the quinazoline derivative in dichloromethane is preferably 5-10 mg/mL; the content of glycolic acid in the suspension of glycolic acid in dichloromethane is preferably 5-10 mg/mL; the molar ratio of the quinazoline derivative to the glycolic acid is preferably 1:2.0-1:2.2; the duration of the reaction is preferably 16-24 hours).

In the method (24), the volume/mass ratio of the dichloromethane to the quinazoline derivative can be 125-250 mL/g.

In the method (24), the temperature of the salt formation can be 10-30° C.

In the method (24), the duration of the salt formation can be 16-24 hours.

The method (24) may comprises the following procedure: mixing the solution of the quinazoline derivative in dichloromethane with the suspension of malonic acid in dichloromethane, reacting, followed by the isolation of the precipitated solids and drying to give the product, wherein the molar ratio of the quinazoline derivative to the malonic acid is 1:1-1:1.2 (wherein, the methods and conditions for mixing are those commonly used in the art. The mixing is preferably that: adding the solution of the quinazoline derivative in dichloromethane dropwise into the suspension of malonic acid in dichloromethane. The molar ratio of the quinazoline derivative to the malonic acid is preferably 1:1.1. The concentration of the solution of the quinazoline derivative in dichloromethane is preferably 5-10 mg/mL; the content of malonic acid in the suspension of malonic acid in dichloromethane is preferably 3-5 mg/mL; the duration of the reaction is preferably 16-24 hours).

In the method (25), the volume/mass ratio of the dichloromethane to the quinazoline derivative can be 125-250 mL/g.

In the method (25), the temperature of the salt formation can be 10-30° C.

In the method (25), the duration of the salt formation can be 16-24 hours.

The method (25) may comprises the following procedure: mixing the solution of the quinazoline derivative in dichloromethane with the suspension of succinic acid in dichloromethane, reacting, followed by the isolation of the precipitated solids and drying to give the product, wherein the molar ratio of the quinazoline derivative to the succinic acid is 1:1-1:1.2 (wherein, the methods and conditions for mixing are those commonly used in the art. The mixing is preferably that: adding the solution of the quinazoline derivative in dichloromethane dropwise into the suspension of succinic acid in dichloromethane. The molar ratio of the quinazoline derivative to the succinic acid is preferably 1:1.1. The concentration of the solution of the quinazoline derivative in dichloromethane is preferably 5-10 mg/mL; the content of succinic acid in the suspension of succinic acid in dichloromethane is preferably 3-5 mg/mL; the duration of the reaction is preferably 16-24 hours).

In the method (26), the volume/mass ratio of the tetrahydrofuran to the quinazoline derivative can be 50-100 mL/g.

In the method (26), the temperature of the salt formation can be 10-30° C.

In the method (26), the duration of the salt formation can be 0.5-24 hours.

The method (26) may comprises the following procedure: mixing the solution of the quinazoline derivative in tetrahydrofuran with the solution of α-ketoglutaric acid in tetrahydrofuran, reacting, followed by the isolation of the precipitated solids and drying to give the product, wherein the molar ratio of the quinazoline derivative to the α-ketoglutaric acid is 1:1-1:1.2 (wherein, the methods and conditions for mixing are those commonly used in the art. The mixing is preferably that: adding the solution of α-ketoglutaric acid in tetrahydrofuran dropwise into the solution of the quinazoline derivative in tetrahydrofuran. The molar ratio of the quinazoline derivative to the α-ketoglutaric acid is preferably 1:1.1. The concentration of the solution of the quinazoline derivative in tetrahydrofuran is preferably 12.5-25 mg/mL; the concentration of the solution of α-ketoglutaric acid in tetrahydrofuran is preferably 15.95-31.9 mg/mL; the duration of the reaction is preferably 0.5-24 hours).

In the method (27), the volume/mass ratio of the tetrahydrofuran to the quinazoline derivative can be 60-120 mL/g.

In the method (27), the molar ratio of the quinazoline derivative to the maleic acid can be 1.1-3.3.

In the method (27), the temperature of the salt formation can be 10-30° C.

In the method (27), the duration of the salt formation can be 0.5-24 hours.

The method (27) may comprises the following procedure: mixing the solution of the quinazoline derivative in tetrahydrofuran with the solution of maleic acid in tetrahydrofuran, reacting, followed by the isolation of the precipitated solids and drying to give the product (wherein, the methods and conditions for mixing are those commonly used in the art. The mixing is preferably that: adding the solution of maleic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of maleic acid in tetrahydrofuran is preferably 12.56-25.32 mg/mL; the molar ratio of the quinazoline derivative to the maleic acid is preferably 1:1.1-1:3.3; the duration of the reaction is preferably 0.5-24 hours).

In the method (28), the volume/mass ratio of the tetrahydrofuran to the quinazoline derivative can be 50-100 mL/g.

In the method (28), the temperature of the salt formation can be 10-30° C.

In the method (28), the duration of the salt formation can be 0.5-24 hours.

The method (28) may comprises the following procedure: mixing the solution of the quinazoline derivative in tetrahydrofuran with the solution of 1,5-naphthalenedisulfonic acid in tetrahydrofuran, reacting, followed by the isolation of the precipitated solids and drying to give the product, wherein the molar ratio of the quinazoline derivative to the 1,5-naphthalenedisulfonic acid is 1:1.1-1:1.5 (wherein, the methods and conditions for mixing are those commonly used in the art. The mixing is preferably that: adding the solution of 1,5-naphthalenedisulfonic acid in tetrahydrofuran dropwise into the solution of the quinazoline derivative in tetrahydrofuran. The molar ratio of the quinazoline derivative to the 1,5-naphthalenedisulfonic acid is preferably 1:1.4. The concentration of the solution of the quinazoline derivative in tetrahydrofuran is preferably 12.5-25 mg/mL; the concentration of the solution of 1,5-naphthalenedisulfonic acid in tetrahydrofuran is preferably 39.3-78.6 mg/mL; the duration of the reaction is preferably 0.5-24 hours).

In the method (29), the volume/mass ratio of the dichloromethane to the quinazoline derivative can be 150-300 mL/g.

In the method (29), the temperature of the salt formation can be 10-30° C.

In the method (29), the duration of the salt formation can be 16-24 hours.

The method (29) may comprises the following procedure: the malonic acid suspension in dichloromethane was mixed with the quinazoline derivative solution in dichloromethane, reacting, followed by the isolation of the precipitated solids and drying to give the product, wherein the molar ratio of the quinazoline derivative to the malonic acid is 1:2.0-1:2.3 (wherein, the methods and conditions for mixing are those commonly used in the art. The mixing is preferably that: adding the solution of the quinazoline derivative in dichloromethane dropwise into the suspension of malonic acid in dichloromethane. The molar ratio of the quinazoline derivative to the malonic acid is preferably 1:2.2. Wherein, the concentration of the solution of the quinazoline derivative in dichloromethane is preferably 5-10 mg/mL; the content of malonic acid in the suspension of malonic acid in dichloromethane is preferably 3-5 mg/mL; the duration of the reaction is preferably 16-24 hours).

In the method (30), the volume/mass ratio of the dichloromethane to the quinazoline derivative can be 150-300 mL/g.

In the method (30), the temperature of the salt formation can be 10-30° C.

In the method (30), the duration of the salt formation can be 16-24 hours.

The method (30) may comprises the following procedure: mixing the solution of the quinazoline derivative in dichloromethane with the suspension of malonic acid in dichloromethane, reacting, followed by the isolation of the precipitated solids and drying to give the product, wherein the molar ratio of the quinazoline derivative to the malonic acid is 1:3.0-1:3.4 (wherein, the methods and conditions for mixing can be those commonly used in the art. The mixing is preferably that: adding the solution of the quinazoline derivative in dichloromethane dropwise into the suspension of malonic acid in dichloromethane. The molar ratio of the quinazoline derivative to the malonic acid is preferably 1:3.3. The concentration of the solution of the quinazoline derivative in dichloromethane is preferably 5-10 mg/mL; the content of the malonic acid in the suspension of malonic acid in dichloromethane is preferably 5-10 mg/mL; the duration of the reaction is preferably 16-24 hours).

In the method (31), the volume/mass ratio of the tetrahydrofuran to the quinazoline derivative can be 60-120 mL/g.

In the method (31), the temperature of the salt formation can be 10-30° C.

In the method (31), the duration of the salt formation can be 0.5-24 hours.

The method (31) may comprises the following procedure: mixing the solution of the quinazoline derivative in tetrahydrofuran with the solution of 1,5-naphthalenedisulfonic acid in tetrahydrofuran, reacting, followed by the isolation of the precipitated solids and drying to give the product, wherein the molar ratio of the quinazoline derivative to the 1,5-naphthalenedisulfonic acid is 1:2.2-1:3.3 (wherein, the methods and conditions for mixing are those commonly used in the art. The mixing is preferably that: adding the solution of 1,5-naphthalenedisulfonic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of 1,5-naphthalenedisulfonic acid in tetrahydrofuran is preferably 39.3-78.6 mg/mL; the duration of the reaction is preferably 0.5-24 hours).

In the method (32), the volume/mass ratio of the dichloromethane to the quinazoline derivative can be 150-300 mL/g.

In the method (32), the temperature of the salt formation can be 10-30° C.

In the method (32), the duration of the salt formation can be 16-24 hours.

The method (32) may comprises the following procedure: mixing the solution of the quinazoline derivative in dichloromethane with the suspension of succinic acid in dichloromethane, reacting, followed by the isolation of the precipitated solids and drying to give the product, wherein the molar ratio of the quinazoline derivative to the succinic acid is 1:2.2-1:3.3 (wherein, the methods and conditions for mixing are those commonly used in the art. The mixing is preferably that: adding the solution of the quinazoline derivative in dichloromethane dropwise into the suspension of succinic acid in dichloromethane. The concentration of the solution of the quinazoline derivative in dichloromethane is preferably 5-10 mg/mL; the content of the succinic acid in the suspension of succinic acid in dichloromethane is preferably 5-10 mg/mL; the duration of the reaction is preferably 16-24 hours).

In the method (33), the volume/mass ratio of the tetrahydrofuran to the quinazoline derivative is 60-120 mL/g.

In the method (33), the temperature of the salt formation can be 10-30° C.

In the method (33), the duration of the salt formation can be 0.5-24 hours.

The method (33) may comprises the following procedure: mixing the solution of the quinazoline derivative in tetrahydrofuran with the solution of α-ketoglutaric acid in tetrahydrofuran reacting, followed by the isolation of the precipitated solids and drying to give the product, wherein the molar ratio of the quinazoline derivative to the α-ketoglutaric acid is 1:2.2-1:3.3 (wherein, the methods and conditions for mixing are those commonly used in the art. The mixing is preferably that: adding the solution of α-ketoglutaric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of α-ketoglutaric acid in tetrahydrofuran is preferably 15.95-31.9 mg/mL; the duration of the reaction is preferably 0.5-24 hours).

In the method (34), the volume/mass ratio of the tetrahydrofuran to the quinazoline derivative can be 50-100 mL/g.

In the method (34), the molar ratio of the p-chlorobenzenesulfonic acid to the quinazoline derivative can be 1-1.2.

In the method (34), the temperature of the salt formation can be 10-30° C.

In the method (34), the duration of the salt formation can be 0.5-24 hours.

The method (34) may comprises the following procedure: mixing the solution of the quinazoline derivative in tetrahydrofuran with the solution of p-chlorobenzenesulfonic acid in tetrahydrofuran, reacting, followed by the isolation of the precipitated solids and drying to give the product (wherein, the methods and conditions for mixing are those commonly used in the art. The mixing is preferably that: adding the solution of p-chlorobenzenesulfonic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of p-chlorobenzenesulfonic acid in tetrahydrofuran is preferably 21-42 mg/mL; the duration of the reaction is preferably 0.5-24 hours. The molar ratio of the quinazoline derivative to the 1,5-naphthalenedisulfonic acid is preferably 1:1-1:1.2).

The present invention also provides a salt of "the quinazoline derivative represented by the formula 1" (the acid in the salt is the acid in the raw materials of the reaction, which may also contain the solvent molecules not shown therein <it may be water or an organic solvent>), which is prepared according to any methods as follows:

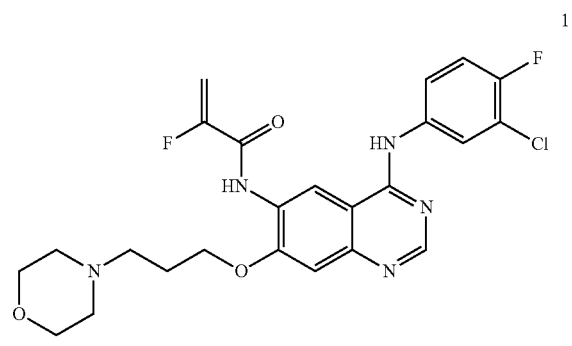 [SMILES: C=C(F)C(=O)Nc1cc2c(Nc3ccc(F)c(Cl)c3)ncnc2cc1OCCCN1CCOCC1]

1

(1) carrying out a salt formation reaction on the quinazoline derivative and the citric acid in tetrahydrofuran to give the salt of the quinazoline derivative;

(2) slurring the monocitrate 2 (e.g. crystal form 1) in ethanol to give the salt of the quinazoline derivative;

(3) slurring the monocitrate 2 (e.g. crystal form 1) in tetrahydrofuran to give the salt of the quinazoline derivative;

(4) recrystalling the monocitrate 2 (e.g. crystal form 1) in 1,4-dioxane to give the salt of the quinazoline derivative;

(5) slurring the monocitrate 2 (e.g. crystal form 1) in n-butanol or water to give the salt of the quinazoline derivative;

(5-1) carrying out evaporative crystallization on the monocitrate 2 (e.g. crystal form 1) in a solvent to give the salt of the quinazoline derivative, wherein the solvent is aqueous methanol solution, aqueous ethanol solution or aqueous isopropanol solution;

(5-2) recrystalling the monocitrate 2 (e.g. crystal form 1) in a solvent to give the salt of the quinazoline derivative, wherein the solvent is methanol and acetone, or 1,4-dioxane and acetone;

(6) slurring the monocitrate 2 (e.g. crystal form 1) in chloroform to give the the salt of the quinazoline derivative;

(7) slurring the monocitrate 2 (e.g. crystal form 1) in chloroform to give the the salt of the quinazoline derivative;

(8) carrying out evaporative crystallization on the monocitrate 2 (e.g. crystal form 1) in a solvent to give the salt of the quinazoline derivative, wherein the solvent is aqueous methanol solution, aqueous n-propanol solution, aqueous tetrahydrofuran solution or aqueous acetonitrile solution;

(9) recrystalling the monocitrate 2 (e.g. crystal form 1) in a solvent to give the salt of the quinazoline derivative, wherein the solvent is methanol and ethanol, nitromethane and ethanol, acetonitrile and ethanol, n-propanol, or isopropanol;

(9-2) slurring the monocitrate 2 (e.g. crystal form 1) in a solvent to give the salt of the quinazoline derivative, wherein the solvent is methanol and ethanol, nitromethane and ethanol, or acetonitrile and ethanol;

(10) recrystalling the monocitrate 2 (e.g. crystal form 1) was subjected to recrystallization in n-butanol to give the salt of the quinazoline derivative;

(10-2) carrying out evaporative crystallization on the monocitrate 2 (e.g. crystal form 1) in water and acetonitrile to give the salt of the quinazoline derivative;

(11) recrystalling the monocitrate 2 (e.g. crystal form 1) in water and dimethyl sulfoxide to give the salt of the quinazoline derivative;

(11-2) carrying out evaporative crystallization on the monocitrate 2 (e.g. crystal form 1) in water and acetone to give the salt of the quinazoline derivative;

(12) carrying out a salt formation reaction on the quinazoline derivative and the ethanedisulfonic acid in tetrahydrofuran to give the salt of the quinazoline derivative;

(13) carrying out a salt formation reaction on the quinazoline derivative and the sulfuric acid in tetrahydrofuran to give the salt of the quinazoline derivative; the molar ratio of the sulfuric acid to the quinazoline derivative is 1-1.3;

(14) carrying out a salt formation reaction on the quinazoline derivative and the sulfuric acid in tetrahydrofuran to give the salt of the quinazoline derivative; the molar ratio of the sulfuric acid to the quinazoline derivative is 2.2-2.3;

(15) carrying out a salt formation reaction on the quinazoline derivative and the benzenesulfonic acid in tetrahydrofuran to give the salt of the quinazoline derivative;

(16) carrying out a salt formation reaction on the quinazoline derivative and the hydrochloride in tetrahydrofuran and water to give the salt of the quinazoline derivative;

(17) carrying out a salt formation reaction on the quinazoline derivative and the D-gluconic acid in dichloromethane to give the salt of the quinazoline derivative;

(18) carrying out a salt formation reaction on the quinazoline derivative and the L-tartaric acid in tetrahydrofuran to give the salt of the quinazoline derivative;

(19) recrystalling the mono-L-tartrate (crystal form 15) in water to give the salt of the quinazoline derivative;

(20) carrying out a salt formation reaction on the quinazoline derivative and the phosphoric acid in tetrahydrofuran to give the salt of the quinazoline derivative;

(21) carrying out a salt formation reaction on the quinazoline derivative and the pamoic acid in tetrahydrofuran to give the salt of the quinazoline derivative;

(22) carrying out a salt formation reaction on the quinazoline derivative and the p-toluenesulfonic acid in chloroform and ethanol to give the salt of the quinazoline derivative;

(23) carrying out a salt formation reaction on the quinazoline derivative and the glycolic acid in dichloromethane to give the salt of the quinazoline derivative;

(24) carrying out a salt formation reaction on the quinazoline derivative and the malonic acid in dichloromethane to give the salt of the quinazoline derivative; the molar ratio of the malonic acid to the quinazoline derivative is 1-1.2;

(25) carrying out a salt formation reaction on the quinazoline derivative and the succinic acid in dichloromethane to give the salt of the quinazoline derivative; the molar ratio of the succinic acid to the quinazoline derivative is 1-1.2;

(26) carrying out a salt formation reaction on the quinazoline derivative and the α-ketoglutaric acid in tetrahydrofuran to give the salt of the quinazoline derivative; the molar ratio of the α-ketoglutaric acid to the quinazoline derivative is 1-1.2;

(27) carrying out a salt formation reaction on the quinazoline derivative and the maleic acid in tetrahydrofuran to give the salt of the quinazoline derivative;

(28) carrying out a salt formation reaction on the quinazoline derivative and the 1,5-naphthalenedisulfonic acid in tetrahydrofuran to give the salt of the quinazoline derivative; the molar ratio of the 1,5-naphthalenedisulfonic acid to the quinazoline derivative is 1.1-1.5;

(29) carrying out a salt formation reaction on the quinazoline derivative and the malonic acid in dichloromethane to give the salt of the quinazoline derivative; the molar ratio of the malonic acid to the quinazoline derivative is 2.0-2.3;

(30) carrying out a salt formation reaction on the quinazoline derivative and the malonic acid in dichloromethane to give the salt of the quinazoline derivative; the molar ratio of the malonic acid to the quinazoline derivative is 3.0-3.4;

(31) carrying out a salt formation reaction on the quinazoline derivative and the 1,5-naphthalenedisulfonic acid in tetrahydrofuran to give the salt of the quinazoline derivative; the molar ratio of the 1,5-naphthalenedisulfonic acid to the quinazoline derivative is 2.2-3.3;

(32) carrying out a salt formation reaction on the quinazoline derivative and the succinic acid in dichloromethane to give the salt of the quinazoline derivative; the molar ratio of the succinic acid to the quinazoline derivative is 2.2-3.3;

(33) carrying out a salt formation reaction on the quinazoline derivative and the α-ketoglutaric acid in tetrahydrofuran to give the salt of the quinazoline derivative; the molar ratio of the α-ketoglutaric acid to the quinazoline derivative is 2.2-3.3;

(34) carrying out a salt formation reaction on the quinazoline derivative and the p-chlorobenzenesulfonic acid in tetrahydrofuran to give the salt of the quinazoline derivative;

wherein, the structure of the quinazoline derivative is represented by formula

1

In the method (1), the volume/mass ratio of the tetrahydrofuran to the quinazoline derivative can be 45-50 mL/g, also can be 45-48 mL/g.

In the method (1), the molar ratio of the citric acid to the quinazoline derivative can be 1-1.5.

In the method (1), the temperature of the salt formation can be 10-30° C.

In the method (1), the duration of the salt formation can be 0.5-24 hours.

In the method (1), the operation of the salt formation reaction can be that commonly used in the art. For example, mixing the solution of citric acid in tetrahydrofuran with the solution of the quinazoline derivative in tetrahydrofuran (for example, adding the solution of citric acid in tetrahydrofuran into the solution of the quinazoline derivative in tetrahydrofuran). The concentration of the solution of the quinazoline derivative in tetrahydrofuran can be 25-50 mg/mL. The concentration of the solution of citric acid in tetrahydrofuran can be 50-100 mg/mL.

In the method (1), the post-treatment of the salt formation reaction can be that commonly used for this kind of reactions in the art, for example, filtration and drying. The temperature for drying can be 40-50° C., also can be 40-45° C. The drying can be vacuum drying.

The method (1) may comprises the following procedure: mixing the solution of citric acid in tetrahydrofuran with the solution of the quinazoline derivative in tetrahydrofuran, reacting, followed by isolating the precipitated solids and drying to give the product (wherein, the concentration of the solution of the quinazoline derivative in tetrahydrofuran is preferably 25-50 mg/mL; the concentration of the solution of citric acid in tetrahydrofuran is preferably 50.8-101.6 mg/mL; the molar ratio of the quinazoline derivative to the citric acid is preferably 1:1-1:1.5; the duration of the reaction is preferably 0.5-24 hours).

In the method (2), the volume/mass ratio of the ethanol to the monocitrate 2 (e.g. crystal form 1) can be 35-45 mL/g, also can be 40-45 mL/g.

In the method (2), the monocitrate 2 (e.g. crystal form 1) can be prepared according to the method (1).

In the method (2), the temperature of the slurring can be 55-65° C., also can be 60° C.

In the method (2), the duration of the slurring can be 8-16 hours.

The method (2) may comprises the following procedure: preparing a suspension by mixing the monocitrate 2 (e.g. crystal form 1) with ethanol and stirring at 55-65° C. to give the product (wherein, the concentration of the monocitrate 2 (e.g. crystal form 1) in the ethanol is preferably 10-50 mg/mL; the duration for stirring is preferably 8-16 hous; the temperature for stirring is preferably 60° C.).

In the method (3), the volume/mass ratio of the tetrahydrofuran to the monocitrate 2 (e.g. crystal form 1) can be 35-45 mL/g, also can be 40-45 mL/g.

In the method (3), the monocitrate 2 (e.g. crystal form 1) can be prepared according to the method (1).

In the method (3), the temperature of the slurring can be 10-60° C.

In the method (3), the duration of the slurring can be 8-16 hours.

The method (3) may comprises the following procedure: preparing a suspension by mixing the monocitrate 2 (e.g. crystal form 1) with tetrahydrofuran and stirring at 10-60° C. to give the product (wherein, the concentration of the monocitrate 2 (e.g. crystal form 1) in the tetrahydrofuran is preferably 10-50 mg/mL; the duration for stirring is preferably 8-16 hous).

In the method (4), the volume/mass ratio of the 1,4-dioxane to the monocitrate 2 (e.g. crystal form 1) can be 80-120 mL/g, also can be 100-120 mL/g.

In the method (4), the monocitrate 2 (e.g. crystal form 1) can be prepared according to the method (1).

In the method (4), the recrystalling can be performed as cooling recrystallization, wherein the temperature for dissolution can be 50-60° C. and the target temperature for cooling can be 10-30° C.

The method (4) may comprises the following procedure: preparing a solution by mixing the monocitrate 2 (e.g. crystal form 1) with the dioxane at the temperature above 60° C. and naturally cooling while stirring to give the product (wherein, the concentration of the monocitrate 2 (e.g. crystal form 1) is preferably 8.3-16.7 mg/mL; the naturally cooling refers to cooling under room temperature).

In the method (5), the volume/mass ratio of the water to the monocitrate 2 (e.g. crystal form 1) can be 60-70 mL/g, also can be 66-70 mL/g.

In the method (5), the volume/mass ratio of the tetrahydrofuran to the monocitrate 2 (e.g. crystal form 1) can be 80-120 mL/g, also can be 100-120 mL/g.

In the method (5), the monocitrate 2 (e.g. crystal form 1) may be prepared according to the method (1).

In the method (5), the temperature of the slurring can be 10-60° C.

In the method (5), the duration of the slurring can be 8-16 hours.

The method (5) may comprises the following procedure: preparing a suspension by mixing the monocitrate 2 (e.g. crystal form 1) with the solvent and stirring at 10-60° C. to give the product; the solvent is water or n-butanol (wherein, the concentration of the monocitrate 2 (e.g. crystal form 1) in the solvent is preferably 5-40 mg/mL, more preferably 10-20 mg/mL; the duration for stirring is preferably 5-16 hous).

In the method (5-1), the volume/mass ratio of the solvent to the monocitrate 2 (e.g. crystal form 1) can be 20-200 mL/g.

In the method (5-1), the volume ratio of the alcohol to the water in the solvent can be 1.

In the method (5-1), the monocitrate 2 (e.g. crystal form 1) may be prepared according to the method (1).

In the method (5-1), the temperature of the evaporation can be 10-60° C.

The method (5-1) may comprises the following procedure: preparing a solution by mixing the monocitrate 2 (e.g. crystal form 1) with the solvent, and the solvent was evaporated to dry at 10-60° C. to give the product; the solvent is aqueous methanol solution, aqueous ethanol solution or aqueous isopropanol solution (wherein, the concentration of the monocitrate 2 (e.g. crystal form 1) is preferably 5-50 mg/mL).

In the method (5-2), the volume/mass ratio of the solvent to the monocitrate 2 (e.g. crystal form 1) can be 160-240 mL/g, also can be 200-240 mL/g.

In the method (5-2), the volume ratio of the methanol to the acetone can be 1.

In the method (5-2), the volume ratio of the 1,4-dioxane to the acetone can be 1.

In the method (5-2), the monocitrate 2 (e.g. crystal form 1) may be prepared according to the method (1).

In the method (5-2), the recrystalling can be performed as cooling crystallization, wherein the temperature for dissolution can be 50-60° C. and the target temperature for cooling can be 10-30° C.

In the method (6), the volume/mass ratio of the chloroform to the monocitrate 2 (e.g. crystal form 1) can be 35-45 mL/g, also can be 40-45 mL/g.

In the method (6), the monocitrate 2 (e.g. crystal form 1) may be prepared according to the method (1).

In the method (6), the temperature of the slurring can be 55-66° C., also can be 60° C.

In the method (6), the duration of the slurring can be 8-16 hours.

The method (6) may comprises the following procedure: preparing a suspension by mixing the monocitrate 2 (e.g. crystal form 1) with the chloroform and stirring at room temperature to give the product (wherein, the concentration of the monocitrate 2 (e.g. crystal form 1) in the chloroform is preferably 10-50 mg/mL; the duration for stirring is preferably 8-16 hous).

In the method (7), the volume/mass ratio of the chloroform to the monocitrate 2 (e.g. crystal form 1) can be 80-120 mL/g, also can be 100-120 mL/g.

In the method (7), the monocitrate 2 (e.g. crystal form 1) may be prepared according to the method (1).

In the method (7), the temperature of the slurring can be 10-30° C.

In the method (7), the duration of the slurring can be 8-16 hours.

The method (7) may comprises the following procedure: preparing a suspension by mixing the monocitrate 2 (e.g. crystal form 1) with the water and stirring at room temperature to give the product (wherein, the concentration of the monocitrate 2 (e.g. crystal form 1) in the water is preferably 5-40 mg/mL, more preferably 10-20 mg/mL; the duration for stirring is preferably 8-16 hous).

In the method (8), the volume/mass ratio of the solvent to the monocitrate 2 (e.g. crystal form 1) can be 100-200 mL/g.

In the method (8), the volume ratio of the non-aqueous solvent to the water in the solvent can be 1.

In the method (8), the monocitrate 2 (e.g. crystal form 1) may be prepared according to the method (1).

In the method (8), the temperature of the evaporation is 10-30° C.

The method (8) may comprises the following procedure: preparing a solution by mixing the monocitrate 2 (e.g. crystal form 1) with the solvent and followed by natural evaporation at room temperature to give the product (wherein, the concentration of the monocitrate 2 (e.g. crystal form 1) is preferably 5-10 mg/mL; the natural evaporation can be the uncovered evaporation or covered evaporation with punching. The volume ratio of the n-propanol to the water in the aqueous n-propanol solution is preferably 1:1; the volume ratio of the tetrahydrofuran to the water in the aqueous tetrahydrofuran solution is preferably 1:1; the volume ratio of the acetonitrile to the water in the aqueous acetonitrile solution is preferably 1:1).

In the method (9), the volume/mass ratio of the solvent to the monocitrate 2 (e.g. crystal form 1) can be 200-600 mL/g, also can be 200-500 mL/g.

In the method (9), the monocitrate 2 (e.g. crystal form 1) may be prepared according to the method (1).

In the method (9), the recrystalling can be performed as cooling crystallization, wherein the temperature for dissolution can be 50-60° C. and the target temperature for cooling can be 10-30° C.

The method (9) may comprises the following procedure: preparing a solution by mixing the monocitrate 2 (e.g. crystal form 1) with the organic solvent containing alcohols at the temperature above 60° C. and naturally cooling while stirring to give the product (wherein, the organic solvent containing alcohols is preferably n-propanol, isopropanol, the solution of methanol in ethanol, the solution of acetonitrile in ethanol or the solution of nitromethane in ethanol; the volume ratio of the methanol to the ethanol in the solution of methanol in ethanol is preferably 1:1; the volume ratio of the acetonitrile to the ethanol in the solution of acetonitrile in ethanol is preferably 1:1; the volume ratio of the nitromethane to the ethanol in the solution of nitromethane in ethanol is preferably 1:1).

In the method (9-2), the volume/mass ratio of the solvent to the monocitrate 2 (e.g. crystal form 1) can be 160-240 mL/g, also can be 200-240 mL/g.

In the method (9-2), the volume ratio of the methanol to the ethanol in the solvent can be 1.

In the method (9-2), the volume ratio of the nitromethane to the ethanol in the solvent can be 1.

In the method (9-2), the volume ratio of the acetonitrile to the ethanol in the solvent can be 1.

In the method (9-2), the monocitrate 2 (e.g. crystal form 1) may be prepared according to the method (1).

In the method (9-2), the temperature of the slurring can be 10-30° C.

In the method (9-2), the duration of the slurring can be 8-16 hours.

The method (9-2) may comprises the following procedure: preparing a suspension by mixing the monocitrate 2 (e.g. crystal form 1) with the organic solvent containing alcohols and stirring at room temperature to give the product (wherein, the organic solvent containing alcohols is preferably the solution of methanol in ethanol, the solution of acetonitrile in ethanol or the solution of nitromethane in ethanol; the volume ratio of the methanol to the ethanol in the solution of methanol in ethanol is preferably 1:1; the volume ratio of the acetonitrile to the ethanol in the solution of acetonitrile in ethanol is preferably 1:1; the volume ratio of the nitromethane to the ethanol in the solution of nitromethane in ethanol is preferably 1:1; the duration for stirring is preferably 8-16 hours).

In the method (10), the volume/mass ratio of the n-butanol to the monocitrate 2 (e.g. crystal form 1) can be 200-300 mL/g, also can be 240-300 mL/g.

In the method (10), the monocitrate 2 (e.g. crystal form 1) may be prepared according to the method (1).

In the method (10), the recrystalling can be performed as cooling crystallization, wherein the temperature for dissolution can be 50-60° C. and the target temperature for cooling can be 10-30° C.

The method (10) may comprises the following procedure: preparing a solution by mixing the monocitrate 2 (e.g. crystal form 1) with the n-butanol at 50-60° C. and naturally cooling to room temperature while stirring to give the product (wherein, the concentration of the monocitrate 2 (e.g. crystal form 1) is preferably 4.1-8.3 mg/mL).

In the method (10-2), the volume/mass ratio of the "water and acetonitrile" to the monocitrate 2 (e.g. crystal form 1) can be 100-200 mL/g.

In the method (10-2), the volume ratio of the acetonitrile to the water in the solvent can be 1.

In the method (10-2), the monocitrate 2 (e.g. crystal form 1) may be prepared according to the method (1).

In the method (10-2), the temperature of the evaporation can be 50-60° C.

The method (10-2) may comprises the following procedure: preparing a solution by mixing the monocitrate 2 (e.g. crystal form 1) with the acetonitrile and water at 55-65° C. and the solvent was evaporated to dry to give the product (wherein, the concentration of the monocitrate 2 (e.g. crystal form 1) is preferably 5-50 mg/mL; the volume ratio of the acetonitrile to the water is preferably 1:1).

In the method (11), the volume/mass ratio of the "water and dimethyl sulfoxide" to the monocitrate 2 (e.g. crystal form 1) can be 200-300 mL/g, also can be 240-300 mL/g.

In the method (11-2), the volume ratio of the water to the dimethyl sulfoxide in the solvent can be 60.

In the method (11), the monocitrate 2 (e.g. crystal form 1) may be prepared according to the method (1).

In the method (11), the recrystalling can be performed as antisolvent recrystallization, for example, dissolving with dimethyl sulfoxide, followed by mixing with water.

The method (11) may comprises the following procedure: preparing a solution by mixing the monocitrate 2 (e.g. crystal form 1) with the dimethyl sulfoxide and then adding into the water, stirring at room temperature to give the product (wherein, the concentration of the monocitrate 2 (e.g. crystal form 1) in the solution is preferably 200-400 mg/mL; the volume ratio of the water to the dimethyl sulfoxide is preferably 5-10; the duration for stirring is preferably 5-30 minutes).

In the method (11-2), the volume/mass ratio of the "water and acetone" to the monocitrate 2 (e.g. crystal form 1) can be 110-200 mL/g.

In the method (11-2), the volume ratio of the acetone to the water in the solvent can be 1.

In the method (11-2), the monocitrate 2 (e.g. crystal form 1) may be prepared according to the method (1).

In the method (11-2), the temperature of the evaporation can be 50-60° C.

In the method (12), the volume/mass ratio of the tetrahydrofuran to the quinazoline derivative can be 20-100 mL/g.

In the method (12), the molar ratio of the ethanedisulfonic acid to the quinazoline derivative can be 1.1-2.2.

In the method (12), the temperature of the salt formation can be 10-30° C.

In the method (12), the duration of the salt formation can be 0.5-24 hours.

In the method (12), the operation of the salt formation reaction can be that commonly used in the art. For example, mixing the solution of ethanedisulfonic acid in tetrahydrofuran with the solution of quinazoline derivative in tetrahydrofuran (for example, adding the solution of ethanedisulfonic acid in tetrahydrofuran into the solution of quinazoline derivative in tetrahydrofuran). The concentration of the solution of quinazoline derivative in tetrahydrofuran can be 12.5-25 mg/mL. The concentration of the solution of ethanedisulfonic acid in tetrahydrofuran can be 20.75-41.5 mg/mL.

The method (12) may comprises the following procedure: mixing the solution of ethanedisulfonic acid in tetrahydrofuran with the solution of quinazoline derivative in tetrahydrofuran, reacting, followed by the isolation of the precipitated solids and drying to give the product (wherein, the methods and conditions for mixing can be those commonly used in the art. The mixing is preferably that: adding the solution of ethanedisulfonic acid in tetrahydrofuran dropwise into the solution of quinazoline derivative in tetrahydrofuran. The concentration of the solution of the quinazoline derivative in tetrahydrofuran is preferably 12.5-25 mg/mL; the concentration of solution of the ethanedisulfonic acid in tetrahydrofuran is preferably 20.75-41.5 mg/mL; the molar ratio of the quinazoline derivative to the ethanedisulfonic acid is preferably 1:1.1-1:2.2; the duration of the reaction is preferably 0.5-24 hours).

In the method (13), the volume/mass ratio of the tetrahydrofuran to the quinazoline derivative can be 50-100 mL/g.

In the method (13), the sulfuric acid is used in form of the concentrated sulfuric acid.

In the method (13), the temperature of the salt formation can be 10-30° C.

In the method (13), the duration of the salt formation can be 0.5-24 hours.

In the method (13), the operation of the salt formation reaction can be that commonly used in the art. For example, mixing the solution of sulfuric acid in tetrahydrofuran with the solution of the quinazoline derivative in tetrahydrofuran (for example, adding the solution of sulfuric acid in tetrahydrofuran into the solution of quinazoline derivative in tetrahydrofuran.). The concentration of the solution of the quinazoline derivative in tetrahydrofuran can be 12.5-25 mg/mL. The concentration of the solution of sulfuric acid in tetrahydrofuran can be 9.75-19.5 mg/mL.

The method (13) may comprises the following procedure: mixing the solution of sulfuric acid in tetrahydrofuran with the solution of the quinazoline derivative in tetrahydrofuran, reacting, followed by the isolation of the precipitated solids and drying to give the product, wherein the molar ratio of the quinazoline derivative to the sulfuric acid is 1:1-1:1.3 (wherein, the methods and conditions for mixing are that commonly used in the art. The mixing is preferably that: adding the solution of sulfuric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of sulfuric acid in tetrahydrofuran is preferably 9.75-19.5 mg/mL; the duration of the reaction is preferably 0.5-24 hours).

In the method (14), the volume/mass ratio of the tetrahydrofuran to the quinazoline derivative can be 50-100 mL/g.

In the method (14), the sulfuric acid is used in form of the concentrated sulfuric acid.

In the method (14), the temperature of the salt formation can be 10-30° C.

In the method (14), the duration of the salt formation can be 0.5-24 hours.

The method (14) may comprises the following procedure: mixing the solution of sulfuric acid in tetrahydrofuran with the solution of the quinazoline derivative in tetrahydrofuran, reacting, followed by the isolation of the precipitated solids and drying to give the product, wherein the molar ratio of the quinazoline derivative to the sulfuric acid is 1:2.2-1:3.3 (wherein, the methods and conditions for mixing are that commonly used in the art. The mixing is preferably that: adding the solution of sulfuric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of sulfuric acid in tetrahydrofuran is preferably 29.25-58.5 mg/mL; the molar ratio of the quinazoline derivative to the sulfuric acid is preferably 1:3.3; the duration of the reaction is preferably 0.5-24 hours).

In the method (15), the volume/mass ratio of the tetrahydrofuran to the quinazoline derivative can be 50-100 mL/g.

In the method (15), the molar ratio of the benzenesulfonic acid to the quinazoline derivative can be 1-1.3.

In the method (15), the temperature of the salt formation can be 10-30° C.

In the method (15), the duration of the salt formation can be 0.5-24 hours.

In the method (15), the operation of the salt formation reaction is that commonly used in the art. For example, mixing the solution of benzenesulfonic acid in tetrahydrofuran with the solution of the quinazoline derivative in tetrahydrofuran (for example, adding the solution of benzenesulfonic acid in tetrahydrofuran into the solution of the quinazoline derivative in tetrahydrofuran). The concentration of the solution of the quinazoline derivative in tetrahydrofuran can be 12.5-25 mg/mL. The concentration of the solution of benzenesulfonic acid in tetrahydrofuran can be 15.7-31.4 mg/mL.

The method (15) may comprises the following procedure: mixing the solution of benzenesulfonic acid in tetrahydrofuran with the solution of the quinazoline derivative in tetrahydrofuran, reacting, followed by the isolation of the precipitated solids and drying to give the product (wherein, the methods and conditions for mixing are that commonly used in the art. The mixing is preferably that: adding the solution of benzenesulfonic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of benzenesulfonic acid in tetrahydrofuran is preferably 15.7-31.4 mg/mL; the molar ratio of the quinazoline derivative to the benzenesulfonic acid is preferably 1:1-1.3; the duration of the reaction is preferably 0.5-24 hours).

In the method (16), the volume/mass ratio of the tetrahydrofuran to the quinazoline derivative can be 50-100 mL/g.

In the method (16), the hydrochloride is used with the water in the form of concentrated hydrochloride acid (saturated aqueous hydrochloride solution).

In the method (16), the molar ratio of the hydrochloride to the quinazoline derivative can be 1.1-3.3.

In the method (16), the temperature of the salt formation can be 10-30° C.

In the method (16), the duration of the salt formation can be 0.5-24 hours.

The method (16) may comprises the following procedure: mixing the solution of the quinazoline derivative in tetrahydrofuran with the solution of hydrochloride acid in tetrahydrofuran, reacting, followed by the isolation of the precipitated solids and drying to give the product (wherein, the methods and conditions for mixing can be those commonly used in the art. The mixing is preferably that: adding the solution of hydrochloride acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of hydrochloride acid in tetrahydrofuran is preferably 11-22 mg/mL; the molar ratio of the quinazoline derivative to the hydrochloride acid is preferably 1:1.1-1:3.3; the duration of the reaction is preferably 0.5-24 hours).

In the method (17), the volume/mass ratio of the tetrahydrofuran to the quinazoline derivative can be 230-400 mL/g.

In the method (17), the molar ratio of the D-gluconic acid to the quinazoline derivative can be 1.1-3.3.

In the method (17), the temperature of the salt formation can be 10-30° C.

In the method (17), the duration of the salt formation can be 0.5-24 hours.

The method (17) may comprises the following procedure: mixing the solution of the quinazoline derivative in dichloromethane with the suspension of D-gluconic acid in dichloromethane, reacting, followed by the isolation of the precipitated solids and drying to give the product (wherein, the methods and conditions for mixing can be those commonly used in the art. The mixing is preferably that: adding the solution of the quinazoline derivative in dichloromethane dropwise into the suspension of D-gluconic acid in dichloromethane. The concentration of the solution of the quinazoline derivative in dichloromethane is preferably 5-10 mg/mL; the content of D-gluconic acid in the suspension of D-gluconic acid in dichloromethane is preferably 3-5 mg/mL; the molar ratio of the quinazoline derivative to the D-gluconic acid is preferably 1:1.1-1:3.3; the duration of the reaction is preferably 16-24 hours).

In the method (18), the volume/mass ratio of the tetrahydrofuran to the quinazoline derivative can be 100-300 mL/g.

In the method (18), the molar ratio of the L-tartaric acid to the quinazoline derivative can be 1-1.3.

In the method (18), the temperature of the salt formation can be 10-30° C.

In the method (18), the duration of the salt formation can be 0.5-24 hours.

The method (18) may comprises the following procedure: mixtin the solution of the quinazoline derivative in tetrahydrofuran with the solution of L-tartaric acid in tetrahydrofuran, reacting, followed by the isolation of the precipitated solids and drying to give the product (wherein, the methods and conditions for mixing can be those commonly used in the art. The mixing is preferably that: adding the solution of L-tartaric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of L-tartaric acid in tetrahydrofuran is preferably 14.9-29.8 mg/mL; the molar ratio of the quinazoline derivative to the L-tartaric acid is preferably 1:1-1:1.3; the duration of the reaction is preferably 0.5-24 hours).

In the method (19), the recrystalling can be performed as stirring recrystallization.

In the method (19), the mono-L-tartrate (crystal form 15) may be prepared according to method (18).

In the method (19), the duration of the recrystallization can be 6-12 hours.

The method (19) may comprises the following procedure: mixing the mono-L-tartrate (crystal form 15) with water to form a clear solution, and stirring until the solid was completely precipitated, followed by the isolation of the precipitated solids and drying to give the product (wherein, the duration for stirring is preferably 6-12 hours).

In the method (20), the volume/mass ratio of the tetrahydrofuran to the quinazoline derivative can be 50-130 mL/g.

In the method (20), the phosphoric acid is used in form of 85% aqueous phosphoric acid solution.

In the method (20), the molar ratio of the phosphoric acid to the quinazoline derivative can be 1.1-3.3.

In the method (20), the temperature of the salt formation can be 10-30° C.

In the method (20), the duration of the salt formation can be 0.5-24 hours.

The method (20) may comprises the following procedure: mixing the solution of the quinazoline derivative in tetrahydrofuran with the solution of phosphoric acid in tetrahydrofuran, reacting, followed by the isolation of the precipitated solids and drying to give the product (wherein, the methods and conditions for mixing are those commonly used in the art. The mixing is preferably that: adding the solution of phosphoric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of phosphoric acid in tetrahydrofuran is preferably 7.75-15.5 mg/mL; the molar ratio of the quinazoline derivative to the phosphoric acid is preferably 1:1.1-1:3.3; the duration of the reaction is preferably 0.5-24 hours).

In the method (21), the volume/mass ratio of the tetrahydrofuran to the quinazoline derivative can be 65-130 mL/g.

In the method (21), the molar ratio of the pamoic acid to the quinazoline derivative can be 1-1.3.

In the method (21), the temperature of the salt formation can be 10-30° C.

In the method (21), the duration of the salt formation can be 16-24 hours.

The method (21) may comprises the following procedure: mixing the solution of the quinazoline derivative in tetrahydrofuran with the suspension of pamoic acid in tetrahydrofuran, reacting, followed by the isolation of the precipitated solids and drying to give the product (wherein, the methods and conditions for mixing are those commonly used in the art. The mixing is preferably that: adding the solution of the quinazoline derivative in tetrahydrofuran dropwise into the suspension of pamoic acid in tetrahydrofuran. The concentration of the solution of the quinazoline derivative in tetrahydrofuran is preferably 12.5-25 mg/mL; the content of the pamoic acid in the suspension of pamoic acid in tetrahydrofuran is preferably 10-20 mg/mL; the molar ratio of the quinazoline derivative to the pamoic acid is preferably 1:1-1:1.3; the duration of the reaction is preferably 16-24 hours).

In the method (22), the volume/mass ratio of the "chloroform and ethanol" to the quinazoline derivative can be 45-90 mL/g.

In the method (22), the volume ratio of the chloroform to the ethanol can be 8-10.

In the method (22), the molar ratio of the p-toluenesulfonic acid to the quinazoline derivative can be 1-1.3.

In the method (22), the temperature of the salt formation can be 10-30° C.

In the method (22), the duration of the salt formation can be 16-24 hours.

The method (22) may comprises the following procedure: mixing the solution of the quinazoline derivative in chloroform with the solution of p-toluenesulfonic acid in ethanol, reacting, followed by the isolation of the precipitated solids and drying to give the product (wherein, the methods and conditions for mixing are those commonly used in the art. The mixing is preferably that: adding the solution of p-toluenesulfonic acid in ethanol dropwise into the solution of the quinazoline derivative in chloroform. The concentration of the solution of the quinazoline derivative in chloroform is preferably 12.5-25 mg/mL; the concentration of the solution of p-toluenesulfonic acid in ethanol is preferably 41-82 mg/mL; the molar ratio of the quinazoline derivative to the p-toluenesulfonic acid is preferably 1:1.1-1:1.3; the duration of the reaction is preferably 16-24 hours).

In the method (23), the volume/mass ratio of the dichloromethane to the quinazoline derivative can be 125-250 mL/g.

In the method (23), the molar ratio of the glycolic acid to the quinazoline derivative can be 2.0-2.2.

In the method (23), the temperature of the salt formation can be 10-30° C.

In the method (23), the duration of the salt formation can be 16-24 hours.

The method (23) may comprises the following procedure: mixing the solution of the quinazoline derivative in dichloromethane with the suspension of glycolic acid in dichloromethane, reacting, followed by the isolation of the precipitated solids and drying to give the product (wherein, the methods and conditions for mixing are those commonly used in the art. The mixing is preferably that: adding the solution of the quinazoline derivative in dichloromethane dropwise into the suspension of glycolic acid in dichloromethane. The concentration of the solution of the quinazoline derivative in dichloromethane is preferably 5-10 mg/mL; the content of glycolic acid in the suspension of glycolic acid in dichloromethane is preferably 5-10 mg/mL; the molar ratio of the quinazoline derivative to the glycolic acid is preferably 1:2.0-1:2.2; the duration of the reaction is preferably 16-24 hours).

In the method (24), the volume/mass ratio of the dichloromethane to the quinazoline derivative can be 125-250 mL/g.

In the method (24), the temperature of the salt formation can be 10-30° C.

In the method (24), the duration of the salt formation can be 16-24 hours.

The method (24) may comprises the following procedure: mixing the solution of the quinazoline derivative in dichloromethane with the suspension of malonic acid in dichloromethane, reacting, followed by the isolation of the precipitated solids and drying to give the product, wherein the molar ratio of the quinazoline derivative to the malonic acid is 1:1-1:1.2 (wherein, the methods and conditions for mixing are those commonly used in the art. The mixing is preferably that: adding the solution of the quinazoline derivative in dichloromethane dropwise into the suspension of malonic acid in dichloromethane. The molar ratio of the quinazoline derivative to the malonic acid is preferably 1:1.1. The concentration of the solution of the quinazoline derivative in dichloromethane is preferably 5-10 mg/mL; the content of malonic acid in the suspension of malonic acid in dichloromethane is preferably 3-5 mg/mL; the duration of the reaction is preferably 16-24 hours).

In the method (25), the volume/mass ratio of the dichloromethane to the quinazoline derivative can be 125-250 mL/g.

In the method (25), the temperature of the salt formation can be 10-30° C.

In the method (25), the duration of the salt formation can be 16-24 hours.

The method (25) may comprises the following procedure: mixing the solution of the quinazoline derivative in dichloromethane with the suspension of succinic acid in dichloromethane, reacting, followed by the isolation of the precipitated solids and drying to give the product, wherein the molar ratio of the quinazoline derivative to the succinic acid is 1:1-1:1.2 (wherein, the methods and conditions for mixing are those commonly used in the art. The mixing is preferably that: adding the solution of the quinazoline derivative in dichloromethane dropwise into the suspension of succinic acid in dichloromethane. The molar ratio of the quinazoline derivative to the succinic acid is preferably 1:1.1. The concentration of the solution of the quinazoline derivative in dichloromethane is preferably 5-10 mg/mL; the content of succinic acid in the suspension of succinic acid in dichloromethane is preferably 3-5 mg/mL; the duration of the reaction is preferably 16-24 hours).

In the method (26), the volume/mass ratio of the tetrahydrofuran to the quinazoline derivative can be 50-100 mL/g.

In the method (26), the temperature of the salt formation can be 10-30° C.

In the method (26), the duration of the salt formation can be 0.5-24 hours.

The method (26) may comprises the following procedure: mixing the solution of the quinazoline derivative in tetrahydrofuran with the solution of α-ketoglutaric acid in tetrahydrofuran, reacting, followed by the isolation of the precipitated solids and drying to give the product, wherein the molar ratio of the quinazoline derivative to the α-ketoglutaric acid is 1:1-1:1.2 (wherein, the methods and conditions for mixing are those commonly used in the art. The mixing is preferably that: adding the solution of α-ketoglutaric acid in tetrahydrofuran dropwise into the solution of the quinazoline derivative in tetrahydrofuran. The molar ratio of the quinazoline derivative to the α-ketoglutaric acid is preferably 1:1.1. The concentration of the solution of the quinazoline derivative in tetrahydrofuran is preferably 12.5-25 mg/mL; the concentration of the solution of α-ketoglutaric acid in tetrahydrofuran is preferably 15.95-31.9 mg/mL; the duration of the reaction is preferably 0.5-24 hours).

In the method (27), the volume/mass ratio of the tetrahydrofuran to the quinazoline derivative can be 60-120 mL/g.

In the method (27), the molar ratio of the quinazoline derivative to the maleic acid can be 1.1-3.3.

In the method (27), the temperature of the salt formation can be 10-30° C.

In the method (27), the duration of the salt formation can be 0.5-24 hours.

The method (27) may comprises the following procedure: mixing the solution of the quinazoline derivative in tetrahydrofuran with the solution of maleic acid in tetrahydrofuran, reacting, followed by the isolation of the precipitated solids and drying to give the product (wherein, the methods and conditions for mixing are those commonly used in the art. The mixing is preferably that: adding the solution of maleic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of maleic acid in tetrahydrofuran is preferably 12.56-25.32 mg/mL; the molar ratio of the quinazoline derivative to the maleic acid is preferably 1:1.1-1:3.3; the duration of the reaction is preferably 0.5-24 hours).

In the method (28), the volume/mass ratio of the tetrahydrofuran to the quinazoline derivative can be 50-100 mL/g.

In the method (28), the temperature of the salt formation can be 10-30° C.

In the method (28), the duration of the salt formation can be 0.5-24 hours.

The method (28) may comprises the following procedure: mixing the solution of the quinazoline derivative in tetrahydrofuran with the solution of 1,5-naphthalenedisulfonic acid in tetrahydrofuran, reacting, followed by the isolation of the precipitated solids and drying to give the product, wherein the molar ratio of the quinazoline derivative to the 1,5-naphthalenedisulfonic acid is 1:1.1-1:1.5 (wherein, the methods and conditions for mixing are those commonly used in the art. The mixing is preferably that: adding the solution of 1,5-naphthalenedisulfonic acid in tetrahydrofuran dropwise into the solution of the quinazoline derivative in tetrahydrofuran. The molar ratio of the quinazoline derivative to the 1,5-naphthalenedisulfonic acid is preferably 1:1.4. The concentration of the solution of the quinazoline derivative in tetrahydrofuran is preferably 12.5-25 mg/mL; the concentration of the solution of 1,5-naphthalenedisulfonic acid in tetrahydrofuran is preferably 39.3-78.6 mg/mL; the duration of the reaction is preferably 0.5-24 hours).

In the method (29), the volume/mass ratio of the dichloromethane to the quinazoline derivative can be 150-300 mL/g.

In the method (29), the temperature of the salt formation can be 10-30° C.

In the method (29), the duration of the salt formation can be 16-24 hours.

The method (29) may comprises the following procedure: the malonic acid suspension in dichloromethane was mixed with the quinazoline derivative solution in dichloromethane, followed by the isolation of the precipitated solids and drying to give the product, wherein the molar ratio of the quinazoline derivative to the malonic acid is 1:2.0-1:2.3 (wherein, the methods and conditions for mixing are those commonly used in the art. The mixing is preferably that: adding the solution of the quinazoline derivative in dichloromethane dropwise into the suspension of malonic acid in dichloromethane. The molar ratio of the quinazoline derivative to the malonic acid is preferably 1:2.2. Wherein, the concentration of the solution of the quinazoline derivative in dichloromethane is preferably 5-10 mg/mL; the content of malonic acid in the suspension of malonic acid in dichloromethane is preferably 3-5 mg/mL; the duration of the reaction is preferably 16-24 hours).

In the method (30), the volume/mass ratio of the dichloromethane to the quinazoline derivative can be 150-300 mL/g.

In the method (30), the temperature of the salt formation can be 10-30° C.

In the method (30), the duration of the salt formation can be 16-24 hours.

The method (30) may comprises the following procedure: mixing the solution of the quinazoline derivative in dichloromethane with the suspension of malonic acid in dichloromethane, reacting, followed by the isolation of the precipitated solids and drying to give the product, wherein the molar ratio of the quinazoline derivative to the malonic acid is 1:3.0-1:3.4 (wherein, the methods and conditions for mixing can be those commonly used in the art. The mixing is preferably that: adding the solution of the quinazoline derivative in dichloromethane dropwise into the suspension of malonic acid in dichloromethane. The molar ratio of the quinazoline derivative to the malonic acid is preferably 1:3.3. The concentration of the solution of the quinazoline derivative in dichloromethane is preferably 5-10 mg/mL; the content of the malonic acid in the suspension of malonic acid in dichloromethane is preferably 5-10 mg/mL; the duration of the reaction is preferably 16-24 hours).

In the method (31), the volume/mass ratio of the tetrahydrofuran to the quinazoline derivative can be 60-120 mL/g.

In the method (31), the temperature of the salt formation can be 10-30° C.

In the method (31), the duration of the salt formation can be 0.5-24 hours.

The method (31) may comprises the following procedure: mixing the solution of the quinazoline derivative in tetrahydrofuran with the solution of 1,5-naphthalenedisulfonic acid in tetrahydrofuran, reacting, followed by the isolation of the precipitated solids and drying to give the product, wherein the molar ratio of the quinazoline derivative to the 1,5-naphthalenedisulfonic acid is 1:2.2-1:3.3 (wherein, the methods and conditions for mixing are those commonly used in the art. The mixing is preferably that: adding the solution of 1,5-naphthalenedisulfonic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of 1,5-naphthalenedisulfonic acid in tetrahydrofuran is preferably 39.3-78.6 mg/mL; the duration of the reaction is preferably 0.5-24 hours).

In the method (32), the volume/mass ratio of the dichloromethane to the quinazoline derivative can be 150-300 mL/g.

In the method (32), the temperature of the salt formation can be 10-30° C.

In the method (32), the duration of the salt formation can be 16-24 hours.

The method (32) may comprises the following procedure: mixing the solution of the quinazoline derivative in dichloromethane with the suspension of succinic acid in dichloromethane, reacting, followed by the isolation of the precipitated solids and drying to give the product, wherein the molar ratio of the quinazoline derivative to the succinic acid is 1:2.2-1:3.3 (wherein, the methods and conditions for mixing are those commonly used in the art. The mixing is preferably that: adding the solution of the quinazoline derivative in dichloromethane dropwise into the suspension of succinic acid in dichloromethane. The concentration of the solution of the quinazoline derivative in dichloromethane is preferably 5-10 mg/mL; the content of the succinic acid in the suspension of succinic acid in dichloromethane is preferably 5-10 mg/mL; the duration of the reaction is preferably 16-24 hours).

In the method (33), the volume/mass ratio of the tetrahydrofuran to the quinazoline derivative is 60-120 mL/g.

In the method (33), the temperature of the salt formation can be 10-30° C.

In the method (33), the duration of the salt formation can be 0.5-24 hours.

The method (33) may comprises the following procedure: mixing the solution of the quinazoline derivative in tetrahydrofuran with the solution of α-ketoglutaric acid in tetrahydrofuran reacting, followed by the isolation of the precipitated solids and drying to give the product, wherein the molar ratio of the quinazoline derivative to the α-ketoglutaric acid is 1:2.2-1:3.3 (wherein, the methods and conditions for mixing are those commonly used in the art. The mixing is preferably that: adding the solution of α-ketoglutaric acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of α-ketoglutaric acid in tetrahydrofuran is preferably 15.95-31.9 mg/mL; the duration of the reaction is preferably 0.5-24 hours).

In the method (34), the volume/mass ratio of the tetrahydrofuran to the quinazoline derivative can be 50-100 mL/g.

In the method (34), the molar ratio of the p-chlorobenzenesulfonic acid to the quinazoline derivative can be 1-1.2.

In the method (34), the temperature of the salt formation can be 10-30° C.

In the method (34), the duration of the salt formation can be 0.5-24 hours.

The method (34) may comprises the following procedure: mixing the solution of the quinazoline derivative in tetrahydrofuran with the solution of p-chlorobenzenesulfonic acid in tetrahydrofuran, reacting, followed by the isolation of the precipitated solids and drying to give the product (wherein, the methods and conditions for mixing are those commonly used in the art. The mixing is preferably that: adding the solution of p-chlorobenzenesulfonic acid in tetrahydrofuran dropwise into the solution of the quinazoline derivative in tetrahydrofuran. The concentration of the solution of the quinazoline derivative in tetrahydrofuran is preferably 12.5-25 mg/mL; the concentration of the solution of p-chlorobenzenesulfonic acid in tetrahydrofuran is preferably 21-42 mg/mL; the duration of the reaction is preferably 0.5-24 hours. The molar ratio of the quinazoline derivative to the 1,5-naphthalenedisulfonic acid is preferably 1:1-1:1.2).

The present invention also provides a use of the salt of the quinazoline derivative as mentioned above in manufacturing an EGFR tyrosine kinase inhibitor, an HER2 tyrosine kinase inhibitor, an HER4 tyrosine kinase inhibitor, or a medicament for preventing or treating tumor diseases.

The present invention also provides a pharmaceutical composition, comprising a therapeutically and/or prophylactically effective dose of the salt of the quinazoline derivative, and at least one kind of pharmaceutically acceptable excipient.

The pharmaceutical composition may further comprise one or more of the quinazoline derivative, the solvate of the quinazoline derivative (including the hydrate and the organic solvate), the pharmaceutically acceptable salt of the other of the quinazoline derivative, and, the solvate of the pharmaceutically acceptable salt of the other of the quinazoline derivative (including the hydrate and the organic solvate).

The quinazoline derivative can exist in any crystal form.

The solvate of the quinazoline derivative can exist in any crystal form.

The pharmaceutically acceptable salt of the other of the quinazoline derivative can exist in any crystal form.

The solvate of the pharmaceutically acceptable salt of the other the quinazoline derivative can exist in any crystal form.

Wherein, the excipient can be that conventionally used in the art. The excipient can generally be selected from the group consisting of sugars, cellulose and derivatives thereof, starch or modified starch, solid inorganic compounds such as calcium phosphate, dicalcium phosphate, hydroxyapatite, calcium sulfate, calcium carbonate, semisolids such as lipid or paraffin, binders such as microcrystalline cellulose, ethyl cellulose, hydroxymethyl cellulose, hydroxypropyl methyl cellulose, hydroxyethyl cellulose, glidants such as colloidal silica, light anhydrous silicic acid, crystalline cellulose, talc or magnesium stearate, disintegrating agents such as sodium starch glycolate, crospovidone, croscarmellose, sodium carboxymethyl cellulose, dry corn starch, lubricants such as stearic acid, magnesium stearate, sodium stearyl fumarate, polyethylene glycol.

The pharmaceutical composition can be in solid or liquid forms, for example, the solid oral dosage forms, including tablets, granules, powders, pills, and capsules; the liquid oral dosage forms, including solutions, syrups, suspensions, dispersions, and emulsions; injectable preparations, including solutions, dispersions, and lyophilizates. The formulation can be adapted for the rapid release, the delayed release or the modified release of the active ingredients, including the conventional, dispersible, chewable, orally dissolved or rapidly melted formulation. The routes of administration include oral administration, intravenous subcutaneous injection, injection into tissue, transdermal administration, rectal administration, intranasal administration, and the like.

The pharmaceutical composition can be prepared via the methods well known to those skilled in the art. When preparing the pharmaceutical composition, the salt of the quinazoline derivative of the present invention or the crystal form thereof is mixed with one or more pharmaceutically acceptable excipients, optionally with other crystal forms, other amorphous or salt forms of the pharmaceutically acceptable quinazoline derivative, optionally with one or more other active ingredients. The solid preparation can be prepared via a process such as direct mixing, granulation, or the like.

In the present invention, the term "crystal form" does not only refer to "crystal type" or "crystal structure"; in the technical solution, "crystal form" also refers to "a substance having a specific crystal structure" or "a crystal in a specific crystal type". For example, in the technical solution, "the crystal form of the monobenzenesulfonate of the quinazoline derivative" refers to "the monophenylsulfonate of the quinazoline derivative having a specific crystal structure" or "the crystal of monophenylsulfonate of quinazoline derivative in a specific crystal type".

In the present invention, all of the X-ray powder diffraction patterns are determined by the Kα radiation from Cu target.

In the present invention, the "crystal form" is characterized by the X-ray diffraction patterns. Those skilled in the art should appreciate that the experimental error therein depends on the conditions of the instrument, the preparation of the samples, and the purity of the samples. In particular, it is well known to those skilled in the art that the X-ray diffraction pattern generally varies with the conditions of the instrument. In addition, the experimental error of the peak angle is usually 5% or less, which should also be taken into account, and an error of ±0.2° is usually allowed. In addition, the overall offset of the peak angle is caused by the experimental factors such as the sample height, and a certain offset is usually allowed. Therefore, those skilled in the art should appreciate that any crystal form having the characteristic which is the same as or similar to the patterns of the present invention is within the scope of the present invention.

In the present invention, the room temperature is in a common sense of the art, which is generally 10-30° C.

In the present invention, according to the common knowledge in the art, the saturation concentration can be measured by the tests at the operating temperature of the preparation method.

In the present invention, according to the common knowledge in the art, stirring can be performed during the mixing and the reaction. The stirring can be performed via a conventional method in the art, for example, including magnetic stirring and mechanical stirring. The rate of stirring is generally 50-1800 RPM, preferably 300-900 RPM.

In the present invention, according to the common knowledge in the art, the methods and conditions for drying can be those commonly used in the art, such as blast drying, drying under reduced pressure, and the like. The temperature for drying is preferably 20-60° C., more preferably 30-50° C.; the duration for drying is preferably 1-24 hours, more preferably 5-18 hours, most preferably 5-10 hours. When the drying is performed under reduced pressure, the pressure is preferably less than 0.09 MPa. The drying can be performed in a fume hood, a forced air oven or a vacuum oven.

In the present invention, the methods and conditions for isolation can be those commonly used in the art. The method for isolation can be filtration, centrifugation or the like. The filtration is generally performed under reduced pressure using a filter paper. The centrifugation is generally performed at a high rotational speed, and the rate of centrifugation can be 6000 RPM.

In the present invention, according to the common knowledge in the art, the amount of water absorption obtained from the dynamic vapor sorption (DVS) pattern is expressed in percentage by weight.

Without violating the common sense in the art, the above preferred conditions can be arbitrarily combined, then preferred embodiments of the present invention are obtained.

The reagents and raw materials used in the present invention are commercially available.

The positive and progressive effect of the present invention is that: compared with a known quinazoline derivative, the water solubility of the quinazoline derivative of the present invention has been improved, wherein the monocitrate, the monobenzenesulfonate and the monoethanedisulphonate thereof further have advantages in good crystallinity and are not easy to absorb moisture.

BRIEF DESCRIPTION OF THE DRAWINGS

FIG. 3 is DSC pattern of the crystal form 1 of the monocitrate of the quinazoline derivative of the present invention.

FIG. 4 is DVS pattern of the crystal form 1 of the monocitrate of the quinazoline derivative of the present invention.

FIG. 23 is DSC pattern of the crystal form 10 of the monocitrate trihydrate of the quinazoline derivative of the present invention.

FIG. 24 is DVS pattern of the crystal form 10 of the monocitrate triihydrate of the quinazoline derivative of the present invention.

FIG. 27 is DSC pattern of the crystal form 11 of the monocitrate dihydrate of the quinazoline derivative of the present invention.

FIG. 28 is DVS pattern of the crystal form 11 of the monocitrate dihydrate of the quinazoline derivative of the present invention.

FIG. 43 is TGA pattern of the monosulfate of the quinazoline derivative of the present invention.

FIG. 44 is DSC pattern of the monosulfate of the quinazoline derivative of the present invention.

FIG. 47 is TGA pattern of the disulfate of the quinazoline derivative of the present invention.

FIG. 48 is DSC pattern of the disulfate of the quinazoline derivative of the present invention.

FIG. 55 is TGA pattern of the monohydrochloride monohydrate of the quinazoline derivative of the present invention.

FIG. 56 is DSC pattern of the monohydrochloride monohydrate of the quinazoline derivative of the present invention.

FIG. 59 is TGA pattern of the mono-D-gluconate of the quinazoline derivative of the present invention.

FIG. 60 is DSC pattern of the mono-D-gluconate of the quinazoline derivative of the present invention.

FIG. 65 is TGA pattern of the mono-L-tartrate tetrahydrate of the quinazoline derivative of the present invention.

FIG. 66 is DSC pattern of the mono-L-tartrate tetrahydrate of the quinazoline derivative of the present invention.

DETAILED DESCRIPTION OF THE PREFERRED EMBODIMENT

Figure 1:
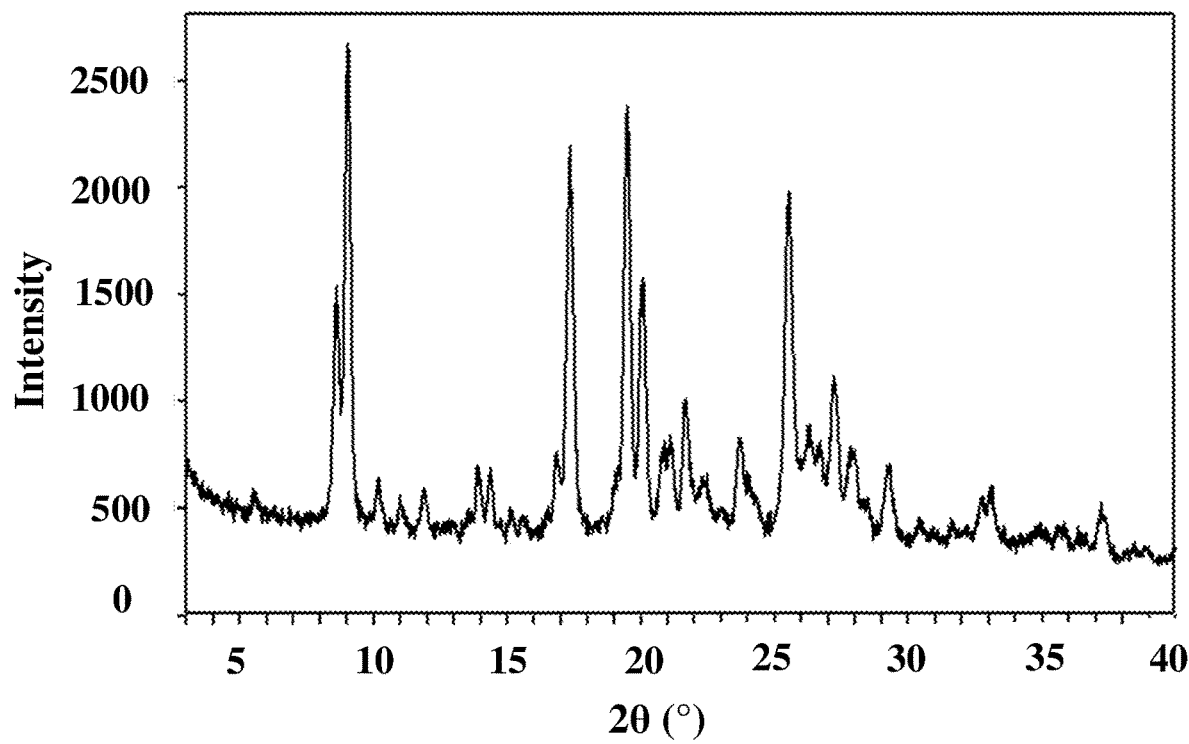
FIG. 1 is XRPD pattern of the crystal form 1 of the monocitrate of the quinazoline derivative of the present invention.

The following embodiments further illustrate the present invention, but the present invention is not limited thereto. The experimental methods that do not specify the specific conditions in the following embodiments are selected according to conventional methods and conditions, or according to the description of the product.

Measurement instruments and methods:

The instrument used for X-ray powder diffraction (XRPD) measurement was Bruker D8 Advance Diffractometer equipped with a θ-2θ goniometer, a Mo monochromator, and a Lynxeye detector. The software for acquisition was Diffrac Plus XRD Commander and the software for analysis was MDI Jade 5.0. The instrument was calibrated with the standard sample (generally, corundum) supplied by the instrument before use. The measurement conditions were: 2θ scanning angle with a range of 3–40°; step size: 0.02°; speed: 0.2 seconds/step. Measurement process: The Kα X-ray generated by a copper target with a wavelength of 1.54 nm was used. Under an operating conditions of 40 kV and 40 mA, the samples were measured at room temperature, and the samples to be measured were placed on a non-reflecting plate. Unless otherwise specified, the samples were unground before measurement.

The differential thermal analysis (DSC) data was collected from TA Instruments Q200 MDSC. The software for instrument control was Thermal Advantage and the software for analysis was Universal Analysis. Generally, 1-10 mg of the sample was placed in an uncovered (unless otherwise specified) aluminum crucible, and the temperature was raised from room temperature to 250° C. with a heating rate of 10° C./min under the protection of 40 ml/min dry $N_2$ gas. At the same time, the heat change of the sample during the heating process was recorded by the TA software.

Thermogravimetric analysis (TGA) data was collected from TA Instruments Q500 TGA. The software for instrument control was Thermal Advantage and software for analysis was Universal Analysis. Generally, 5-15 mg of the sample was placed in a platinum crucible, and the temperature was raised from room temperature to 300° C. with a heating rate of 10° C./min under the protection of 40 ml/min dry $N_2$ gas. At the same time, the weight change of the sample during the heating process was recorded by the TA software.

The isothermal absorption analysis (DVS) data was collected from TA Instruments Q5000 TGA. The software for instrument control was Thermal Advantage and software for analysis was Universal Analysis. 1-10 mg of the sample was generally placed in a platinum crucible, and the weight change of the sample during the relative humidity changing from 20% to 80% was recorded by the TA software. Depending on the specifics of the sample, different steps of sample adsorption and desorption were also involved.

Bruker Ascend TM500 was used for 41 NMR measurement, generally using full-frequency excitation, single pulse, excitation angle of 30°, 16-times scanning, digital orthogonal detection, temperature control at 298K, DMSO as deuterated reagent.

The HPLC measurement conditions are as follows:
Mobile phase A, formic acid:water=0.1:99.9;
Mobile phase B, formic acid:acetonitrile=0.1:99.9;
Elution gradient:
0 min 10% B;
0.5 min 10% B;
4 min 80% B;
4.5 min 80% B;
6 min 10% B;
6.5 min 10% B;
Flow rate: 0.3 mL/min; column: Eclipse Plus-C18 2.1 mm*50.0 mm*1.8 μm; column temperature: 40° C.; wavelength: 254 nm.

Unless otherwise specified, the embodiments were all operated at room temperature.

Unless otherwise specified, the various reagents used in the embodiments are commercially available.

In the following examples, the quinazoline derivative (i.e., the compound represented by formula 1) used was given according to the method described in CN102898386. The mixing and the reaction were accompanied by stirring, and the stirring rate was generally 50-1800 RPM. The duration of "overnight" was generally 12-24 hours.

Embodiment 1: Synthesis of the Crystal Form 1 of the Monocitrate of the Quinazoline Derivative 2 g of the compound represented by formula 1 was dissolved in 80 mL of tetrahydrofuran and 0.762 g of citric acid was dissolved in 15 mL of tetrahydrofuran, and the acid solution was added dropwise to the alkali solution. The mixture was stirred at room temperature for 0.5 hour to precipitate a solid, stirred overnight, filtered, and dried in a vacuum oven at 45° C. 2.466 g of the crystal form 1 of the monocitrate of the quinazoline derivative was given in a yield of 89.3%.

The XRPD pattern is shown in FIG. 1.

Figure 2:
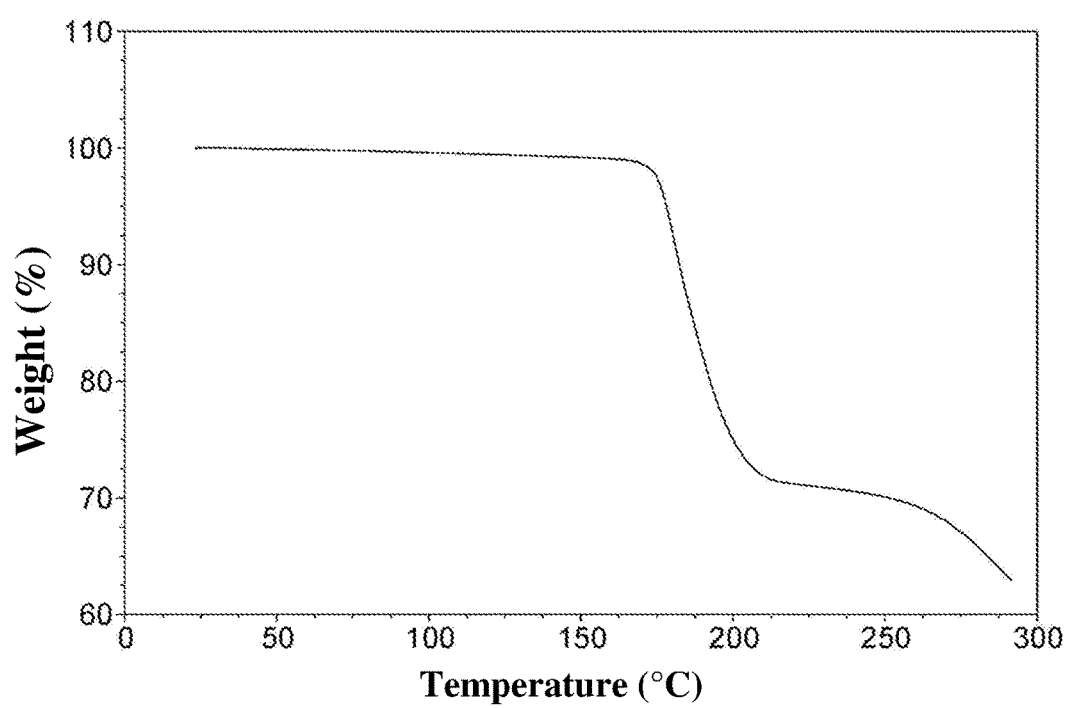
FIG. 2 is TGA pattern of the crystal form 1 of the monocitrate of the quinazoline derivative of the present invention.

As the TGA pattern shown in FIG. 2, the decomposition temperature is 175° C.

As the DSC pattern shown in FIG. 3, the melting point is 165-169° C.

As the DVS pattern shown in FIG. 4, the weight change in the RH range of 20-80% is 0.21%.

4 g of the compound represented by formula 1 was dissolved in 80 mL of tetrahydrofuran, 2.288 g of citric acid was dissolved in 22.5 mL of tetrahydrofuran, and the other conditions remained the same, and the given product was still the crystal form 1.

Embodiment 2: Synthesis of the Crystal Form 5 of the Monocitrate Dihydrate of the Quinazoline Derivative 30 mg of the crystal form 1 prepared in embodiment 1 was taken and 2 mL of water was added thereto, followed by crystallization at 60° C. for 16 hours, centrifugation, and vacuum drying at room temperature. 26 mg of the crystal form 5 of the monocitrate dihydrate of the quinazoline derivative was given in a molar yield of 82.4%.

Figure 5:
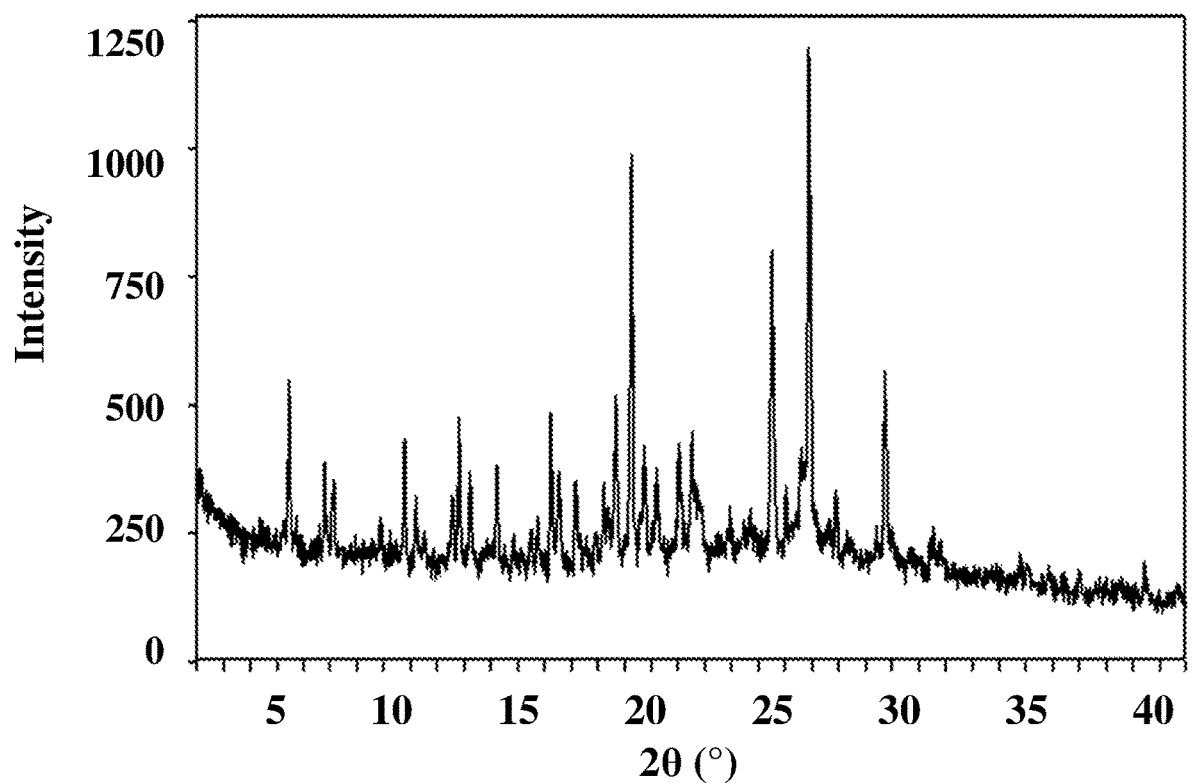
FIG. 5 is XRPD pattern of the crystal form 5 of the monocitrate dihydrate of the quinazoline derivative of the present invention.

The XRPD pattern was shown in FIG. 5.

Figure 6:
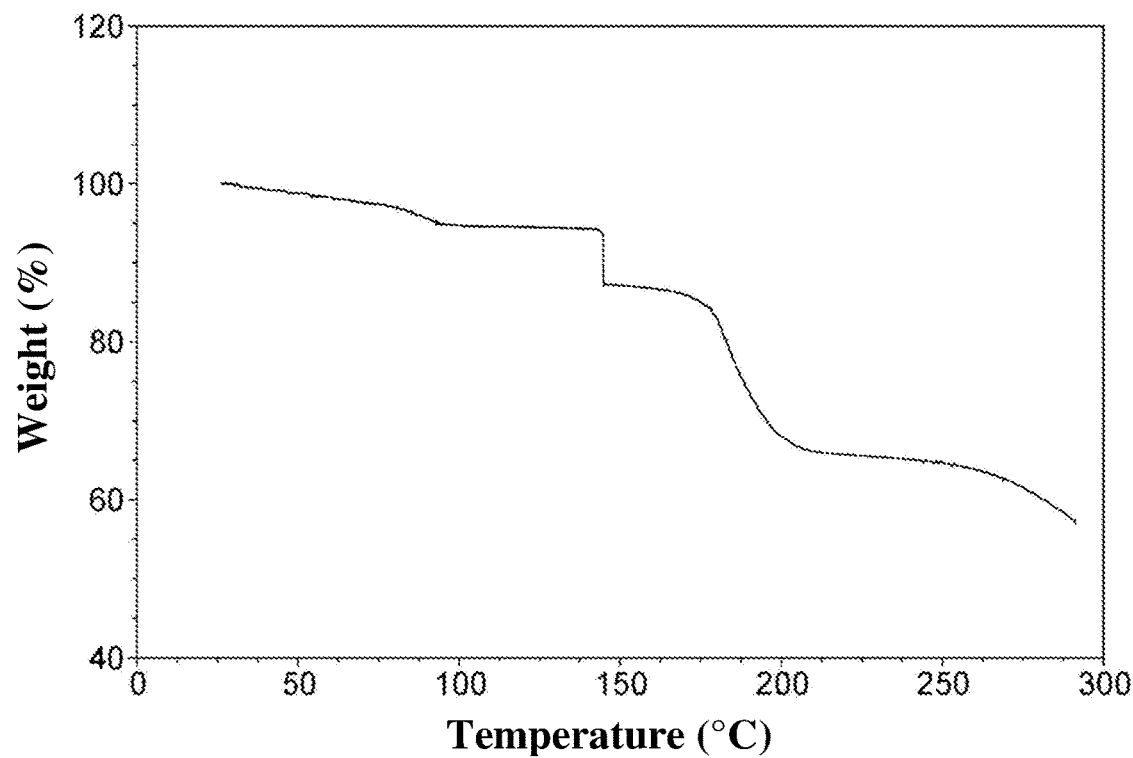
FIG. 6 is TGA pattern of the crystal form 5 of the monocitrate dihydrate of the quinazoline derivative of the present invention.

As the TGA pattern shown in FIG. 6, the decomposition temperature is 145° C. and the weight loss before decomposition is 5.3%, containing 2 moles of water.

Figure 7:
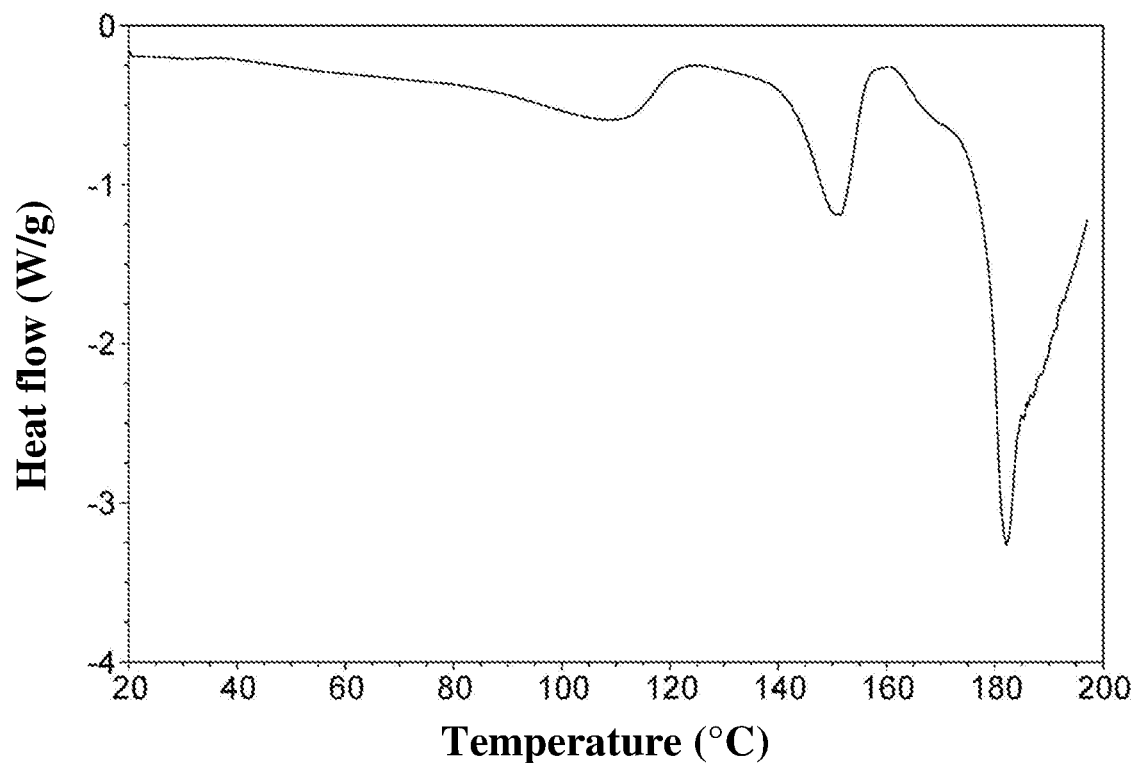
FIG. 7 is DSC pattern of the crystal form 5 of the monocitrate dihydrate of the quinazoline derivative of the present invention.

As the DSC pattern shown in FIG. 7, there is an endothermic peak of water elimination before 123° C.

Figure 8:
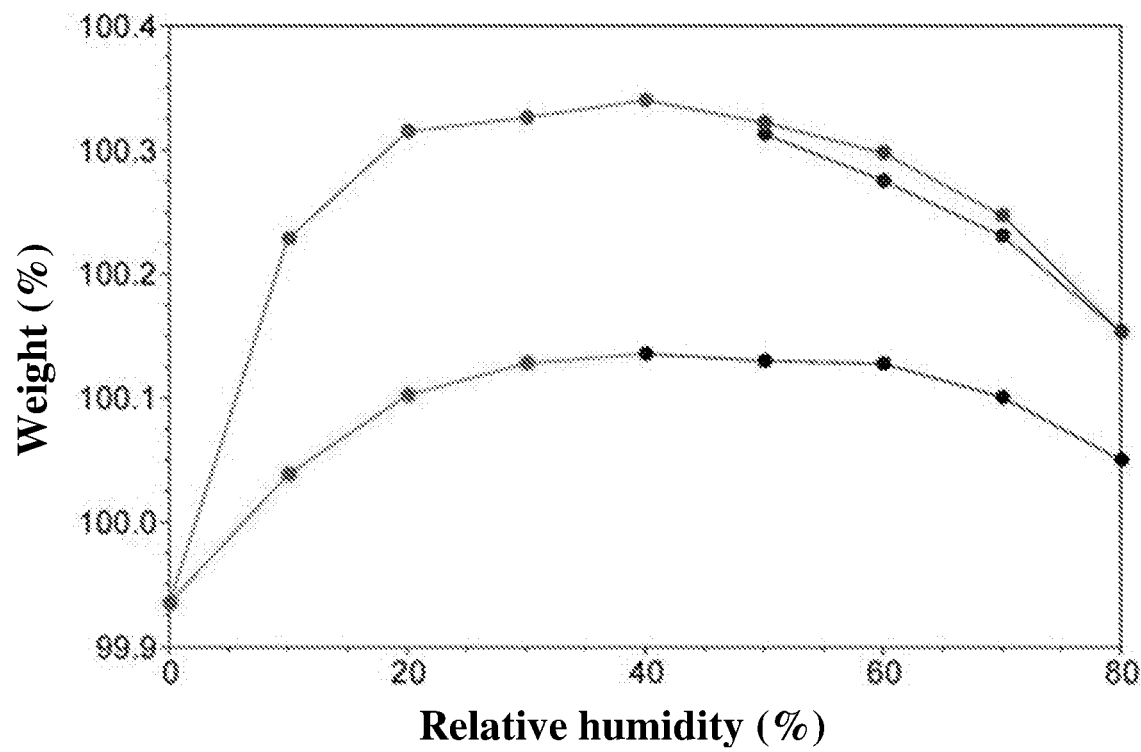
FIG. 8 is DVS pattern of the crystal form 5 of the monocitrate dihydrate of the quinazoline derivative of the present invention.

As the DVS pattern shown in FIG. 8, the weight change in the RH range of 0-80% is 0.4%.

Embodiment 3: Synthesis of the Crystal Form 5 of the Monocitrate Dihydrate of the Quinazoline Derivative 30 mg of the crystal form 1 prepared in embodiment 1 was taken and 3 mL of n-butanol was added thereto, followed by crystallization at room temperature for 16 hours, centrifugation, and vacuum drying at room temperature. 24 mg of the crystal form 5 of the dihydrate was given in a molar yield of 76.1%.

Embodiment 4: Synthesis of the Crystal Form 5 of the Monocitrate Dihydrate of the Quinazoline Derivative 10 mg of the crystal form 1 prepared in embodiment 1 was taken and 1 mL of water and 1 mL of methanol was added thereto, followed by uncovered evaporation of the solvent to dry at room temperature. 7 mg of the crystal form 5 of the dihydrate was given in a molar yield of 66.7%.

100 mg of the crystal form 1 prepared in embodiment 1 was taken and 1 mL of water and 1 mL of methanol was added thereto, wherein other conditions remained the same. The given product was still the crystal form 5 of the dihydrate.

Embodiment 5: Synthesis of the Crystal Form 5 of the Monocitrate Dihydrate of the Quinazoline Derivative The "methanol" in embodiment 4 was replaced with the "ethanol", and the other operations remained the same as that in embodiment 4 to give the crystal form 5 of the dihydrate.

Embodiment 6: Synthesis of the Crystal Form 5 of the Monocitrate Dihydrate of the Quinazoline Derivative The "methanol" in embodiment 4 was replaced with the "isopropanol", and the other operations remained the same as that in embodiment 4 to give the crystal form 5 of the dihydrate.

Embodiment 7: Synthesis of the Crystal Form 5 of the Monocitrate Dihydrate of the Quinazoline Derivative 10 mg of the crystal form 1 prepared in embodiment 1 was taken and 1 mL of water and 1 mL of methanol was added thereto, followed by uncovered evaporation of the solvent to dry at 60° C. 8 mg of the crystal form 5 of the dihydrate was given in a molar yield of 76.1%.

Embodiment 8: Synthesis of the Crystal Form 5 of the Monocitrate Dihydrate of the Quinazoline Derivative The "methanol" in embodiment 7 was replaced with the "ethanol", and the other operations remained the same as that in embodiment 7 to give the crystal form 5 of the dihydrate.

Embodiment 9: Synthesis of the Crystal Form 5 of the Monocitrate Dihydrate of the Quinazoline Derivative The "methanol" in embodiment 7 was replaced with the "isopropanol", and the other operations remained the same as that in embodiment 7 to give the crystal form 5 of the dihydrate.

Embodiment 10: Synthesis of the Crystal Form 5 of the Monocitrate Dihydrate of the Quinazoline Derivative 10 mg of the crystal form 1 prepared in embodiment 1 was taken and 1 mL of methanol and 1 mL of acetone was added thereto, followed by stirring in water bath at 60° C. for 5 minutes to keep the solution clear and naturally cooling to room temperature. The precipitated solids were centrifuged and dried in vacuum at room temperature. 6 mg of the crystal form 5 of the dihydrate was given in a molar yield of 57.0%.

Embodiment 11: Synthesis of the Crystal Form 5 of the Monocitrate Dihydrate of the Quinazoline Derivative The "methanol" in embodiment 10 was replaced with the "dioxane", and the other operations remained the same as that in embodiment 10 to give the crystal form 5 of the dihydrate.

The XRPD patterns and the DSC patterns of the samples prepared in embodiments 3-11 (not shown) are similar to those of embodiment 2, indicating that the samples prepared in these embodiments are the same as that in embodiment 2.

Embodiment 12: Synthesis of the Crystal Form 13 of the Monocitrate of the Quinazoline Derivative 10 mg of the crystal form 1 prepared in embodiment 1 was taken and 2.4 mL of n-butanol was added thereto, followed by stirring in water bath at 60° C. for 5 minutes to keep the solution clear and naturally cooling to room temperature. The precipitated solids were centrifuged and dried in vacuum at room temperature. 8 mg of the crystal form 13 was given in a yield of 80%.

Figure 9:
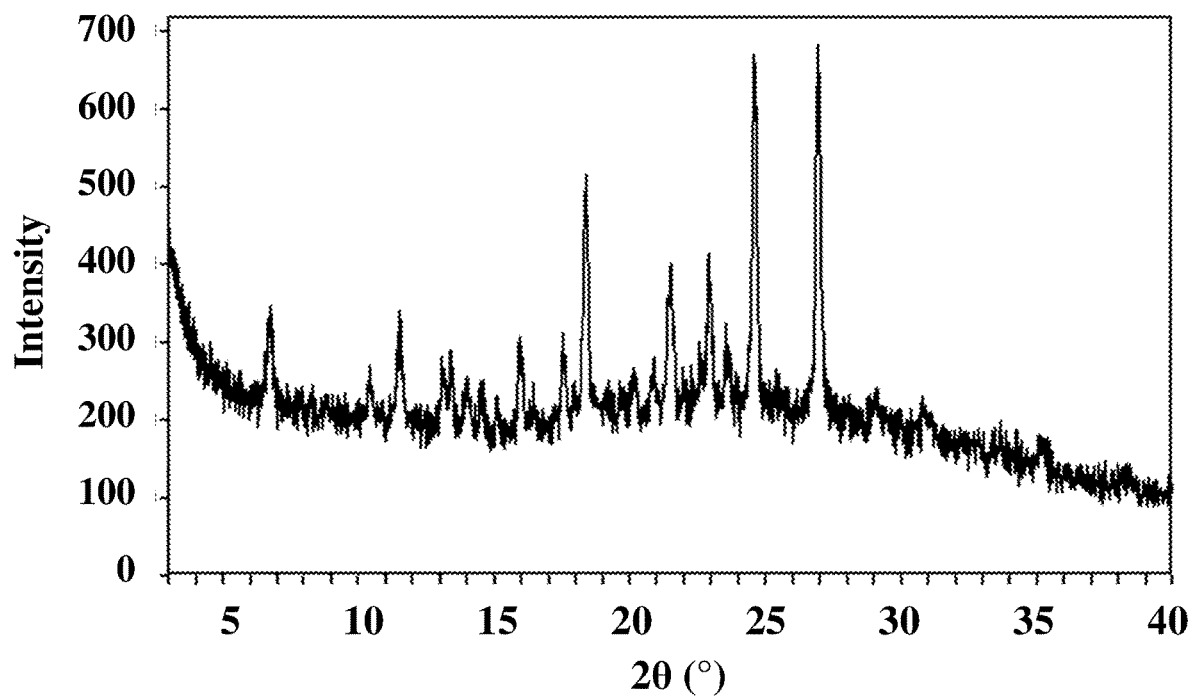
FIG. 9 is XRPD pattern of the crystal form 13 of the monocitrate of the quinazoline derivative of the present invention.

The XRPD pattern is shown in FIG. 9.

Figure 10:
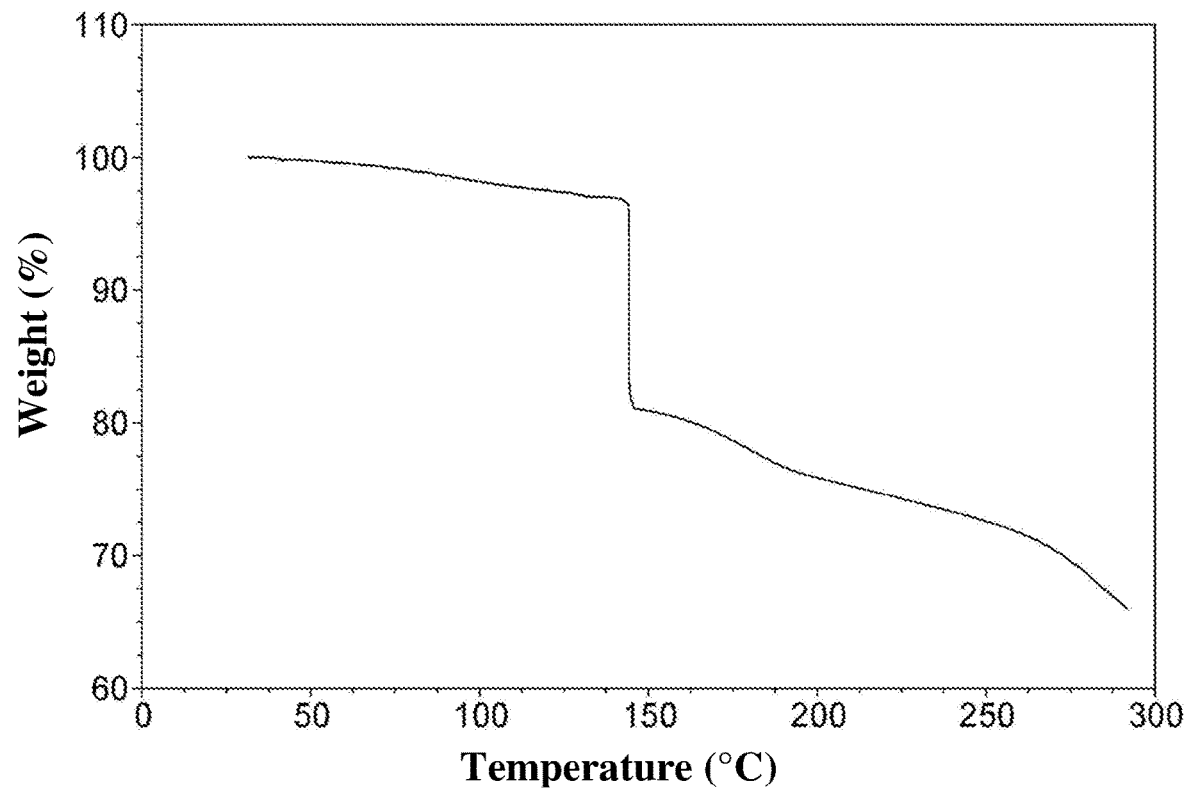
FIG. 10 is TGA pattern of the crystal form 13 of the monocitrate of the quinazoline derivative of the present invention.

As the TGA pattern shown in FIG. 10, the decomposition temperature is 144° C.

Figure 11:
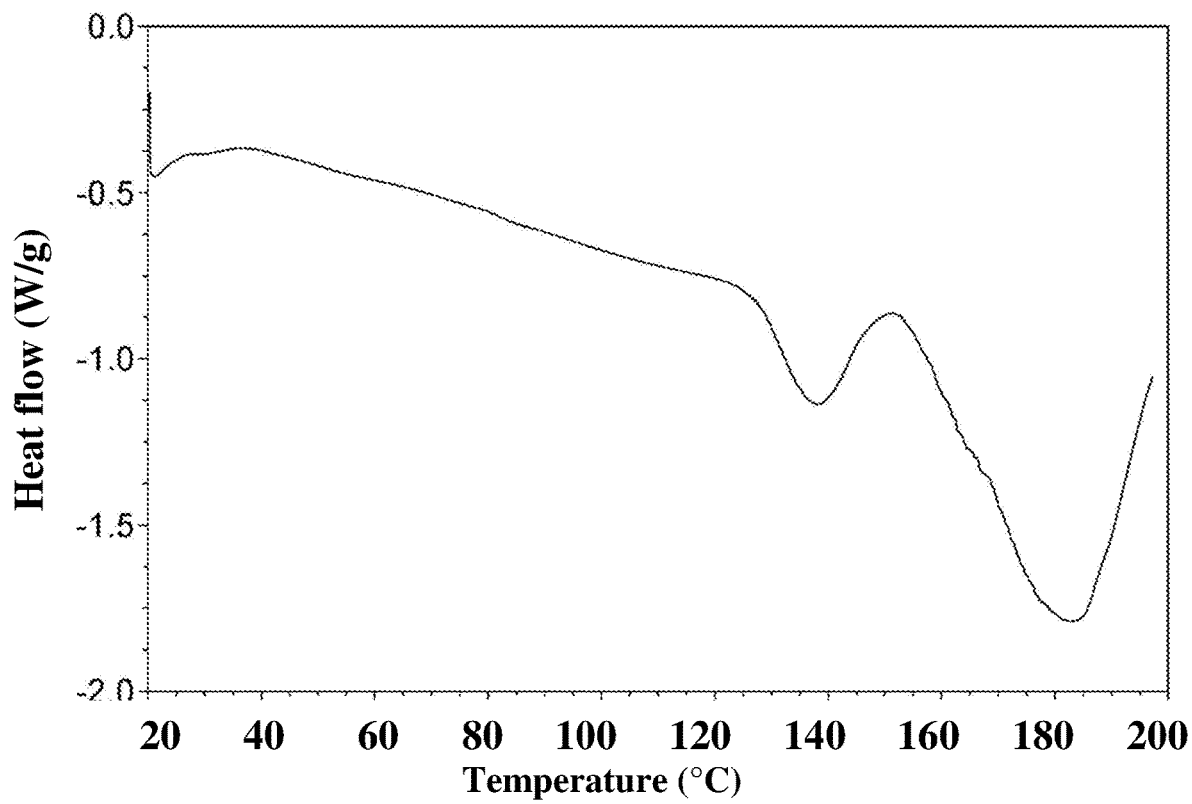
FIG. 11 is DSC pattern of the crystal form 13 of the monocitrate of the quinazoline derivative of the present invention.

As the DSC pattern shown in FIG. 11, the melting point is 127-138° C.

Figure 12:
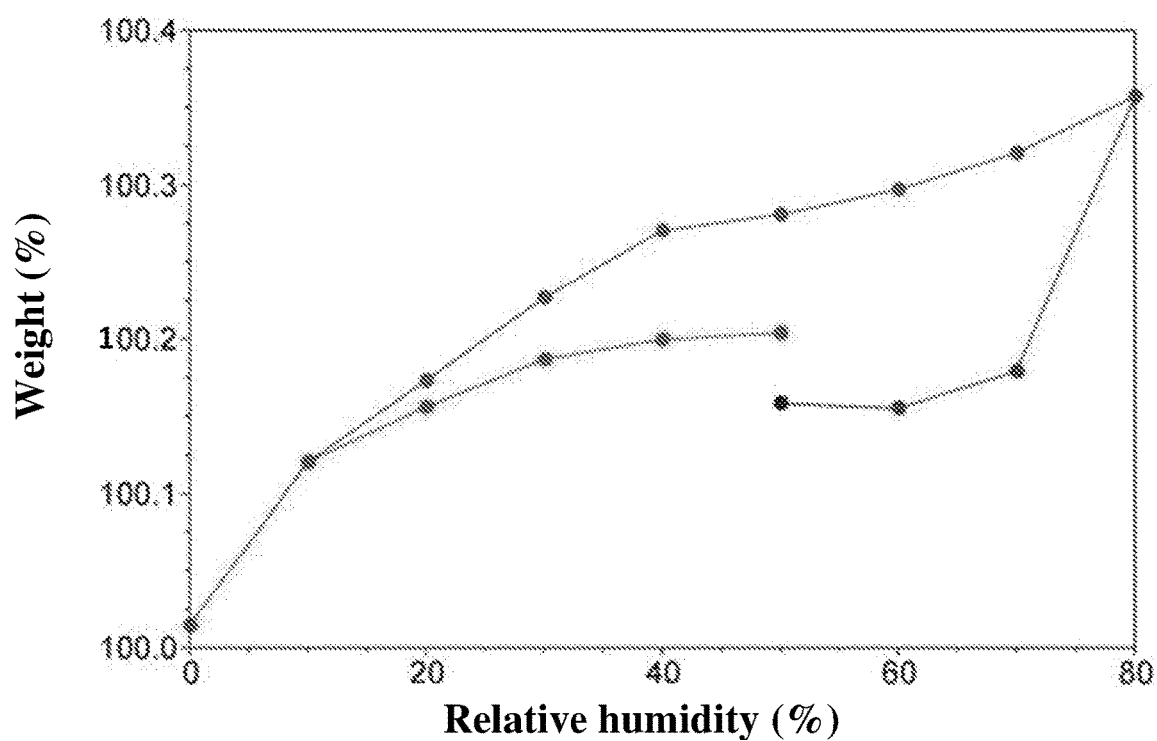
FIG. 12 is DVS pattern of the crystal form 13 of the monocitrate of the quinazoline derivative of the present invention.

As the DVS pattern shown in FIG. 12, the weight change in the range of 20-80% RH is 0.2%.

20 mg of the crystal form 1 prepared in embodiment 1 was taken, and the other conditions remained the same, and the given product was still the crystal form 13.

Embodiment 13: Synthesis of the Crystal Form 13 of the Monocitrate of the Quinazoline Derivative 10 mg of the crystal form 1 prepared in embodiment 1 was taken and 1 mL of water and 1 mL of acetonitrile was added thereto, followed by uncovered evaporation of the solvent to dry at 60° C. 7 mg of the crystal form 13 was given in a yield of 70%.

The XRPD pattern and the DSC pattern of the sample prepared in embodiment 13 (not shown) are similar to those of embodiment 12, indicating that the sample prepared in the example is the same as that in embodiment 12.

100 mg of the crystal form 1 prepared in embodiment 1 was taken, and other conditions remained the same. The given product was still the crystal form 13.

Embodiment 14: Synthesis of the Crystal Form 14 of the Monocitrate Hemi(Pentahydrate) of the Quinazoline Derivative 10 mg of the crystal form 1 prepared in embodiment 1 was taken and 0.05 mL of dimethyl sulfoxide was added thereto with ultrasound to keep the solution clear, followed by rapid addition into a flask with 3 mL of water with stirring for 5 minutes, centrifugation and vacuum drying at room temperature. 8.3 mg of the crystal form 14 of the hemi(pentahydrate) was given in a molar yield of 78.0%.

Figure 13:
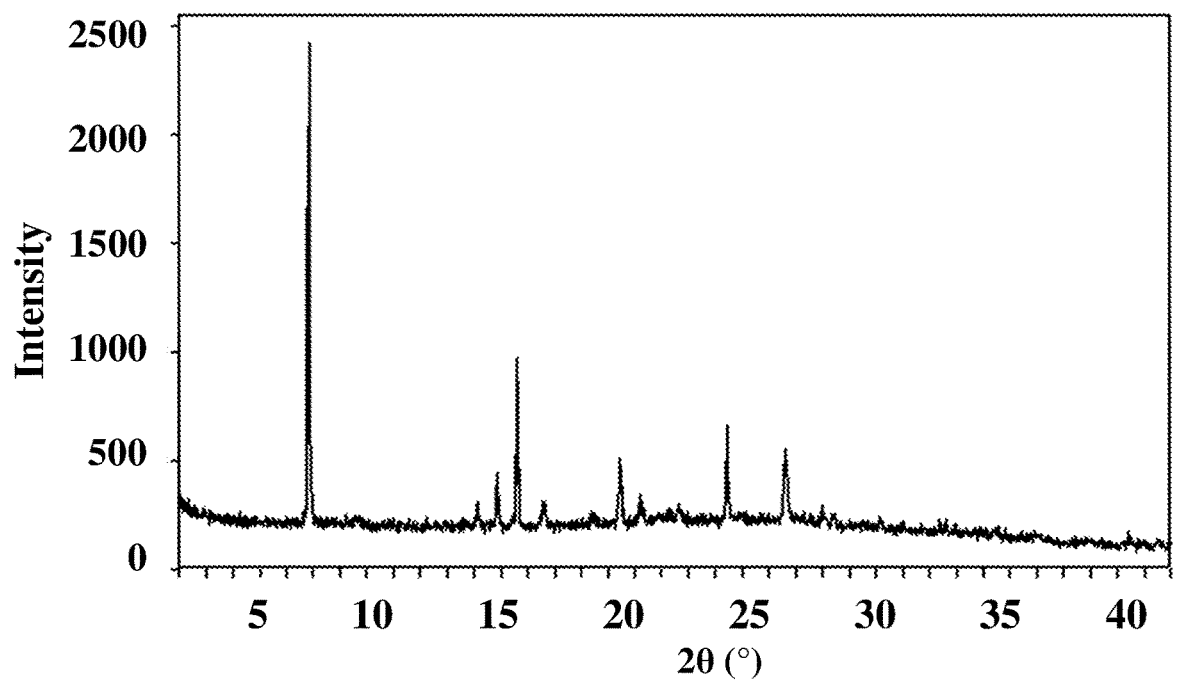
FIG. 13 is XRPD pattern of the crystal form 14 of the monocitrate hemi(pentahydrate) of the quinazoline derivative of the present invention.

The XRPD pattern is shown in FIG. 13.

Figure 14:
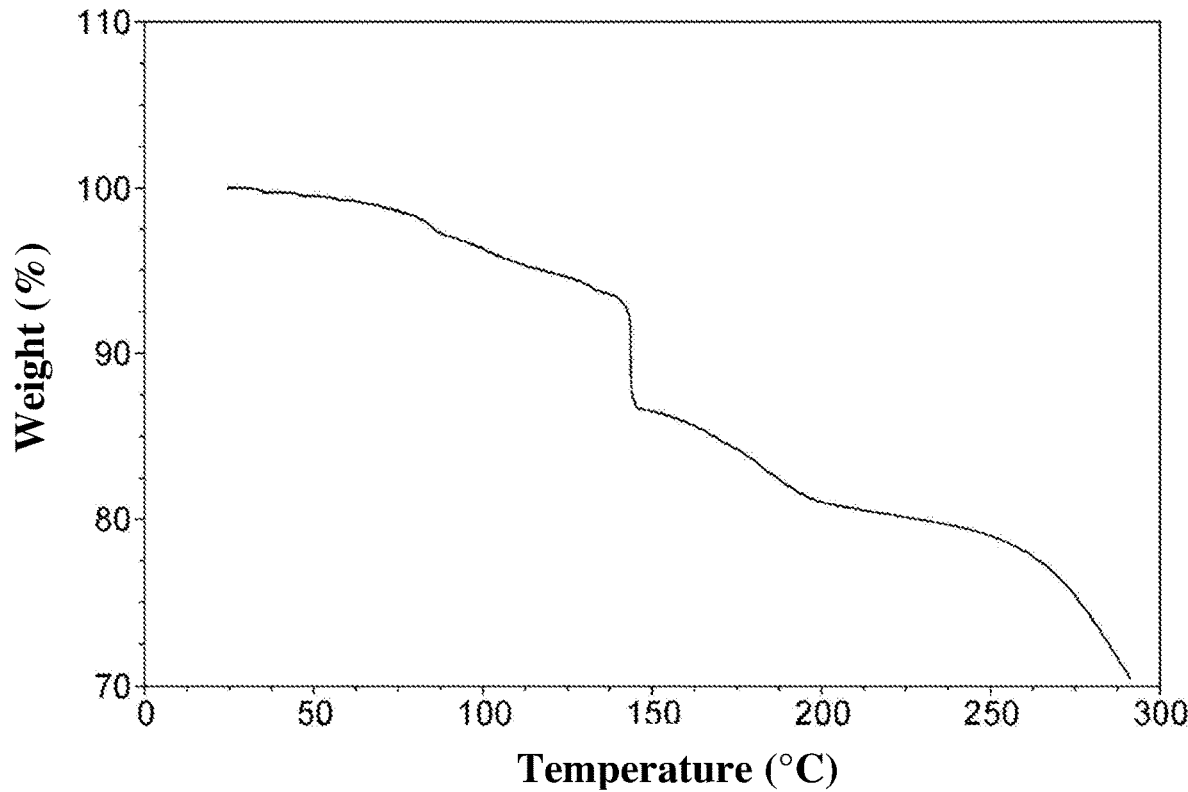
FIG. 14 is TGA pattern of the crystal form 14 of the monocitrate hemi(pentahydrate) of the quinazoline derivative of the present invention.

As the TGA pattern shown in FIG. 14, the decomposition temperature is 144° C., and the weight loss before decomposition is 6.3%, containing 2.5 moles of water.

Figure 15:
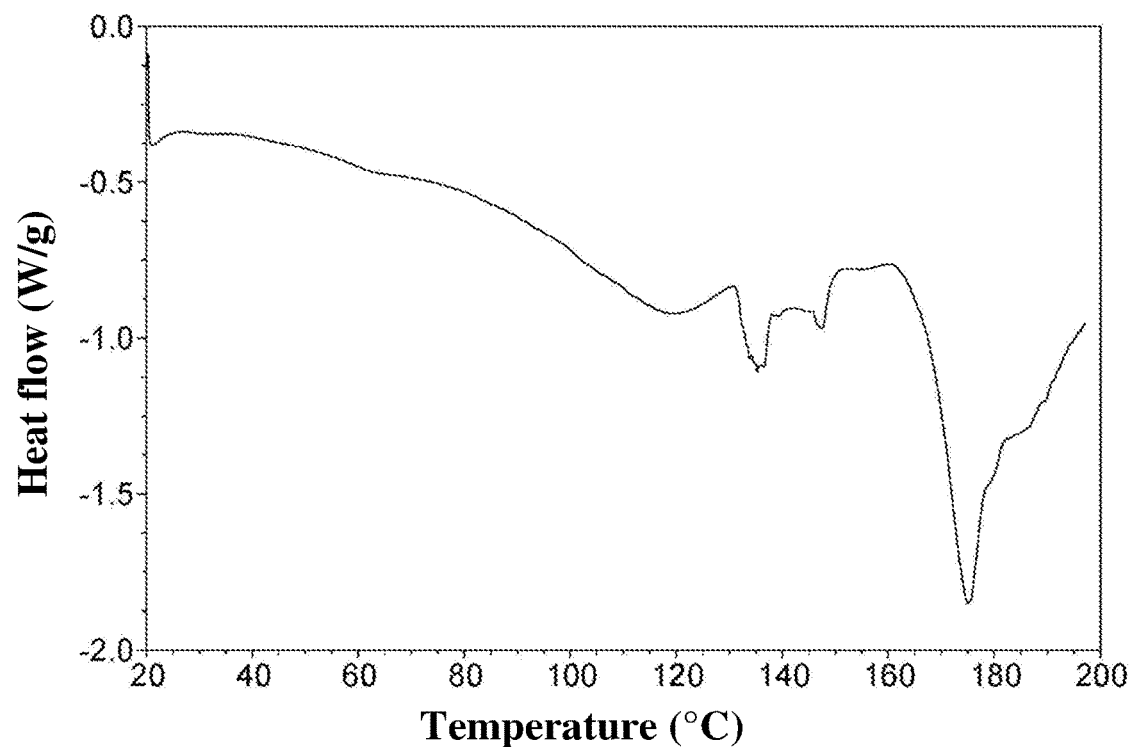
FIG. 15 is DSC pattern of the crystal form 14 of the monocitrate hemi(pentahydrate) of the quinazoline derivative of the present invention.

As the DSC pattern shown in FIG. 15, there is an endothermic peak of water elimination below 130° C.

Figure 16:
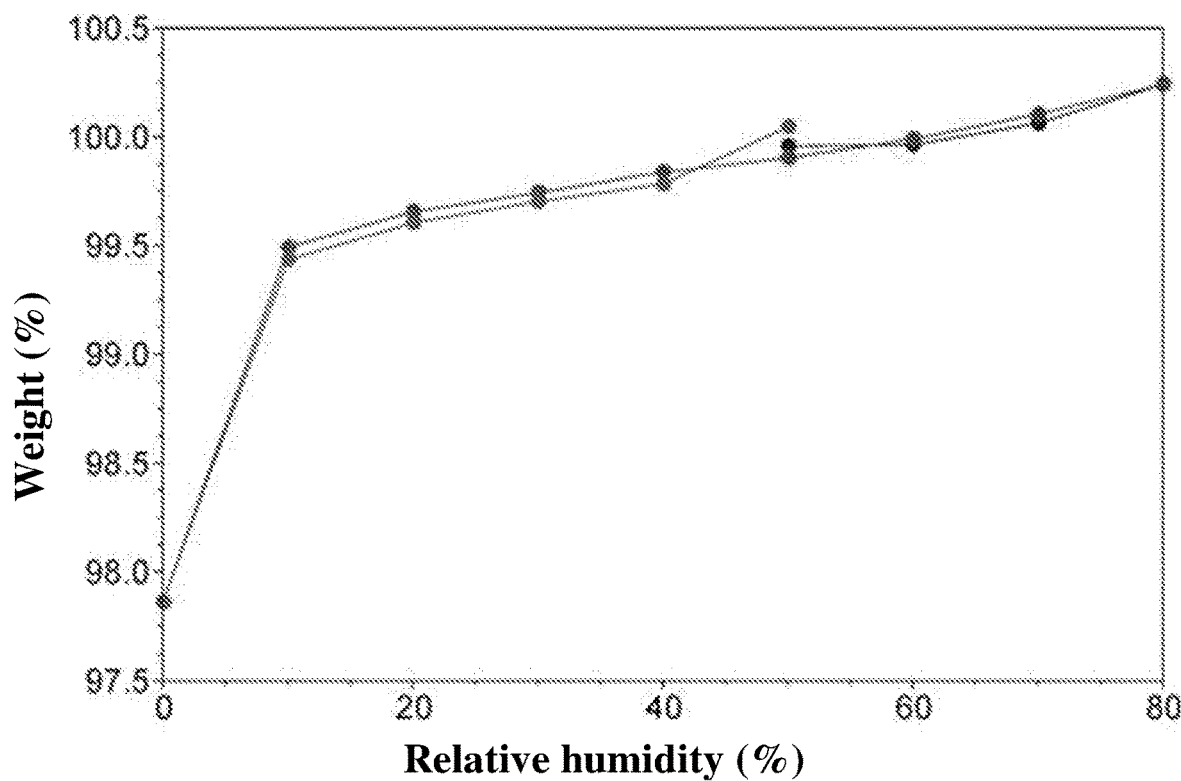
FIG. 16 is DVS pattern of the crystal form 14 of the monocitrate hemi(pentahydrate) of the quinazoline derivative of the present invention.

As the DVS pattern shown in FIG. 16, the weight change in the RH range of 10-80% is 0.7% and the hydrate water was partially eliminated below the RH of 10%.

20 mg of the crystal form 1 prepared in embodiment 1 was taken, and the other conditions remained the same, and the given product was still the crystal form 14 of the hemi (pentahydrate).

Embodiment 15: Synthesis of the Crystal Form 14 of the Monocitrate Hemi(Pentahydrate) of the Quinazoline Derivative 10 mg of the crystal form 1 prepared in embodiment 1 was taken and 1 mL of acetone and 1 mL of water was added thereto, followed by uncovered evaporation of the solvent to dry at 60° C. 8 mg of the crystal form 14 of the hemi (pentahydrate) was given in a yield of 75.1%.

The XRPD pattern and the DSC pattern of the sample prepared in embodiment 15 (not shown) are similar to those of embodiment 14, indicating that the sample prepared in the embodiment is the same as that in embodiment 14.

Embodiment 16: Synthesis of the Crystal Form 7 of the Monocitrate Dihydrate of the Quinazoline Derivative 10 mg of the crystal form 1 prepared in embodiment 1 was taken and 1 mL of water was added thereto, followed by crystallization at room temperature for 16 hours, centrifugation, and vacuum drying at room temperature. 9 mg of the crystal form 7 of the dihydrate was given in a molar yield of 85.6%.

Figure 17:
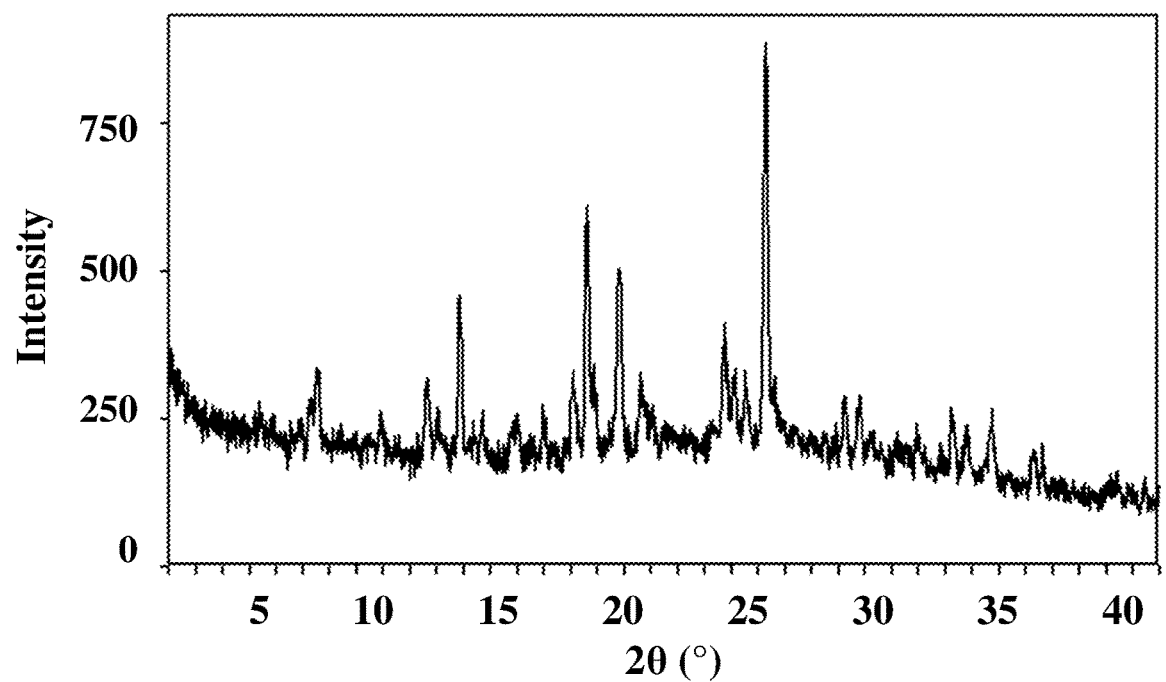
FIG. 17 is XRPD pattern of the crystal form 7 of the monocitrate dihydrate of the quinazoline derivative of the present invention.

The XRPD pattern is shown in FIG. 17.

Figure 18:
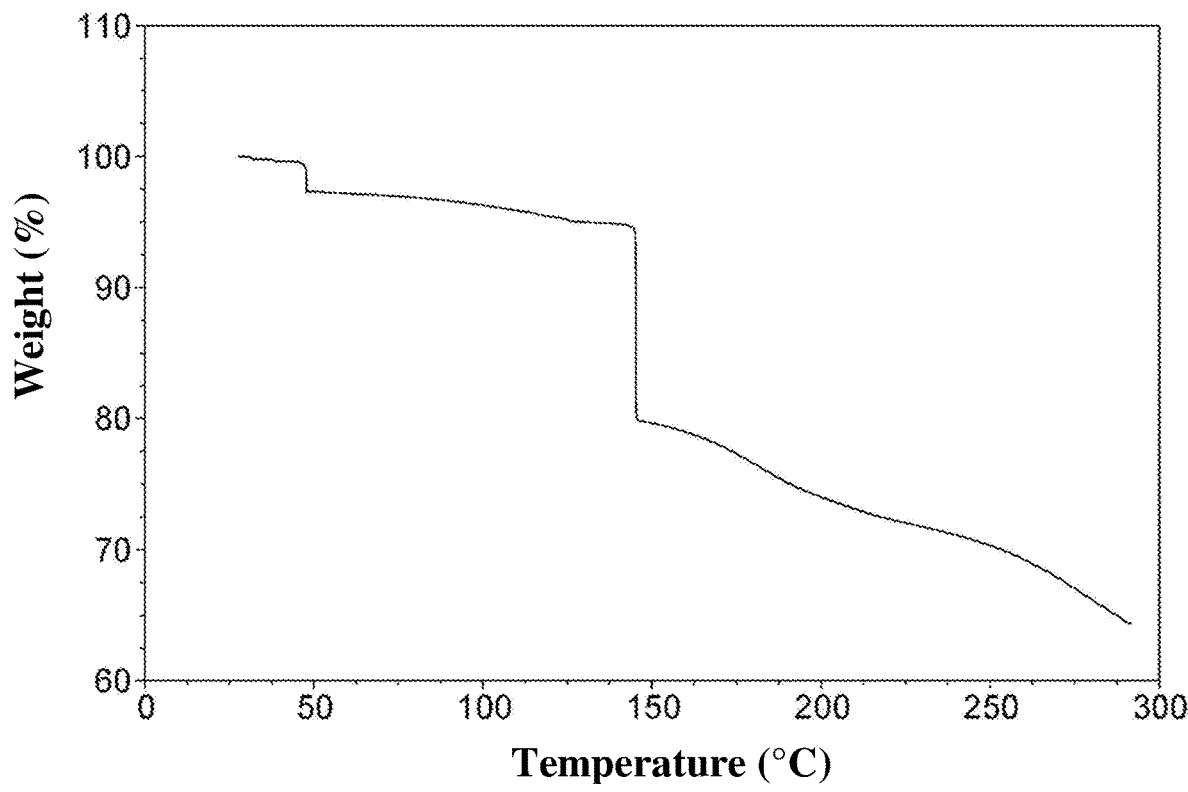
FIG. 18 is TGA pattern of the crystal form 7 of the monocitrate dihydrate of the quinazoline derivative of the present invention.

As the TGA pattern shown in FIG. 18, the decomposition temperature is 145° C., and the weight loss before decomposition is 4.7%, containing 2 moles of water.

Figure 19:
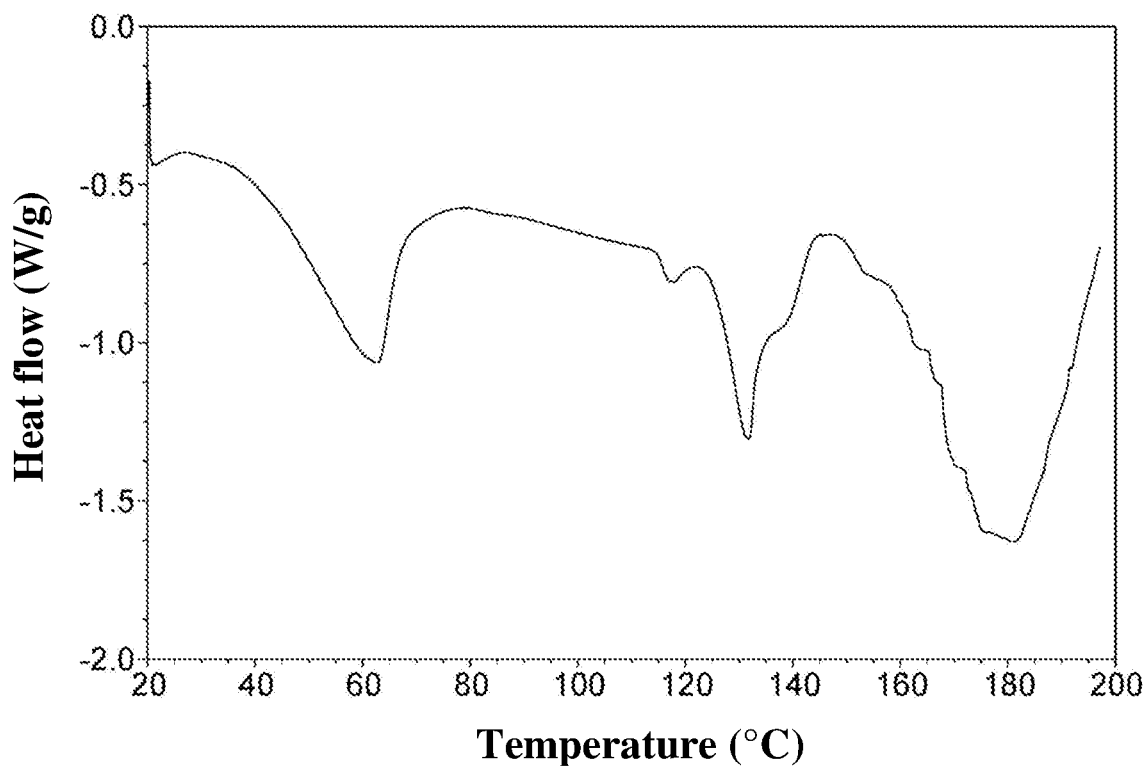
FIG. 19 is DSC pattern of the crystal form 7 of the monocitrate dihydrate of the quinazoline derivative of the present invention.

As the DSC pattern shown in FIG. 19, there is two endothermic peaks of water elimination below 79° C. and between 115-117° C.

Figure 20:
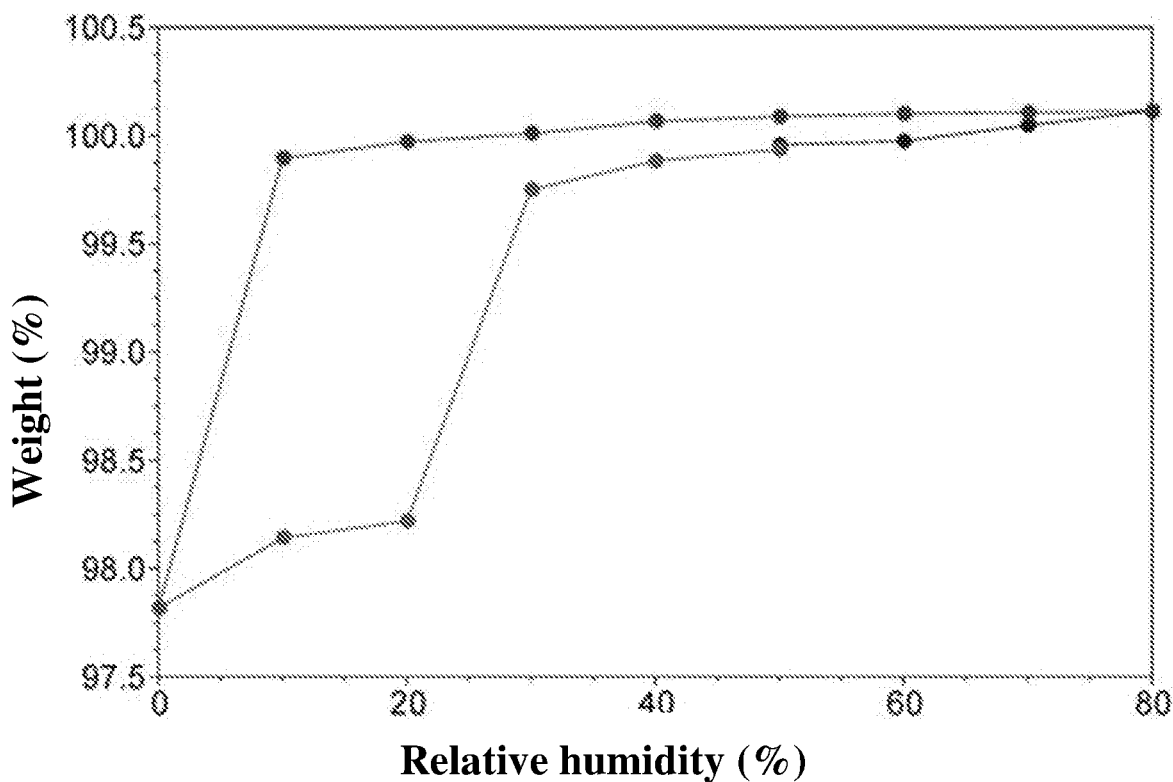
FIG. 20 is DVS pattern of the crystal form 7 of the monocitrate dihydrate of the quinazoline derivative of the present invention.

As the DVS pattern shown in FIG. 20, the weight change in the RH range of 10-80% is 0.38% and one water molecule is eliminated below a relative humidity of 10%. The eliminated water molecules were recombined at the relative humidity of 30%.

Embodiment 17: Synthesis of the Crystal Form 10 of the Monocitrate Trihydrate of the Quinazoline Derivative 10 mg of the crystal form 1 prepared in embodiment 1 was taken and 2 mL of methanol was added thereto, followed by uncovered evaporation of the solvent to dry at room temperature. 8 mg of the crystal form 10 of the trihydrate was given in a molar yield of 74.2%.

Figure 21:
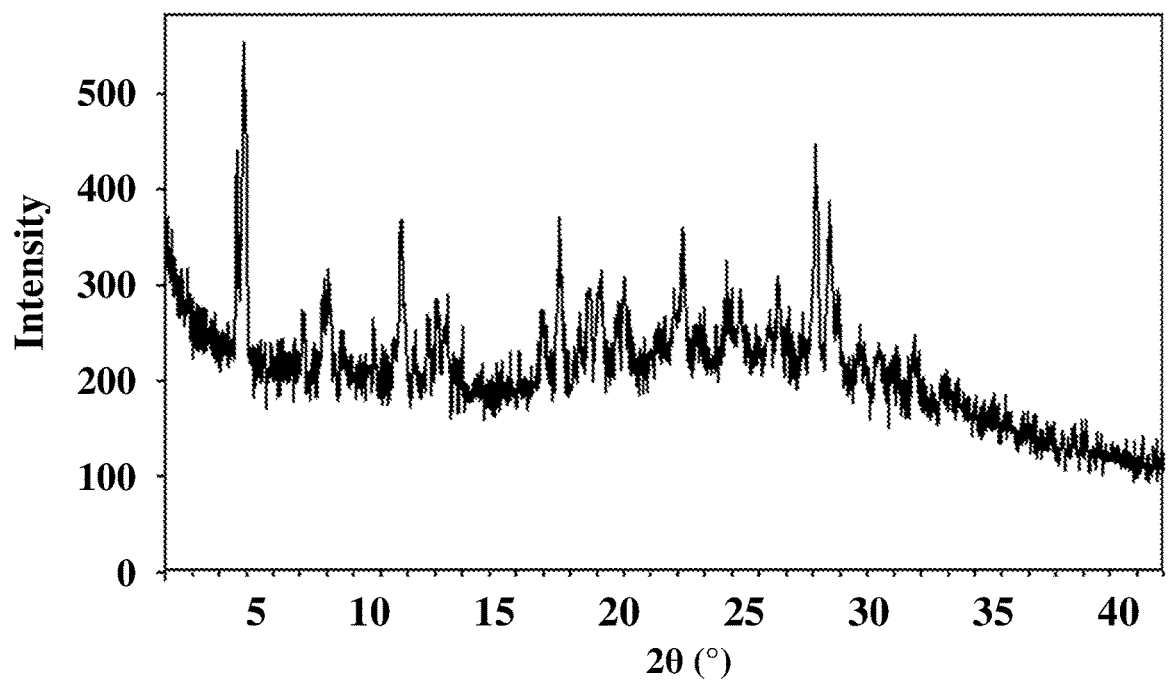
FIG. 21 is XRPD pattern of the crystal form 10 of the monocitrate trihydrate of the quinazoline derivative of the present invention.

The XRPD pattern is shown in FIG. 21.

Figure 22:
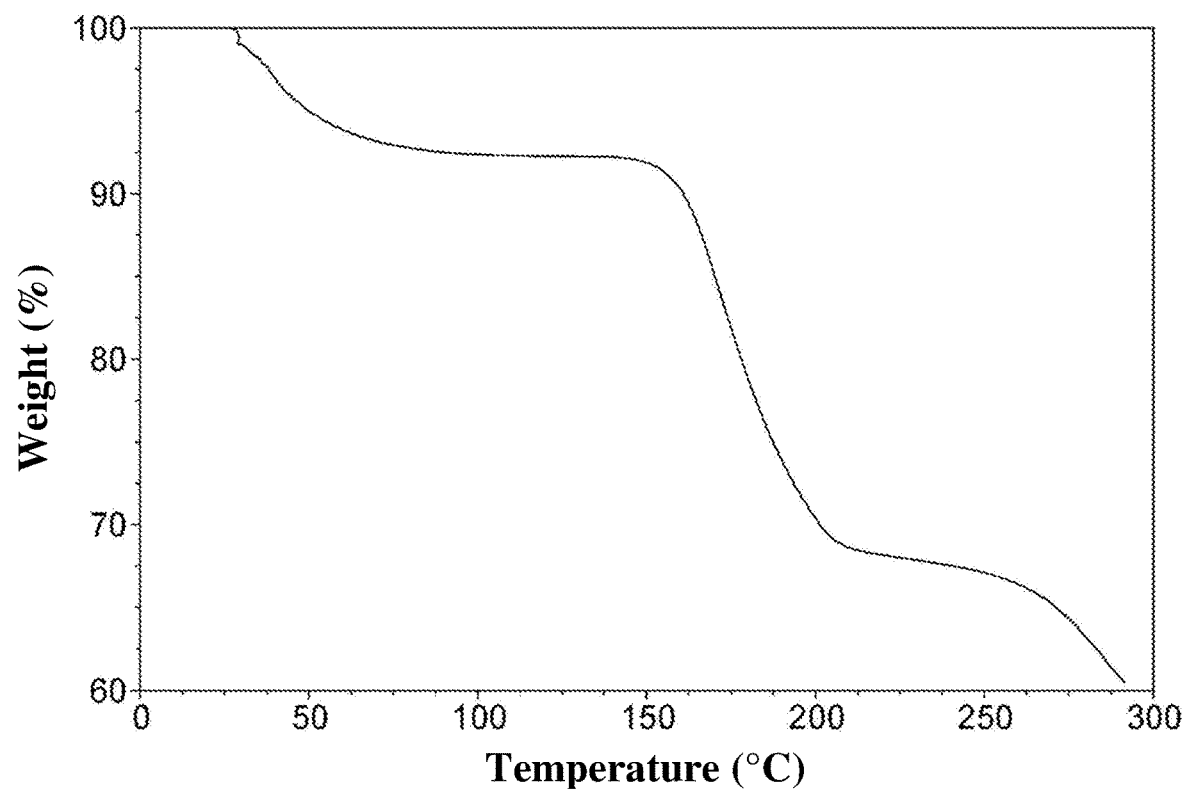
FIG. 22 is TGA pattern of the crystal form 10 of the monocitrate trihydrate of the quinazoline derivative of the present invention.

As the TGA pattern shown in FIG. 22, the decomposition temperature is 159° C., and the weight loss before decomposition is 7.7%, containing 3 moles of water.

As the DSC pattern shown in FIG. 23, there is an endothermic peak of water elimination below 117° C.

As the DVS pattern shown in FIG. 24, 3.5% of hydrate water is eliminated below a relative humidity of 50%. However, the hydrate is stable in a relative humidity range of 50-80% and the weight change is 1.1%.

Embodiment 18: Synthesis of the Crystal Form 10 of the Monocitrate Trihydrate of the Quinazoline Derivative 10 mg of the crystal form 1 prepared in embodiment 1 was taken and 1 mL of water and 1 mL of n-propanol was added thereto, followed by uncovered evaporation of the solvent to dry at room temperature. 8 mg of the crystal form 10 of the trihydrate was given in a molar yield of 74.2%.

20 mg of the crystal form 1 prepared in embodiment 1 was taken, and the other conditions remained the same, and the given product was still the crystal form 10 of the trihydrate.

Embodiment 19: Synthesis of the Crystal Form 10 of the Monocitrate Trihydrate of the Quinazoline Derivative The "n-propanol" in embodiment 18 was replaced with the "tetrahydrofuran", and the other operations remained the same as that in embodiment 18 to give the crystal form 10 of the trihydrate.

Embodiment 20: Synthesis of the Crystal Form 10 of the Monocitrate Trihydrate of the Quinazoline Derivative The "n-propanol" in embodiment 18 was replaced with the "acetonitrile", and the other operations remained the same as that in embodiment 18 to give the crystal form 10 of the trihydrate.

The XRPD patterns and the DSC patterns of the samples prepared in embodiments 18-20 (not shown) are similar to those of embodiment 17, indicating that the samples prepared in these embodiments are the same as that in embodiment 17.

Embodiment 21: Synthesis of the Crystal Form 11 of the Monocitrate Dihydrate of the Quinazoline Derivative 10 mg of the crystal form 1 prepared in embodiment 1 was taken and 5 mL of isopropanol was added thereto, followed by stirring in water bath at 60° C. for 5 minutes to keep the solution clear and naturally cooling to room temperature. The precipitated solids were centrifuged and dried in vacuum at room temperature. 7.5 mg of the crystal form 11 of the dihydrate was given in a molar yield of 71.3%.

Figure 25:
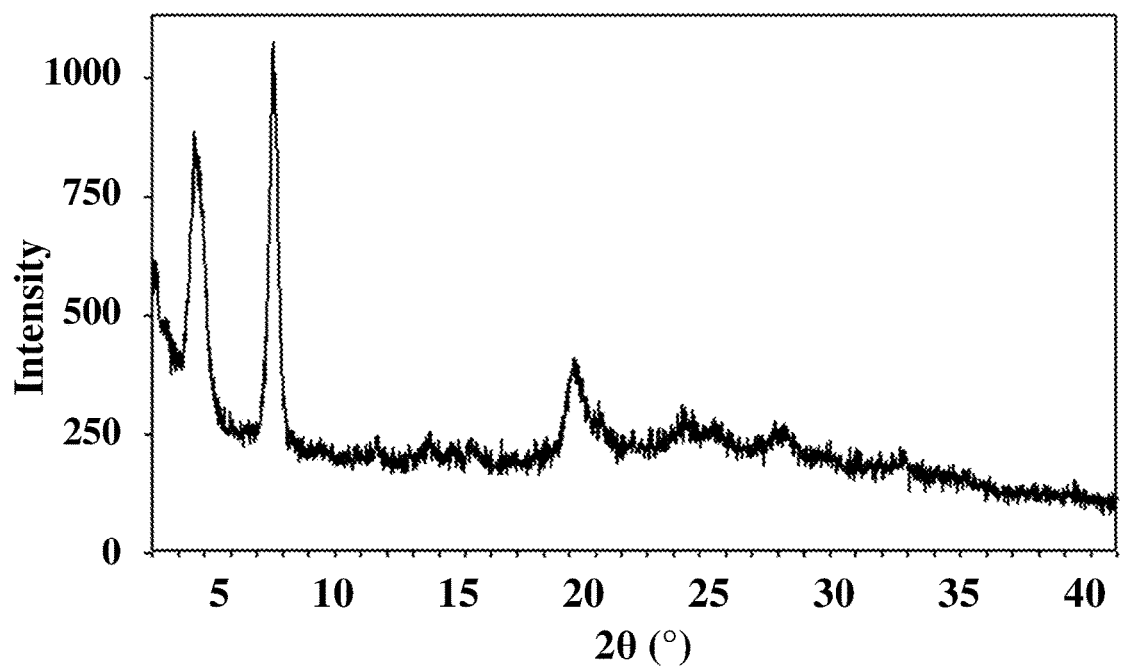
FIG. 25 is XRPD pattern of the crystal form 11 of the monocitrate dihydrate of the quinazoline derivative of the present invention.

The XRPD pattern is shown in FIG. 25.

Figure 26:
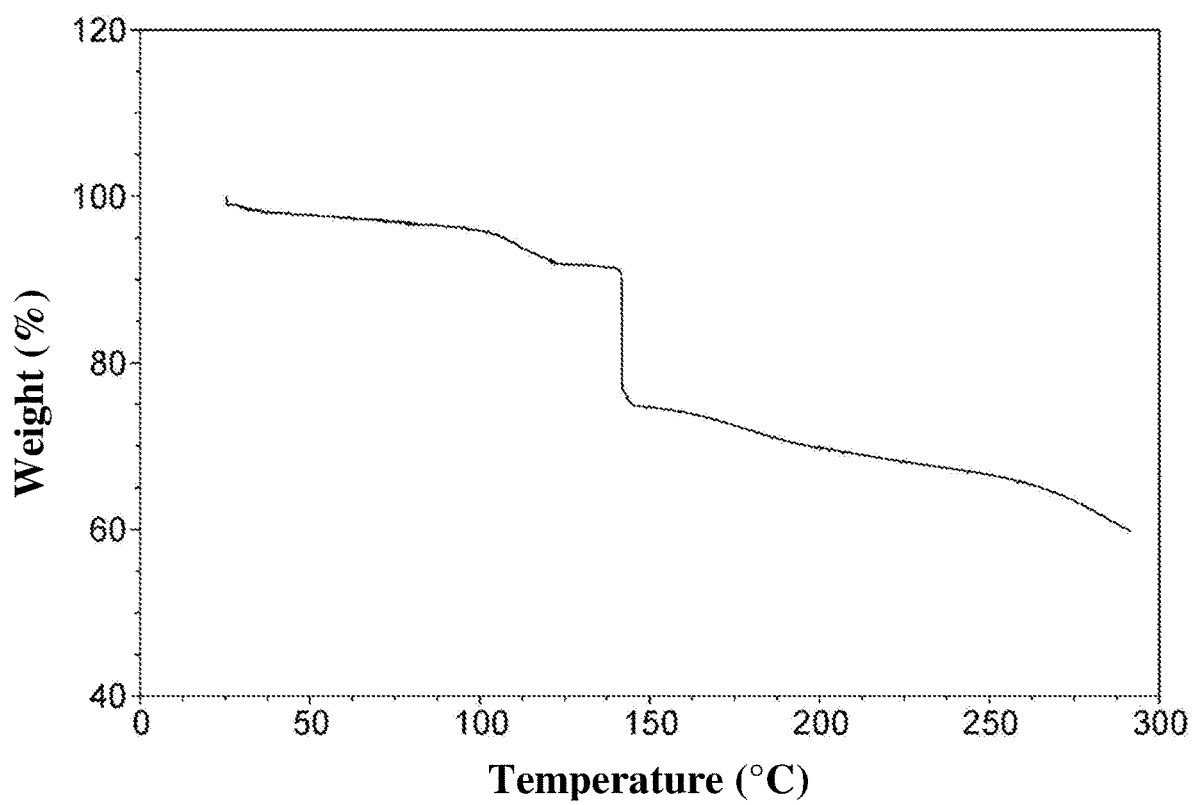
FIG. 26 is TGA pattern of the crystal form 11 of the monocitrate dihydrate of the quinazoline derivative of the present invention.

As the TGA pattern shown in FIG. 26, the decomposition temperature is 142° C., and the weight loss before decomposition is 4.8%, containing 2 moles of water.

As the DSC pattern shown in FIG. 27, there is an endothermic peak of water elimination below 71° C.

As the DVS pattern shown in FIG. 28, the hydrate is stable in a relative humidity range of 50-80% and the weight change therein is 5.3%. The hydrate water is eliminated below the relative humidity of 50%.

Embodiment 22: Synthesis of the Crystal Form 11 of the Monocitrate Dihydrate of the Quinazoline Derivative The "isopropanol" in embodiment 21 was replaced with the "n-propanol", and the other operations remained the same as that in embodiment 21 to give the crystal form 11 of the dihydrate.

Embodiment 23: Synthesis of the Crystal Form 11 of the Monocitrate Dihydrate of the Quinazoline Derivative 10 mg of the crystal form 1 prepared in embodiment 1 was taken and 1 mL of methanol and 1 mL of ethanol were added thereto, followed by crystallization at room temperature for 16 hours, centrifugation, and vacuum drying at room temperature. 6.8 mg of the crystal form 11 of the dihydrate was given in a yield of 64.7%.

Embodiment 24: Synthesis of the Crystal Form 11 of the Monocitrate Dihydrate of the Quinazoline Derivative The "methanol" in embodiment 23 was replaced with the "nitromethane", and the other operations remained the same as that in embodiment 23 to give the crystal form 11 of the dihydrate.

Embodiment 25: Synthesis of the Crystal Form 11 of the Monocitrate Dihydrate of the Quinazoline Derivative The "methanol" in embodiment 23 was replaced with the "acetonitrile", and the other operations remained the same as that in embodiment 23 to give the crystal form 11 of the dihydrate.

Embodiment 26: Synthesis of the Crystal Form 11 of the Monocitrate Dihydrate of the Quinazoline Derivative 10 mg of the crystal form 1 prepared in embodiment 1 was taken and 1 mL of methanol and 1 mL of ethanol were added thereto, followed by stirring in water bath at 60° C. for 5 minutes to keep the solution clear and naturally cooling to room temperature. The precipitated solids were centrifuged and dried in vacuum at room temperature. 7 mg of the crystal form 11 of the dihydrate was given in a molar yield of 66.6%.

Embodiment 27: Synthesis of the Crystal Form 11 of the Monocitrate Dihydrate of the Quinazoline Derivative The "methanol" in embodiment 26 was replaced with the "nitromethane", and the other operations remained the same as that in embodiment 26 to give the crystal form 11 of the dihydrate.

Embodiment 28: Synthesis of the Crystal Form 11 of the Monocitrate Dihydrate of the Quinazoline Derivative The "methanol" in embodiment 26 was replaced with the "acetonitrile", and the other operations remained the same as that in embodiment 26 to give the crystal form 11 of the dihydrate.

The XRPD patterns and the DSC patterns of the samples prepared in embodiments 22-28 (not shown) are similar to those of embodiment 21, indicating that the samples prepared in these embodiments are the same as that in embodiment 21.

Embodiment 29: Synthesis of the Crystal Form 2 of the Monocitrate Hemiethanolate of the Quinazoline Derivative 10 mg of the crystal form 1 prepared in embodiment 1 was taken and 0.4 mL of ethanol was added thereto, followed by stirring at 60° C. for 16 hours, centrifugation and vacuum drying at room temperature. 8 mg of the crystal form 2 of the hemiethanolate was given in a molar yield of 77.4%.

Figure 29:
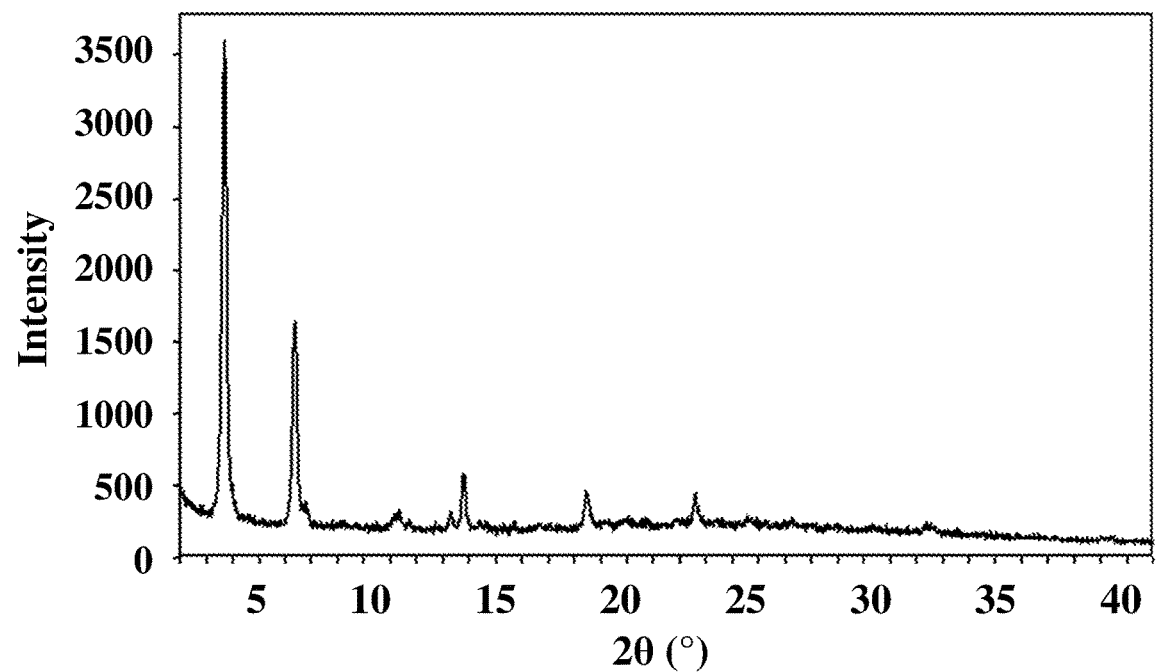
FIG. 29 is XRPD pattern of the crystal form 2 of the monocitrate hemiethanolate of the quinazoline derivative of the present invention.

The XRPD pattern is shown in FIG. 29.

Figure 30:
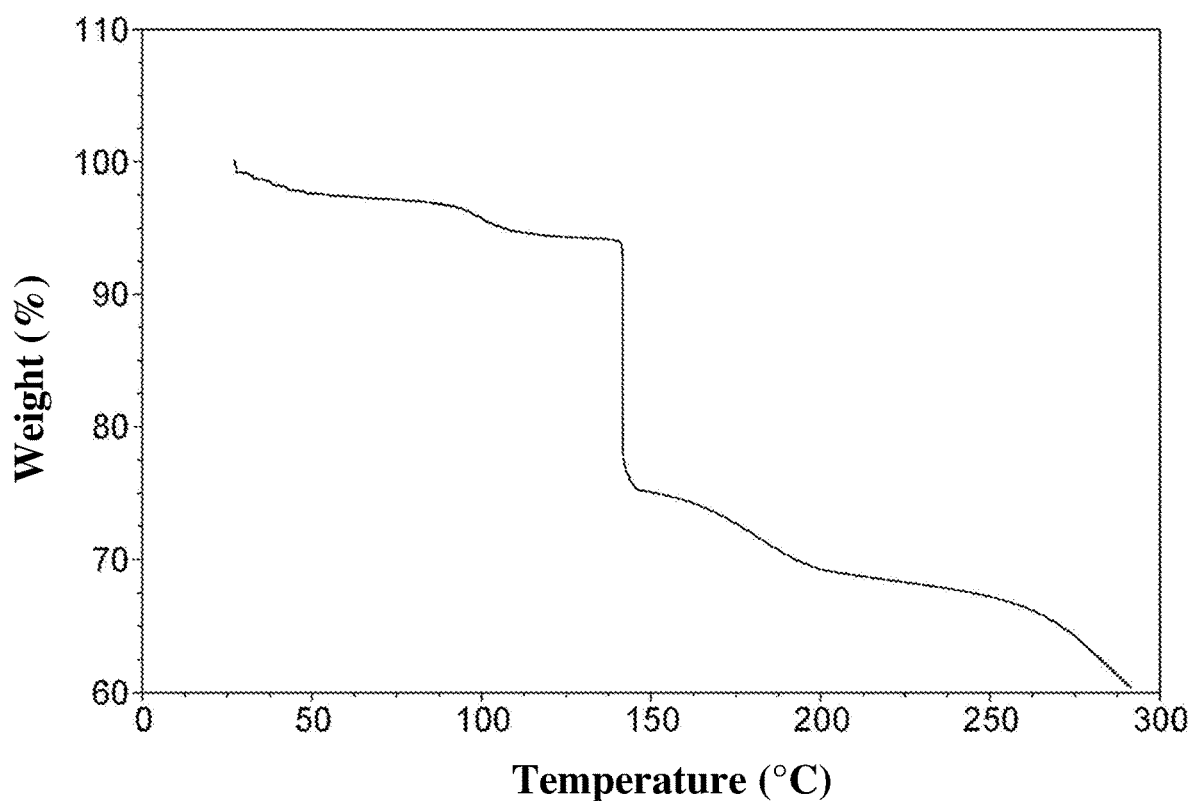
FIG. 30 is TGA pattern of the crystal form 2 of the monocitrate hemiethanolate of the quinazoline derivative of the present invention.

As the TGA pattern shown in FIG. 30, the decomposition temperature is 142° C., and the weight loss before decomposition is 3.2%, containing 0.5 mole of ethanol.

Figure 31:
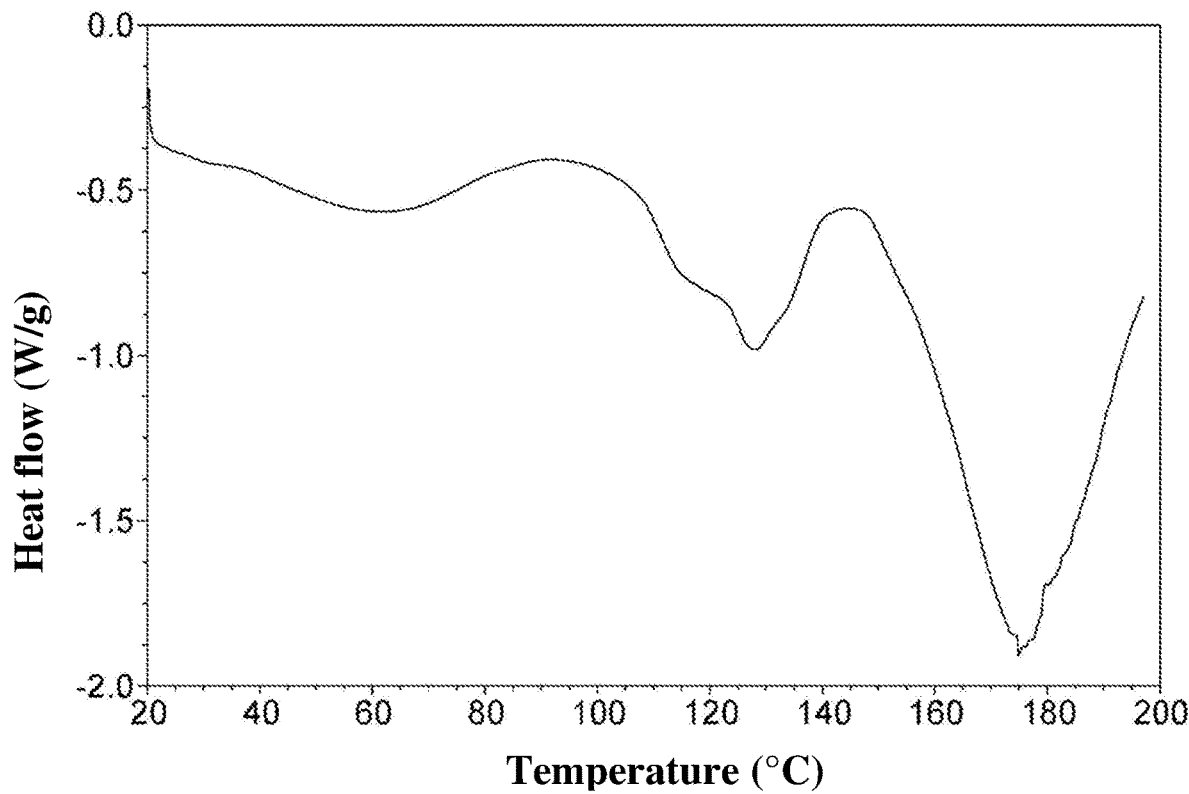
FIG. 31 is DCS pattern of the crystal form 2 of the monocitrate hemiethanolate of the quinazoline derivative of the present invention.

As the DSC pattern shown in FIG. 31, there is an endothermic peak of ethanol elimination between 89-120° C.

Embodiment 30: Synthesis of the Crystal Form 2 of the Monocitrate Ditetrahydrofuran Complex of the Quinazoline Derivative 10 mg of the crystal form 1 prepared in embodiment 1 was taken and 0.4 mL of tetrahydrofuran was added thereto, followed by stirring at room temperature for 16 hours, centrifugation and vacuum drying at room temperature. 9 mg of the crystal form 3 of the ditetrahydrofuran complex was given in a molar yield of 73.7%.

Figure 32:
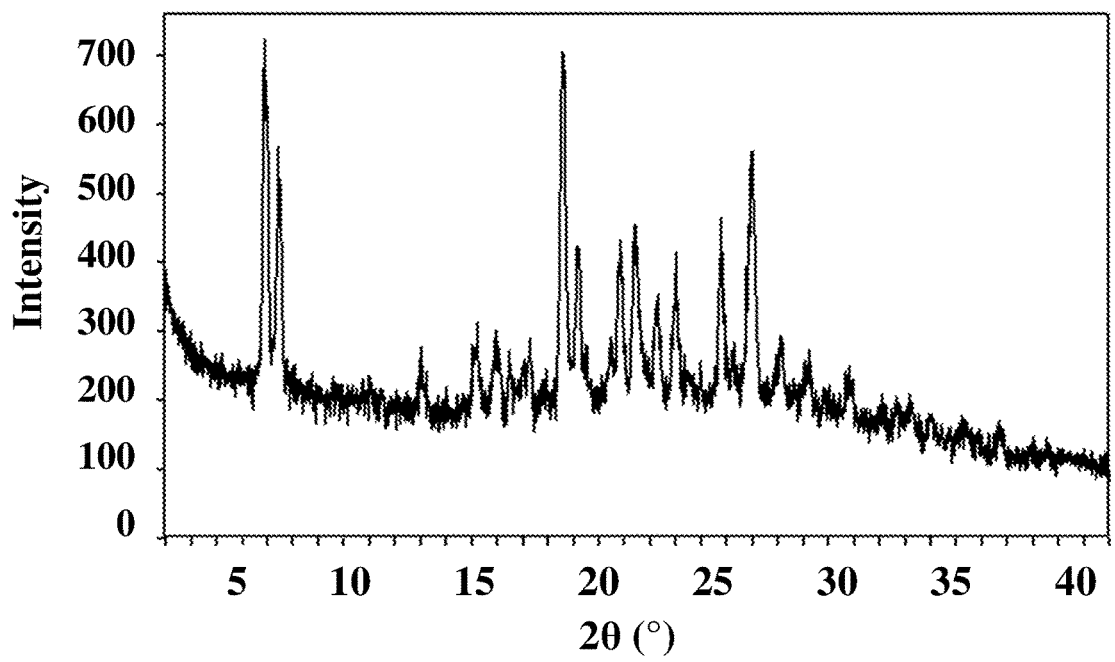
FIG. 32 is XRPD pattern of the crystal form 3 of the monocitrate ditetrahydrofuran complex of the quinazoline derivative of the present invention.

The XRPD pattern is shown in FIG. 32.

Figure 33:
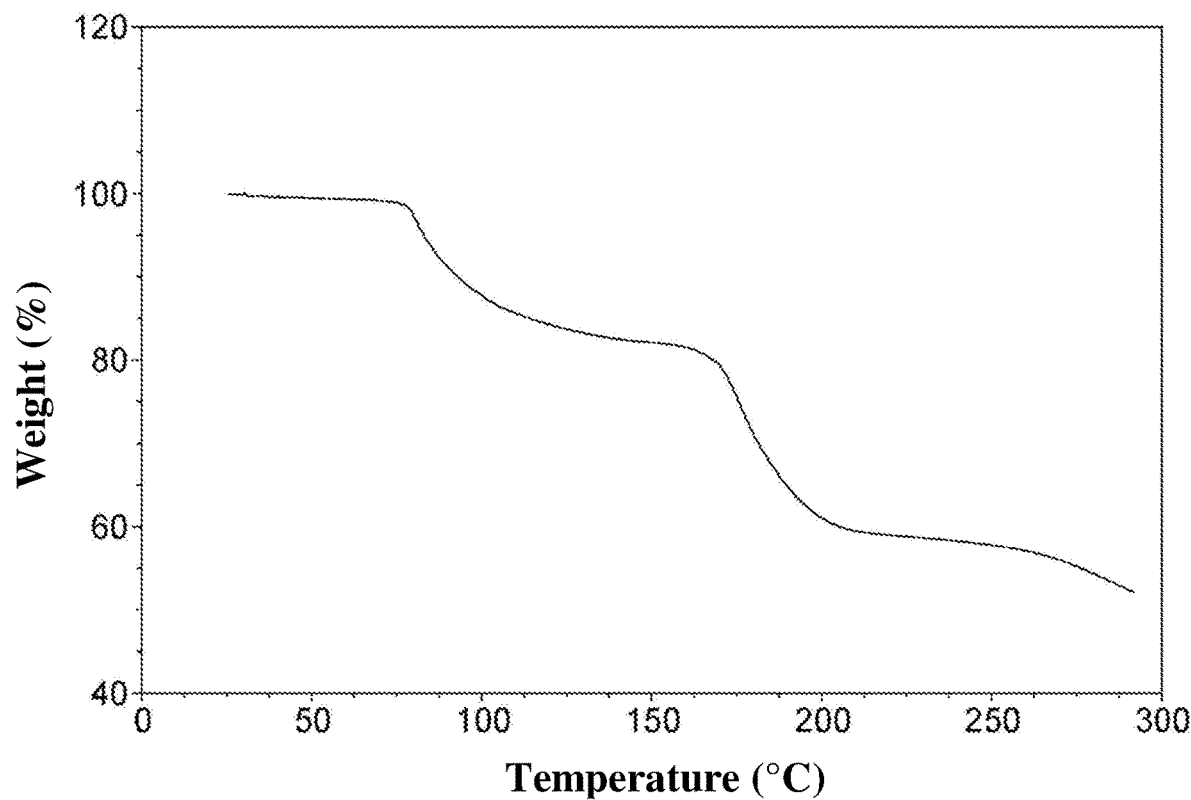
FIG. 33 is TGA pattern of the crystal form 3 of the monocitrate ditetrahydrofuran complex of the quinazoline derivative of the present invention.

As the TGA pattern shown in FIG. 33, the decomposition temperature is 169° C., and the weight loss before decomposition is 17.3%, containing 2 moles of tetrahydrofuran.

Embodiment 31: Synthesis of the Crystal Form 2 of the Monocitrate Ditetrahydrofuran Complex of the Quinazoline Derivative 10 mg of the crystal form 1 prepared in embodiment 1 was taken and 0.4 mL of tetrahydrofuran was added thereto, followed by stirring at 60° C. for 16 hours, centrifugation and vacuum drying at room temperature to give the crystal form 3 of the ditetrahydrofuran complex.

The XRPD patterns and the DSC patterns of the samples prepared in embodiment 31 (not shown) are similar to those of embodiment 30, indicating that the sample prepared in the embodiment are the same as that in embodiment 30.

Embodiment 32: Synthesis of the Crystal Form 2 of the Monocitrate Hemi-1,4-Dioxane Complex of the Quinazoline Derivative 10 mg of the crystal form 1 prepared in embodiment 1 was taken and 1.2 mL of dioxane was added thereto, followed by stirring in water bath at 60° C. for 5 minutes to keep the solution clear and naturally cooling to room temperature. The precipitated solids were centrifuged and dried in vacuum at room temperature. 6 mg of the crystal form 4 of the hemi-1,4-dioxane compound was given in a molar yield of 56.4%.

Figure 34:
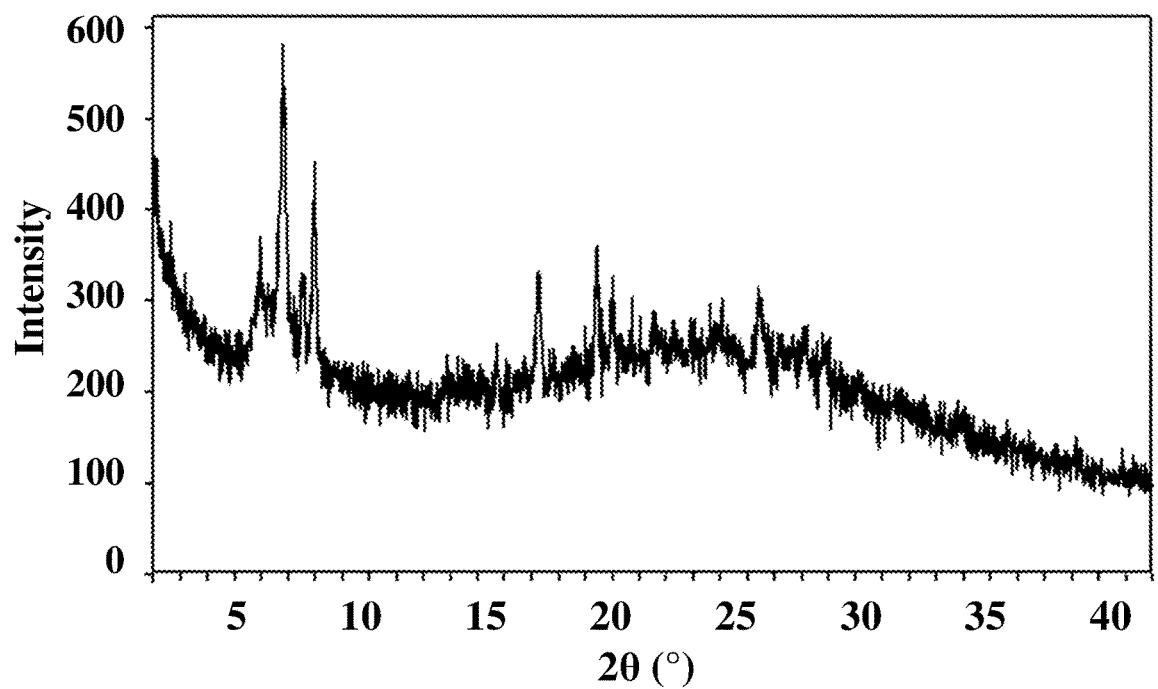
FIG. 34 is XRPD pattern of the crystal form 4 of the monocitrate hemi-1,4-dioxane complex of the quinazoline derivative of the present invention.

The XRPD pattern is shown in FIG. 34.

Figure 35:
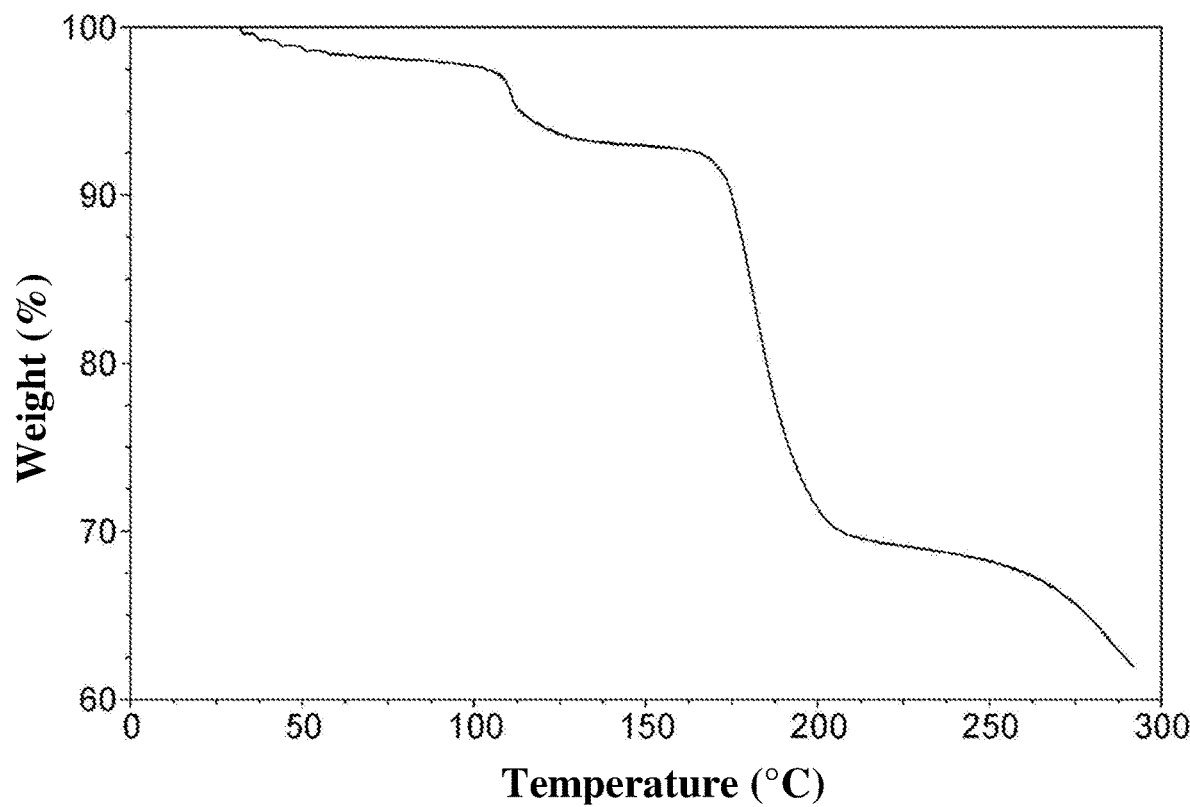
FIG. 35 is TGA pattern of the crystal form 4 of the monocitrate hemi-1,4-dioxane complex of the quinazoline derivative of the present invention.

As the TGA pattern shown in FIG. 35, the decomposition temperature is 173° C., and the weight loss before decomposition is 6.6%, containing 0.5 mole of dioxane.

20 mg of the crystal form 1 prepared in embodiment 1 was taken, followed by the addition of 1.2 mL of dioxane, and the other conditions remained the same, and the given product was still the crystal form 4 of the hemi-1,4-dioxane complex.

Embodiment 33: Synthesis of the Crystal Form 6 of the Monocitrate Hemichloroform Complex of the Quinazoline Derivative 10 mg of the crystal form 1 prepared in embodiment 1 was taken and 0.4 mL of chloroform was added thereto, followed by stirring at room temperature for 16 hours, centrifugation and vacuum drying at room temperature. 7 mg of the crystal form 6 of the hemichloroform complex was given in a molar yield of 64.4%.

Figure 36:
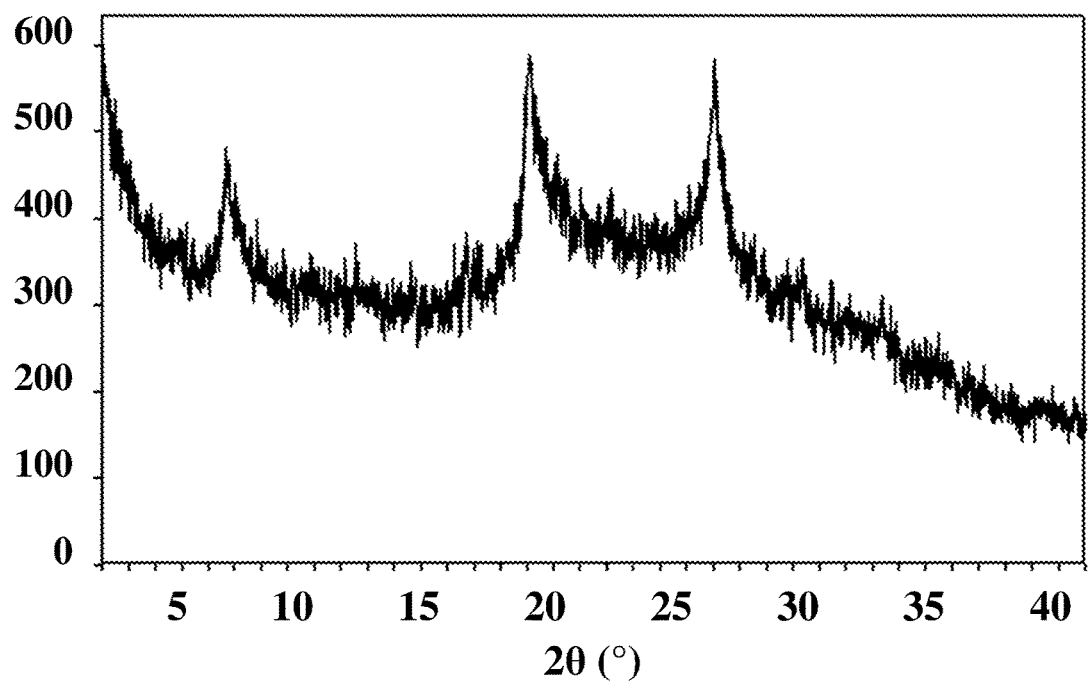
FIG. 36 is XRPD pattern of the crystal form 6 of the monocitrate hemichloroform complex of the quinazoline derivative of the present invention.

The XRPD pattern is shown in FIG. 36.

Figure 37:
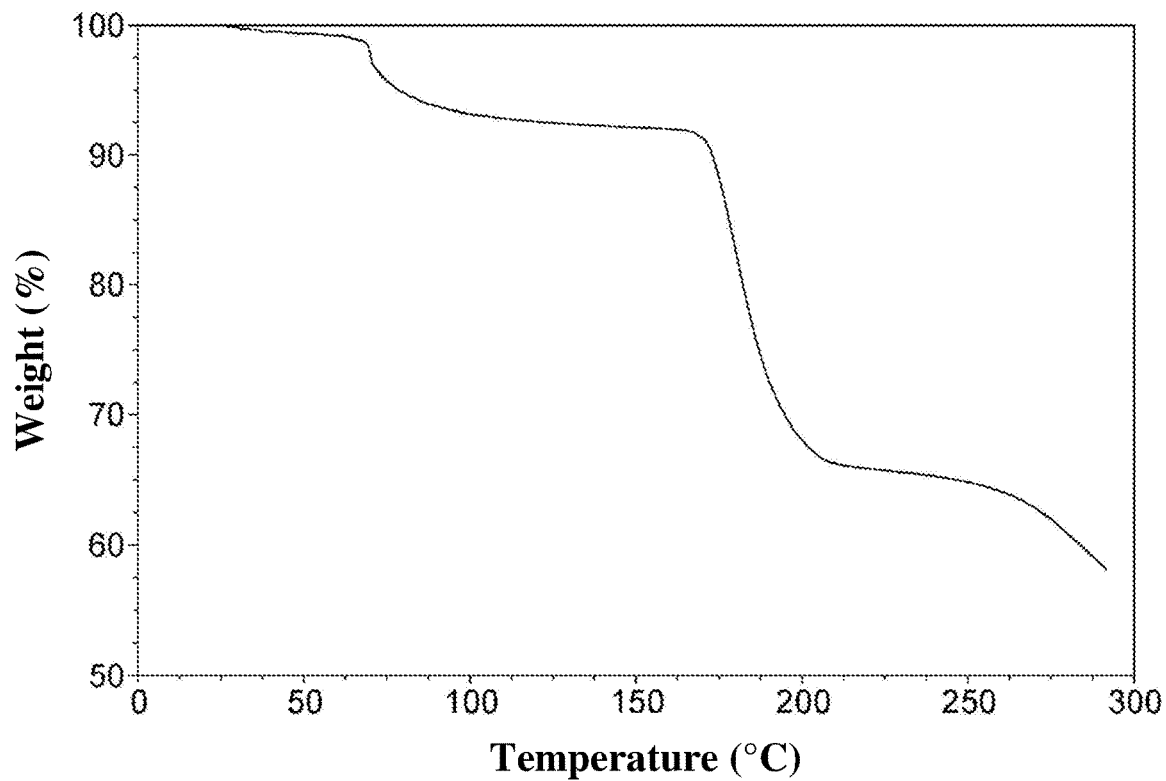
FIG. 37 is TGA pattern of the crystal form 6 of the monocitrate hemichloroform complex of the quinazoline derivative of the present invention.

As the TGA pattern shown in FIG. 37, the decomposition temperature is 173° C., and the weight loss before decomposition is 7.3%, containing 0.5 mole of chloroform.

Embodiment 34: Synthesis of the Monoethanedisulfonate of the Quinazoline Derivative 10 mg of the compound represented by formula 1 was dissolved in 0.8 mL of tetrahydrofuran and 4.15 mg of ethanedisulfonic acid was dissolved in 0.2 mL of tetrahydrofuran. The solution of ethanedisulfonic acid in tetrahydrofuran was added dropwise to the solution of the compound represented by formula 1 in tetrahydrofuran, accompanied by the precipitation of the solids, followed by stirring overnight, centrifugation, rinsing and drying to give the salt.

Figure 38:
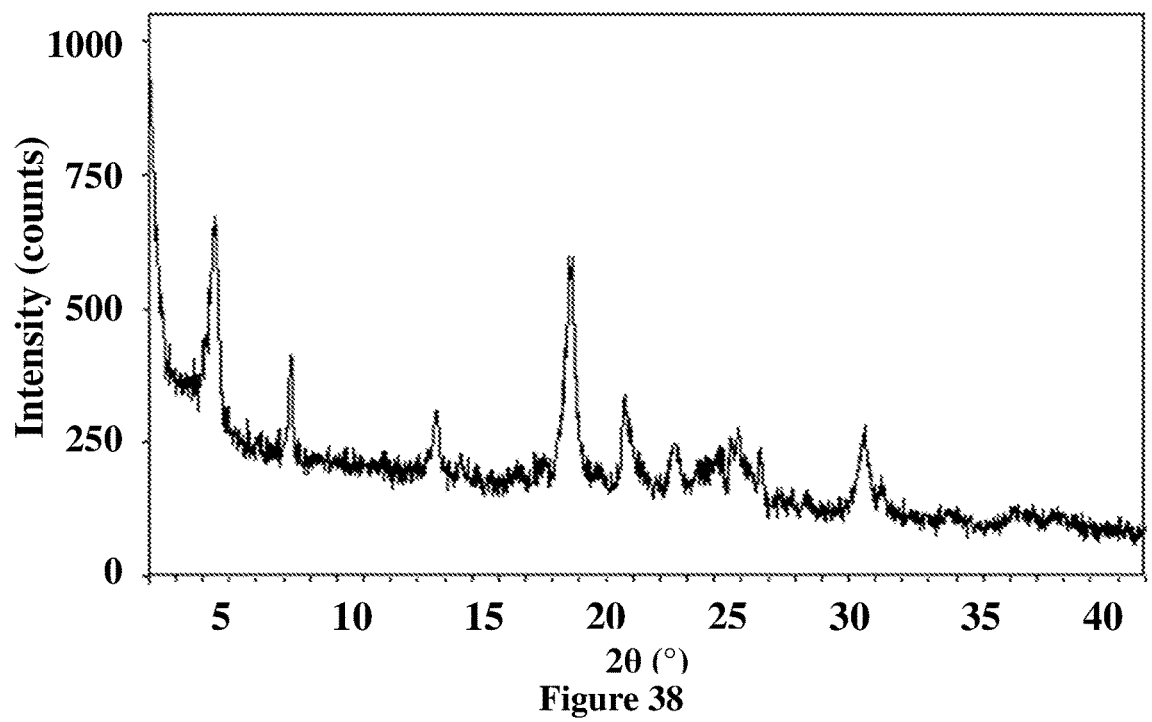
FIG. 38 is XRPD pattern of the monoethanedisulfonate of the quinazoline derivative of the present invention.

The XRPD pattern is shown in FIG. 38.

Figure 39:
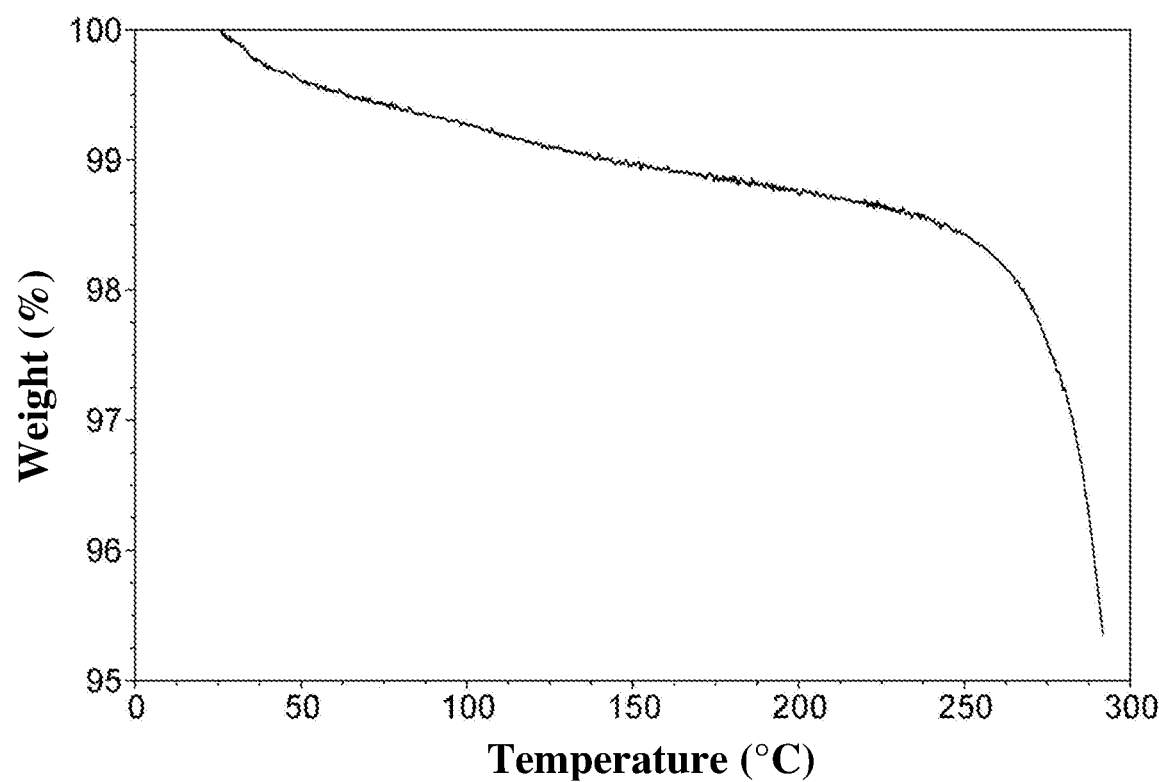
FIG. 39 is TGA pattern of the monoethanedisulfonate of the quinazoline derivative of the present invention.

As the TGA pattern shown in FIG. 39, the decomposition temperature is 250° C., and the weight loss before decomposition is 1.2%. The actual content of the free base determined by HPLC is 74.2%, which is close to the theoretical value of 72.6%, so the acid/base molar ratio of the salt is 1:1.

Figure 40:
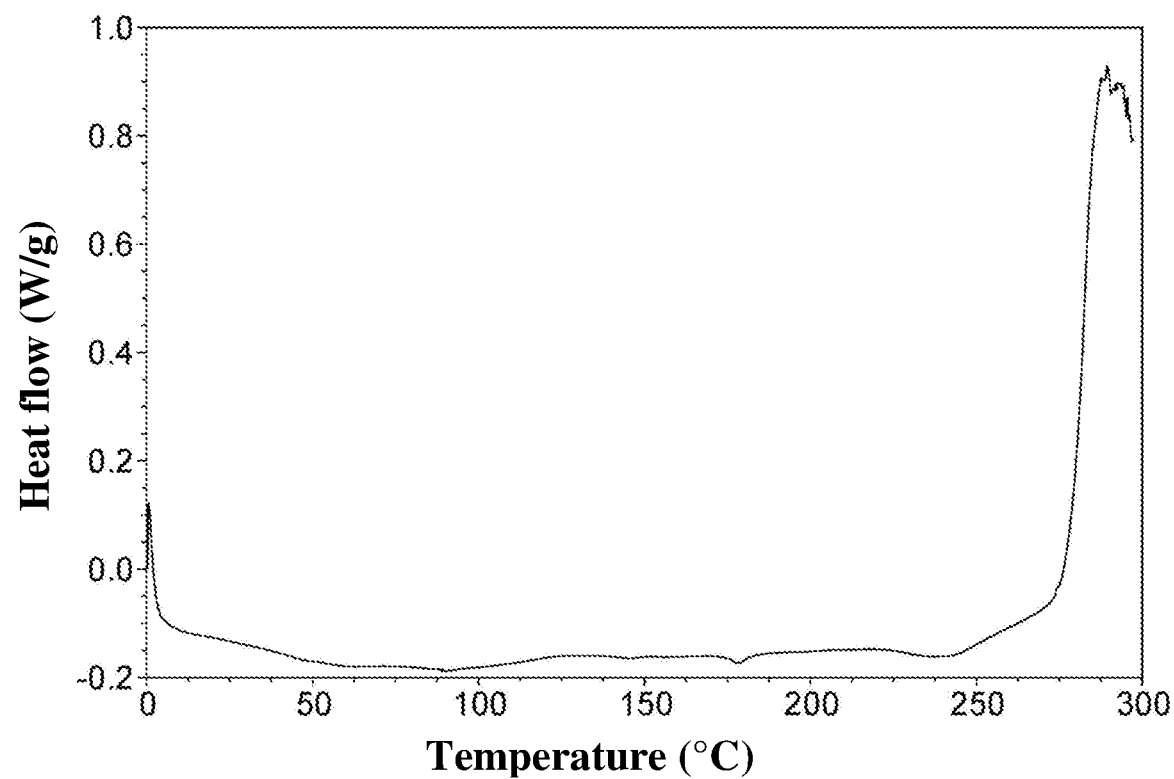
FIG. 40 is DSC pattern of the monoethanedisulfonate of the quinazoline derivative of the present invention.

As the DSC pattern shown in FIG. 40, the sample has no melting point.

Figure 41:
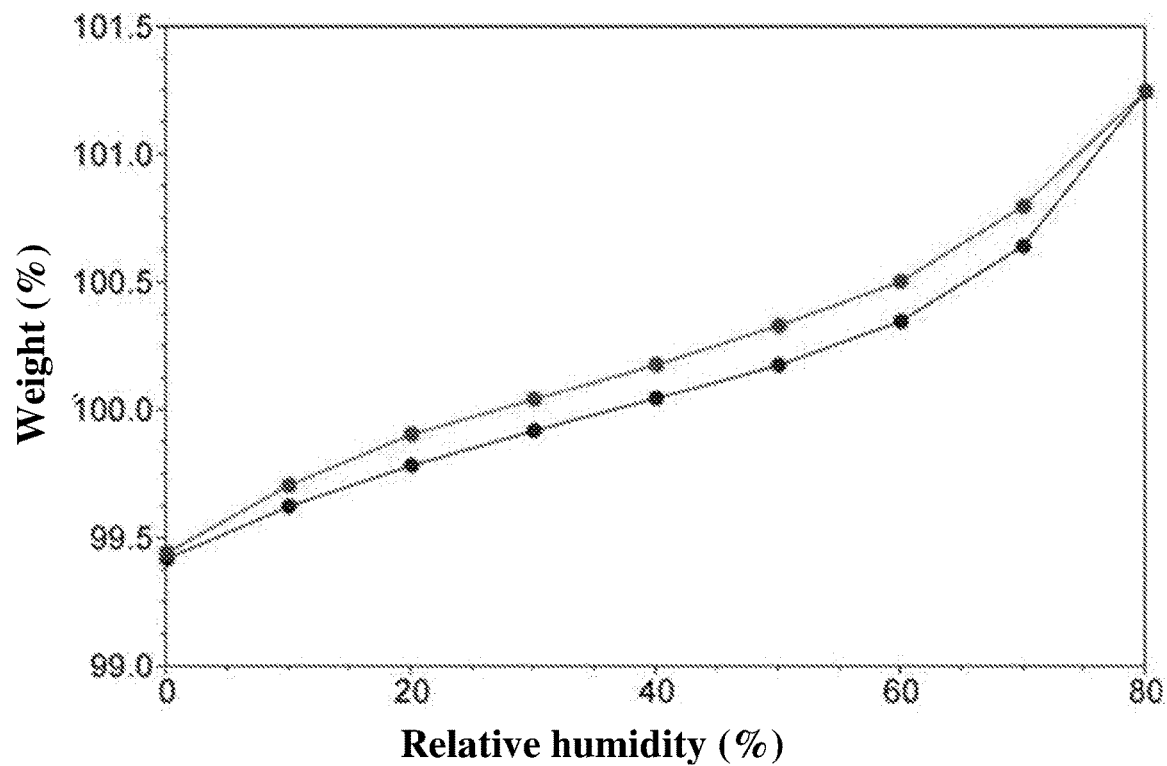
FIG. 41 is DVS pattern of the monoethanedisulfonate of the quinazoline derivative of the present invention.

As the DVS pattern shown in FIG. 41, the weight change in a relative humidity range of 20-80% is 1.46%.

20 mg of the compound represented by formula 1 was taken, followed by dissolving 16.6 mg of ethanedisulfonic acid in 0.4 mL of tetrahydrofuran, and the other conditions remained the same, and the given product was still the monoethanedisulfonate of the quinazoline derivative with the same XRPD.

Embodiment 35: Synthesis of the Monosulfate of the Quinazoline Derivative 10 mg of the compound represented by formula 1 was dissolved in 0.8 mL of tetrahydrofuran and the concentrated sulfuric acid containing 1.95 mg of $H_2SO_4$ was dissolved in 0.2 mL of tetrahydrofuran. The solution of sulfuric acid in tetrahydrofuran was added dropwise to the solution of the compound represented by formula 1 in tetrahydrofuran, accompanied by the turbidity formation, followed by stirring overnight, centrifugation, rinsing and drying to give the salt.

Figure 42:
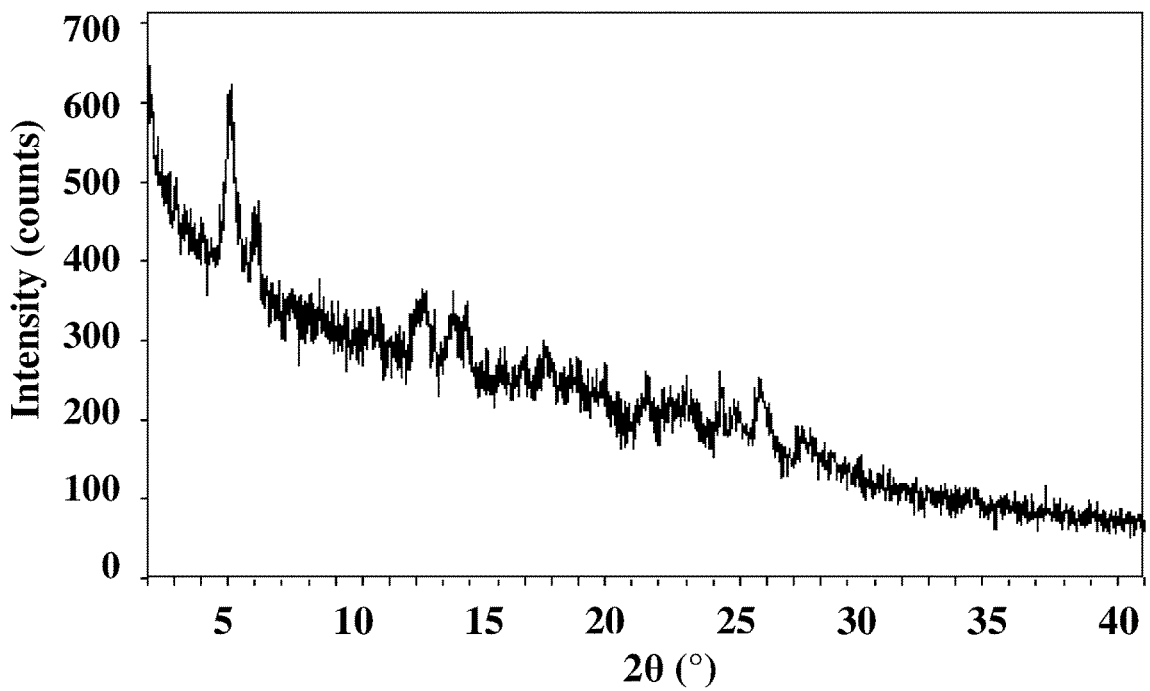
FIG. 42 is XRPD pattern of the monosulfate of the quinazoline derivative of the present invention.

The XRPD pattern is shown in FIG. 42.

As the TGA pattern shown in FIG. 43, the decomposition temperature is 230° C., and the weight loss before decomposition is 7.5%. The actual content of the free base determined by HPLC is 87.2%, which is close to the theoretical value of 83.6%, so the acid/base molar ratio of the salt is 1:1.

As the DSC pattern shown in FIG. 44, there is an endothermic peak below 124° C. and the melting point of the sample is 165° C.

Figure 45:
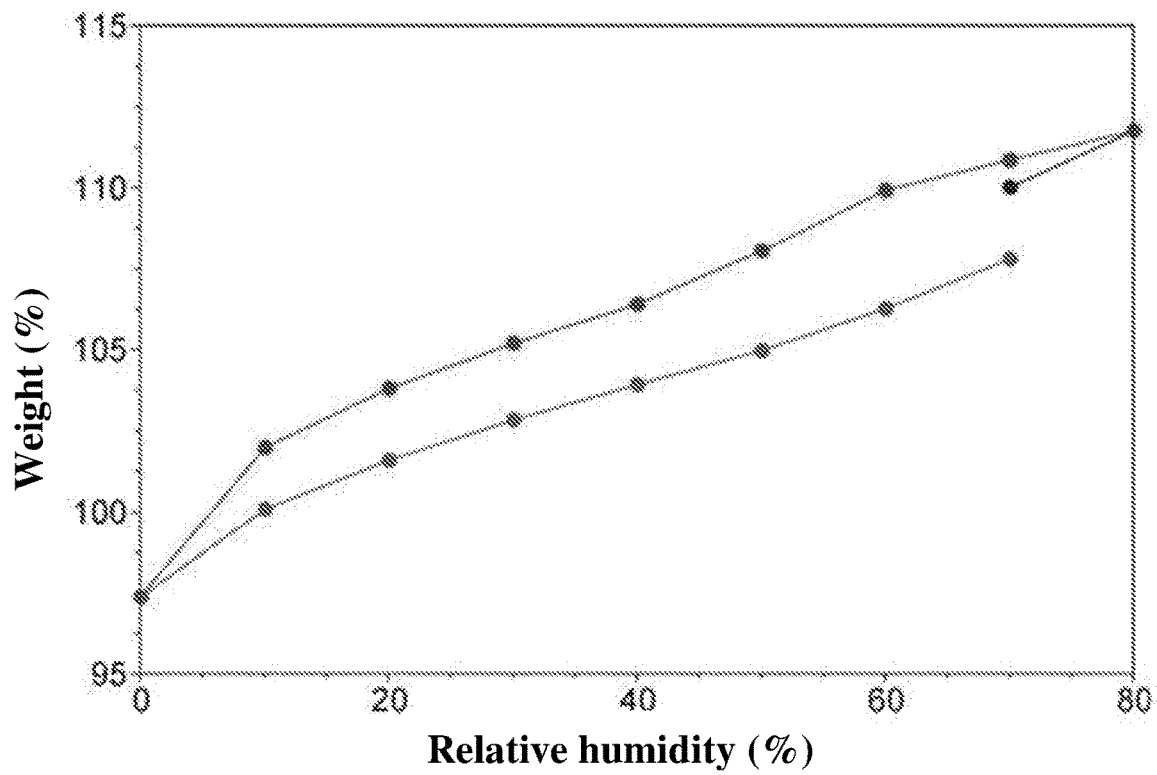
FIG. 45 is DVS pattern of the monosulfate of the quinazoline derivative of the present invention.

As the DVS pattern shown in FIG. 45, the weight change in a relative humidity range of 20-80% is 11.68%.

20 mg of the compound represented by formula 1 and the concentrated sulfuric acid containing 3.9 mg of $H_2SO_4$ were taken, and the other conditions remained the same, and the given product was still the monosulfate of the quinazoline derivative with the same XRPD.

20 mg of the compound represented by formula 1 was taken, followed by dissolving the concentrated sulfuric acid containing 5.06 mg of H$_2$SO$_4$ in 0.26 mL of tetrahydrofuran, and the other conditions remained the same, and the given product was still the monosulfate of the quinazoline derivative with the same XRPD.

Embodiment 36: Synthesis of the Disulfate of the Quinazoline Derivative 10 mg of the compound represented by formula 1 was dissolved in 0.8 mL of tetrahydrofuran and the concentrated sulfuric acid containing 5.85 mg of H$_2$SO$_4$ was dissolved in 0.2 mL of tetrahydrofuran. The solution of sulfuric acid in tetrahydrofuran was added dropwise to the solution of the compound represented by formula 1 in tetrahydrofuran, accompanied by the turbidity formation, followed by stirring overnight, centrifugation, rinsing and drying to give the salt.

Figure 46:
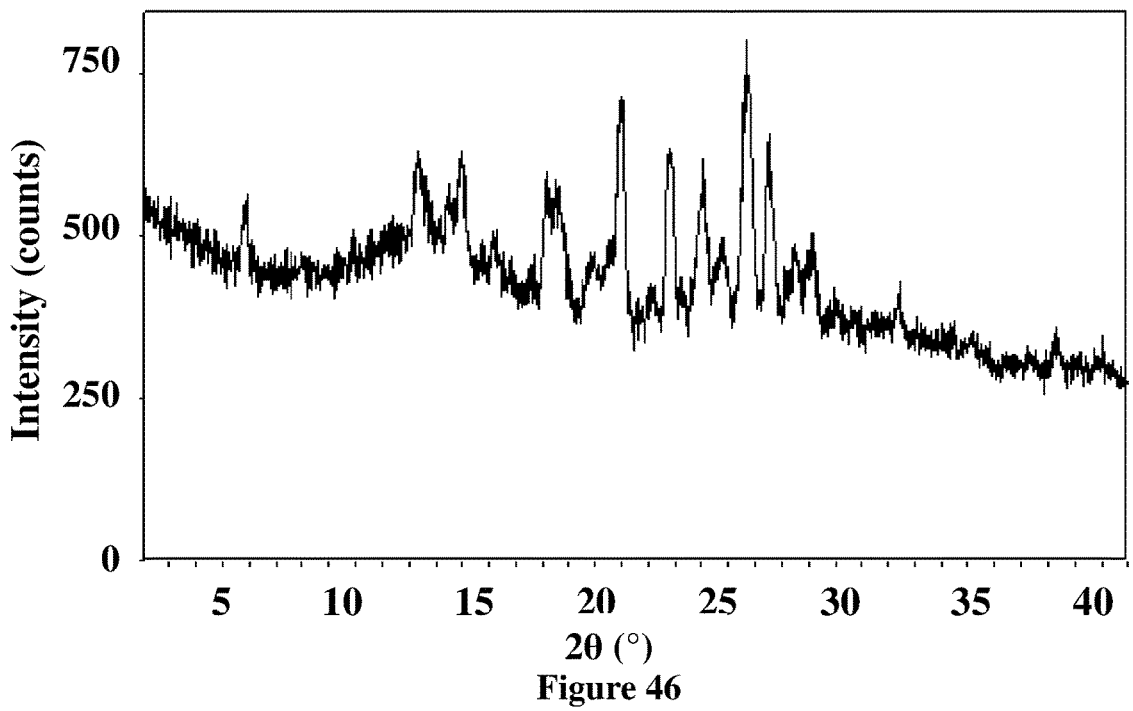
FIG. 46 is XRPD pattern of the disulfate of the quinazoline derivative of the present invention.

The XRPD pattern is shown in FIG. 46.

As the TGA pattern shown in FIG. 47, the decomposition temperature is 250° C., and the weight loss below 130° C. is 3.0%. The actual content of the free base determined by HPLC is 76.7%, which is close to the theoretical value of 72.0%, so the acid/base molar ratio of the salt is 2:1.

As the DSC pattern shown in FIG. 48, there are endothermic peaks below 74° C. and between 114-160° C. No melting peak appears within the range of 200° C.

Figure 49:
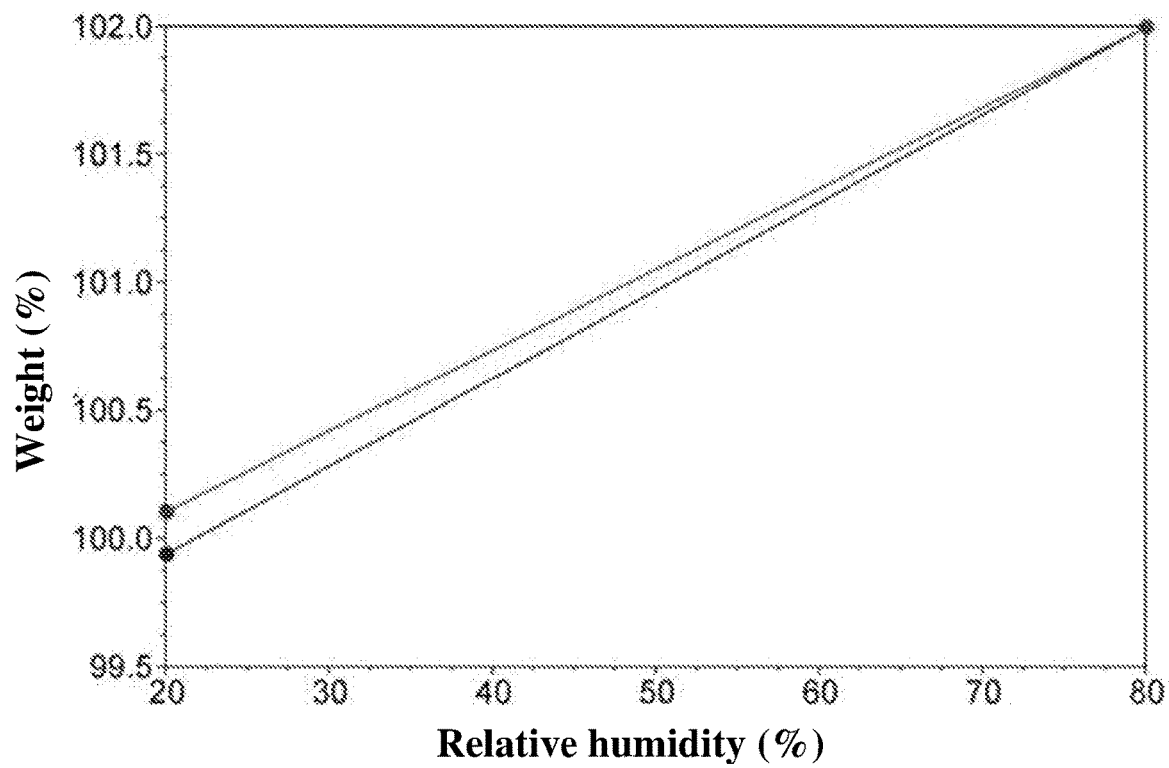
FIG. 49 is DVS pattern of the disulfate of the quinazoline derivative of the present invention.

As the DVS pattern shown in FIG. 49, the weight change in a relative humidity range of 20-80% is 2.0%.

20 mg of the compound represented by formula 1 was taken, followed by dissolving the concentrated sulfuric acid containing 8.56 mg of H$_2$SO$_4$ in 0.15 mL of tetrahydrofuran, and the other conditions remained the same, and the given product was still the disulfate of the quinazoline derivative with the same XRPD.

10 mg of the compound represented by formula 1 was taken, followed by dissolving the concentrated sulfuric acid containing 6.42 mg of H$_2$SO$_4$ in 0.2 mL of tetrahydrofuran, and the other conditions remained the same, and the given product was still the disulfate of the quinazoline derivative with the same XRPD.

Embodiment 37: Synthesis of the Monobenzenesulfonate of the Quinazoline Derivative 10 mg of the compound represented by formula 1 was dissolved in 0.8 mL of tetrahydrofuran and 3.14 mg of the benzenesulfonic acid was dissolved in 0.2 mL of tetrahydrofuran. The solution of benzenesulfonic acid in tetrahydrofuran was added dropwise to the solution of the compound represented by formula 1 in tetrahydrofuran, followed by stirring overnight accompanied by precipitation of the solids, centrifugation, rinsing and drying to give the salt.

Figure 50:
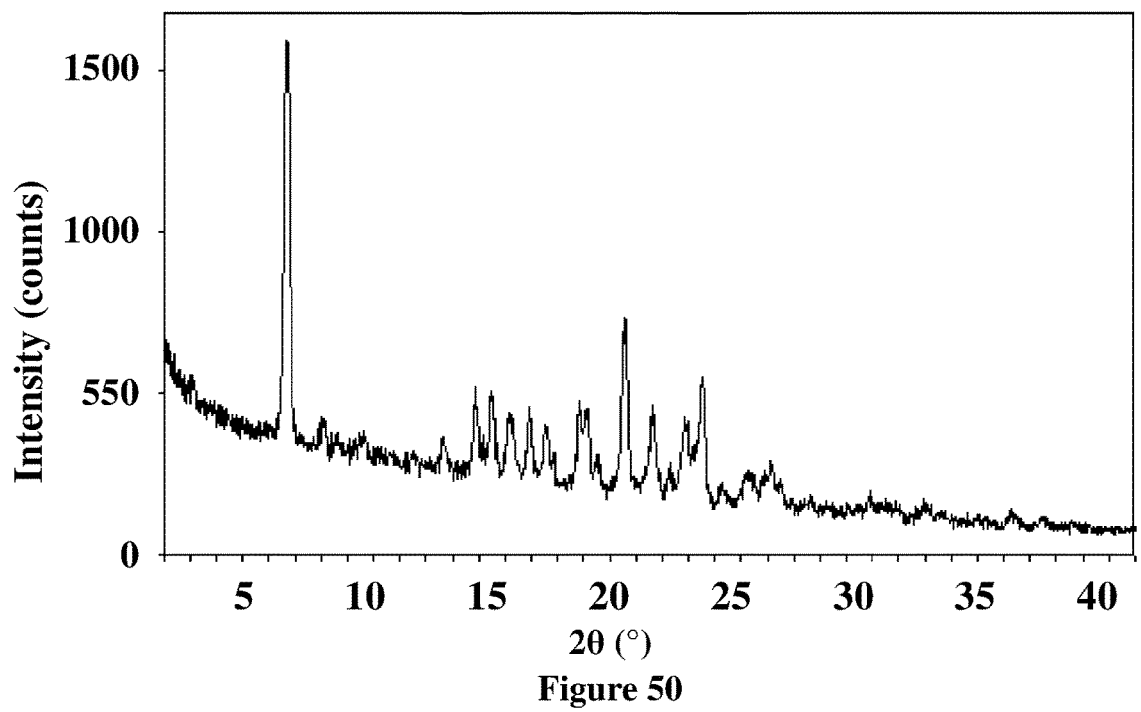
FIG. 50 is XRPD pattern of the monobenzenesulfonate of the quinazoline derivative of the present invention.

The XRPD pattern is shown in FIG. 50.

Figure 51:
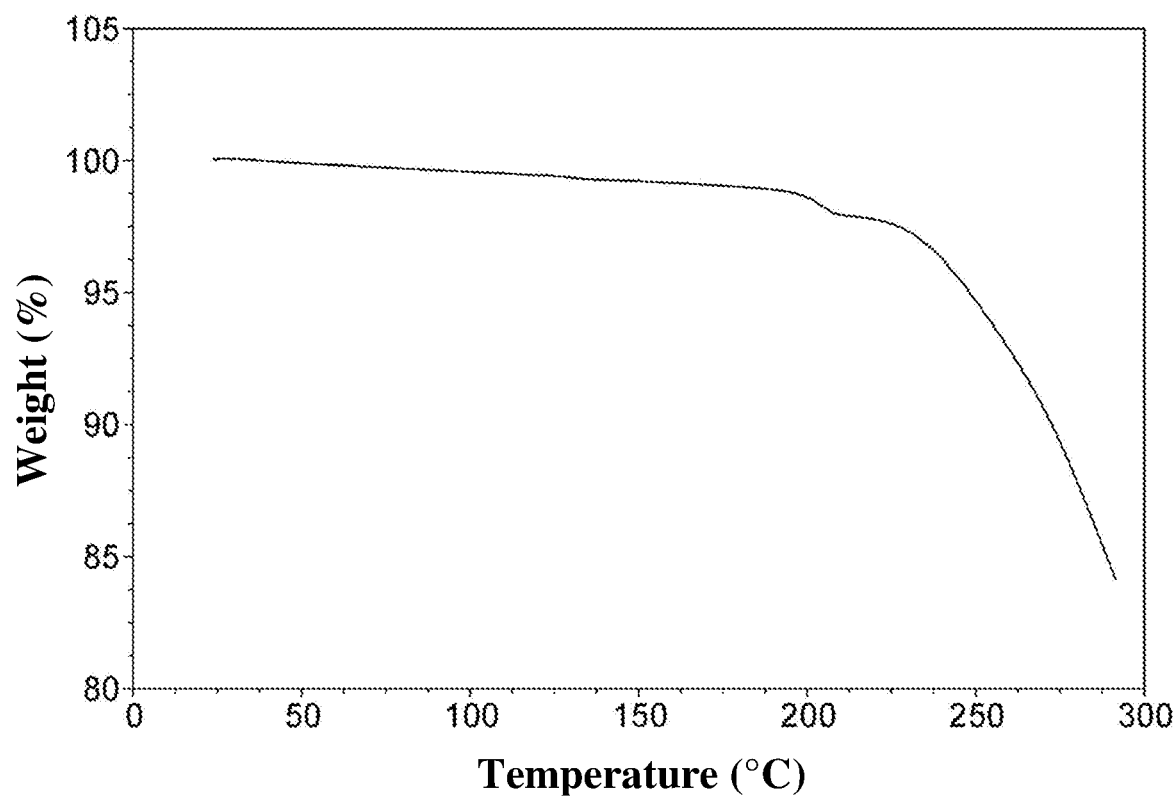
FIG. 51 is TGA pattern of the monobenzenesulfonate of the quinazoline derivative of the present invention.

As the TGA pattern shown in FIG. 51, the decomposition temperature is 199° C., and there is no significant weight loss before the decomposition.

Figure 52:
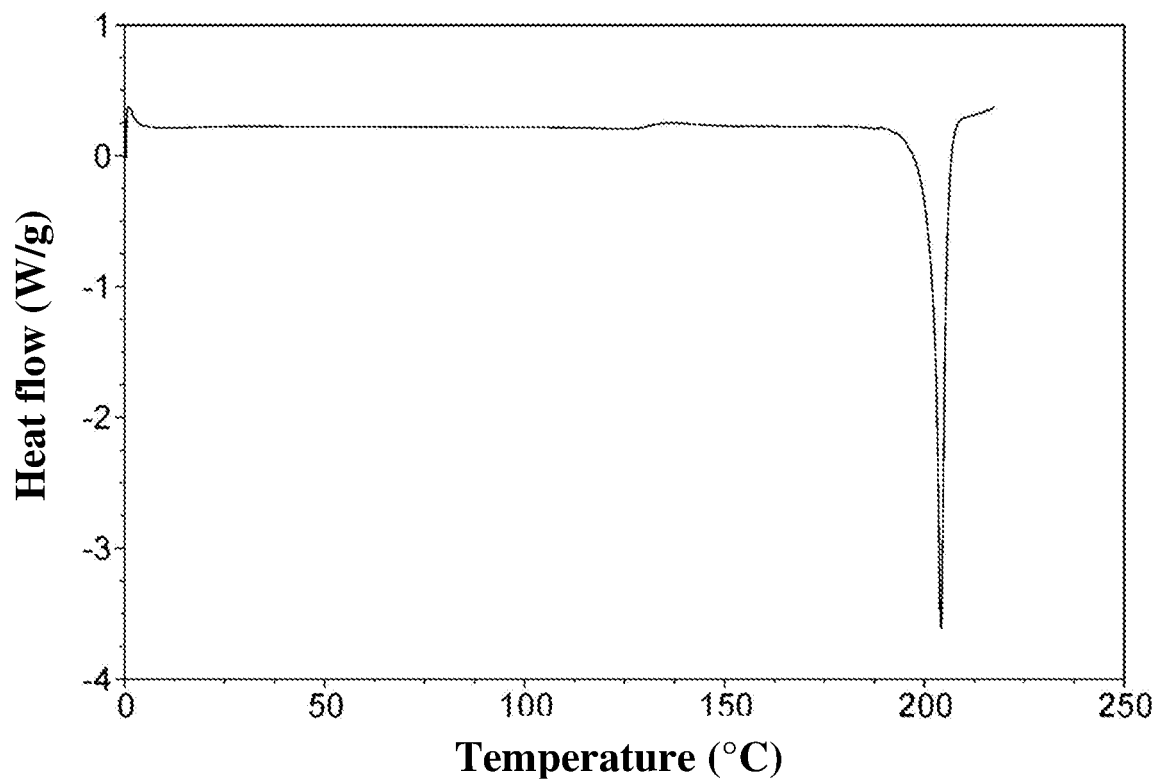
FIG. 52 is DSC pattern of the monobenzenesulfonate of the quinazoline derivative of the present invention.

As the DSC pattern shown in FIG. 52, the melting point of the sample is 199° C. and the decomposition occurs spontaneously after melting.

Figure 53:
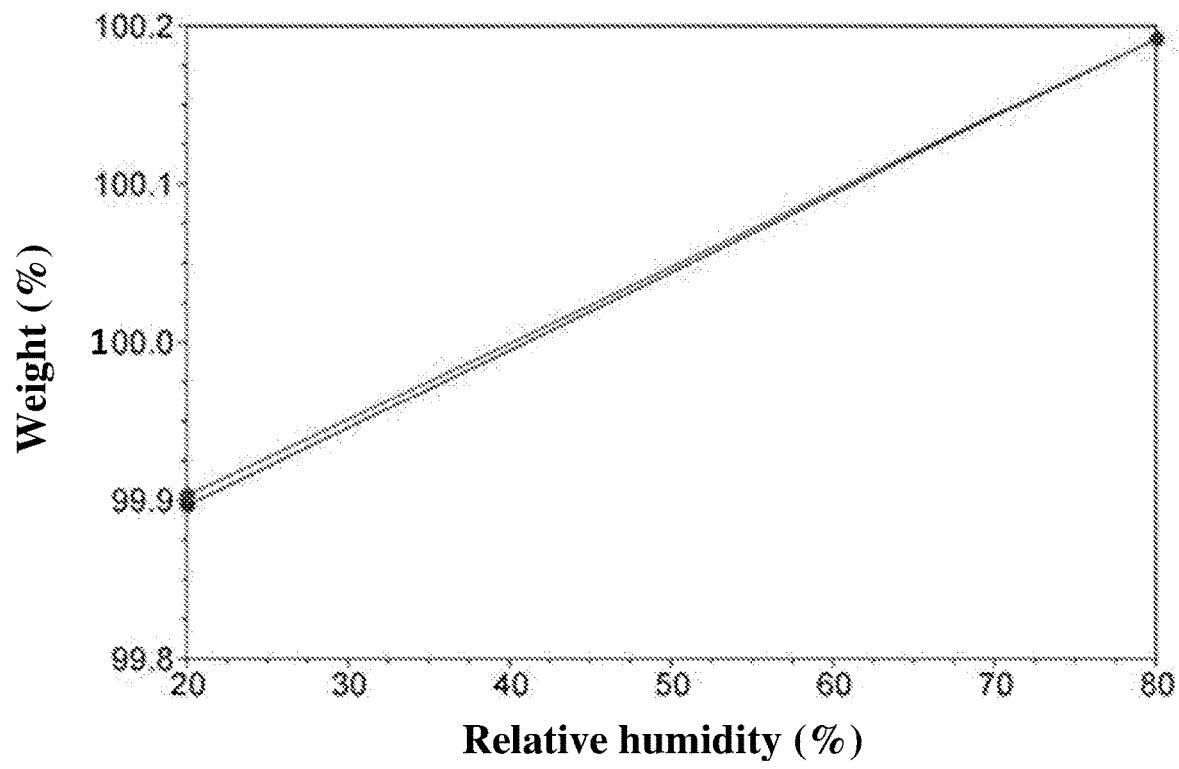
FIG. 53 is DVS pattern of the monobenzenesulfonate of the quinazoline derivative of the present invention.

As the DVS pattern shown in FIG. 53, the weight change in a relative humidity range of 20-80% is 0.3%.

20 mg of the compound represented by formula 1 and 6.28 mg of the benzenesulfonic acid were taken, and the other conditions remained the same, and the given product was still the monobenzenesulfonate of the quinazoline derivative with the same XRPD.

20 mg of the compound represented by formula 1 was taken, followed by dissolving 8.17 mg of the benzenesulfonic acid in 0.26 mL of tetrahydrofuran, and the other conditions remained the same, and the given product was still the monobenzenesulfonate of the quinazoline derivative with the same XRPD.

Embodiment 38: Synthesis of the Monohydrochloride Monohydrate of the Quinazoline Derivative 10 mg of the compound represented by formula 1 was dissolved in 0.8 mL of tetrahydrofuran and the concentrated hydrochloride acid containing 2.2 mg of HCl was dissolved in 0.2 mL of tetrahydrofuran. The solution of hydrochloride acid in tetrahydrofuran was added dropwise to the solution of the compound represented by formula 1 in tetrahydrofuran, accompanied by precipitation of the solids, followed by stirring overnight, centrifugation, rinsing and drying to give the salt.

Figure 54:
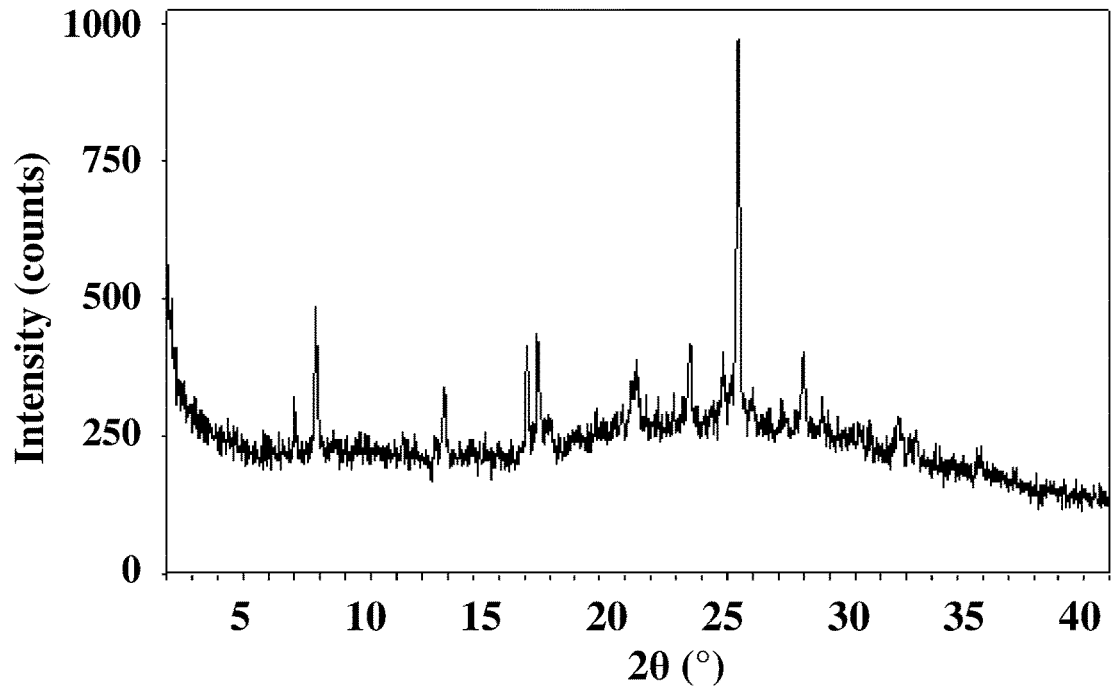
FIG. 54 is XRPD pattern of the monohydrochloride monohydrate of the quinazoline derivative of the present invention.

The XRPD pattern is shown in FIG. 54.

As the TGA pattern shown in FIG. 55, the decomposition of the sample occurs slightly at 156° C. and massively at 228° C., and the weight loss before decomposition is 3.3%, containing 1 mole of water. The actual content of the free base determined by HPLC is 93.4%, which is close to the theoretical value of 93.2%, so the acid/base molar ratio of the salt is 1:1.

As the DSC pattern shown in FIG. 56, the sample has no melting point.

Figure 57:
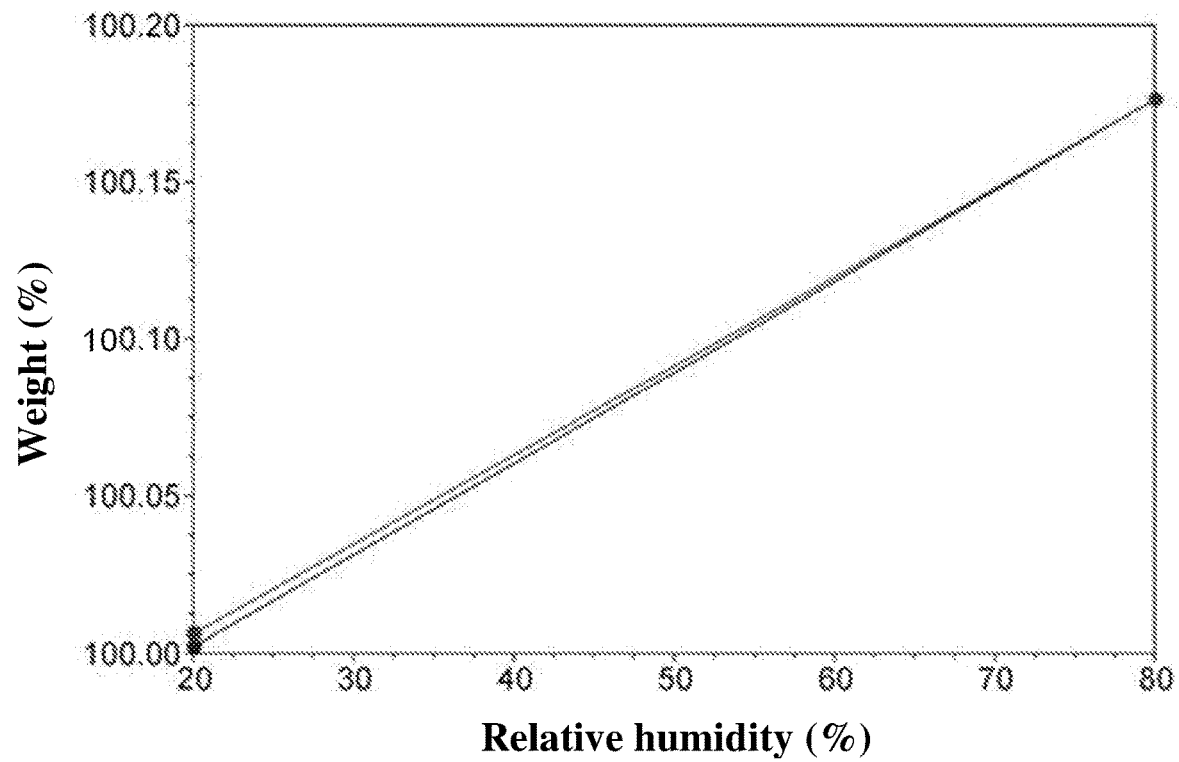
FIG. 57 is DVS pattern of the monohydrochloride monohydrate of the quinazoline derivative of the present invention.

As the DVS pattern shown in FIG. 57, the weight change in a relative humidity range of 20-80% is 0.17%.

20 mg of the compound represented by formula 1 was taken, followed by dissolving the concentrated hydrochloride acid containing 1.59 mg of HCl in 0.072 mL of tetrahydrofuran, and the other conditions remained the same, and the given product was still the monohydrochloride monohydrate of the quinazoline derivative with the same XRPD.

10 mg of the compound represented by formula 1 was taken, followed by dissolving the concentrated hydrochloride acid containing 2.39 mg of HCl in 0.21 mL of tetrahydrofuran, and the other conditions remained the same, and the given product was still the monohydrochloride monohydrate of the quinazoline derivative with the same XRPD.

Embodiment 39: Synthesis of the Mono-D-Gluconate Monohydrate of the Quinazoline Derivative 10 mg of the compound represented by formula 1 was dissolved in 2 mL of dichloromethane and 3.89 mg of the D-gluconic acid was dissolved in 1 mL of dichloromethane. The solution of the compound represented by formula 1 in dichloromethane was added dropwise to the solution of D-gluconic acid in dichloromethane, followed by stirring overnight accompanied by precipitation of the solids, centrifugation, rinsing and drying to give the salt.

Figure 58:
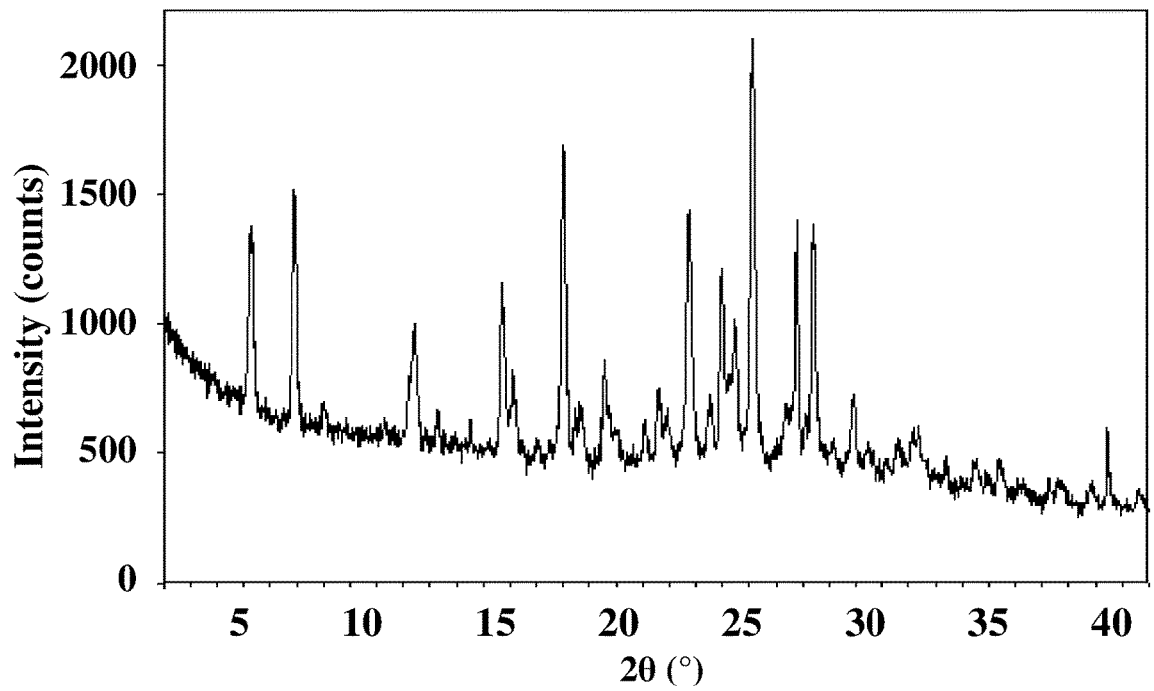
FIG. 58 is XRPD pattern of the mono-D-gluconate of the quinazoline derivative of the present invention.

The XRPD pattern is shown in FIG. 58.

As the TGA pattern shown in FIG. 59, the decomposition temperature is 180° C., and there is no significant weight loss before decomposition. The actual content of the free base determined by HPLC is 64.5%, which is close to the theoretical value of 72.0%. Moreover, the DSC pattern of FIG. 60 shows that the product contains some free D-gluconic acids (having an endothermic peak at melting point of D-gluconic acid of 131° C.), so the acid/base molar ratio of the salt is 1:1.

As the DSC pattern shown in FIG. 60, the melting point of the sample is 193° C., and the decomposition of the sample occurs after melting.

Figure 61:
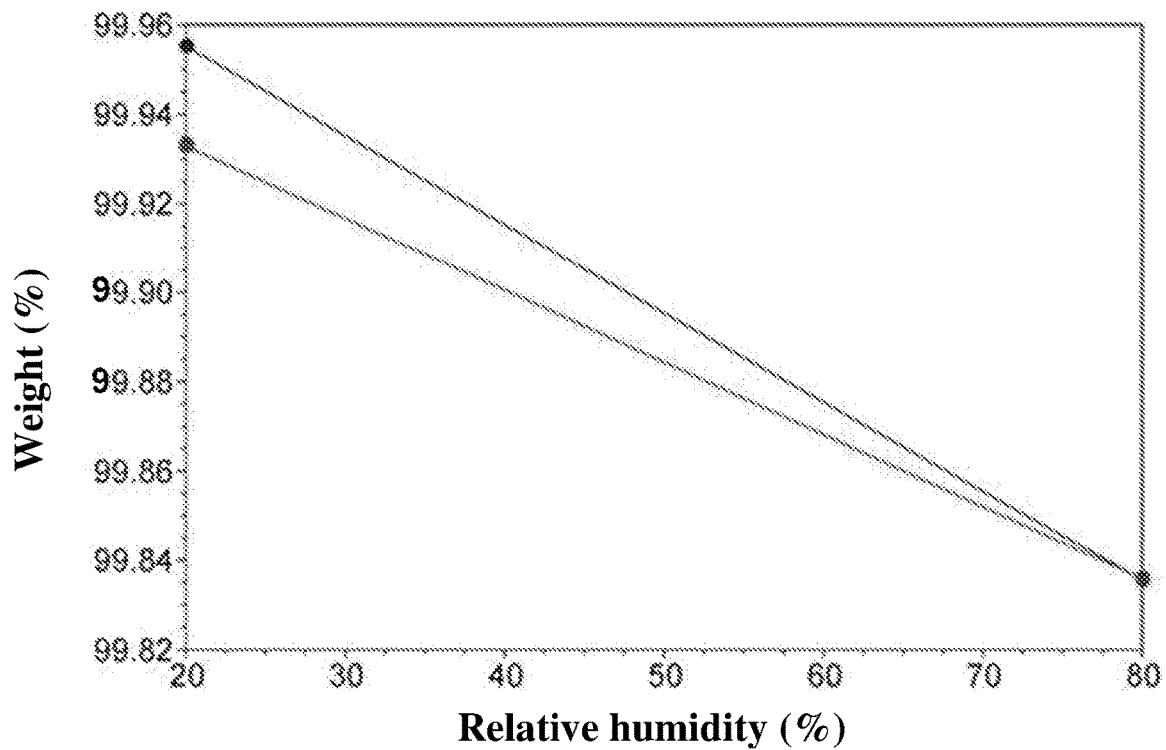
FIG. 61 is DVS pattern of the mono-D-gluconate of the quinazoline derivative of the present invention.

As the DVS pattern shown in FIG. 61, the weight change in a relative humidity range of 20-80% is 0.12%.

20 mg of the compound represented by formula 1 was taken, followed by dissolving 23.62 mg of the D-gluconic acid in 7.87 mL of dichloromethane, or in 4.72 mL of dichloromethane to form a suspension, and the other conditions remained the same, and the given product was still the mono-D-gluconate of the quinazoline derivative with the same XRPD.

Embodiment 40: Synthesis of the Mono-L-Tartrate (Crystal Form 15) of the Quinazoline Derivative 10 mg of the compound represented by formula 1 was dissolved in 0.8 mL of tetrahydrofuran and 2.98 mg of the L-tartaric acid was dissolved in 0.2 mL of tetrahydrofuran. The solution of L-tartaric acid in tetrahydrofuran was added dropwise to the solution of the compound represented by formula 1 in tetrahydrofuran, followed by stirring overnight accompanied by precipitation of the solids, centrifugation, rinsing and drying to give the salt.

Figure 62:
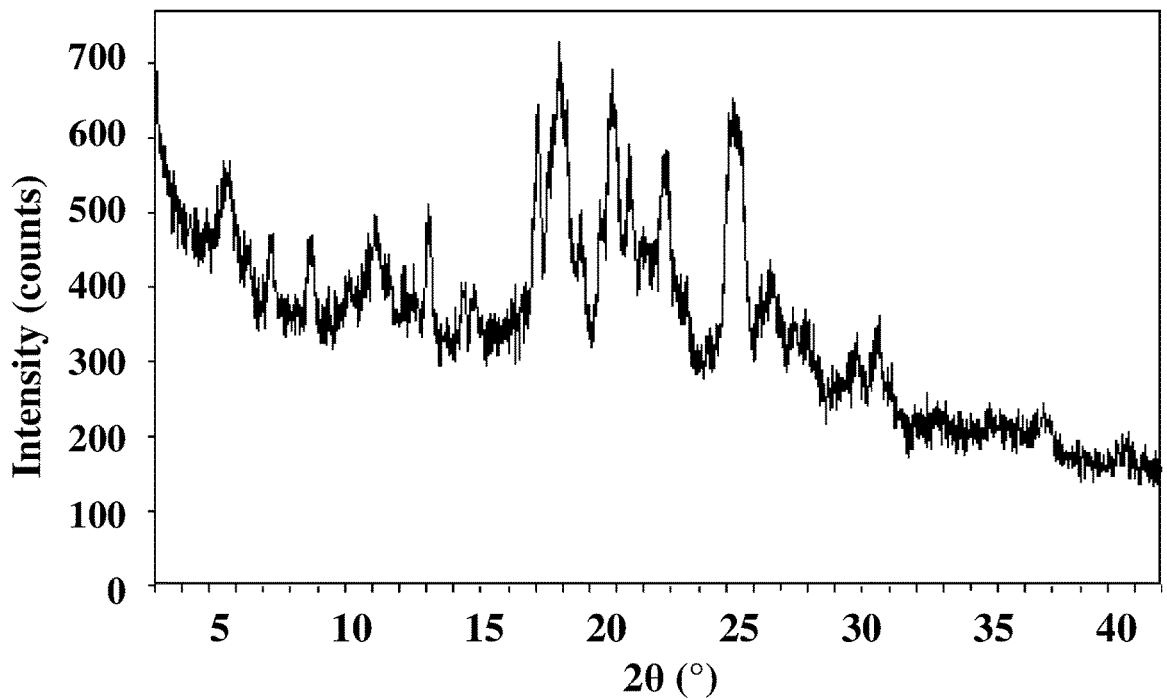
FIG. 62 is XRPD pattern of the mono-L-tartrate of the quinazoline derivative of the present invention.

The XRPD pattern is shown in FIG. 62.

Figure 63:
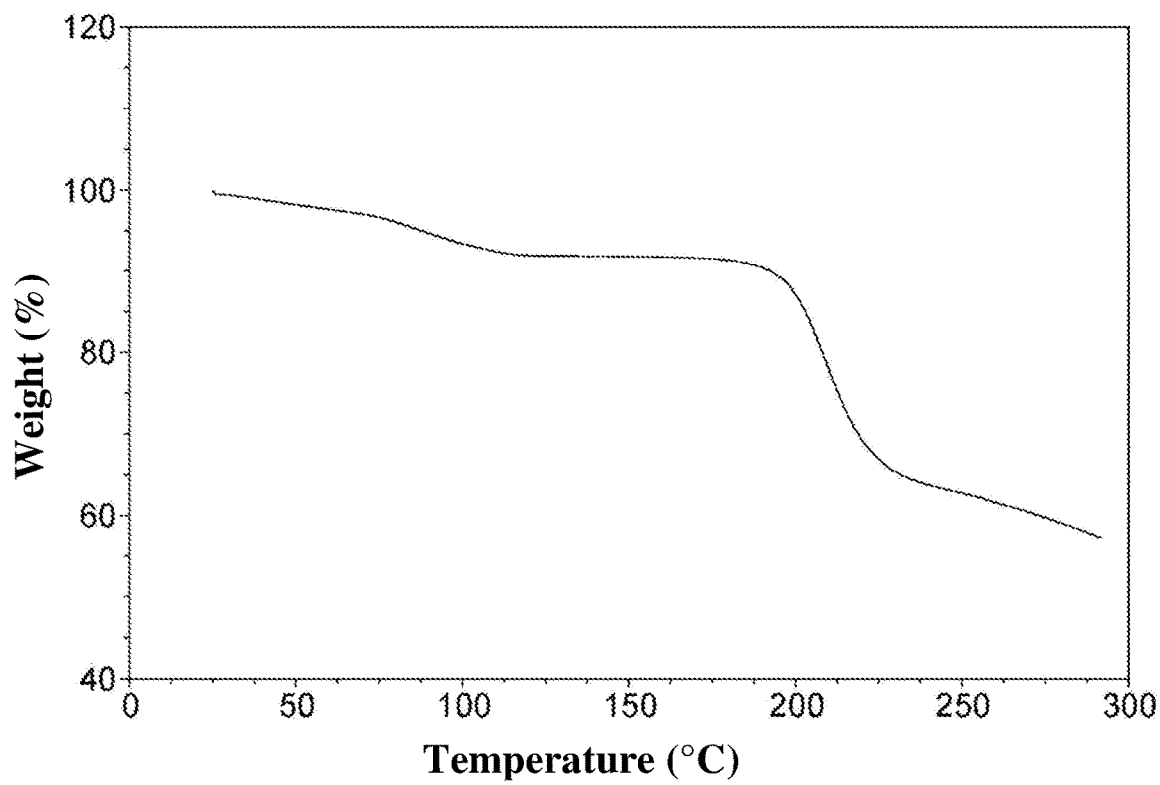
FIG. 63 is TGA pattern of the mono-L-tartrate of the quinazoline derivative of the present invention.

As the TGA pattern shown in FIG. 63, the decomposition of the sample occurs at 198° C., and the weight loss before decomposition is 8.1%. The actual content of the free base determined by HPLC is 72.0%, which is close to the theoretical value of 77.0%, so the acid/base molar ratio of the salt is 1:1.

20 mg of the compound represented by formula 1 and 5.96 mg of the L-tartaric acid were taken, and the other conditions remained the same, and the given product was still the mono-L-tartrate (crystal form 15) of the quinazoline derivative with the same XRPD.

Embodiment 41: Synthesis of the Mono-L-Tartrate Tetrahydrate (Crystal Form 16) Monohydrate of the Quinazoline Derivative 30 mg of the compound represented by formula 1 was dissolved in 2.5 mL of tetrahydrofuran and 17.87 mg of the L-tartaric was dissolved in 1 mL of tetrahydrofuran. The solution of the compound represented by formula 1 in tetrahydrofuran was added dropwise to the solution of L-tartaric acid in tetrahydrofuran, followed by stirring overnight accompanied by precipitation of the solids, centrifugation and rinsing. Water was added thereto for dissolving and stirred for 6 hours until the complete precipitation of the solids, followed by centrifugation removing the water to give the salt.

Figure 64:
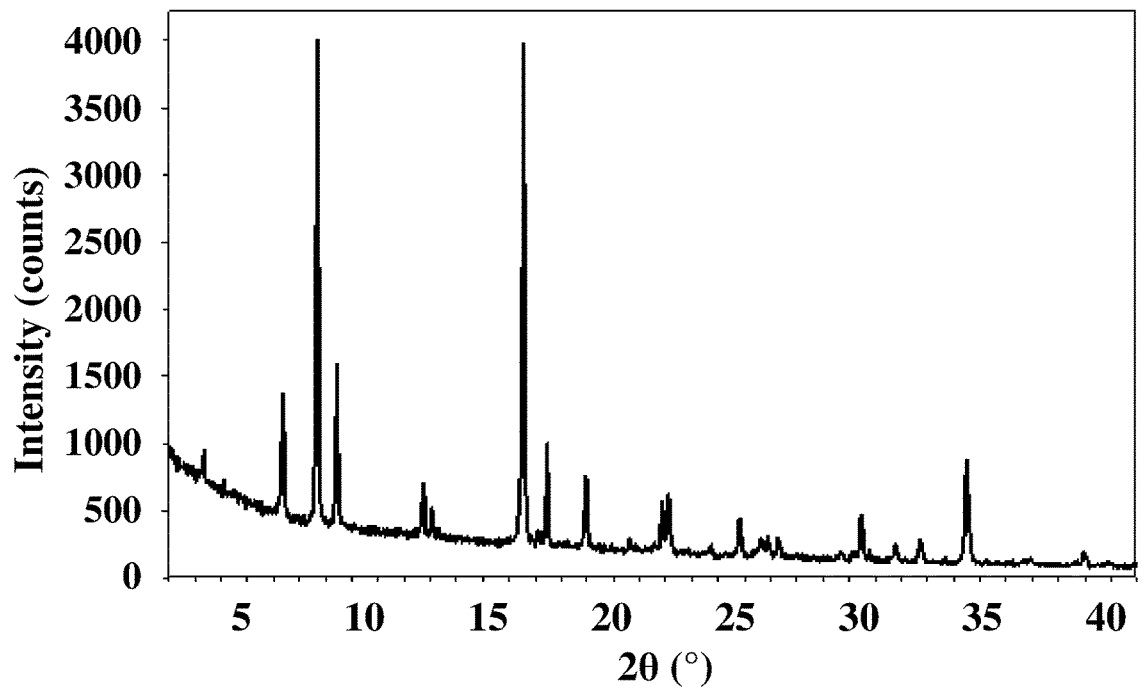
FIG. 64 is XRPD pattern of the mono-L-tartrate tetrahydrate of the quinazoline derivative of the present invention.

The XRPD pattern is shown in FIG. 64.

As the TGA pattern shown in FIG. 65, the decomposition of the sample occurs at 194° C., and the weight loss before decomposition is 9.5%.

As the DSC pattern shown in FIG. 66, there is an endothermic peak below 106° C. and the sample has no melting point.

Figure 67:
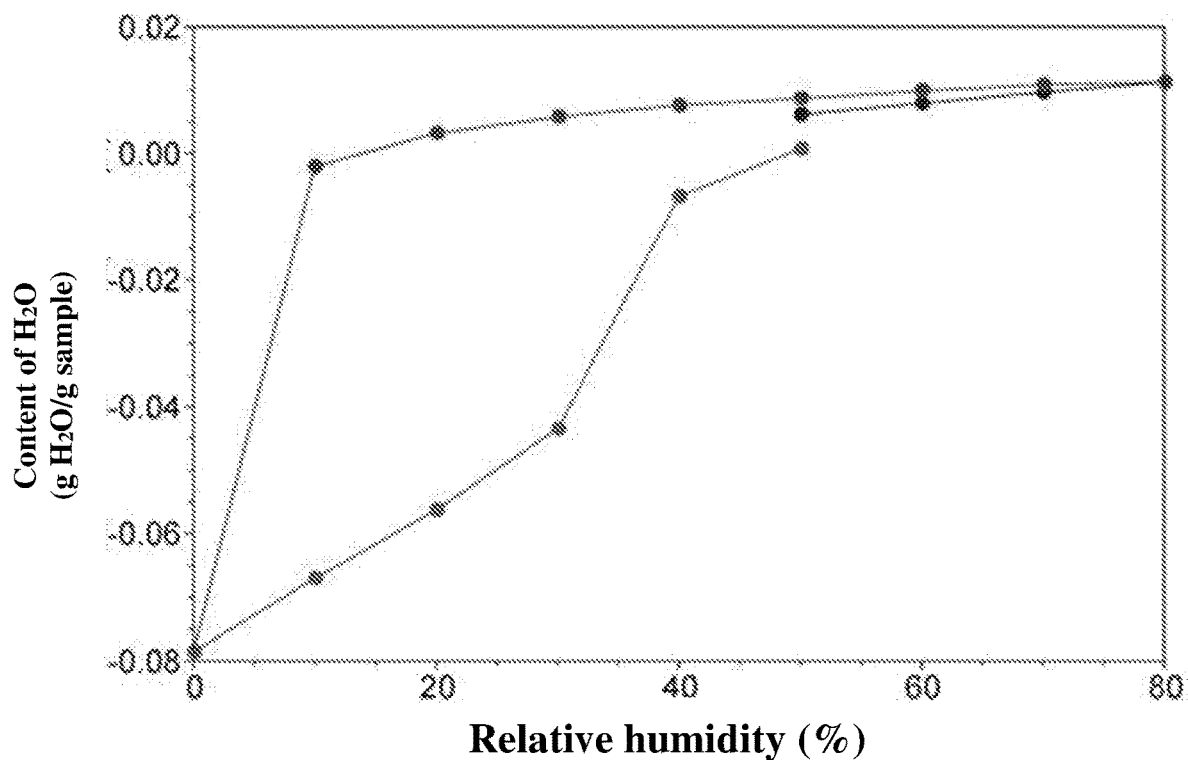
FIG. 67 is DVS pattern of the mono-L-tartrate tetrahydrate of the quinazoline derivative of the present invention.

As the DVS pattern shown in FIG. 67, the weight change in a relative humidity range of 20-80% is 0.8% and large amounts of water is eliminated rapidly at the relative humidity of 10%.

Embodiment 42: Synthesis of the Diphosphonate of the Quinazoline Derivative 10 mg of the compound represented by formula 1 was dissolved in 0.8 mL of tetrahydrofuran and 4.56 mg of 85% phosphoric acid was dissolved in 0.5 mL of tetrahydrofuran. The solution of phosphoric acid in tetrahydrofuran was added dropwise to the solution of the compound represented by formula 1 in tetrahydrofuran, accompanied by the simultaneous precipitation of the solids, followed by stirring overnight, centrifugation, rinsing and drying to give the salt.

Figure 68:
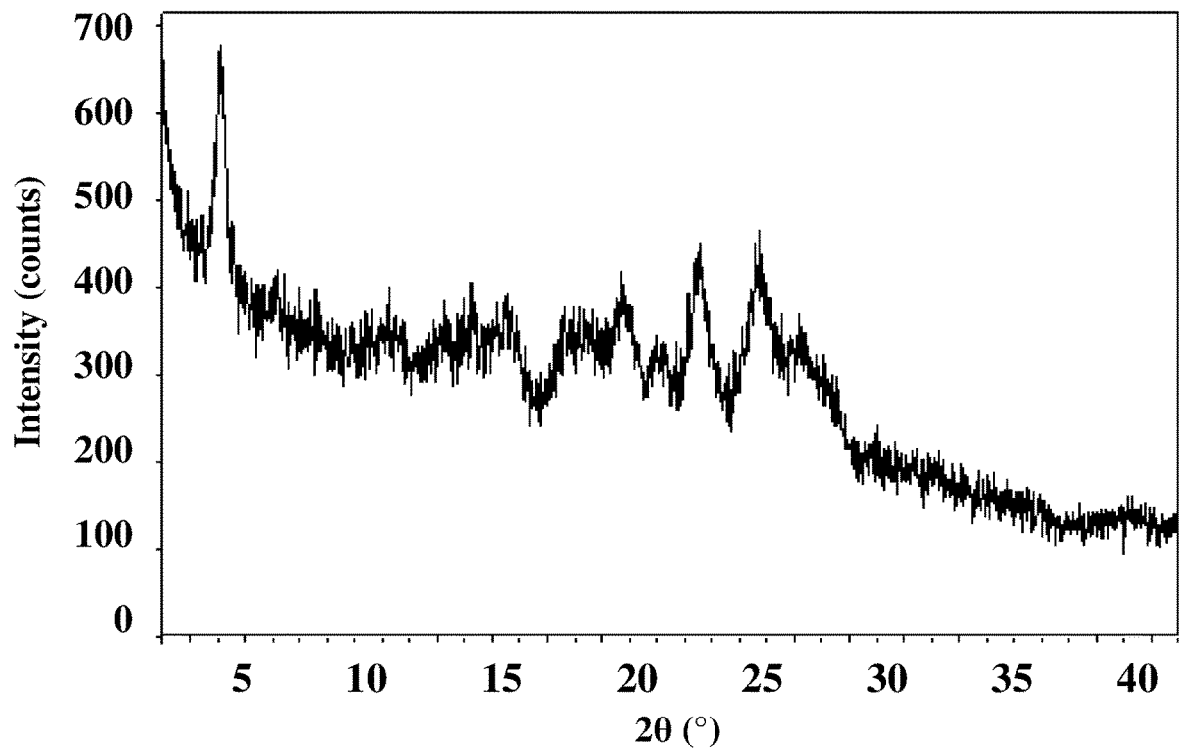
FIG. 68 is XRPD pattern of the diphosphonate of the quinazoline derivative of the present invention.

The XRPD pattern is shown in FIG. 68.

Figure 69:
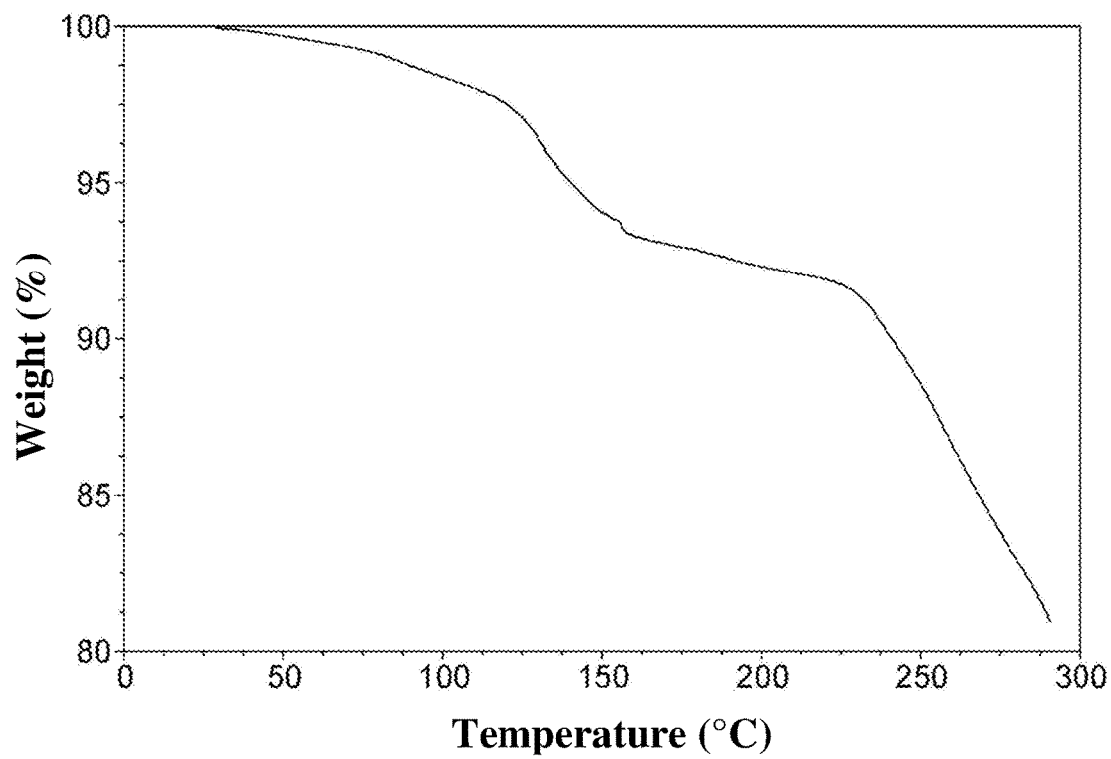
FIG. 69 is TGA pattern of the diphosphonate of the quinazoline derivative of the present invention.

As the TGA pattern shown in FIG. 69, the decomposition of the sample occurs at 234° C., and the weight loss before decomposition is 7.1%. The actual content of the free base determined by HPLC is 73.3%, which is close to the theoretical value of 72.0%, so the acid/base molar ratio of the salt is 2:1.

20 mg of the compound represented by formula 1 was taken, followed by dissolving 4.28 mg of 85% phosphoric acid in 0.28 mL of tetrahydrofuran, and the other conditions remained the same, and the given product was still the diphosphonate of the quinazoline derivative with the same XRPD.

10 mg of the compound represented by formula 1 was taken, followed by dissolving 6.42 mg of 85% phosphoric acid in 0.5 mL of tetrahydrofuran, and the other conditions remained the same, and the given product was still the diphosphonate of the quinazoline derivative with the same XRPD.

Embodiment 43: Synthesis of the Monopamoate of the Quinazoline Derivative 10 mg of the compound represented by formula 1 was dissolved in 0.8 mL of tetrahydrofuran and 7.71 mg of the pamoic acid was dissolved in 0.5 mL of tetrahydrofuran to form a suspension. The solution of the compound represented by formula 1 in tetrahydrofuran was added dropwise to the suspension of pamoic acid in tetrahydrofuran, accompanied by the dissolving of the pamoic acid and the precipitation of the solids after stirring for 1 hour, followed by stirring overnight, centrifugation, rinsing and drying to give the salt.

Figure 70:
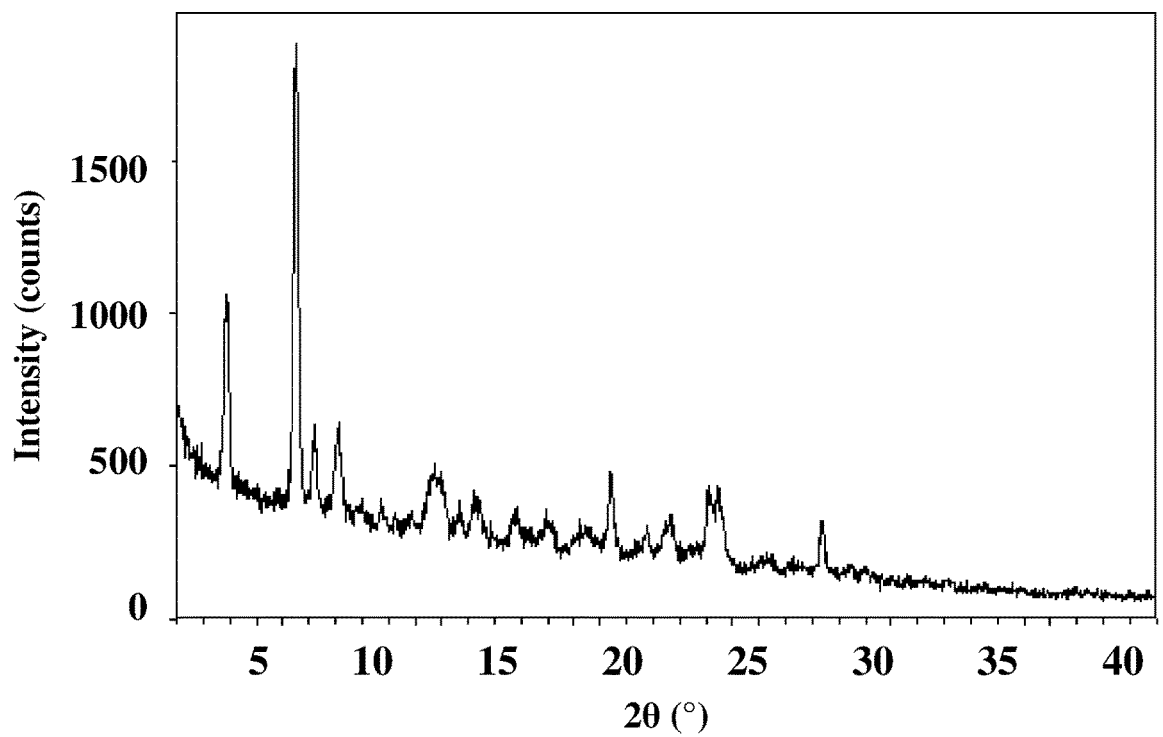
FIG. 70 is XRPD pattern of the monopamoate of the quinazoline derivative of the present invention.

The XRPD pattern is shown in FIG. 70.

20 mg of the compound represented by formula 1 and 5 mg or 10 mg of pamoic acid were taken, and the other conditions remained the same, and the given product was still the monopamoate of the quinazoline derivative with the same XRPD.

Embodiment 44: Synthesis of the Mono-p-Toluenesulfonate of the Quinazoline Derivative 10 mg of the compound represented by formula 1 was dissolved in 0.8 mL of chloroform and 4.53 mg of the p-toluenesulfonate monohydrate was dissolved in 0.1 mL of ethanol. The solution of p-toluenesulfonic acid in ethanol was added dropwise to the solution of the compound represented by formula 1 in chloroform, followed by stirring overnight accompanied by the precipitation of the solids, centrifugation, rinsing and drying to give the salt.

Figure 71:
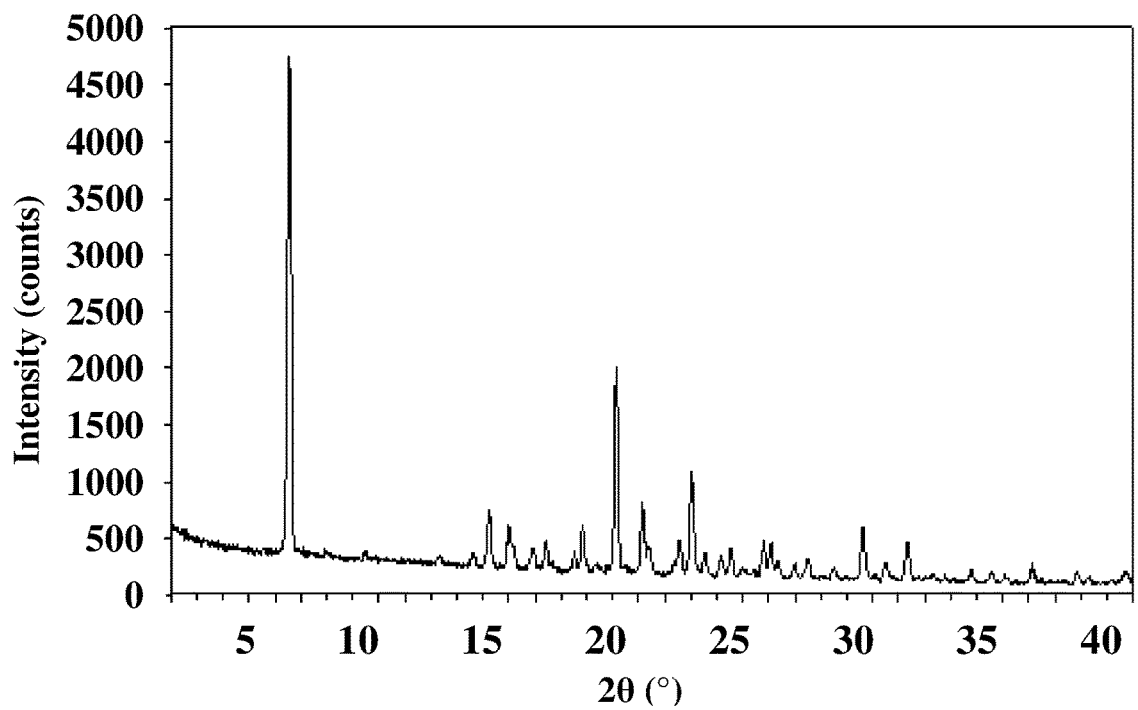
FIG. 71 is XRPD pattern of the mono-p-toluenesulfonate of the quinazoline derivative of the present invention.

The XRPD pattern is shown in FIG. 71.

Figure 72:
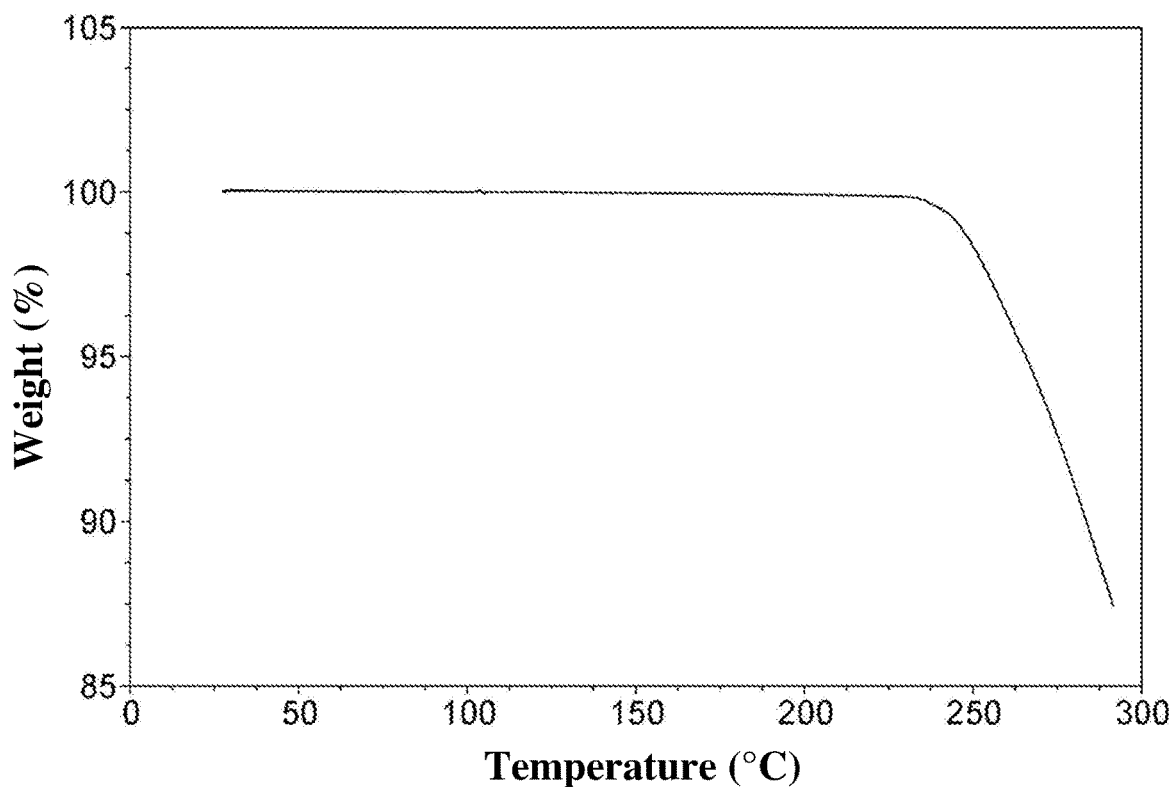
FIG. 72 is TGA pattern of the mono-p-toluenesulfonate of the quinazoline derivative of the present invention.

As the TGA pattern shown in FIG. 72, the decomposition of the sample occurs at 245° C., and there is no weight loss before decomposition. The actual content of the free base determined by HPLC is 77.4%, which is close to the theoretical value of 74.6%, so the acid/base molar ratio of the salt is 1:1.

20 mg of the compound represented by formula 1 and 9.06 mg of the p-toluenesulfonate monohydrate were taken, and the other conditions remained the same, and the given product was still the mono-p-toluenesulfonate of the quinazoline derivative with the same XRPD.

Embodiment 45: Synthesis of the Diglycolate of the Quinazoline Derivative 10 mg of the compound represented by formula 1 was dissolved in 2 mL of dichloromethane and 3.1 mg of the glycolic acid was added in 0.5 mL of dichloromethane to form a suspension. The solution of the compound represented by formula 1 in dichloromethane was added dropwise to the suspension of glycolic acid in dichloromethane, followed by stirring overnight accompanied by the precipitation of the solids, centrifugation, rinsing and drying to give the salt.

Figure 73:
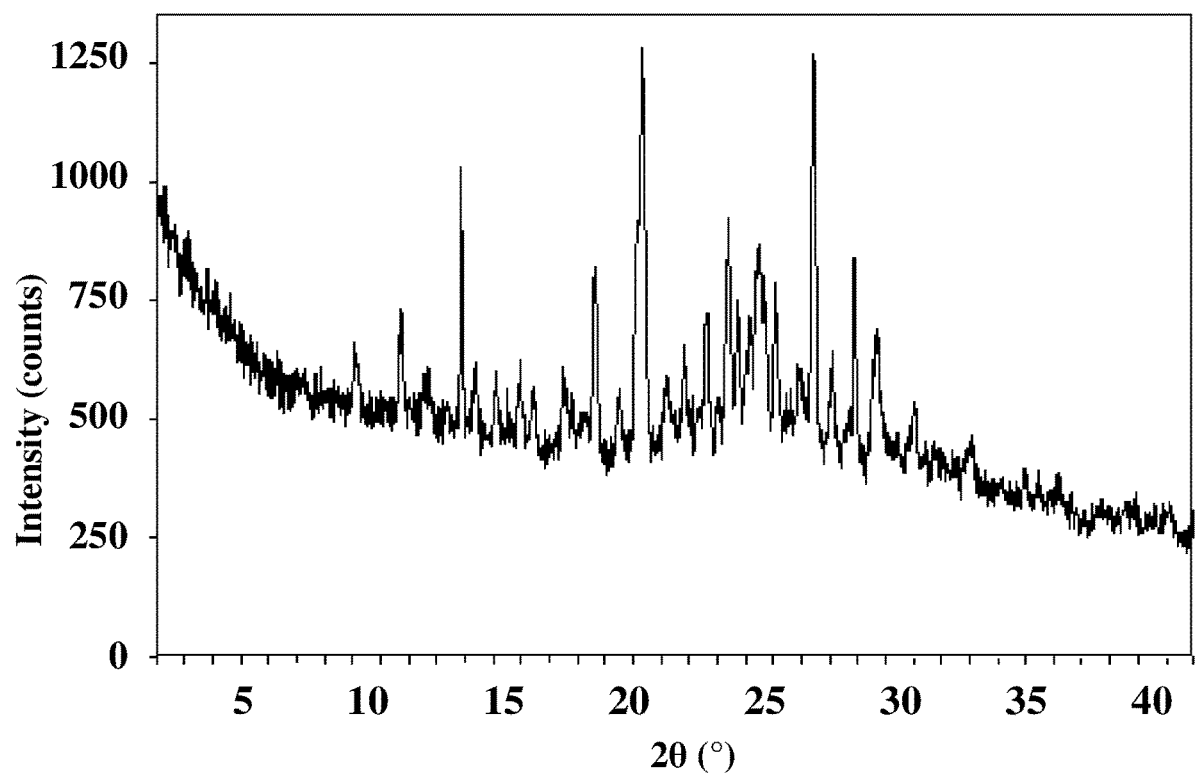
FIG. 73 is XRPD pattern of the diglycolate of the quinazoline derivative of the present invention.

The XRPD pattern is shown in FIG. 73.

20 mg of the compound represented by formula 1 and 2.5 mg or 5 mg of glycolic acid were taken, and the other conditions remained the same, and the given product was still the diglycolate of the quinazoline derivative with the same XRPD.

Embodiment 46: Synthesis of the Monomalonate of the Quinazoline Derivative 10 mg of the compound represented by formula 1 was dissolved in 2 mL of dichloromethane and 2.06 mg of the malonic acid was added in 0.5 mL of dichloromethane to form a suspension. The solution of the compound represented by formula 1 in dichloromethane was added dropwise to the suspension of malonic acid in dichloromethane, followed by stirring overnight, centrifugation, rinsing and drying to give the salt.

Figure 74:
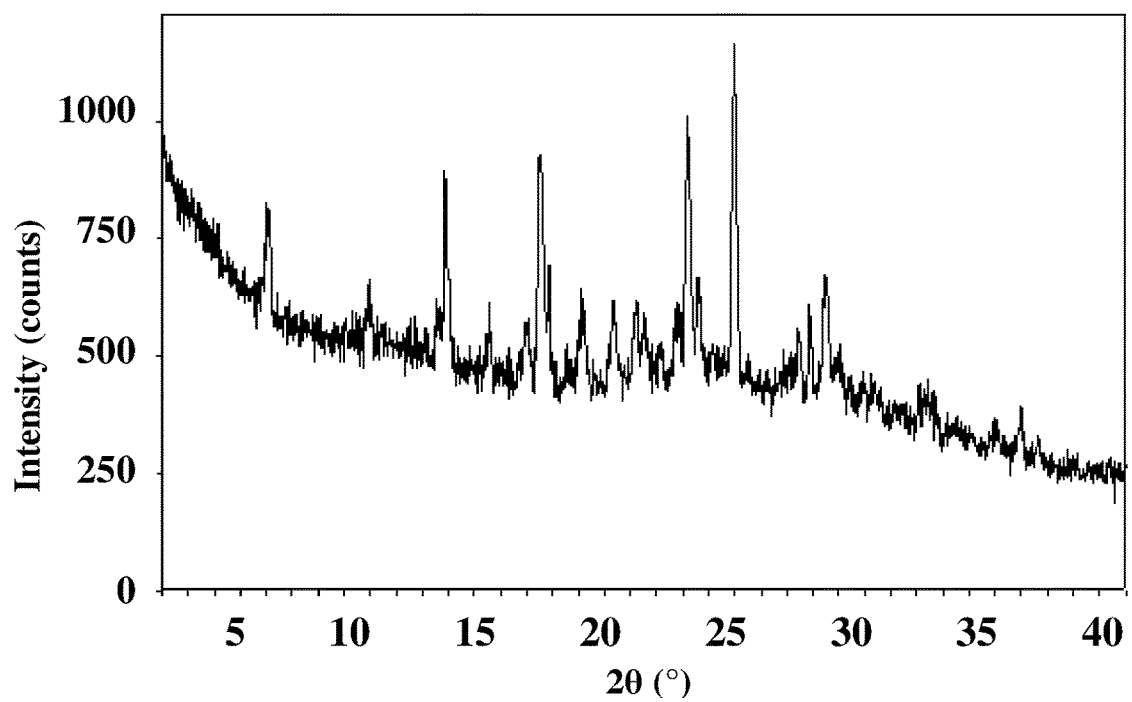
FIG. 74 is XRPD pattern of the monomalonate of the quinazoline derivative of the present invention.

The XRPD pattern is shown in FIG. 74.

Figure 75:
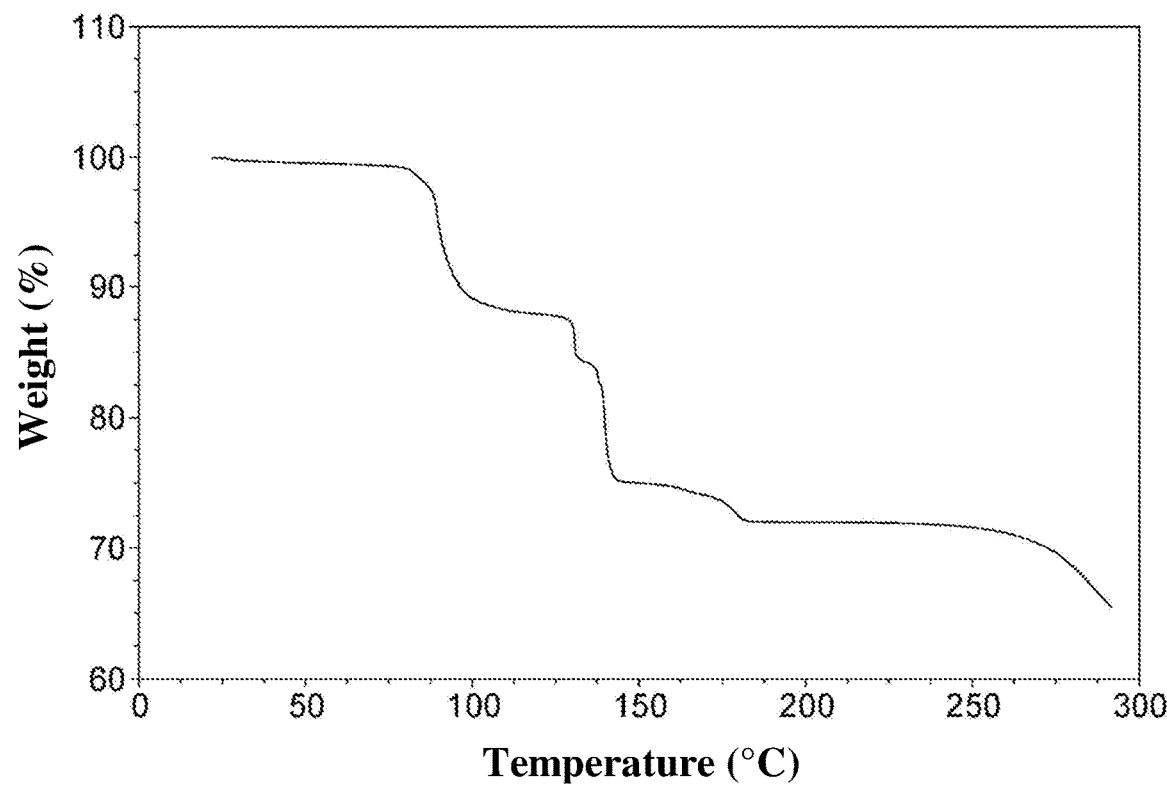
FIG. 75 is TGA pattern of the monomalonate of the quinazoline derivative of the present invention.

As the TGA pattern shown in FIG. 75, the decomposition of the sample occurs at 88° C.

20 mg of the compound represented by formula 1 and 1.5 mg or 2.5 mg of the malonic acid were taken, and the other conditions remained the same, and the given product was still the monomalonate of the quinazoline derivative with the same XRPD.

Embodiment 47: Synthesis of the Monosuccinate of the Quinazoline Derivative 10 mg of the compound represented by formula 1 was dissolved in 2 mL of dichloromethane and 2.34 mg of the succinic acid was added in 0.5 mL of dichloromethane to form a suspension. The solution of the compound represented by formula 1 in dichloromethane was added dropwise to the suspension of succinic acid in dichloromethane, followed by stirring overnight, centrifugation, rinsing and drying to give the salt.

Figure 76:
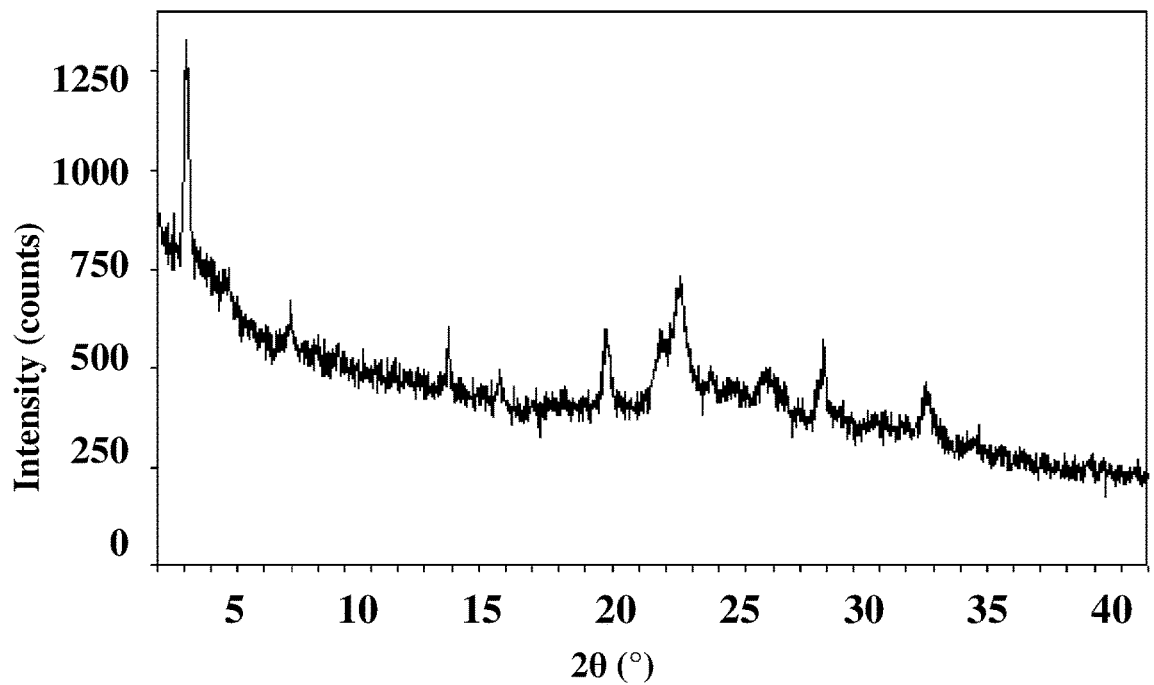
FIG. 76 is XRPD pattern of the monosuccinate of the quinazoline derivative of the present invention.

The XRPD pattern is shown in FIG. 76.

20 mg of the compound represented by formula 1 and 1.5 mg or 2.5 mg of the succinic acid were taken, and the other conditions remained the same, and the given product was still the monosuccinate of the quinazoline derivative with the same XRPD.

Embodiment 48: Synthesis of the Mono-α-Ketoglutarate of the Quinazoline Derivative 10 mg of the compound represented by formula 1 was dissolved in 0.8 mL of tetrahydrofuran and 3.19 mg of the α-ketoglutaric acid was dissolved in 0.2 mL of tetrahydrofuran. The solution of α-ketoglutaric acid in tetrahydrofuran was added dropwise to the solution of the compound represented by formula 1 in tetrahydrofuran, accompanied by the simultaneous precipitation of the solids, followed by centrifugation, rinsing and drying to give the salt.

Figure 77:
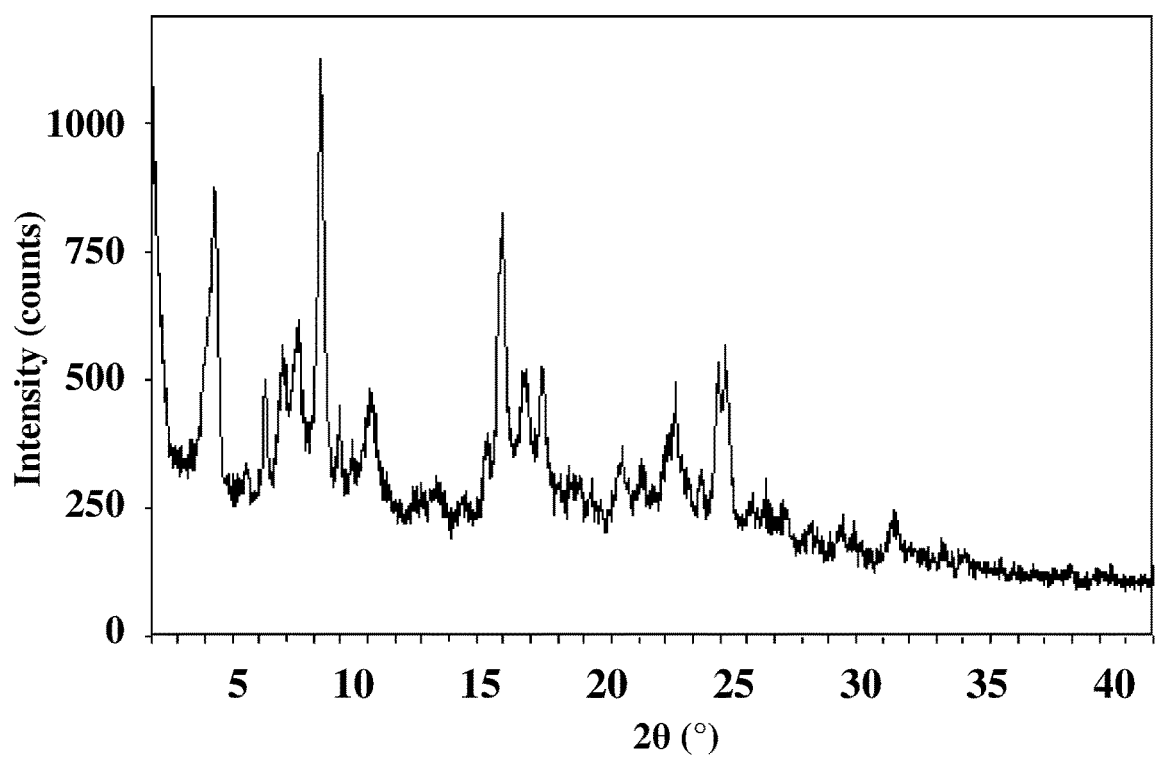
FIG. 77 is XRPD pattern of the mono-α-ketoglutarate of the quinazoline derivative of the present invention.

The XRPD pattern is shown in FIG. 77.

Figure 78:
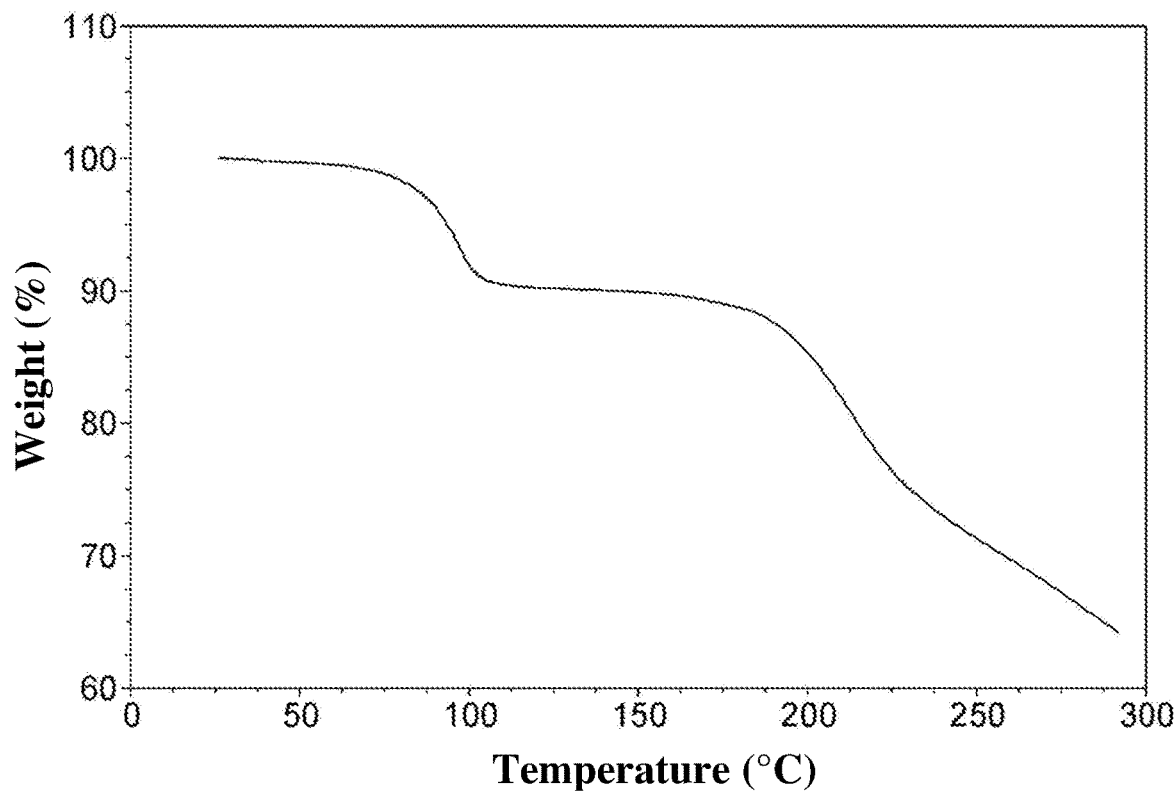
FIG. 78 is TGA pattern of the mono-α-ketoglutarate of the quinazoline derivative of the present invention.

As the TGA pattern shown in FIG. 78, the decomposition of the sample occurs at 193° C., and the weight loss before decomposition is 9.8%. The actual content of the free base determined by HPLC is 82.1%, which is close to the theoretical value of 77.5%, so the acid/base molar ratio of the salt is 1:1.

20 mg of the compound represented by formula 1 and 6.38 mg of the α-ketoglutaric acid were taken, and the other conditions remained the same, and the given product was still the mono-α-ketoglutarate of the quinazoline derivative with the same XRPD.

Embodiment 49: Synthesis of the Dimaleate of the Quinazoline Derivative 10 mg of the compound represented by formula 1 was dissolved in 0.8 mL of tetrahydrofuran and 5.06 mg of the maleic acid was dissolved in 0.4 mL of tetrahydrofuran. The solution of maleic acid in tetrahydrofuran was added dropwise to the solution of the compound represented by formula 1 in tetrahydrofuran, accompanied by the simultaneous precipitation of the solids, followed by centrifugation, rinsing and drying to give the salt.

Figure 79:
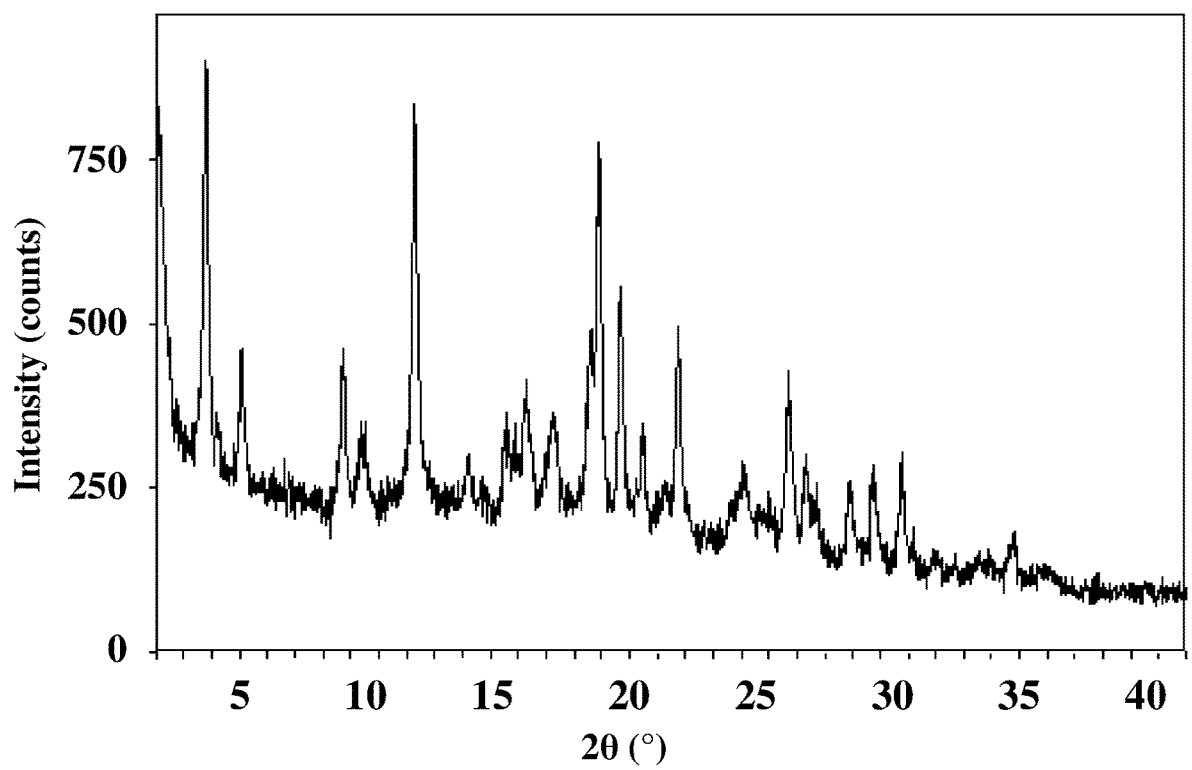
FIG. 79 is XRPD pattern of the dimaleate of the quinazoline derivative of the present invention.

The XRPD pattern is shown in FIG. 79.

Figure 80:
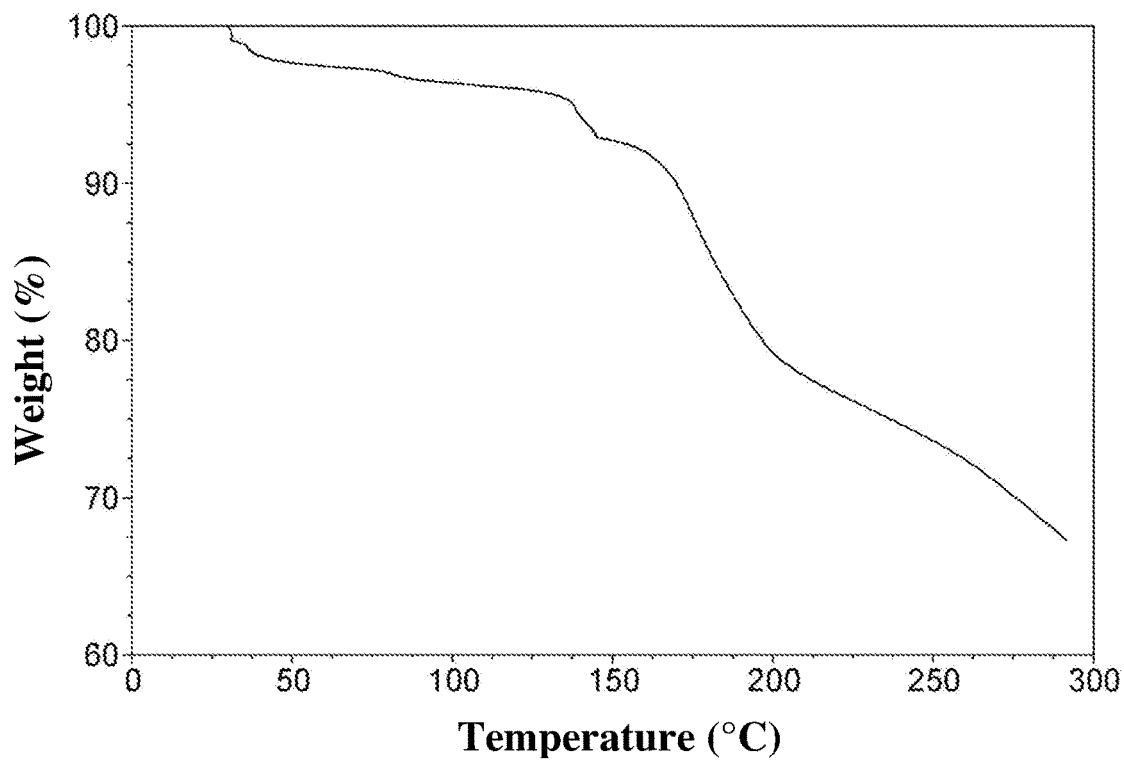
FIG. 80 is TGA pattern of the dimaleate of the quinazoline derivative of the present invention.

As the TGA pattern shown in FIG. 80, the stagewise weight loss of the sample occurs at 75° C. and 136° C., and the decomposition thereof occurs massively at 167° C. The actual content of the free base determined by HPLC is 71.3%, which is close to the theoretical value of 68.5%, so the acid/base molar ratio of the salt is 2:1.

20 mg of the compound represented by formula 1 was taken, and the other conditions remained the same, and the given product was still the dimaleate of the quinazoline derivative with the same XRPD.

10 mg of the compound represented by formula 1 was taken, followed by dissolving 7.59 mg of the maleic acid in 0.3 mL of tetrahydrofuran, and the other conditions remained the same, and the given product was still the dimaleate of the quinazoline derivative with the same XRPD.

Embodiment 50: Synthesis of the Mono-1,5-Naphthalenedisulfonate of the Quinazoline Derivative 10 mg of the compound represented by formula 1 was dissolved in 0.8 mL of tetrahydrofuran and 7.86 mg of the 1,5-naphthalenedisulfonic acid was dissolved in 0.2 mL of tetrahydrofuran. The solution of 1,5-naphthalenedisulfonic acid in tetrahydrofuran was added dropwise to the solution of the compound represented by formula 1 in tetrahydrofuran, accompanied by the simultaneous precipitation of the solids, followed by stirring overnight, centrifugation, rinsing and drying to give the salt.

Figure 81:
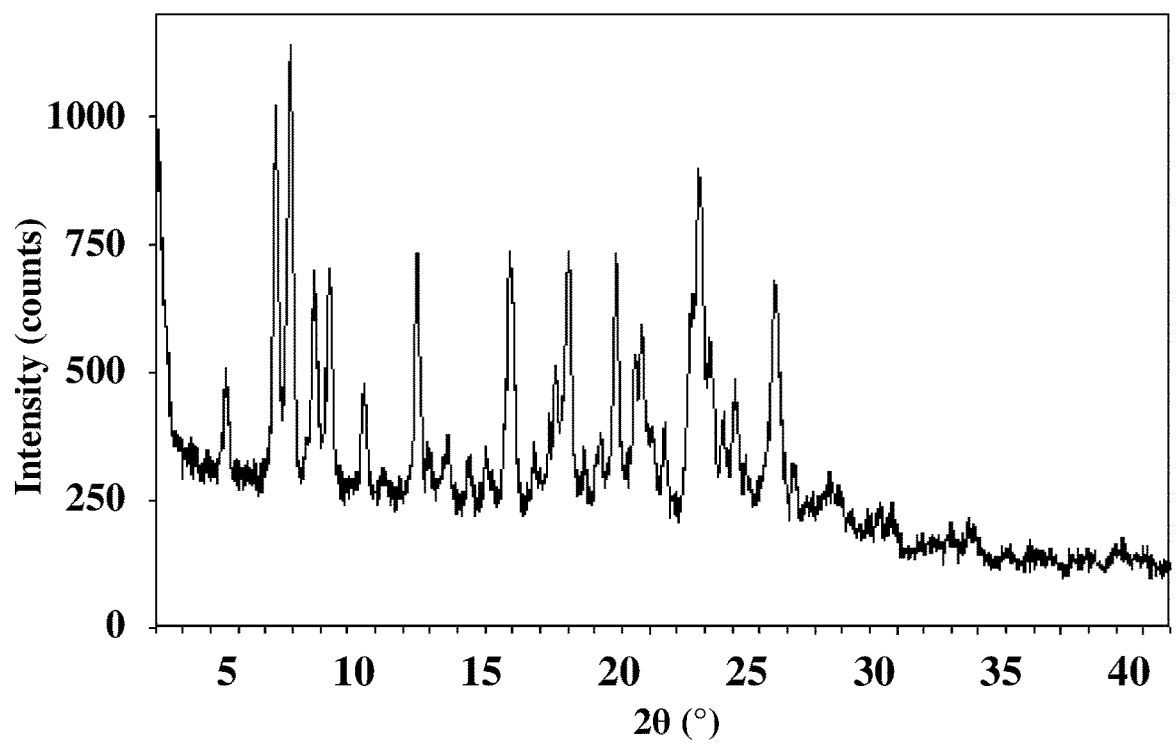
FIG. 81 is XRPD pattern of the mono-1,5-naphthalene-disulfonate of the quinazoline derivative of the present invention.

The XRPD pattern is shown in FIG. 81.

20 mg of the compound represented by formula 1 and 15.72 mg of the 1,5-naphthalenedisulfonic acid were taken, and the other conditions remained the same, and the given product was still the mono-1,5-naphthalenedisulfonate of the quinazoline derivative with the same XRPD.

Embodiment 51: Synthesis of the Dimalonate of the Quinazoline Derivative 10 mg of the compound represented by formula 1 was dissolved in 2 mL of dichloromethane and 4.13 mg of the malonic acid was added in 1 mL of dichloromethane to form a suspension. The solution of the compound represented by formula 1 in dichloromethane was added dropwise to the suspension of malonic acid in dichloromethane, followed by stirring overnight, centrifugation, rinsing and drying to give the salt.

Figure 82:
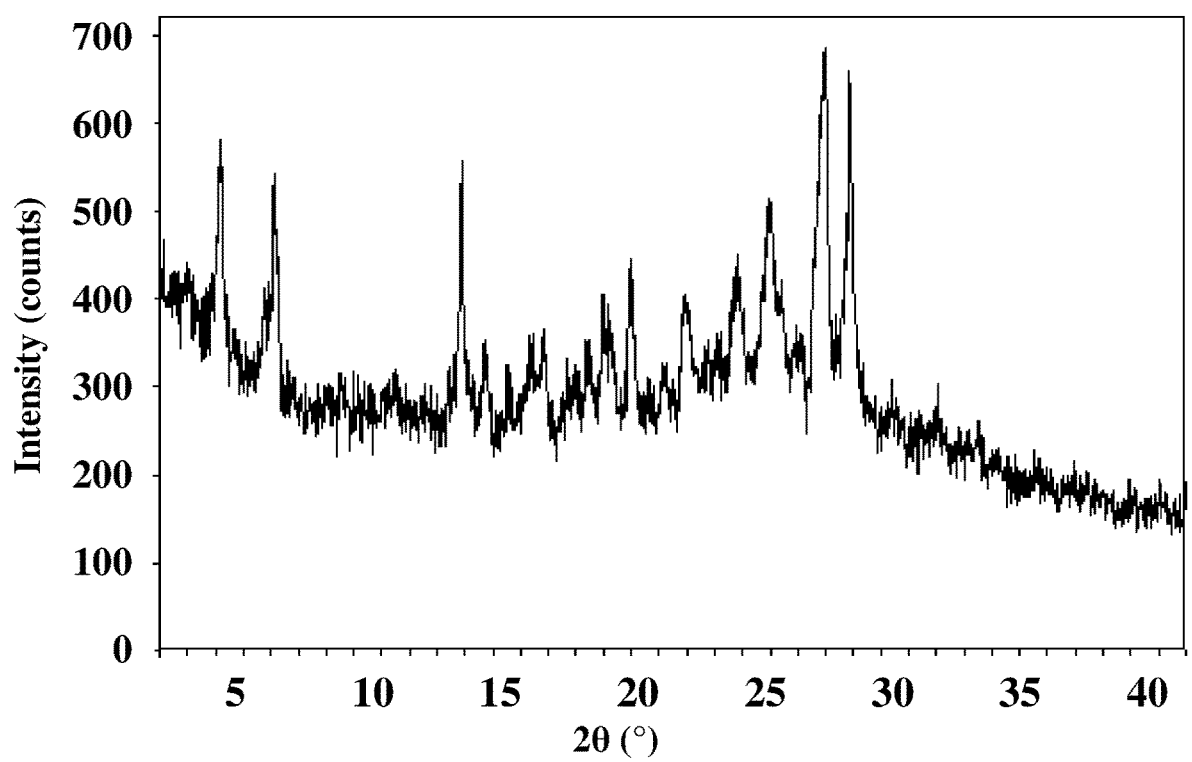
FIG. 82 is XRPD pattern of the dimalonate of the quinazoline derivative of the present invention.

The XRPD pattern is shown in FIG. 82.

Figure 83:
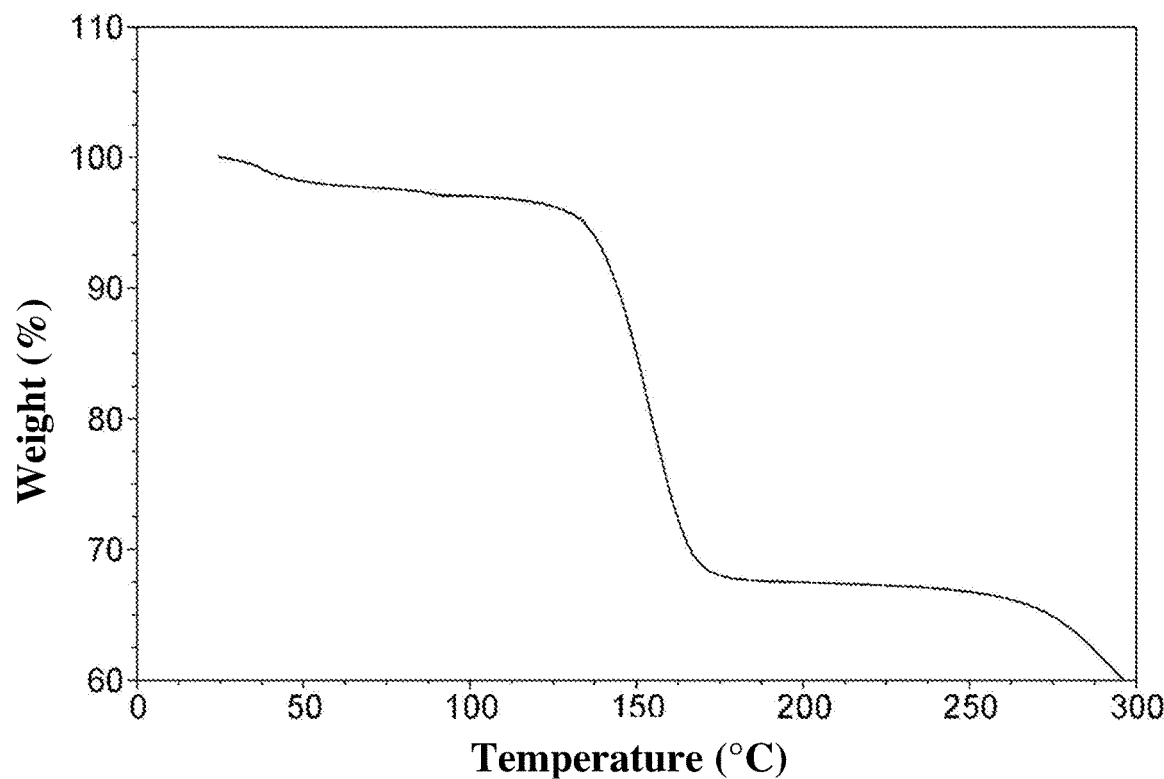
FIG. 83 is TGA pattern of the dimalonate of the quinazoline derivative of the present invention.

As the TGA pattern shown in FIG. 83, the decomposition of the sample occurs at 135° C. The actual content of the free base determined by HPLC is 74.9%, which is close to the theoretical value of 70.8%, so the acid/base molar ratio of the salt is 2:1.

20 mg of the compound represented by formula 1, and 3 mg/mL or 5 mg/mL of the suspension of malonic acid in dichloromethane were taken, and the molar ratio of the compound represented by formula 1 to the malonic acid in the reaction is 1:2.2. The other conditions remained the same, and the given product was still the dimalonate of the quinazoline derivative with the same XRPD.

Embodiment 52: Synthesis of the Trimalonate of the Quinazoline Derivative 10 mg of the compound represented by formula 1 was dissolved in 2 mL of dichloromethane and 6.19 mg of the malonic acid was added in 1 mL of dichloromethane to form a suspension. The solution of the compound represented by formula 1 in dichloromethane was added dropwise to the suspension of malonic acid in dichloromethane, followed by stirring overnight, centrifugation, rinsing and drying to give the salt.

Figure 84:
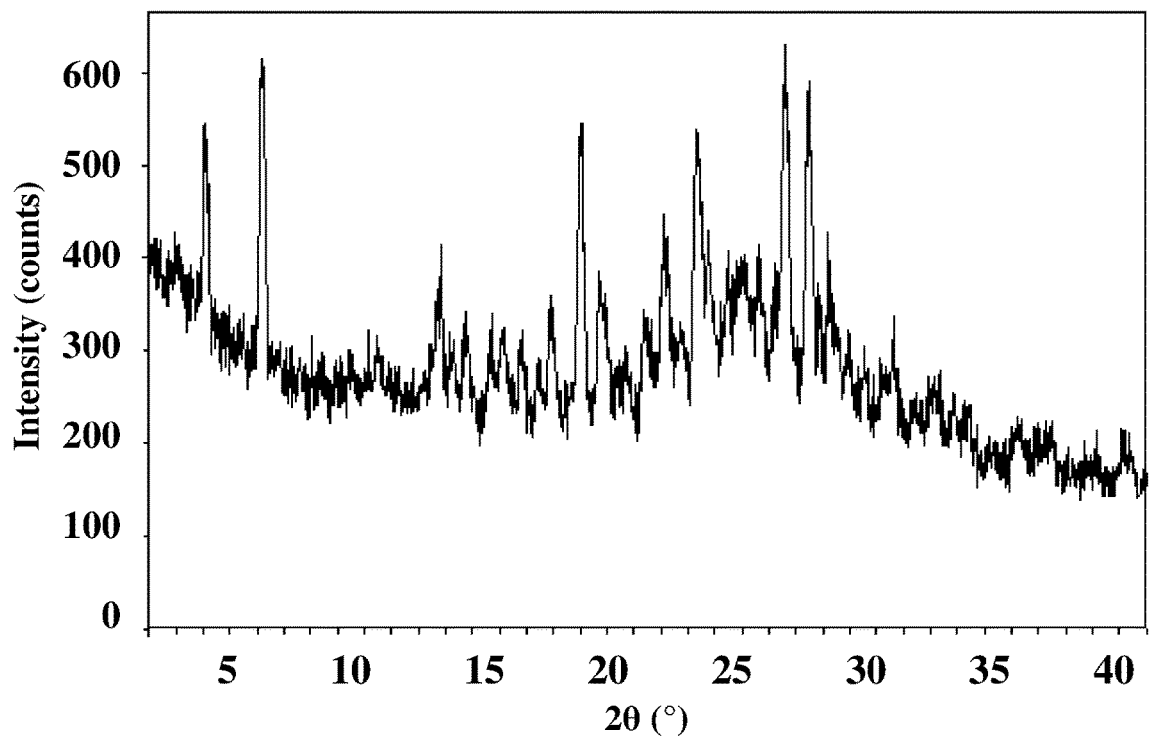
FIG. 84 is XRPD pattern of the trimalonate of the quinazoline derivative of the present invention.

The XRPD pattern is shown in FIG. 84.

Figure 85:
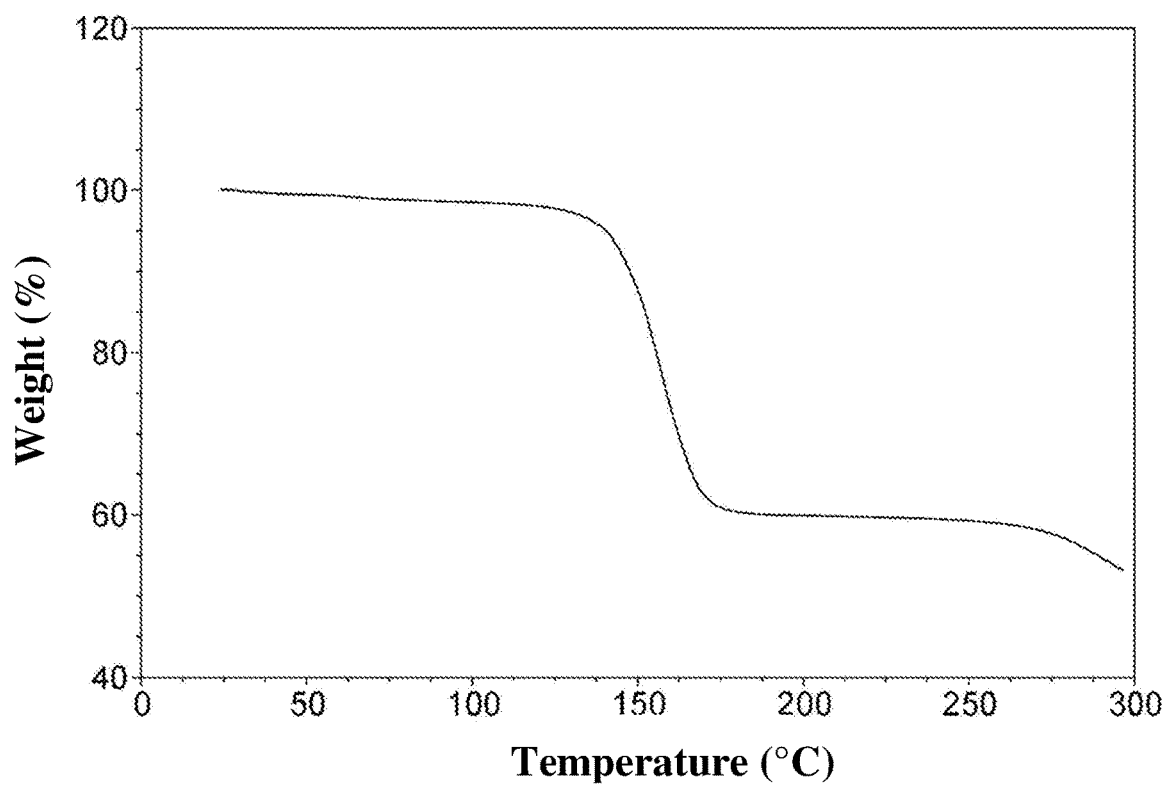
FIG. 85 is TGA pattern of the trimalonate of the quinazoline derivative of the present invention.

As the TGA pattern shown in FIG. 85, the decomposition of the sample occurs at 140° C. The actual content of the free base determined by HPLC is 61.8%, which is close to the theoretical value of 65.6%, so the acid/base molar ratio of the salt is 3:1.

20 mg of the compound represented by formula 1, and 5 mg/mL or 10 mg/mL of the suspension of malonic acid in dichloromethane were taken, and the molar ratio of the compound represented by formula 1 to the malonic acid in the reaction is 1:3.3. The other conditions remained the same, and the given product was still the trimalonate of the quinazoline derivative with the same XRPD.

Embodiment 53: Synthesis of the Di-1,5-Naphthalenedisulfonate of the Quinazoline Derivative 10 mg of the compound represented by formula 1 was dissolved in 0.8 mL of tetrahydrofuran and 15.72 mg of the 1,5-naphthalenedisulfonic acid was dissolved in 0.4 mL of tetrahydrofuran. The solution of the compound represented by formula 1 in tetrahydrofuran was added dropwise to the solution of 1,5-naphthalenedisulfonic acid in tetrahydrofuran, accompanied by the simultaneous precipitation of the solids, followed by stirring overnight, centrifugation, rinsing and drying to give the salt.

Figure 86:
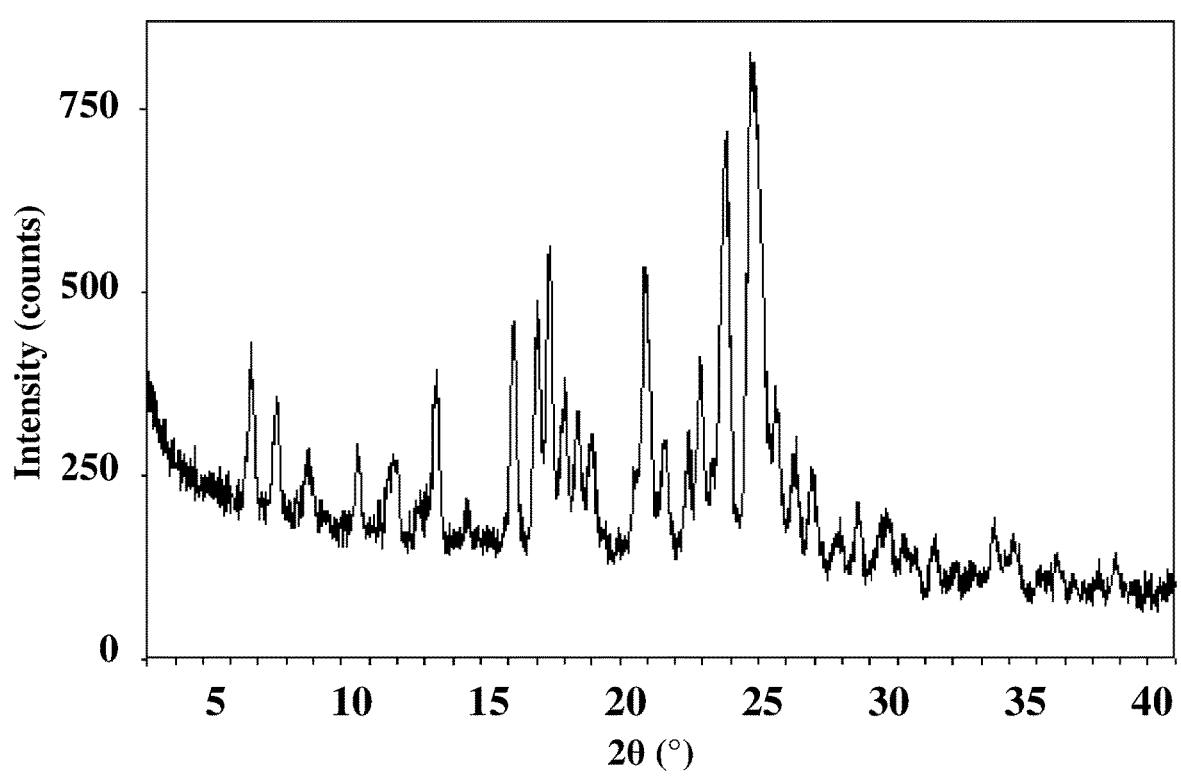
FIG. 86 is XRPD pattern of the di-1,5-naphthalenedisulfonate of the quinazoline derivative of the present invention.

The XRPD pattern is shown in FIG. 86.

Figure 87:
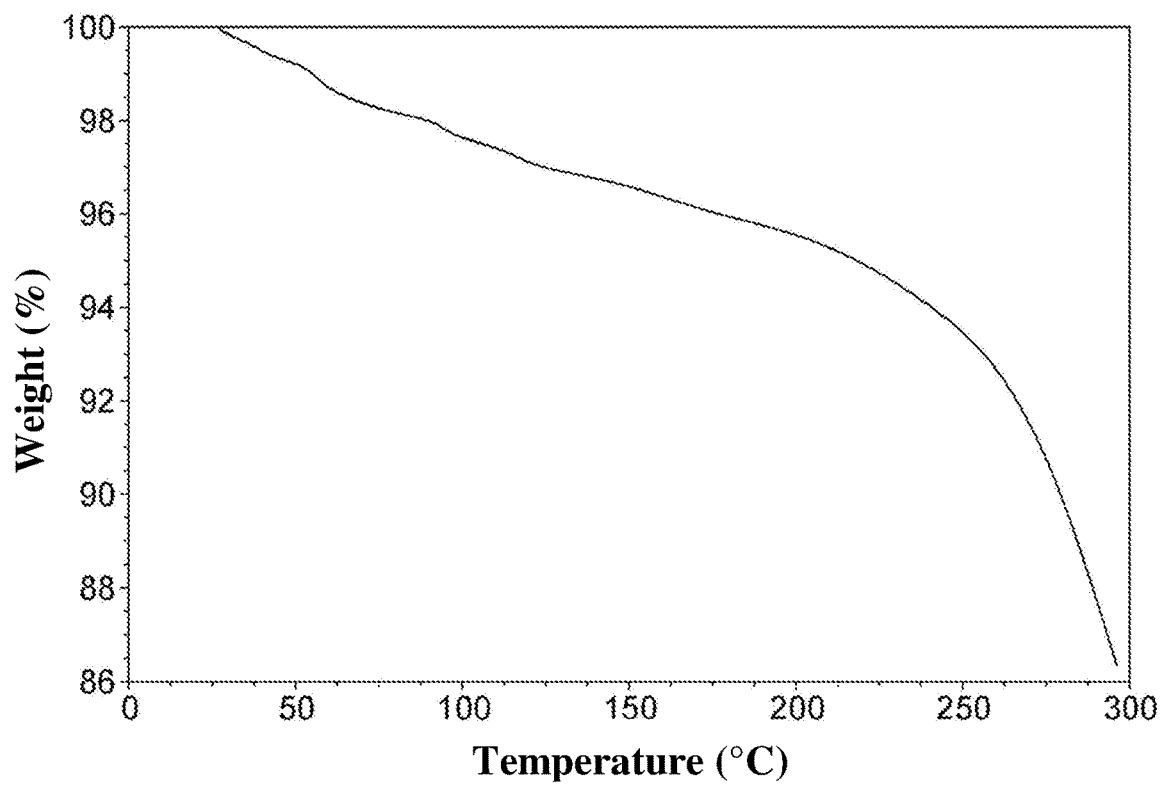
FIG. 87 is TGA pattern of the di-1,5-naphthalenedisulfonate of the quinazoline derivative of the present invention.

As the TGA pattern shown in FIG. 87, the decomposition of the sample occurs at 223° C., and there is a slight weight loss of 3.4% below 150° C. The actual content of the free base determined by HPLC is 54.8%, which is close to the theoretical value of 59.3%, so the acid/base molar ratio of the salt is 1:1.

20 mg of the compound represented by formula 1 was taken, followed by dissolving 25.17 mg of the 1,5-naphthalenedisulfonic acid in 0.32 mL of tetrahydrofuran, and the other conditions remained the same, and the given product was still the di-1,5-naphthalenedisulfonate of the quinazoline derivative with the same XRPD.

10 mg of the compound represented by formula 1 was taken, followed by dissolving 18.88 mg of the 1,5-naphthalenedisulfonic acid in 0.32 mL of tetrahydrofuran, and the other conditions remained the same, and the given product was still the di-1,5-naphthalenedisulfonate of the quinazoline derivative with the same XRPD.

Embodiment 54: Synthesis of the Trisuccinate of the Quinazoline Derivative 10 mg of the compound represented by formula 1 was dissolved in 2 mL of dichloromethane and 7.03 mg of the succinic acid was added in 1 mL of dichloromethane to form a suspension. The solution of the compound represented by formula 1 in dichloromethane was added dropwise to the suspension of succinic acid in dichloromethane, followed by stirring overnight, centrifugation, rinsing and drying to give the salt.

Figure 88:
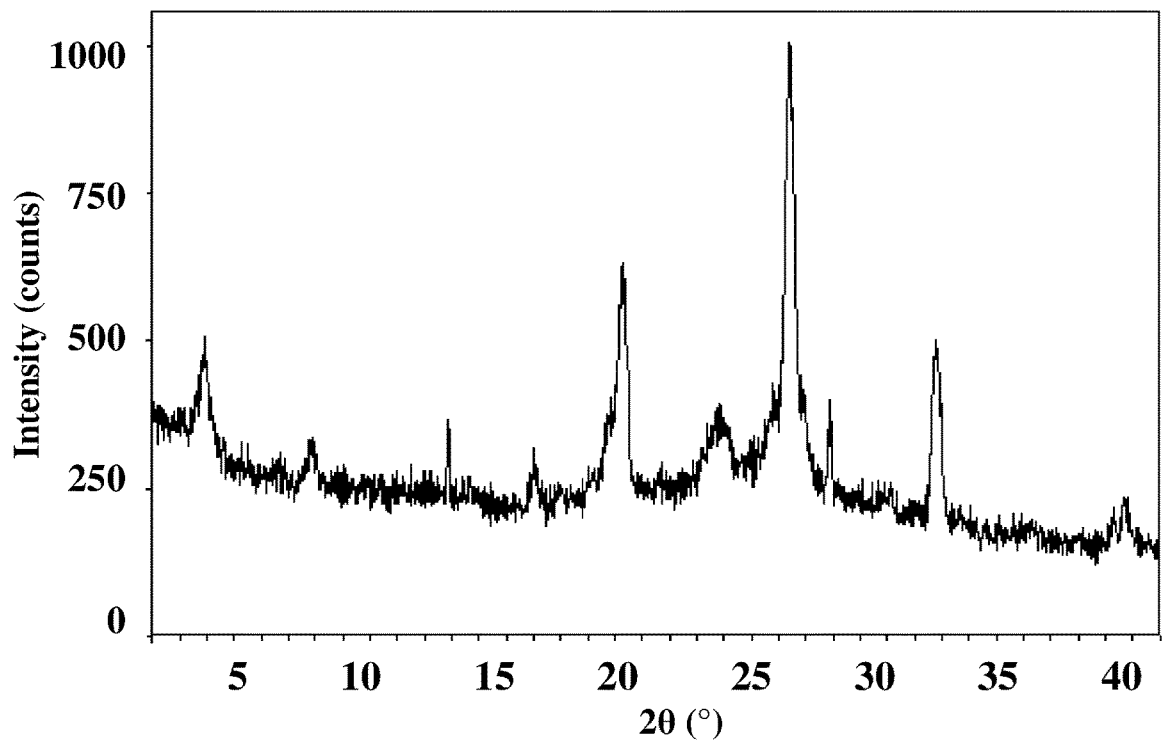
FIG. 88 is XRPD pattern of the trisuccinate of the quinazoline derivative of the present invention.

The XRPD pattern is shown in FIG. 88.

Figure 89:
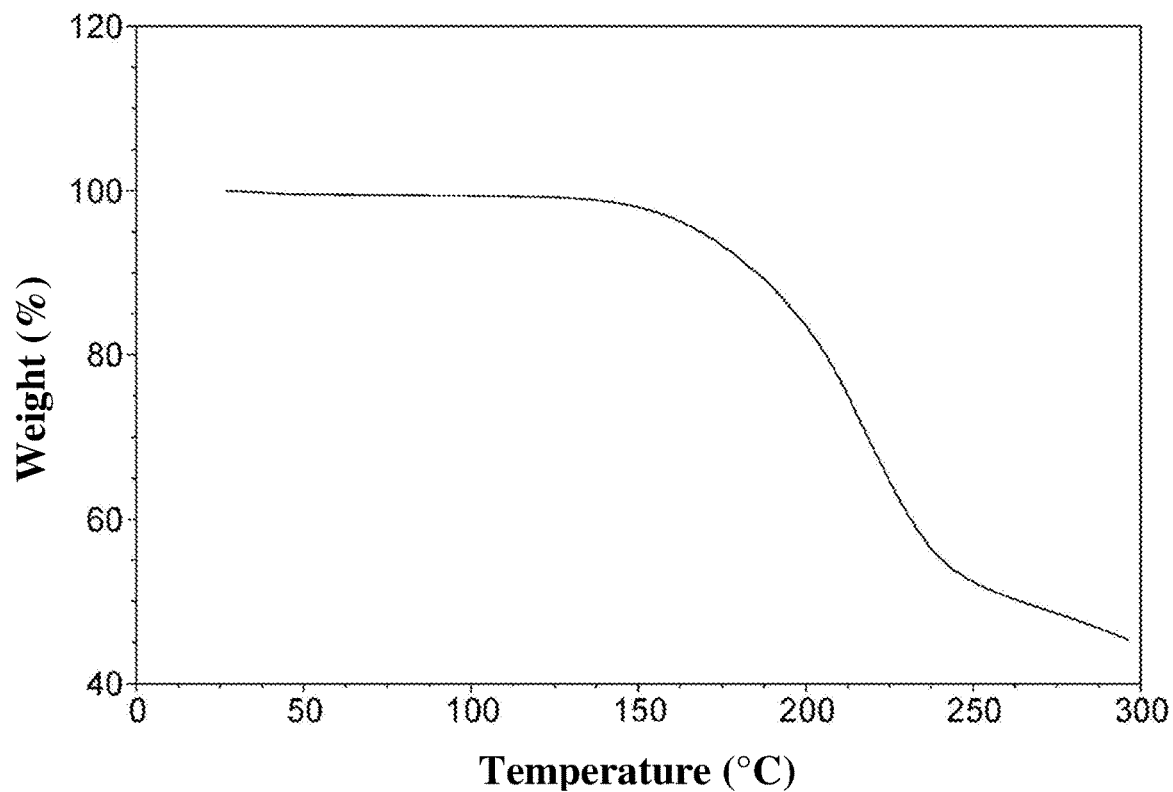
FIG. 89 is TGA pattern of the trisuccinate of the quinazoline derivative of the present invention.

As the TGA pattern shown in FIG. 89, the decomposition of the sample occurs at 173° C. The actual content of the free base determined by HPLC is 58.7%, which is close to the theoretical value of 57.2%, so the acid/base molar ratio of the salt is 3:1.

20 mg of the compound represented by formula 1, and 5 mg/mL of the suspension of succinic acid in dichloromethane were taken, and the molar ratio of the compound represented by formula 1 to the succinic acid in the reaction is 1:2.2. The other conditions remained the same, and the given product was still the trisuccinate of the quinazoline derivative with the same XRPD.

10 mg of the compound represented by formula 1, and 10 mg/mL of the suspension of succinic acid in dichloromethane were taken, and the molar ratio of the compound represented by formula 1 to the succinic acid in the reaction is 1:3.3. The other conditions remained the same, and the given product was still the trisuccinate of the quinazoline derivative with the same XRPD.

Embodiment 55: Synthesis of the Di-α-Ketoglutarate of the Quinazoline Derivative 10 mg of the compound represented by formula 1 was dissolved in 0.8 mL of tetrahydrofuran and 6.38 mg of the α-ketoglutaric acid was dissolved in 0.4 mL of tetrahydrofuran. The solution of the compound represented by formula 1 in tetrahydrofuran was added dropwise to the solution of α-ketoglutaric acid in tetrahydrofuran, accompanied by the simultaneous precipitation of the solids, followed by centrifugation, rinsing and drying to give the salt.

Figure 90:
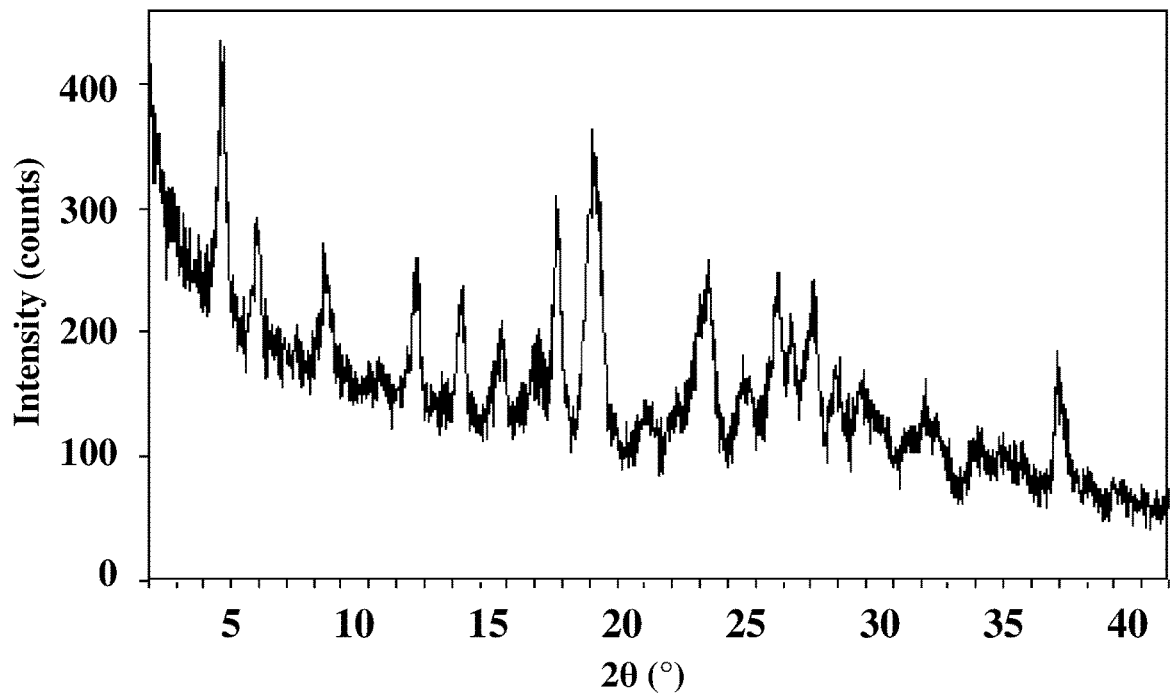
FIG. 90 is XRPD pattern of the di-α-ketoglutarate of the quinazoline derivative of the present invention.

The XRPD pattern is shown in FIG. 90.

Figure 91:
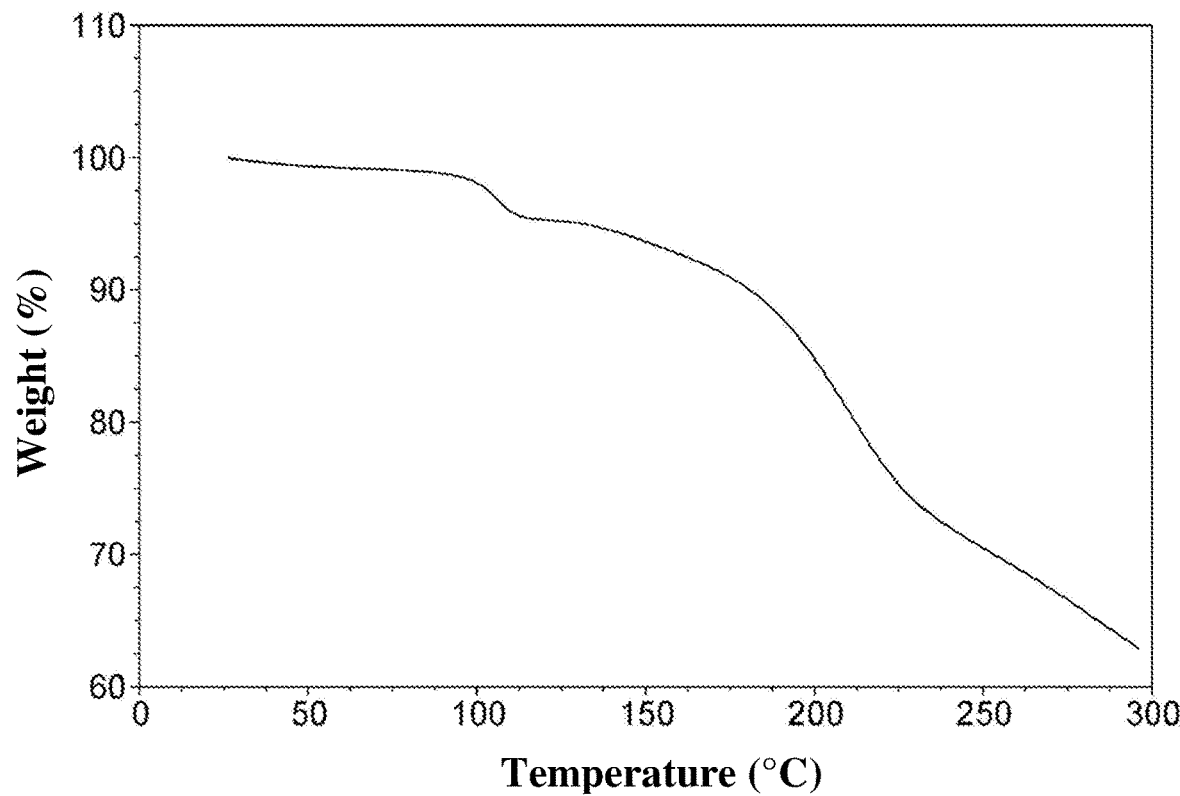
FIG. 91 is TGA pattern of the di-α-ketoglutarate of the quinazoline derivative of the present invention.

As the TGA pattern shown in FIG. 91, the decomposition of the sample occurs at 140° C., and the weight loss before decomposition is 4.7%. The actual content of the free base determined by HPLC is 64.3%, which is close to the theoretical value of 63.3%, so the acid/base molar ratio of the salt is 1:1.

20 mg of the compound represented by formula 1 was taken, followed by dissolving 19.14 mg of the α-ketoglutaric acid in 0.6 mL of tetrahydrofuran, and the other conditions remained the same, and the given product was still the di-α-ketoglutarate of the quinazoline derivative with the same XRPD.

Embodiment 56: Synthesis of the Mono-p-Chlorobenzenesulfonate of the Quinazoline Derivative 10 mg of the compound represented by formula 1 was dissolved in 0.8 mL of tetrahydrofuran and 4.2 mg of the p-chlorobenzenesulfonic acid was dissolved in 0.2 mL of tetrahydrofuran. The solution of p-chlorobenzenesulfonic acid in tetrahydrofuran was added dropwise to the solution of the compound represented by formula 1 in tetrahydrofuran, followed by stirring overnight, centrifugation of the precipitated solids, rinsing and drying to give the salt.

Figure 92:
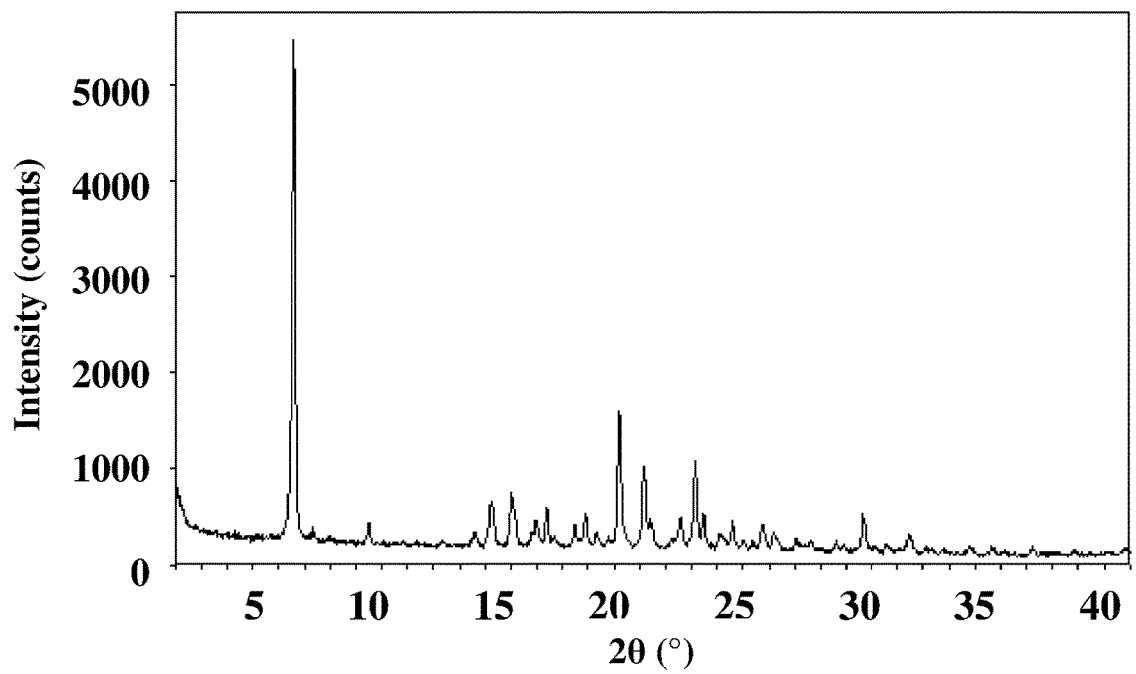
FIG. 92 is XRPD pattern of the mono-p-chlorobenzenesulfonate of the quinazoline derivative of the present invention.

The XRPD pattern is shown in FIG. 92.

20 mg of the compound represented by formula 1 and 8.4 mg of the p-chlorobenzenesulfonic acid were taken, and the other conditions remained the same, and the given product was still the mono-p-chlorobenzenesulfonate of the quinazoline derivative with the same XRPD.

Effectiveness Embodiment 1: Solid-State Stability Test

An appropriate amount of the drugs were placed in the surface dish, spread to a thickness of 3-5 mm, and exposed in high temperature, high temperature and high humidity, illumination and oxidation conditions for 10 days respectively, and the solid-state characterization was performed. The purity and the number of impurities 0.05%) of the samples for testing were determined by HPLC, and compared with the samples on day 0. The exposure conditions are:

High temperature (an oven with T=60° C.);

High temperature and high humidity (40° C., a chamber with constant temperature and 75% relative humidity);

Illumination (25° C., a 4500±500 lx light incubator);

Oxidation (25° C., a closed container containing urea hydrogen peroxide).

The results are shown in Table 1.

TABLE 1

| Sample for testing | Time and conditions | | High temperature | High temperature and high humidity | Illumination | Oxidation |
|---|---|---|---|---|---|---|
| The quinazoline derivative compound represented by formula 1 | 0 d | Purity | | | 99.1% | |
| | | Number of impurities | | | 1 | |
| | 10 d | Purity | 99.0% | 99.0% | 99.0% | 99.0% |
| | | Number of impurities | 2 | 3 | 2 | 3 |
| The monocitrate of the quinazoline derivative (crystal form 1) | 0 d | Purity | | | 99.2% | |
| | | Number of impurities | | | 1 | |
| | 10 d | Purity | 99.1% | 99.2% | 98.9% | 98.9% |
| | | Number of impurities | 1 | 1 | 4 | 3 |
| The monobenzenesulfonate of the quinazoline derivative | 0 d | Purity | | | 98.5% | |
| | | Number of impurities | | | 2 | |
| | 10 d | Purity | 98.5% | 98.5% | 98.5% | 98.5% |
| | | Number of impurities | 2 | 2 | 2 | 2 |
| The monoethanedisulfonate of the quinazoline derivative | 0 d | Purity | | | 99.0% | |
| | | Number of impurities | | | 2 | |
| | 10 d | Purity | 99.0% | 99.0% | 99.0% | 99.0% |
| | | Number of impurities | 2 | 2 | 2 | 2 |

Effectiveness Embodiment 2: Solution Stability Test

About 15 mg of the sample was weighed accurately, dissolved with 25 mL of the test solvent (10% aqueous acetone solution, pH=4.0 B-R buffer solution, SGF, SIF) via ultrasound for 20 minutes. The solution was divided into four portions and placed in the clear glass vials, followed by sealing. The samples were exposed in different environments and sampled on day 0 and day 5. The purity of each sample was determined by HPLC, and the number of impurities greater than 0.05% was calculated and compared with the samples on day 0. The exposure environments are:

Room temperature and light-proof test, 25° C.;

High temperature and light-proof test, 60° C.;

Illumination experiment (4500±500 lx), 25° C.;

Oxidation experiment (3% v/v hydrogen peroxide), 25° C.

The results are shown in Table 2.

TABLE 2

| Name | Media | Time | Testing target | High temperature | High temperature and high humidity | Illumination | Oxidation |
|---|---|---|---|---|---|---|---|
| The quinazoline derivative compound represented by formula 1 | 10% aqueous acetone solution | 0 d | Purity | | | 93.4% | |
| | | | Number of impurities | | | 2 | |
| | | 5 d | Purity | 83.1% | 13.3% | 61.5% | Complete decomposition |
| | | | Number of impurities | 2 | 6 | 4 | |
| | B-R Buffer solution | 0 d | Purity | | | 99.0% | |
| | | | Number of impurities | | | 1 | |
| | | 5 d | Purity | 99.0% | 95.0% | 99.0% | 40.6% |
| | | | Number of impurities | 1 | 4 | 1 | 13 |
| | SGF | 0 d | Purity | | | 99.0% | |
| | | | Number of impurities | | | 2 | |
| | | 5 d | Purity | 99.0% | 94.2% | 99.0% | 84.3% |
| | | | Number of impurities | 2 | 4 | 2 | 3 |
| | SIF | 0 d | Purity | | | 88.9% | |
| | | | Number of impurities | | | 1 | |
| | | 5 d | Purity | 85.6% | 81.9% | 50.0% | 62.7% |
| | | | Number of impurities | 2 | 4 | 18 | 5 |
| The monocitrate of the quinazoline derivative (crystal form 1) | 10% aqueous acetone solution | 0 d | Purity | | | 98.6% | |
| | | | Number of impurities | | | 1 | |
| | | 5 d | Purity | 98.5% | 96.8% | 98.5% | 62.8% |
| | | | Number of impurities | 1 | 2 | 2 | 8 |
| | B-R Buffer solution | 0 d | Purity | | | 98.8% | |
| | | | Number of impurities | | | 1 | |
| | | 5 d | Purity | 98.7% | 97.0% | 98.6% | 38.8% |
| | | | Number of impurities | 1 | 4 | 1 | 13 |
| | SGF | 0 d | Purity | | | 99.2% | |
| | | | Number of impurities | | | 1 | |
| | | 5 d | Purity | 99.0% | 94.6% | 99.0% | 80.8% |
| | | | Number of impurities | 2 | 2 | 2 | 4 |
| | SIF | 0 d | Purity | | | 81.4% | |
| | | | Number of impurities | | | 1 | |
| | | 5 d | Purity | 56.8% | 54.0% | 24.8% | 36.4% |
| | | | Number of impurities | 1 | 6 | 12 | 6 |
| The monobenzenesulfonate of the quinazoline derivative | 10% aqueous acetone solution | 0 d | Purity | | | 98.2% | |
| | | | Number of impurities | | | 1 | |
| | | 5 d | Purity | 97.9% | 96.8% | 97.6% | 60.8% |
| | | | Number of impurities | 1 | 3 | 1 | 7 |
| | B-R Buffer solution | 0 d | Purity | | | 98.5% | |
| | | | Number of impurities | | | 2 | |
| | | 5 d | Purity | 97.2% | 97.2% | 98.5% | 38.1% |
| | | | Number of impurities | 3 | 3 | 1 | 12 |
| | SGF | 0 d | Purity | | | 98.9% | |
| | | | Number of impurities | | | 1 | |
| | | 5 d | Purity | 98.8% | 94.4% | 98.9% | 81.7% |
| | | | Number of impurities | 2 | 2 | 1 | 3 |
| | SIF | 0 d | Purity | | | 80.2 | |
| | | | Number of impurities | | | 2 | |
| | | 5 d | Purity | 58.7% | 42.0% | 10.0% | Complete decomposition |
| | | | Number of impurities | 1 | 8 | 9 | |

TABLE 2-continued

| Name | Media | Time | Testing target | High temperature | High temperature and high humidity | Illumination | Oxidation |
|---|---|---|---|---|---|---|---|
| The monoethanedisulfonate of the quinazoline derivative | 10% aqueous acetone solution | 0 d | Purity<br>Number of impurities | | | 99.1%<br>1 | |
| | | 5 d | Purity<br>Number of impurities | 99.0%<br>1 | 98.1%<br>3 | 99.1%<br>1 | 70.8%<br>7 |
| | B-R Buffer solution | 0 d | Purity<br>Number of impurities | | | 99.0%<br>1 | |
| | | 5 d | Purity<br>Number of impurities | 99.0%<br>1 | 97.7%<br>3 | 99.0%<br>1 | 44.0%<br>15 |
| | SGF | 0 d | Purity<br>Number of impurities | | | 99.0%<br>1 | |
| | | 5 d | Purity<br>Number of impurities | 98.9%<br>2 | 94.5%<br>2 | 98.9%<br>2 | 80.8%<br>3 |
| | SIF | 0 d | Purity<br>Number of impurities | | | 74.8%<br>2 | |
| | | 5 d | Purity<br>Number of impurities | 50.0%<br>1 | 36.5%<br>6 | 25.2%<br>13 | 30.8%<br>7 |

Effectiveness Embodiment 3: $^1$H NMR Measurement of the Salt of the Quinazoline Derivative and Solubility Determination by HPLC Method The partially salts of the quinazoline derivatives were subjected to $^1$H NMR measurement and solubility determination by HPLC method.

The solubility was determined as follows: a certain amount of the sample was weighed and the solvent was added thereto in portions with stirring or ultrasonication to accelerate dissolution; the amount of the consumed solvent was recorded once the sample was dissolved. If the sample was still not dissolved at a specific concentration, the solubility thereof was expressed as "<" such specific concentration; when the solubility of the sample was relatively low, the amount of the solvent could be amplified multiple times, followed by the addition of an excess of sample and stirring overnight. A certain volume of the solution was taken, followed by filtration, concentration, dissolved with a certain volume of other suitable solvents and subjected to HPLC measurement to obtain accurate data of the solubility.

Figure 93:
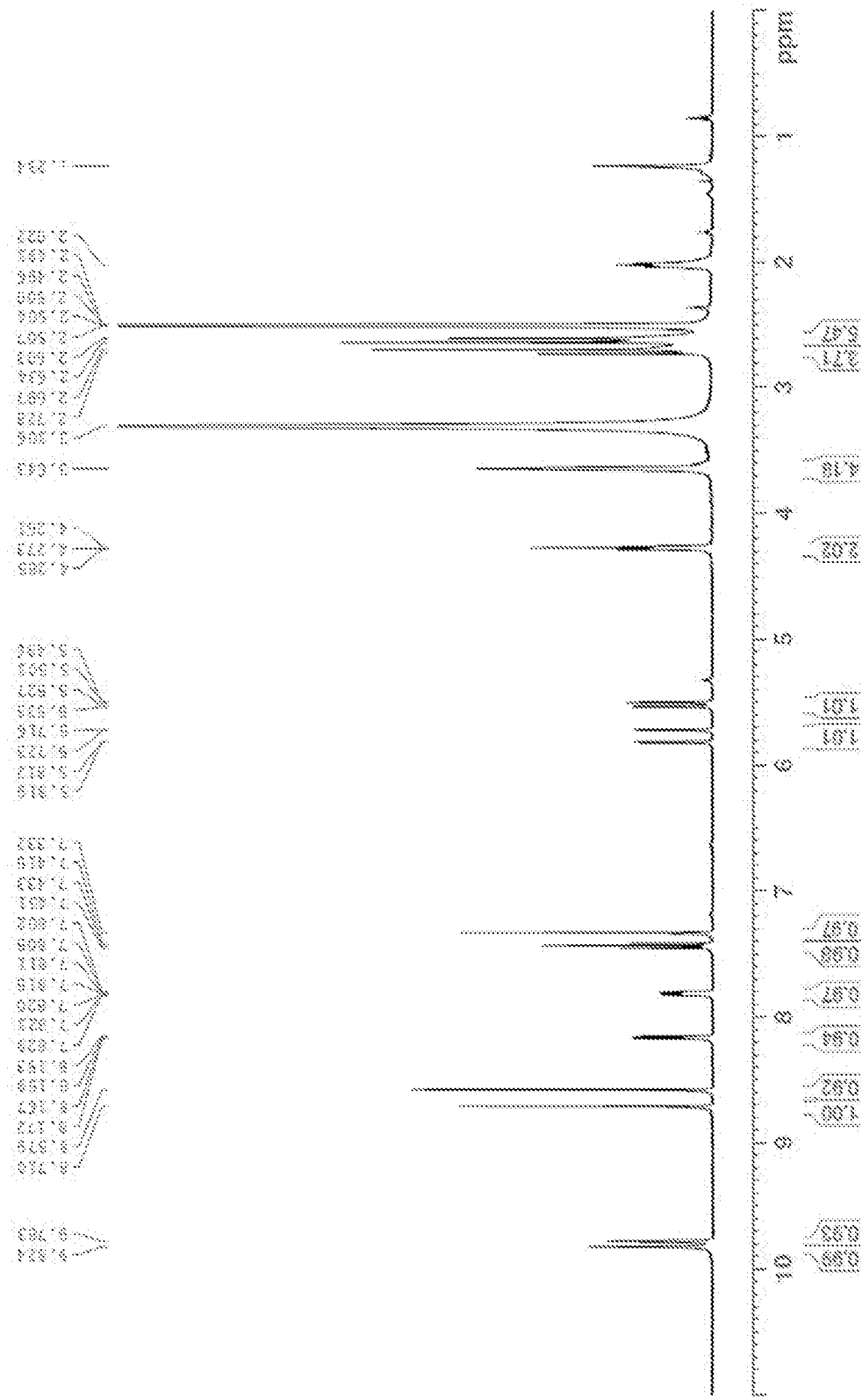
FIG. 93 is $^1$H NMR pattern of the monocitrate of the quinazoline derivative of the present invention.

The specific test results are as follows:

FIG. 93 is $^1$H NMR pattern of the monocitrate of the quinazoline derivative of the present invention (including crystal form 1 and 13). ($^1$H NMR (500 MHz, DMSO) δ 9.82 (s, 1H), 9.78 (s, 1H), 8.71 (s, 1H), 8.58 (s, 1H), 8.16 (dd, J=6.5, 2.5 Hz, 1H), 7.81 (ddd, J=9.0, 4.2, 2.7 Hz, 1H), 7.43 (t, J=9.0 Hz, 1H), 7.33 (s, 1H), 5.77 (dd, J=48.0, 3.5 Hz, 1H), 5.52 (dd, J=16.0, 3.5 Hz, 1H), 4.27 (t, J=6.0 Hz, 2H), 3.64 (s, 4H), 2.73-2.69 (m, 4H), 2.63-2.60 (m, 5H), 2.05-1.99 (m, 2H)); it is indicated that the molar ratio of the citric acid to the compound represented by formula 1 in the monocitrate of the quinazoline derivative is 1:1. The water solubility of the crystal form 1 of the monocitrate of the quinazoline derivative at 20° C. determined by HPLC is 84.3 µg/mL.

Figure 94:
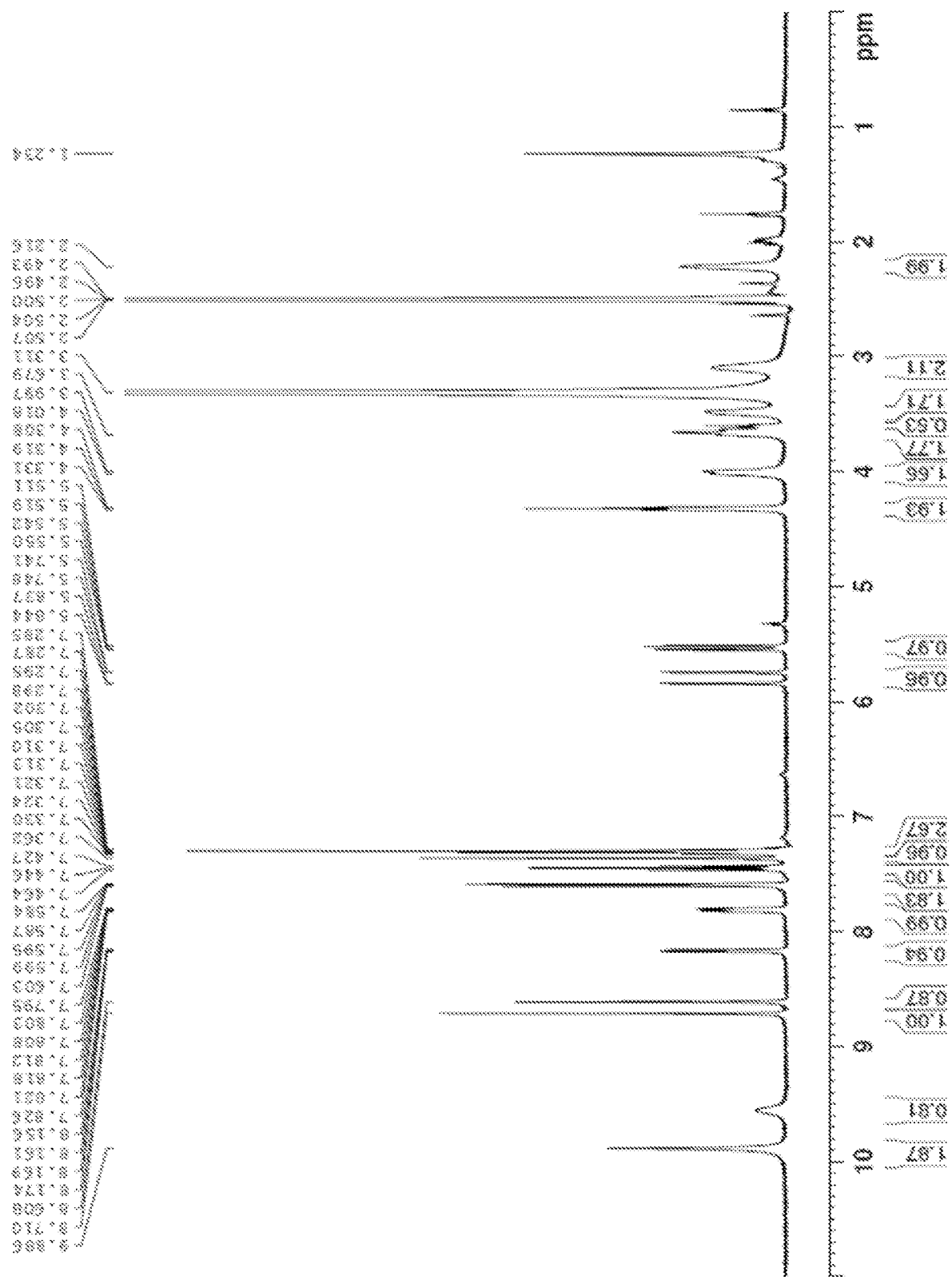
FIG. 94 is $^1$H NMR pattern of the monobenzenesulfonate of the quinazoline derivative of the present invention.

FIG. 94 is $^1$H NMR pattern of the monobenzenesulfonate of the quinazoline derivative of the present invention. ($^1$H NMR (500 MHz, DMSO) δ 9.89 (s, 2H), 9.55 (s, 1H), 8.71 (s, 1H), 8.61 (s, 1H), 8.17 (dd, J=6.8, 2.5 Hz, 1H), 7.81 (ddd, J=8.8, 4.2, 2.7 Hz, 1H), 7.60 (d, J=2.0 Hz, 1H), 7.58 (d, J=1.5 Hz, 1H), 7.45 (t, J=9.0 Hz, 1H), 7.36 (s, 1H), 7.34-7.27 (m, 2H), 5.79 (dd, J=48.0, 3.5 Hz, 1H), 5.53 (dd, J=15.5, 4.0 Hz, 1H), 4.32 (t, J=5.5 Hz, 2H), 4.02-3.99 (m, 2H), 3.66 (t, J=12.0 Hz, 2H), 3.49-3.47 (m, 2H), 3.10 m, 2H), 2.21 (m, 2H)); it is indicated that the molar ratio of the benzenesulfonic acid to the compound represented by formula 1 in the monobenzenesulfonate of the quinazoline derivative is 1:1. The water solubility of the monobenzenesulfonate of the quinazoline derivative at 20° C. determined by HPLC is 60.4 µg/mL.

The water solubility of the monohydrochloride monohydrate of the quinazoline derivative at 20° C. determined by HPLC is 51.5 µg/mL.

The water solubility of the mono-D-gluconate of the quinazoline derivative at 20° C. determined by HPLC is 51.4 µg/mL.

The water solubility of the diphosphate of the quinazoline derivative at 20° C. determined by HPLC is 25.0 µg/mL.

Figure 95:
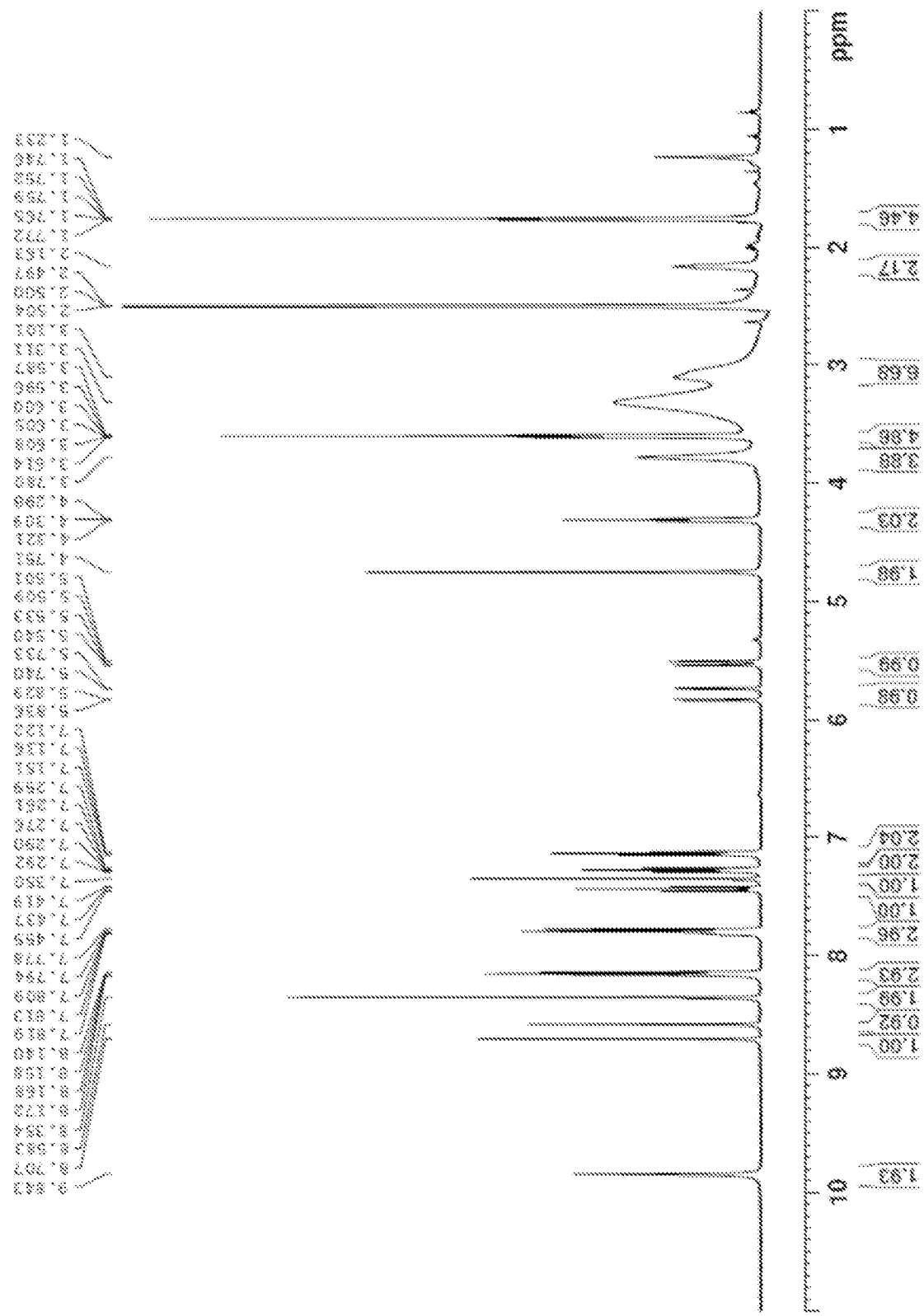
FIG. 95 is $^1$H NMR pattern of the monopamoate of the quinazoline derivative of the present invention.

FIG. 95 is $^1$H NMR pattern of the monopamoate of the quinazoline derivative of the present invention. It is indicated that the molar ratio of the pamoic acid to the compound represented by formula 1 in the monopamoate of the quinazoline derivative is 1:1. The water solubility of the monopamoate of the quinazoline derivative at 20° C. was determined by HPLC, wherein no absorption peak was detected, indicating that it is almost insoluble.

Figure 96:
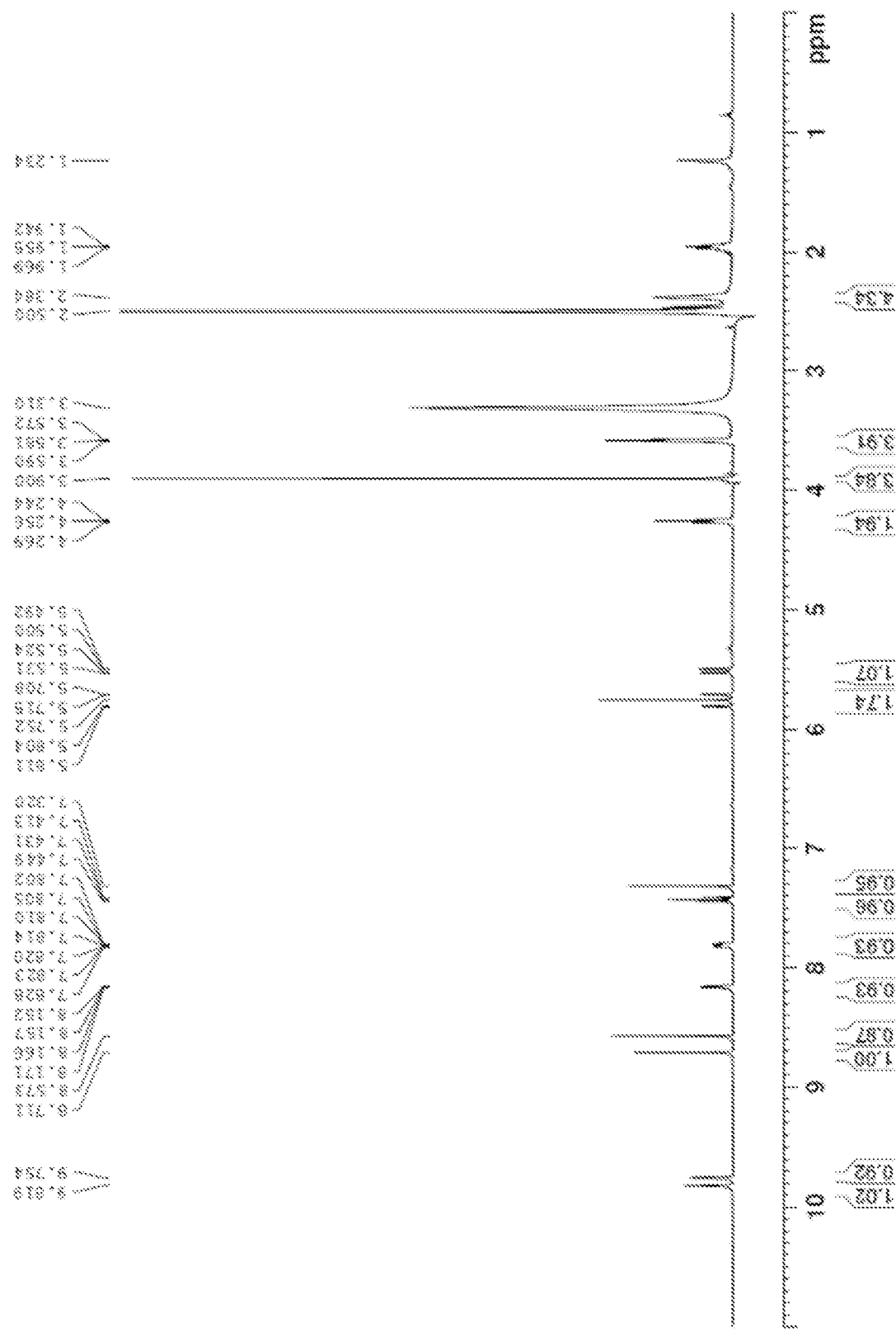
FIG. 96 is $^1$H NMR pattern of the diglycolate of the quinazoline derivative of the present invention.

FIG. 96 is 41 NMR pattern of the diglycolate of the quinazoline derivative of the present invention. It is indicated that the molar ratio of the glycolic acid to the compound represented by formula 1 in the diglycolate of the quinazoline derivative is 1:1. The water solubility of the diglycolate of the quinazoline derivative at 20° C. determined by HPLC is 24.2 µg/mL.

Figure 97:
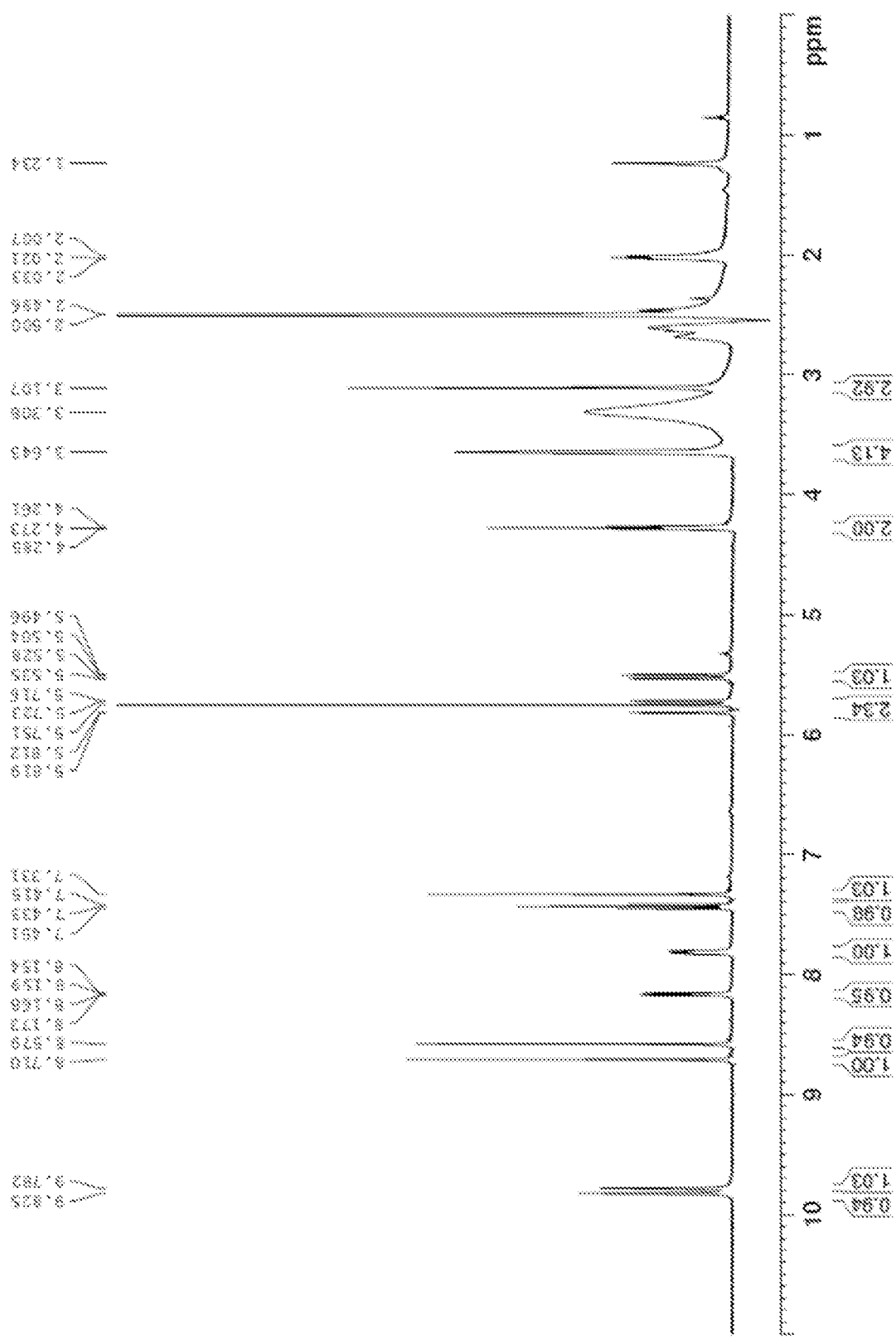
FIG. 97 is $^1$H NMR pattern of the monomalonate of the quinazoline derivative of the present invention.

FIG. 97 is $^1$H NMR pattern of the monomalonate of the quinazoline derivative of the present invention. It is indicated that the molar ratio of the malonic acid to the compound represented by formula 1 in the monomalonate of the quinazoline derivative is 1:1. The water solubility of the monomalonate of the quinazoline derivative at 20° C. determined by HPLC is 41 μg/mL.

Figure 98:
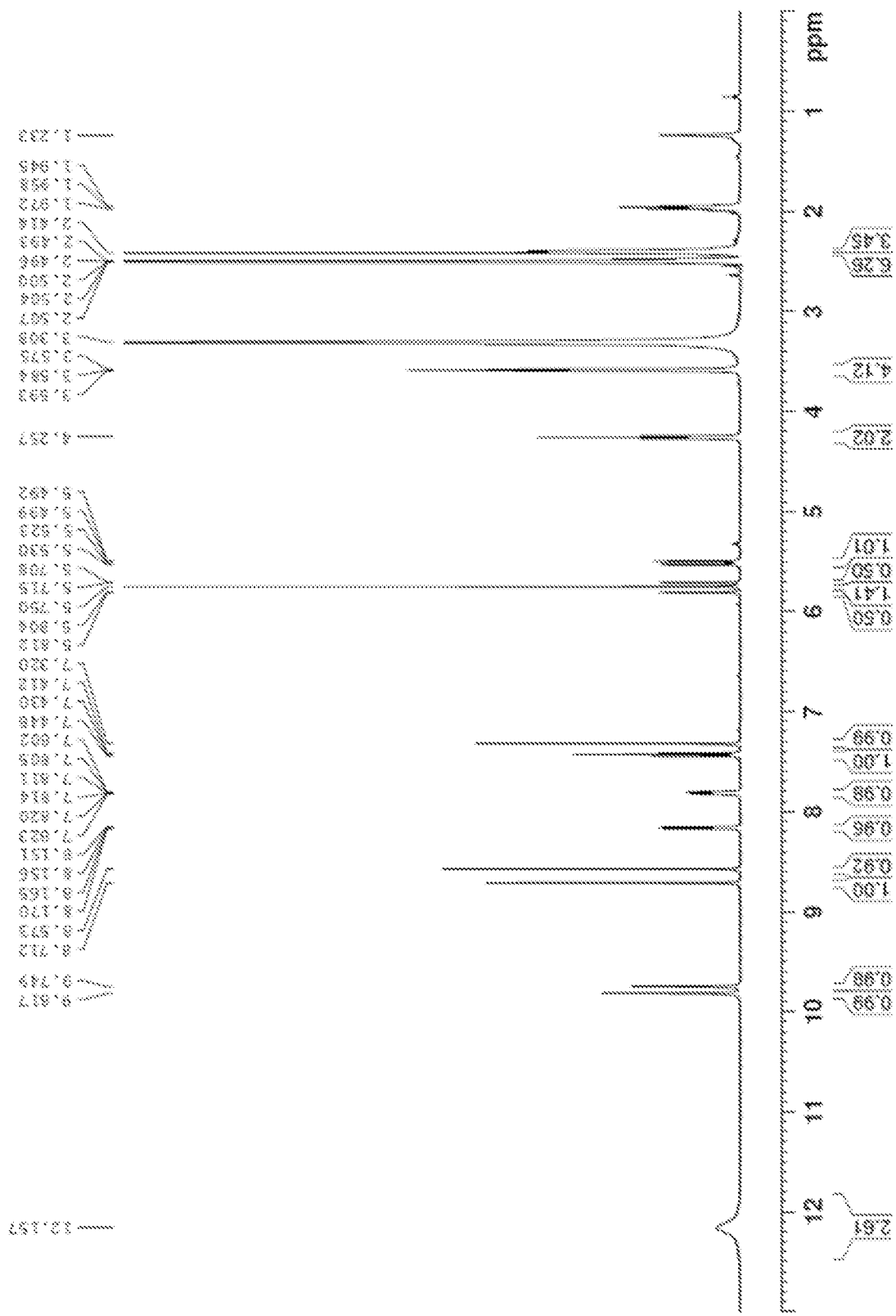
FIG. 98 is $^1$H NMR pattern of the monosuccinate of the quinazoline derivative of the present invention.

FIG. 98 is $^1$H NMR pattern of the monosuccinate of the quinazoline derivative of the present invention. It is indicated that the molar ratio of the succinic acid to the compound represented by formula 1 in the monosuccinate of the quinazoline derivative is 1:1. The water solubility of the monosuccinate of the quinazoline derivative at 20° C. determined by HPLC is 32 μg/mL.

The water solubility of the dimaleate of the quinazoline derivative at 20° C. determined by HPLC is 25.7 μg/mL.

Figure 99:
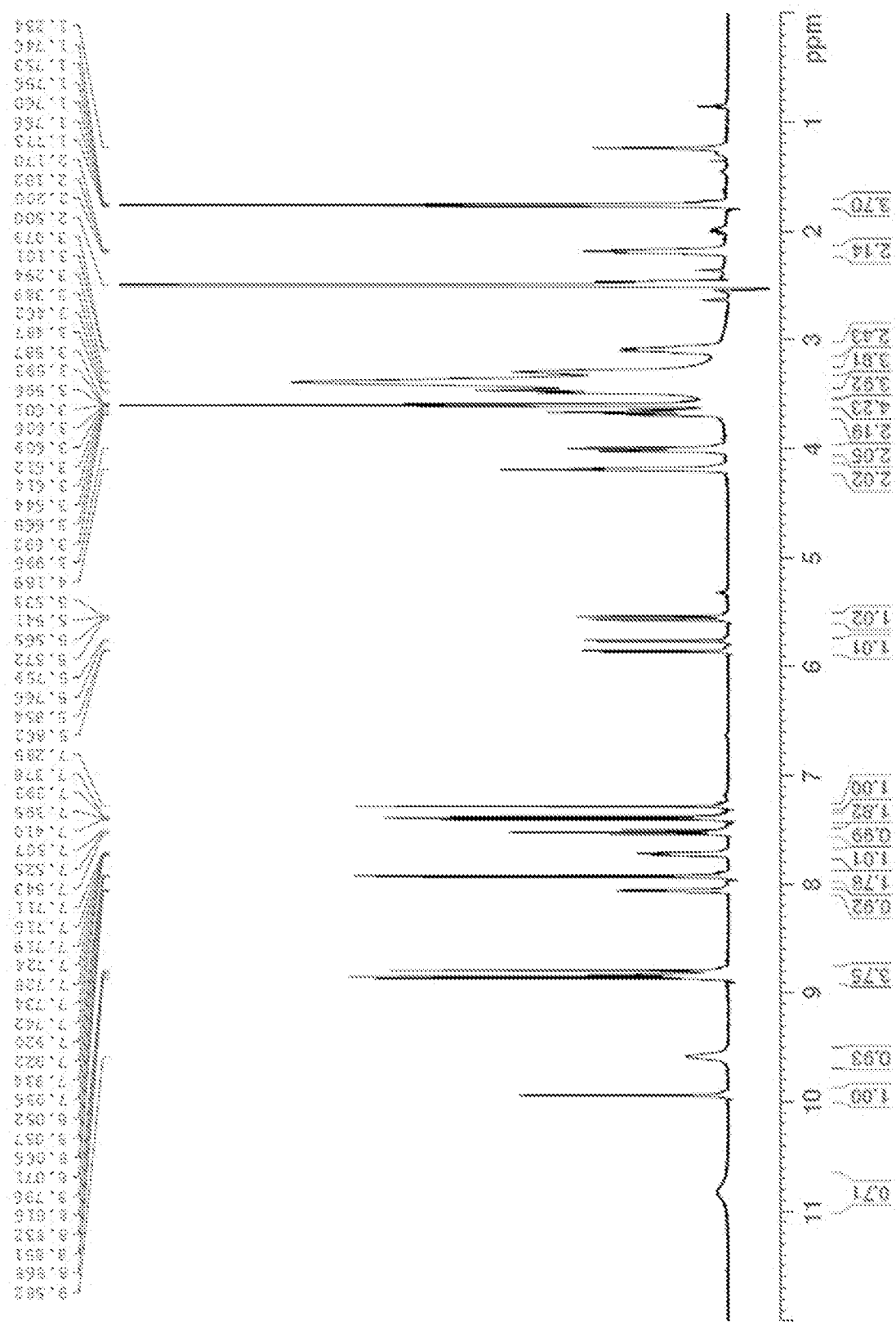
FIG. 99 is $^1$H NMR pattern of the mono-1,5-naphthalene-disulfonate of the quinazoline derivative of the present invention.

FIG. 99 is $^1$H NMR pattern of the mono-1,5-naphthalenedisulfonate of the quinazoline derivative of the present invention. It is indicated that the molar ratio of the 1,5-naphthalenedisulfonic acid to the compound represented by formula 1 in the mono-1,5-naphthalenedisulfonate of the quinazoline derivative is 1:1. The water solubility of the mono-1,5-naphthalenedisulfonate of the quinazoline derivative at 20° C. was determined by HPLC, wherein no absorption peak was detected, indicating that it is almost insoluble.

The water solubility of the trisuccinate of the quinazoline derivative at 20° C. determined by HPLC is 8.6 μg/mL.

The solubility of crystal form 1 in different solvents at 20° C. determined by HPLC is shown in Table 3.

TABLE 3

| Abbreviation | Solubility mg/mL |
| --- | --- |
| MeOH | 5-12.5 |
| EtOH | <1 |
| IPA | <1 |
| BtOH | <1 |
| H$_2$O | <1 |
| THF | <1 |
| Dioxane | 1-2.5 |
| ACN | <1 |
| CH$_2$Cl$_2$ | <1 |
| CHCl$_3$ | <1 |
| DMSO | 100-200 |

In addition, the results of the solubility determined by visual inspection are as follows:

(1) The monoethanedisulfonate of the quinazoline derivative: the visual solubility of the salt in water at room temperature of 1-2 mg/mL.

(2) The monosulfate of the quinazoline derivative: the visual solubility of the sample in water at 20° C. is 1-2 mg/mL.

(3) The disulfate of the quinazoline derivative: the visual solubility of the sample in water at 20° C. is 0.91-1 mg/mL.

(4) The mono-L-tartrate tetrahydrate of the quinazoline derivative: the visual solubility of the hydrate in water at room temperature is 0.625-0.667 mg/mL.

(5) The dimalonate of the quinazoline derivative: the visual solubility of the sample in water at room temperature is 2-2.5 mg/mL.

(6) The trimalonate of the quinazoline derivative: the visual solubility of the sample in water at room temperature was 1.67-2 mg/mL.

The above is only the specific embodiments of the present invention, but the scope of the present invention is not limited thereto. Any changes or alternatives made by those skilled in the art according to the technical scope of the present invention without creativity are intended to fall within the scope of the present invention.

Figure 100:
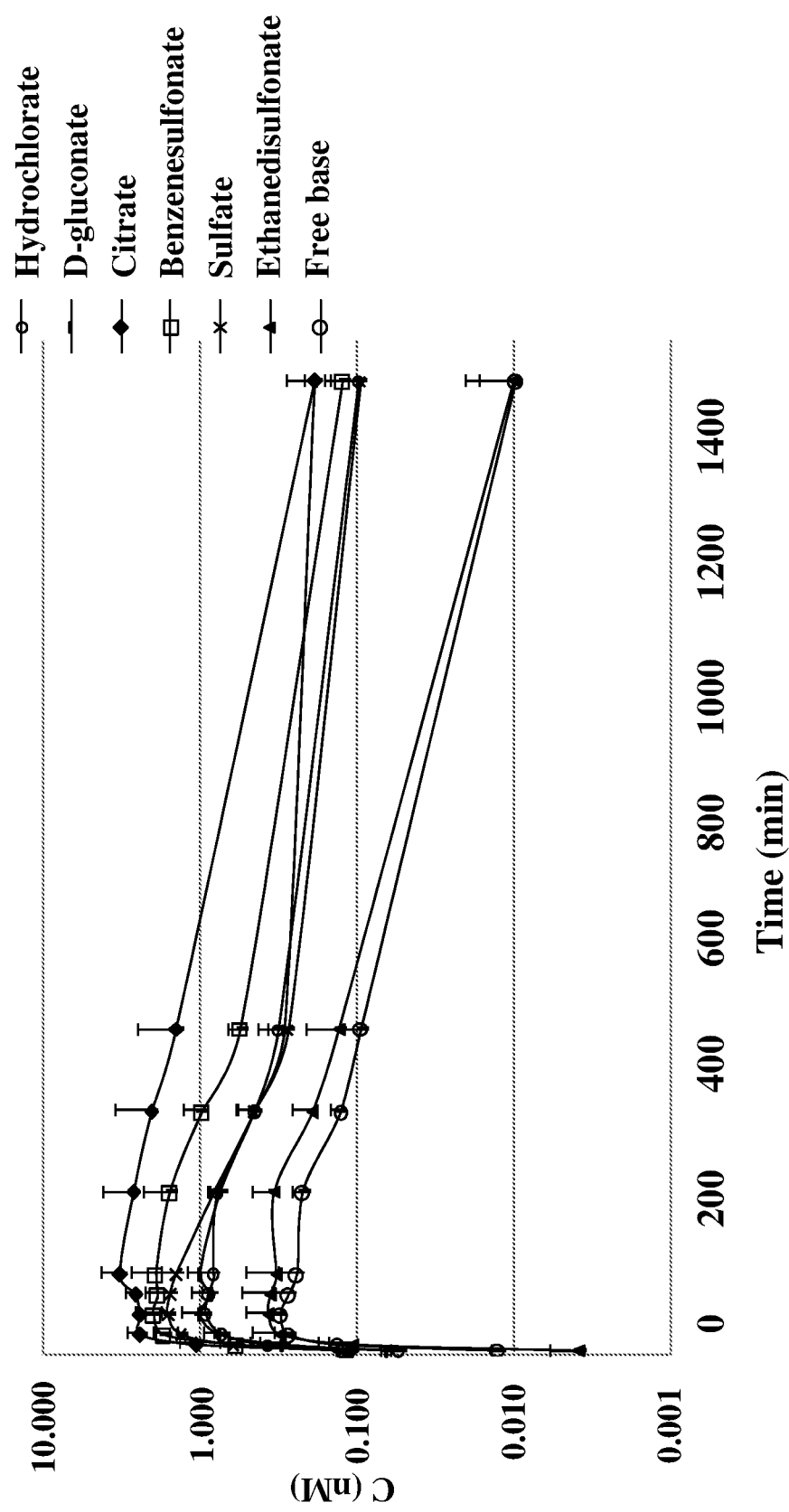
FIG. 100 is the drug concentration-time curve of each salt of the quinazoline derivative of the present invention.

Effectiveness Embodiment 4: Comparison of Absorption in Rats after Administration of Free Base and Salt 21 SD rats were divided into 7 groups, and 20 μmol/kg of the free base and 6 salts of the above quinazoline derivative compound represented by formula 1 (8 mL/kg, 2.5 mM) were given by means of intragastric administration (see Table 4). 0.4 mL of blood was taken from the fundus venous plexus of rats before administration and 5, 15, 30, 60, 90, 120, 240, 360, 480, and 1440 minutes after administration, respectively. The blood sample was centrifuged at 8000 RPM for 5 minutes, followed by the isolation of the upper plasma. 200 μL of the acetonitrile containing internal standard (Ponatinib, 0.25 μM) was added to 50 μL of the plasma sample to precipitate the protein, followed by vortexing for 10 minutes and centrifugation at 6000 g for 10 minutes. 200 μL of the supernatant was taken and centrifuged again for 10 minutes. 50 μL of the supernatant was injected in a 96-well plate. The plasma drug concentration was determined by LC/MS/MS, and the corresponding pharmacokinetic parameters were calculated. See Table 5 and FIG. 100.

TABLE 4

| Compound | Preparation of the test agents | Subject dose (μmol/kg) | Concentration of the dosing solution (mM) | Dose volume (mL/kg) | Route of administration | Number of animals/gender |
| --- | --- | --- | --- | --- | --- | --- |
| The monohydrochloride monohydrate | CMC-Na (containing 0.4% Tween80) | 20 | 2.5 | 8 | Intragastric administration | 3/male |
| mono-D-gluconate | CMC-Na (containing 0.4% Tween80) | 20 | 2.5 | 8 | Intragastric administration | 3/male |
| The monocitrate (crystal form 1) | CMC-Na (containing 0.4% Tween80) | 20 | 2.5 | 8 | Intragastric administration | 3/male |

TABLE 4-continued

| Compound | Preparation of the test agents | Subject dose (μmol/kg) | Concentration of the dosing solution (mM) | Dose volume (mL/kg) | Route of administration | Number of animals/ gender |
|---|---|---|---|---|---|---|
| The monobenzene-sulfonate | CMC-Na (containing 0.4% Tween80) | 20 | 2.5 | 8 | Intragastric administration | 3/male |
| The monosulfate | CMC-Na (containing 0.4% Tween80) | 20 | 2.5 | 8 | Intragastric administration | 3/male |
| The monoethane-disulfonate | CMC-Na (containing 0.4% Tween80) | 20 | 2.5 | 8 | Intragastric administration | 3/male |
| The quinazoline derivative compound represented by formula 1 | CMC-Na (containing 0.4% Tween80) | 20 | 2.5 | 8 | Intragastric administration | 3/male |

TABLE 5

| | Dose (μmol/kg) | Cmax (μM) | Tmax (min) | AUC (0-t) (μM*min) | MRT (0-T) (min) | t1/2 (min) |
|---|---|---|---|---|---|---|
| The monohydrochloride monohydrate | 20.00 | 0.98 ± 0.06 | 70.00 ± 17.32 | 507.89 ± 66.81 | 408.76 ± 81.85 | 270.47 ± 93.62 |
| mono-D-gluconate | 20.00 | 1.12 ± 0.28 | 80.00 ± 34.64 | 484.40 ± 201.71 | 375.68 ± 153.09 | 213.43 ± 20.92 |
| The monocitrate (crystal form 1) | 20.00 | 3.35 ± 1.00 | 100.00 ± 34.64 | 1894.24 ± 1131.20 | 359.24 ± 37.56 | 217.25 ± 91.84 |
| The monobenzenesulfonate | 20.00 | 2.30 ± 0.47 | 80.00 ± 34.64 | 972.26 ± 291.88 | 357.13 ± 15.20 | 305.38 ± 127.64 |
| The monosulfate | 20.00 | 1.66 ± 0.27 | 70.00 ± 17.32 | 591.00 ± 29.76 | 343.51 ± 42.43 | 230.81 ± 162.24 |
| The monoethanedisulfonate | 20.00 | 0.39 ± 0.16 | 80.00 ± 17.32 | 195.56 ± 84.51 | 319.90 ± 59.62 | 224.64 ± 54.99 |
| The quinazoline derivative compound represented by formula 1 | 20.00 | 0.31 ± 0.07 | 60.00 | 122.73 ± 28.00 | 399.30 ± 91.28 | 256.89 ± 105.96 |

By comparison, the free base and the 6 salts were orally administered to rats at the same dose. It is indicated that the citrate, the monobenzenesulfonate and the monosulfate are better absorbed, while the AUC (0-t) and Cmax of the monohydrochloride monohydrate, the mono-D-gluconate and the monoethanedisulfonate are relatively low. Among them, the citrate has the highest AUC (0-t) and Cmax.

It is to be understood that the foregoing description of the embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A crystal form 1 of the monocitrate represented by formula 2, wherein the crystal form 1 has an X-ray powder diffraction pattern comprising characteristic peaks at diffraction angle 2θ of 8.280±0.2°, 8.720±0.2°, 16.962±0.2°, 19.124±0.2°, 19.742±0.2° and 25.222±0.2°

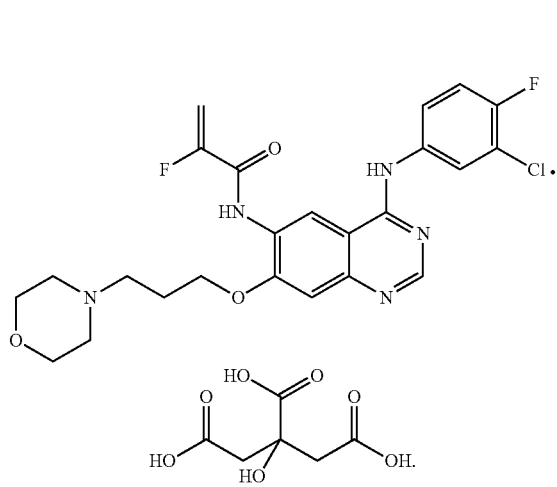

2. The crystal form 1 of the monocitrate represented by formula 2 according to claim 1, wherein the crystal form 1 has an X-ray powder diffraction pattern comprising characteristic peaks at diffraction angle 2θ of 8.280±0.2°, 8.720±0.2°, 13.621±0.2°, 14.043±0.2°, 16.522±0.2°, 16.962±0.2°, 19.124±0.2°, 19.742±0.2°, 21.367±0.2°, 23.439±0.2°, 25.222±0.2° and 26.842±0.2°.

3. The crystal form 1 of the monocitrate represented by formula 2 according to claim 1, wherein the crystal form 1 has an X-ray powder diffraction pattern comprising characteristic peaks at diffraction angle 2θ of 5.278±0.2°, 8.280±0.2°, 8.720±0.2°, 9.862±0.2°, 10.740±0.2°, 11.564±0.2°, 13.621±0.2°, 14.043±0.2°, 14.853±0.2°, 16.522±0.2°, 16.962±0.2°, 19.124±0.2°, 19.742±0.2°, 20.501±0.2°, 20.802±0.2°, 21.367±0.2°, 23.439±0.2°, 23.799±0.2°, 25.222±0.2°, 26.359±0.2°, 26.842±0.2°, 27.494±0.2°, 28.919±0.2°, 32.383±0.2° and 32.764±0.2°.

4. The crystal form 1 of the monocitrate represented by formula 2 according to claim 1, wherein the crystal form 1 has an X-ray powder diffraction pattern comprising characteristic peaks at diffraction angle 2θ of 8.280±0.2°, 8.720±0.2°, 9.862±0.2°, 10.740±0.2°, 11.564±0.2°, 13.621±0.2°, 14.043±0.2°, 16.522±0.2°, 16.962±0.2°, 19.124±0.2°, 19.742±0.2°, 20.802±0.2°, 21.367±0.2°, 23.439±0.2° and 25.222±0.2°.

5. The crystal form 1 of the monocitrate represented by formula 2 according to claim 1, wherein the crystal form 1 has one or more of the parameters as follows: the XRPD pattern shown as FIG. 1, the TGA pattern shown as FIG. 2, the DSC pattern shown as FIG. 3 and the DVS pattern shown as FIG. 4.

6. The crystal form 1 of the monocitrate represented by formula 2 according to claim 1, wherein the melting point of the crystal form 1 is 165-169° C.;
or, the water absorption of the crystal form 1 in a relative humidity range of 20-80% is 0.21%.

7. A preparation method for the crystal form 1 of the monocitrate represented by formula 2 according to claim 1, comprising the following procedure: carrying out a salt formation reaction on the quinazoline derivative and the citric acid in tetrahydrofuran to give the crystal form 1 of the monocitrate represented by formula 2
wherein, the structure of the quinazoline derivative is represented by formula

1

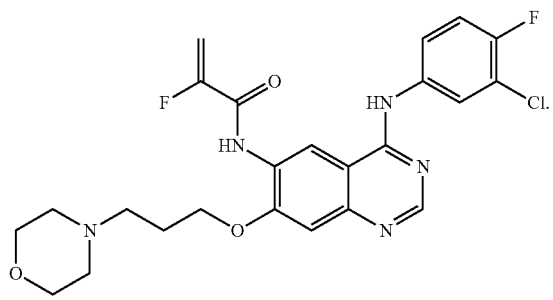

8. The preparation method according to claim 7, wherein, the volume/mass ratio of the tetrahydrofuran to the quinazoline derivative is 25-50 mL/g;
or, the molar ratio of the citric acid to the quinazoline derivative is 1-1.5;
or, the temperature of the salt formation is 10-30° C.;
or, the duration of the salt formation is 0.5-24 hours;
or, the operation of the salt formation reaction is mixing the solution of citric acid in tetrahydrofuran with the solution of the quinazoline derivative in tetrahydrofuran;
or, the post-treatment of the salt formation reaction is filtration and drying;
or, the method comprises the following procedure: mixing the solution of citric acid in tetrahydrofuran with the solution of the quinazoline derivative in tetrahydrofuran, reacting, followed by the isolation of the precipitated solids and drying to give the product.

9. The preparation method according to claim 8, wherein, the volume/mass ratio of the tetrahydrofuran to the quinazoline derivative is 26-48 mL/g;
or, the operation of the salt formation reaction is that adding the solution of citric acid in tetrahydrofuran into the solution of the quinazoline derivative in tetrahydrofuran; the concentration of the quinazoline derivative solution in tetrahydrofuran is 25-50 mg/mL; concentration of the citric acid solution in tetrahydrofuran is 50-100 mg/mL;
or, the post-treatment of the salt formation reaction is filtration and drying;
or, the method comprises the following procedure: mixing the solution of citric acid in tetrahydrofuran with the solution of the quinazoline derivative in tetrahydrofuran, reacting, followed by the isolation of the precipitated solids and drying to give the product; the temperature for the drying is 40-45° C.; the drying is vacuum drying.

10. A pharmaceutical composition, comprising a therapeutically and/or prophylactically effective dose of the salt of the crystal form 1 of the monocitrate represented by formula 2 according to claim 1, and at least one kind of pharmaceutically acceptable excipient.

11. A method for treating tumor diseases in a subject in need thereof, comprising: administering an effective amount of the crystal form 1 of the monocitrate represented by formula 2 according to claim 1 to the subject.

12. A method for treating a patient in need of a medicament for EGFR tyrosine kinase inhibitor HER2 tyrosine kinase inhibitor or HER4 tyrosine kinase inhibitor comprising: administering an effective amount of the crystal form 1 of the monocitrate represented by formula 2 according to claim 1 to the patient.

* * * * *